(12) United States Patent
Blumstein et al.

(10) Patent No.: US 10,314,823 B2
(45) Date of Patent: Jun. 11, 2019

(54) SUBSTITUTED 1,2-DIHYDRO-3H-PYRROLO[1,2-C]IMIDAZOL-3-ONE ANTIBACTERIAL COMPOUNDS

(71) Applicant: IDORSIA PHARMACEUTICALS LTD, Allschwil (CH)

(72) Inventors: Anne-Catherine Blumstein, Allschwil (CH); Gaelle Mathieu, Allschwil (CH); Loïc Jacob, Allschwil (CH); Florence Masse, Allschwil (CH); Azely Mirre, Allschwil (CH); Philippe Panchaud, Allschwil (CH); Christine Schmitt, Allschwil (CH); Jean-Luc Specklin, Allschwil (CH); Jean-Philippe Surivet, Allschwil (CH)

(73) Assignee: IDORSIA PHARMACEUTICALS LTD, Allschwil (CH)

( * ) Notice: Subject to any disclaimer, the term of this patent is extended or adjusted under 35 U.S.C. 154(b) by 0 days.

(21) Appl. No.: 15/756,366

(22) PCT Filed: Sep. 2, 2016

(86) PCT No.: PCT/EP2016/070695
§ 371 (c)(1),
(2) Date: Feb. 28, 2018

(87) PCT Pub. No.: WO2017/037221
PCT Pub. Date: Mar. 9, 2017

(65) Prior Publication Data
US 2018/0250273 A1    Sep. 6, 2018

(30) Foreign Application Priority Data

Sep. 3, 2015  (WO) ................. PCT/EP2015/070144

(51) Int. Cl.
*A61K 31/4188*  (2006.01)
*A61K 31/397*   (2006.01)
(Continued)

(52) U.S. Cl.
CPC ........ *A61K 31/4188* (2013.01); *A61K 31/397* (2013.01); *A61K 31/4439* (2013.01);
(Continued)

(58) Field of Classification Search
CPC .............. A61K 31/397; A61K 31/4188; A61K 31/4439; A61P 31/04; C07D 487/04; C07D 519/00
See application file for complete search history.

(56) References Cited

U.S. PATENT DOCUMENTS 9,624,206 B2    4/2017  Chapoux et al.
9,796,686 B2    10/2017 Chapoux et al.
(Continued)

FOREIGN PATENT DOCUMENTS

WO    WO 03/077914 A1    9/2003
WO    WO 2005/036964 A1  4/2005
(Continued)

OTHER PUBLICATIONS

Bellina et al., "Palladium Catalysts for the Suzuki Cross-Coupling Reaction: An Overview of Recent Advances," Synthesis, 2004, pp. 2419-2440.
(Continued)

*Primary Examiner* — Erich A Leeser
(74) *Attorney, Agent, or Firm* — Arent Fox LLP

(57) ABSTRACT

The invention relates to antibacterial compounds of formula I wherein M is one of the groups $M^A$, $M^B$ and $M^C$ represented below wherein $R^1$, $M^A$, $M^B$ and $M^C$ are as defined in the specification;
and to salts thereof.

39 Claims, No Drawings

(51) Int. Cl.
A61K 31/4439 (2006.01)
C07D 487/04 (2006.01)
C07D 519/00 (2006.01)
A61P 31/04 (2006.01)
(52) U.S. Cl.
CPC ............ A61P 31/04 (2018.01); C07D 487/04 (2013.01); C07D 519/00 (2013.01)

(56) References Cited

U.S. PATENT DOCUMENTS

| 9,802,901 | B2 | 10/2017 | Gauvin et al. |
| 2016/0221959 | A1 | 8/2016 | Gauvin et al. |
| 2017/0029411 | A1 | 2/2017 | Chapoux et al. |
| 2017/0081292 | A1 | 3/2017 | Chapoux et al. |
| 2017/0107223 | A1 | 4/2017 | Chapoux et al. |
| 2017/0355687 | A1 | 12/2017 | Chapoux et al. |

FOREIGN PATENT DOCUMENTS

| WO | WO 2015/036964 A | * | 4/2005 | ............ A01N 43/90 |
| WO | WO 2010/060785 A1 | | 6/2010 | |
| WO | WO 2011/045703 A2 | | 4/2011 | |
| WO | WO 2011/073845 A1 | | 6/2011 | |
| WO | WO 2012/093809 A2 | | 7/2012 | |
| WO | WO 2012/120397 A1 | | 9/2012 | |
| WO | WO 2012/137094 A1 | | 10/2012 | |
| WO | WO 2012/137099 A1 | | 10/2012 | |
| WO | WO 2013/170165 A1 | | 11/2013 | |
| WO | WO 2014/078609 A1 | | 5/2014 | |
| WO | WO 2014/165075 A1 | | 10/2014 | |
| WO | WO 2015/036964 A1 | | 3/2015 | |
| WO | WO 2015/066413 A1 | | 5/2015 | |
| WO | WO 2015/091741 A1 | | 6/2015 | |
| WO | WO 2015/132228 A1 | | 9/2015 | |
| WO | WO 2015/173329 A1 | | 11/2015 | |
| WO | WO 2016/079688 A1 | | 5/2016 | |
| WO | WO 2017/025562 A1 | | 2/2017 | |
| WO | WO 2017/036968 A1 | | 3/2017 | |
| WO | WO 2017/037039 A1 | | 3/2017 | |
| WO | WO 2017/098440 A1 | | 6/2017 | |
| WO | WO 2017/198647 A1 | | 11/2017 | |

OTHER PUBLICATIONS

Benz, "Synthesis of Amides and Related Compounds," Comprehensive Organic Systems, New York, 1991, vol. 6, pp. 381-417.
Chodkiewicz et al., "Nouvelle Synthése de composes polyacétyléniques conjugués symétriques et dissymétriques," C.R. Hebd. Seances Acad. Sci., 1955, vol. 241, pp. 1055-1057 (8 pages total).
Fu, "The Development of Versatile Methods for Palladium-Catalyzed Coupling Reactions of Aryl Electrophiles through the Use of P(t-BU)3 and PCy3 as Ligands," Accounts of Chemical Research, 2008, vol. 41(11), pp. 1555-1564.
International Search Report and Written Opinion issued in International Patent Application No. PCT/EP2016/070695, dated Oct. 27, 2016 (6 pages).
Kantchev et al., "Pd—N-Heterocyclic Carbene (NHC) Catalysts for Cross-Coupling Reactions," Aldrichimica ACTA, vol. 39(4), 2006, pp. 97-111.
Ko et al., "Total Synthesis of (−)-Blepharocalyxin D" Organic Letters, 2007, vol. 9(1), pp. 141-144.
Larock, "Comprehensive Organic Transformations, A Guide to Functional Group Preparations," 2nd Edition, 1999, Section Nitriles, Carboxylic Acids and Derivatives, pp. 1941-1949.
Lee et al., N-[4-(Methylsulfonylamino)benzyl]thiourea analogues as vanilloid receptor antagonists: analysis of structure-activity relationships for the 'C-Region,' Bioorganic and Medicinal Chemistry, vol. 12, 2004, pp. 371-385.
Longshaw et al., "Design and Synthesis of Potent "Sulfur-Free" Transition State Analogue Inhibitors of 5'-Methylthioadenosine Nucleosidase and 5'Methylthioadenosine Phosphorylase,"J. Med. Chem., 2010, vol. 53, pp. 6730-6746.
Marmer et al., "The Preparation and Reactions of Novel O-Acylhydroxylamines," J. Org. Chem., vol. 37(22), 1972, pp. 3520-3523.
Mauger et al., "Synthetic Applications of Buchwald's Phosphines in Palladium-Catalyzed Aromatic-Bond-Forming Reactions," Aldrichimica ACTA, vol. 39(1), 2006, pp. 17-24.
Methods for Dilution Antimicrobial Susceptibility Tests for Bacteria That Grow Aerobically; Approved Standard—Seventh Ed. vol. 26(2), 2006, pp. 1-64.
Miyaura et al., "Palladium-Catalyzed Cross-Coupling Reactions of Organoboron Compounds," Chem. Rev. 1995, vol. 95, pp. 2457-2483.
Montgomery et al., "Pyridone Methylsulfone Hydroxamate LpxC Inhibitors for the Treatment of Serious Gram-Negative Infections," J. of Medicinal Chem., vol. 55(4), 2012, pp. 1662-1670.
Remington, The Science and Practice of Pharmacy, 21st Edition, 2005, pp. 1-5.
Sanford et al., The Sanford Guide to Antimicrobial Therapy 2012, 42nd Edition, pp. 1-4.
Sleveland et al., "Synthesis of Phenylboronic Acids in Continuous Flow by Means of a Multijet Oscillating Disc Reactor System Operating at Cryogenic Temperatures," Organic Process & Res. Development, 2012, vol. 16, pp. 1121-1130.
Sonogashira, Cross-Coupling Reactions to sp Carbon Atoms, 1998, pp. 203-229.
Stahl et al., Handbook of Pharmaceutical Salts, 2008, pp. 329-350.
Sugano et al., "Total Synthesis of (+)-Polygaloide A and (+)-Polygalolide B: Elucidation of the Absolute Stereochemistry and Biogenetic Implications," Chem., A European Journal, vol. 18(31), 2012, pp. 9682-9690.
Sugisaki et al., "Direct Access to Furanosidic Eight-Membered Ulosonic Esters from cis-theta, Beta-Epoxy Aldehydes," Eur. J. of Org. Chem., 2003, pp. 672-688.
T.W. Greene and P.G.M. Wuts, Protecting Groups in Orgnaic Synthesis, 3rd Ed., 1999, pp. 23-147.
T.W. Greene and P.G.M. Wuts, Protecting Groups in Organic Synthesis, 3rd Ed., 1999, Wiley-Interscience, pp. 1-3.
T.W. Greene et al., Protective Groups in Organic Synthesis, 3rd Eds., Publisher: John Wiley and Sons, Inc., New York, NY, 1999, pp. 369-441.
Wang et al., "Copper(I) Iodide Catalyzed Cross-Coupling Reaction of Terminal Alkynes with 1-Bromoalkynes: A Simple Synthesis of Unsymmetrical Buta-1,3-diynes," 2011, pp. 1541-1546.
Wouters et al., Pharmaceutical Salts and Co-crystals, 2012, pp. 1-10.

* cited by examiner

SUBSTITUTED 1,2-DIHYDRO-3H-PYRROLO[1,2-C]IMIDAZOL-3-ONE ANTIBACTERIAL COMPOUNDS

CROSS REFERENCE TO RELATED APPLICATIONS

This application is a 35 U.S.C. 371 National Phase of PCT Application No. PCT/EP2016/070695 filed Sep. 2, 2016, which claims benefit to PCT Application No. PCT/EP2015/070144 filed Sep. 3, 2015, the disclosure of each of which is hereby incorporated by reference in its entirety.

The present invention concerns substituted 1,2-dihydro-3H-pyrrolo[1,2-c]imidazol-3-one antibacterial compounds, pharmaceutical compositions containing them and uses of these compounds in the manufacture of medicaments for the treatment of bacterial infections. These compounds are useful antimicrobial agents effective against a variety of human and veterinary pathogens, especially Gram negative aerobic and anaerobic bacteria. The compounds of the present invention can optionally be employed in combination, either sequentially or simultaneously, with one or more therapeutic agents effective against bacterial infections.

The intensive use of antibiotics has exerted a selective evolutionary pressure on microorganisms to produce genetically based resistance mechanisms. Modern medicine and socio-economic behaviour exacerbate the problem of resistance development by creating slow growth situations for pathogenic microbes, e.g. in artificial joints, and by supporting long-term host reservoirs, e.g. in immune-compromised patients.

In hospital settings, an increasing number of strains of *Staphylococcus aureus, Streptococcus pneumoniae, Enterococcus* spp., Enterobacteriaceae such as *Klebsiella pneumoniae, Acinetobacter baumannii* and *Pseudomonas aeruginosa*, major sources of infections, are becoming multi-drug resistant and therefore difficult if not impossible to treat. This is particularly the case for Gram-negative organisms where the situation is getting worrisome since no novel agents have been approved for decades and the development pipeline looks empty.

Therefore, there is an important medical need for new antibacterial compounds addressing Gram-negative resistant bacteria, in particular third generation cephalosporins- and carbapenem-resistant *Klebsiella pneumoniae* and multi-drug-resistant *Pseudomonas aeruginosa* and *Acinetobacter baumannii*. One way to tackle the problem of cross resistance to established classes of antibiotics is to inhibit a new essential target. In this respect, LpxC, which is an enzyme in the biosynthesis of lipopolysaccharides (a major constituent of the outer membrane of Gram-negative bacteria), has received some attention and several patent applications relating to LpxC inhibitors have been published recently.

For example, WO 2011/045703, WO 2011/073845, WO 2012/120397, WO 2012/137094, WO 2012/137099, WO 2013/170165 and WO 2015/066413 describe antibacterial compounds having a N-hydroxy-2-methyl-2-(methylsulfonyl)butanamide side chain bound to a monocyclic aromatic or heteroaromatic ring system.

Furthermore WO 2013/170165 describes notably antibacterial compounds of formula (A0)

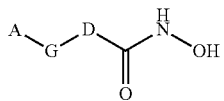

(A0)

wherein A is a substituted alkyl group, wherein at least one substituent is hydroxy, or A is a substituted cycloalkyl group, wherein at least one substituent is hydroxy or hydroxyalkyl; G is a group comprising at least one carbon-carbon double or triple bond and/or a phenyl ring; D represents a group selected from

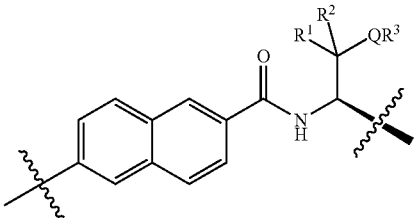

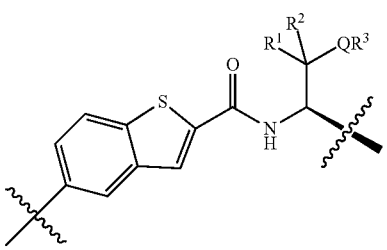

Q is O or NR, wherein R is H or an unsubstituted ($C_1$-$C_3$) alkyl; $R^1$ and $R^2$ independently are selected from the group consisting of H and substituted or unsubstituted ($C_1$-$C_3$) alkyl, or $R^1$ and $R^2$, together with the carbon atom to which they are attached, form an unsubstituted ($C_3$-$C_4$)cycloalkyl group or an unsubstituted 4-6 membered heterocyclic group; and $R^3$ is selected from the group consisting of hydrogen, substituted or unsubstituted ($C_1$-$C_3$)alkyl, substituted or unsubstituted cycloalkyl, substituted or unsubstituted cycloalkylalkyl, substituted or unsubstituted aryl, substituted or unsubstituted arylalkyl, substituted or unsubstituted heterocyclyl, substituted or unsubstituted heterocyclylalkyl, substituted or unsubstituted heteroaryl, and substituted or unsubstituted heteroarylalkyl.

In WO 2015/036964, we have reported antibacterial 2H-indazole derivatives of general formula (A1)

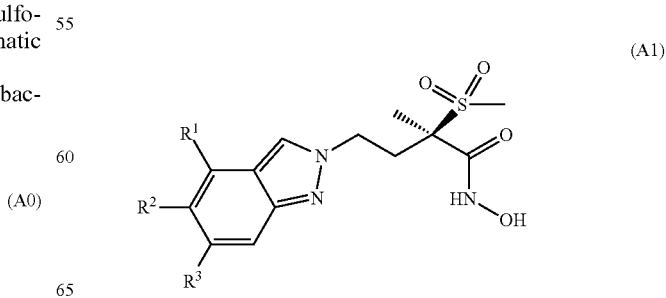

(A1)

wherein
R¹ is H or halogen; R² is (C₃-C₄)alkynyloxy or the group M; R³ is H or halogen; M is one of the groups $M^A$ and $M^B$ represented below

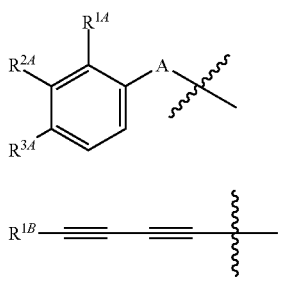

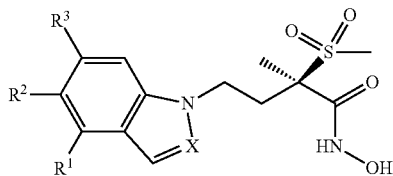

wherein A is a bond, CH₂CH₂, CH=CH or C≡C; $R^{1A}$ represents H or halogen; $R^{2A}$ represents H, alkoxy or halogen; $R^{3A}$ represents H, alkoxy, hydroxyalkoxy, thioalkoxy, trifluoromethoxy, amino, dialkylamino, hydroxyalkyl, 1-hydroxymethyl-cycloprop-1-yl, trans-2-hydroxymethyl-cycloprop-1-yl, 1,2-dihydroxyethyl, 3-hydroxyoxetan-3-yl, 3-(hydroxyalkyl)oxetan-3-yl, 3-aminooxetan-3-yl, 3-(dialkylamino)oxetan-3-yl, 3-hydroxythietan-3-yl, morpholin-4-ylalkoxy, morpholin-4-ylalkyl, oxazol-2-yl or [1,2,3]triazol-2-yl; and $R^{1B}$ represents 3-hydroxyoxetan-3-yl, 3-hydroxythietan-3-yl, hydroxyalkyl, aminoalkyl, trans-2-hydroxymethyl-cycloprop-1-yl or 4-hydroxytetrahydro-2H-pyran-4-yl.

In WO 2015/091741, we have reported antibacterial 1H-indazole derivatives of general formula (A2)

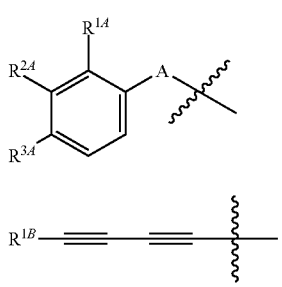
(A2)

wherein
X represents N or CH;
R¹ represents H or halogen;
R² represents (C₃-C₄)alkynyloxy or the group M;
R³ represents H or halogen;
M is one of the groups $M^A$ and $M^B$ represented below

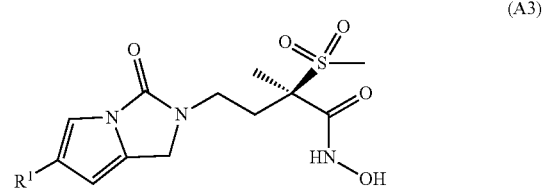

wherein A represents a bond, CH₂CH₂, CH=CH or C≡C; $R^{1A}$ represents H or halogen;
$R^{2A}$ represents H, (C₁-C₃)alkoxy or halogen;
$R^{3A}$ represents H, (C₁-C₃)alkoxy, hydroxy(C₁-C₄)alkoxy, (C₁-C₃)thioalkoxy, trifluoromethoxy, amino, hydroxy(C₁-C₄)alkyl, 2-hydroxyacetamido, 1-hydroxymethyl-cycloprop-1-yl, trans-2-hydroxymethyl-cycloprop-1-yl, 1,2-dihydroxyethyl, 3-hydroxyoxetan-3-yl, 3-(hydroxy(C₁-C₃)alkyl)oxetan-3-yl, 3-aminooxetan-3-yl, 3-hydroxythietan-3-yl, morpholin-4-yl(C₂-C₃)alkoxy, morpholin-4-yl-(C₁-C₂)alkyl, oxazol-2-yl or [1,2,3]triazol-2-yl; and
$R^{1B}$ represents 3-hydroxyoxetan-3-yl, 3-hydroxythietan-3-yl, hydroxy(C₁-C₃)alkyl, amino(C₁-C₃)alkyl, 1-hydroxymethyl-cycloprop-1-yl or trans-2-hydroxymethyl-cycloprop-1-yl.

In WO 2015/132228, we have reported antibacterial 1,2-dihydro-3H-pyrrolo[1,2-c]imidazol-3-one derivatives of general formula (A3)

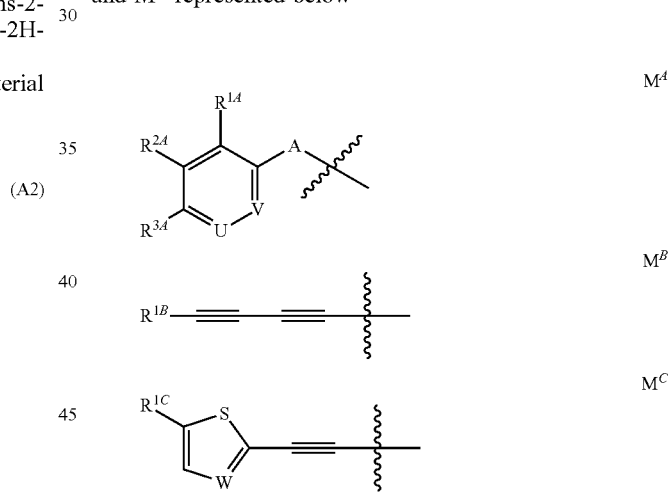
(A3)

wherein R¹ is the group M; M is one of the groups $M^A$, $M^B$ and $M^C$ represented below wherein A is a bond, CH=CH or C≡C; U is N or CH; V is N or CH; $R^{1A}$ is H or halogen; $R^{2A}$ is H, (C₁-C₃)alkoxy or halogen; $R^{3A}$ is H, (C₁-C₃)alkoxy, hydroxy(C₂-C₄)alkoxy, dihydroxy(C₃-C₄)alkoxy, (C₁-C₃)alkoxy(C₁-C₃)alkoxy, (C₁-C₃)thioalkoxy, trifluoromethoxy, trifluoromethyl, amino, hydroxy(C₁-C₄)alkyl, 1,2-dihydroxyethyl, 1-hydroxy-2,2-difluoroethyl, (C₁-C₃)alkoxy(C₁-C₄)alkyl, 2-hydroxy-1-oxoethyl, [(C₁-C₄)alkoxy]carbonyl, methylsulfonamidomethyl, 3-hydroxy-3-methylbut-1-yn-1-yl, 2-hydroxyacetamido, (carbamoyloxy)methyl, 1-aminocyclopropyl, 1-hydroxymethyl-cycloprop-1-yl, 1-aminomethyl-cycloprop-1-yl, 1-(((dimethylglycyl)oxy)methyl)-cycloprop-1-yl, 1-aminomethyl-cycloprop-1-yl, 1-(carbamoyloxy)methyl-cycloprop-1-yl, 1-(morpholin-4-yl)methylcycloprop-1-yl, trans-2-hydroxymethyl-cycloprop-1-yl, 1-(hydroxymethyl)-cyclobut-1-yl, 1-(2-hydroxyacetyl)azetidin-3-yl, (1-tert-butyloxycarbonyl)-3-hydroxyazetidin-3-yl, 3-hydroxyoxetan-3-yl, 3-(hydroxy ($C_1$-$C_3$)alkyl)oxetan-3-yl, 3-aminooxetan-3-yl, 3-hydroxythietan-3-yl, 4-aminopiperidin-1-yl, morpholin-4-yl($C_2$-$C_3$)alkoxy, [4-N—($C_1$-$C_3$)alkylpiperazin-1-yl]($C_1$-$C_3$)alkyl, morpholin-4-yl-($C_1$-$C_2$)alkyl, [1,2,3]triazol-2-yl, 3-[hydroxy($C_2$-$C_3$)alkyl]-2-oxo-imidazolidin-1-yl, (1s,3r)-(1-hydroxy-3-(hydroxymethyl)cyclobutyl)methyl, (4-hydroxypiperidinyl)methyl or (4-aminopiperidinyl)methyl; and $R^{1B}$ is 3-hydroxyoxetan-3-yl, 3-hydroxythietan-3-yl, 3-(hydroxy($C_1$-$C_3$)alkyl)oxetan-3-yl, hydroxy($C_1$-$C_3$)alkyl, 1,2-dihydroxyethyl, amino($C_1$-$C_3$)alkyl, (dimethylamino)methyl, methylsulfonamidomethyl, 1-aminocyclopropyl, 1-hydroxymethyl-cycloprop-1-yl, 1-(carbamoyloxy)methyl-cycloprop-1-yl, 1-(((dimethylglycyl)oxy)methyl)-cycloprop-1-yl, 1-((phosphonooxy)methyl)-cycloprop-1-yl, 1-((((phosphonooxy)methoxy)carbonyl)oxymethyl)-cycloprop-1-yl, 1-((((phosphonooxy)methoxy)carbonyl)amino)-cycloprop-1-yl, trans-2-hydroxymethyl-cycloprop-1-yl, 1-fluoro-2-hydroxymethyl-cycloprop-1-yl, 2-fluoro-2-hydroxymethyl-cycloprop-1-yl, 1-methyl-2-hydroxymethyl-cycloprop-1-yl, 2-hydroxymethyl-2-methylcycloprop-1-yl, (1R*,2S*,3s*)-1,2-bis-(hydroxymethyl)-cycloprop-3-yl, 1-(hydroxymethyl)cyclobut-1-yl, 3-amino-oxetan-3-yl, 3-(hydroxy($C_1$-$C_3$)alkyl)oxetan-3-yl, 1-(2-hydroxyacetyl)-azetidin-3-yl, trans-(cis-3,4-dihydroxy)-cyclopent-1-yl, 3-hydroxymethylbicyclo[1,1,1]pentan-1-yl, 4-hydroxy-tetrahydro-2H-pyran-4-yl, 5-aminotetrahydro-2H-pyran-2-yl, 3-hydroxyoxetan-3-ylmethyl, 1-cyclobutyl-2-hydroxyethyl or 1-(oxetan-3-yl)-azetidin-3-yl.

In WO 2015/173329, we have reported antibacterial quinazoline-4(3H)-one derivatives of general formula (A4)

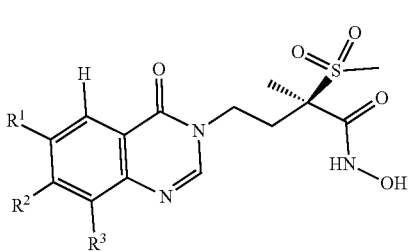

(A4)

wherein $R^1$ is H or halogen; $R^2$ is the group M; $R^3$ is H or halogen; M is one of the groups $M^A$ and $M^B$ represented below

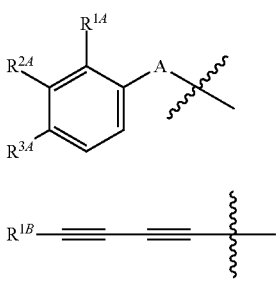

$M^A$ $M^B$ wherein A represents a bond or C≡C; $R^{1A}$ is H or halogen; $R^{2A}$ is H, ($C_1$-$C_3$)alkoxy or halogen; $R^{3A}$ is H, ($C_1$-$C_3$)alkoxy, hydroxy($C_2$-$C_4$)alkoxy, hydroxy($C_1$-$C_4$)alkyl, 1,2-dihydroxyethyl, di($C_1$-$C_3$)alkylamino, 1-hydroxymethyl-cycloprop-1-yl, 1-((dimethylglycyl)oxy)methyl-cycloprop-1-yl, 3-hydroxyoxetan-3-yl, morpholin-4-yl-($C_1$-$C_2$)alkyl or morpholin-4-yl($C_2$-$C_3$)alkoxy; and $R^{1B}$ is hydroxy($C_1$-$C_3$)alkyl, amino($C_1$-$C_3$)alkyl, [di($C_1$-$C_3$)alkylamino]-($C_1$-$C_3$)alkyl, 1,2-dihydroxyprop-3-yl, 1-amino-cycloprop-1-yl, 1-hydroxymethyl-cycloprop-1-yl, 1-((phosphonooxy)methyl)cycloprop-1-yl, trans-2-hydroxymethyl-cycloprop-1-yl, trans-2-aminomethyl-cycloprop-1-yl, 1-fluoro-2-hydroxymethyl-cycloprop-1-yl, trans-2-hydroxymethyl-1-methyl-cycloprop-1-yl, 2-fluoro-2-hydroxymethyl-cycloprop-1-yl, trans-2-hydroxymethyl-2-methyl-cycloprop-1-yl, 1-(1,2-dihydroxyethyl)-cycloprop-1-yl, trans-2-(1,2-dihydroxyethyl)-cycloprop-1-yl, 1-(hydroxymethyl)cyclobut-1-yl, 3-hydroxyoxetan-3-yl, 3-(hydroxy($C_1$-$C_3$)alkyl)oxetan-3-yl, 3-hydroxythietan-3-yl, trans-(cis-3,4-dihydroxy)-cyclopent-1-yl, 3-(2-aminoacetamido)cyclopentyl or 3-hydroxymethylbicyclo[1,1,1]pentan-1-yl.

In WO 2016/079688, we have reported antibacterial benzothiazole derivatives of general formula (A5)

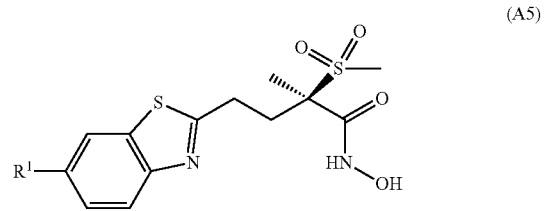

(A5)

wherein
$R^1$ is the group M, whereby M is one of the groups $M^A$ and $M^B$ represented below

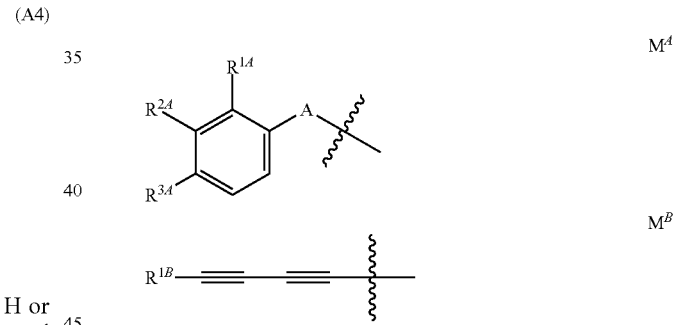

$M^A$ $M^B$ wherein A represents a bond or C≡C;
$R^{1A}$ is H or halogen;
$R^{2A}$ is H or halogen; and
$R^{3A}$ is H, ($C_1$-$C_3$)alkoxy, hydroxy($C_2$-$C_4$)alkoxy, hydroxy($C_1$-$C_4$)alkyl, dihydroxy($C_2$-$C_4$)alkyl, 2-hydroxyacetamido, 1-hydroxymethyl-cycloprop-1-yl, trans-2-hydroxymethyl-cycloprop-1-yl, 3-hydroxyoxetan-3-yl, 3-(hydroxy($C_1$-$C_3$)alkyl)oxetan-3-yl, 3-aminooxetan-3-yl or 1-aminocycloprop-1-yl;
and wherein $R^{1B}$ is hydroxy($C_1$-$C_4$)alkyl, dihydroxy($C_2$-$C_4$)alkyl, amino($C_1$-$C_4$)alkyl, di($C_1$-$C_4$)alkylamino($C_1$-$C_3$)alkyl, 1-amino-cycloprop-1-yl, 1-hydroxymethyl-cycloprop-1-yl, trans-2-hydroxymethyl-cycloprop-1-yl, trans-2-aminomethyl-cycloprop-1-yl, trans-2-hydroxymethyl-1-methyl-cycloprop-1l-yl, trans-2-hydroxymethyl-2-methyl-cycloprop-1-yl, cis-1-fluoro-2-(hydroxymethyl)cycloprop-1-yl, cis-2-fluoro-2-(hydroxymethyl)cycloprop-1l-yl, 2-(1,2-dihydroxyethyl)-cycloprop-1-yl, 1-(hydroxymethyl)-cyclobutan-1-yl, cis-3-(hydroxymethyl)-1-hydroxycyclobutan-1-yl, 3-hydroxyoxetan-3-yl, 3-hydroxyoxetan-3-yl-($C_1$-$C_3$)alkyl, 3-aminooxetan-3-yl, 3-hydroxymethyloxetan-3-yl, trans-(cis-3,4-dihydroxy)-cyclopent-1-yl, 3-hydroxymethylbicyclo[1,1,1]pentan-1-yl, 4-hydroxytetrahydro-2H-pyran-4-yl, (3R,6S)-3-aminotetrahydro-2H-pyran-6-yl, piperidin-4-yl, 1-(2-hydroxyacetyl)piperidin-4-yl, 3-hydroxythietan-3-yl, 1-(2-hydroxyacetyl)azetidin-3-yl or 1-glycylazetidin-3-yl;
and salts thereof.

Besides, in Montgomery et al., *J. Med. Chem.* (2012), 55(4), 1662-1670, yet further LpxC inhibitors are disclosed, among others the compound of formula (A6)

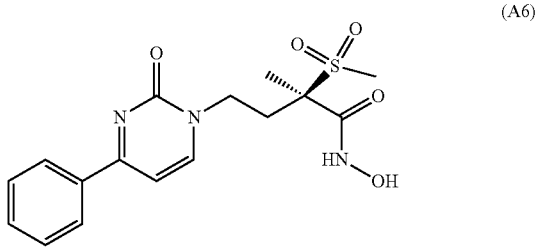 [SMILES: C[C@@](CCn1ccc(-c2ccccc2)nc1=O)(C(=O)NO)S(C)(=O)=O]

(A6)

The instant invention provides new substituted 1,2-dihydro-3H-pyrrolo[1,2-c]imidazol-3-one antibacterial compounds, namely the compounds of formula I described herein.

Various embodiments of the invention are presented hereafter:
1) The invention relates to compounds of formula I

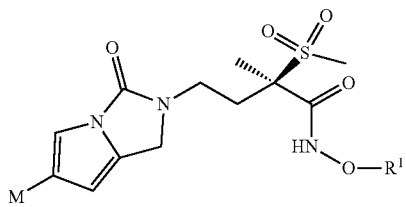

I wherein
M is one of the groups $M^A$, $M^B$ and $M^C$ represented below

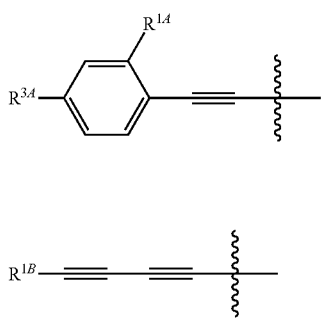

wherein
$R^{1A}$ represents hydrogen or fluorine;
$R^{3A}$ represents 3-fluoroazetidin-3-yl, 3-fluoro-1-methyl-azetidin-3-yl, 1-acetyl-3-hydroxyazetidin-3-yl, 3-fluoro-1-(oxetan-3-yl)azetidin-3-yl, (3-fluoroazetidin-1-yl)methyl, (3-hydroxyazetidin-1-yl)methyl, (5-(hydroxymethyl)-2-oxooxazolidin-3-yl)methyl, (4-hydroxy-3-fluoropiperidin-1-yl)methyl, (4-amino-3-fluoropiperidin-1-yl)methyl, (4-hydroxy-3,3-difluoropiperidin-1-yl)methyl, (4-amino-3,3-difluoropiperidin-1-yl)methyl, (6-amino-3-azabicyclo[3.1.0]hexan-3-yl)methyl, (2-oxa-6-azaspiro[3.3]heptan-6-yl)methyl, 2-morpholino-1-hydroxyethyl, 2-(methylsulfonyl)ethoxy, (3-hydroxyazetidin-1-yl)carbonyloxymethyl, (4-hydroxypiperidin-1-yl)carbonyloxymethyl, (4-methylpiperazin-1-yl)carbonyloxymethyl, N-(2-hydroxyethyl)-N-(methyl)carbamoyloxymethyl, 1-hydroxy-2-[(2-methoxyethyl)(methyl)amino]ethyl, azetidin-3-yloxycarbonylaminomethyl or (N-methylazetidin-3-yl)oxycarbonylaminomethyl;
$R^{1B}$ represents trans-2-(1,2-dihydroxyethyl)cycloprop-1-yl, 1-(methylamino)cycloprop-1-yl, 1-(dimethylamino)cycloprop-1-yl, 2-(dimethylaminomethyl)cycloprop-1-yl, 1-((3-hydroxyazetidinyl)-1-carbonyloxymethyl)cycloprop-1-yl, 2-(morpholinomethyl)cycloprop-1l-yl, 1-((4-methylpiperazinyl)-1-carbonyloxymethyl)cycloprop-1-yl, 4-fluoropyrrolidin-2-yl, (2-oxooxazolidin-3-yl)methyl, 1-(3-hydroxyazetidine)-1-carbonyloxymethyl, (4-hydroxypiperidin-1-yl)carbonyloxymethyl, 1-(4-methylpiperazine)-1-carbonyloxymethyl or N-methylazetidin-3-yl)oxycarbonylaminomethyl, or $R^{1B}$ represents a group Q, Q being one of the groups $Q^A$, $Q^B$ and $Q^C$ represented below

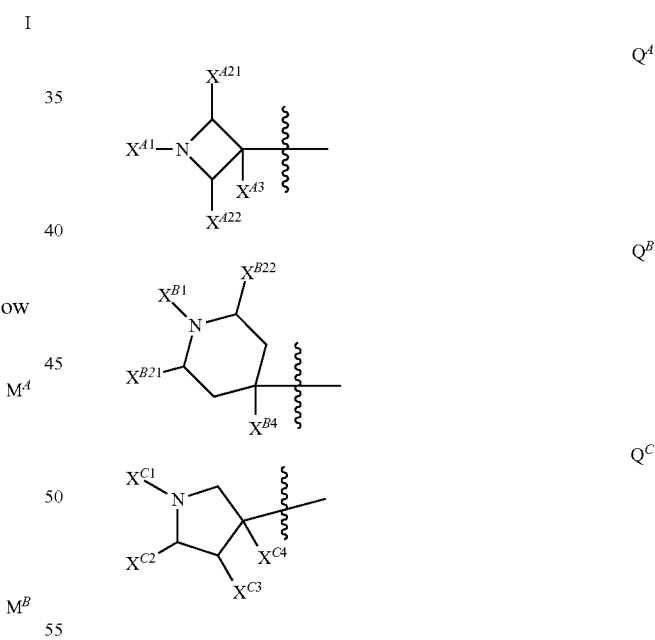

wherein
$X^{A1}$ represents H, methyl-d, methyl-d2, $(C_1-C_4)$alkyl, acetyl, ω-$(C_2-C_3)$haloalkyl, ω-hydroxy$(C_2-C_3)$alkyl, 2,3-dihydroxyprop-1-yl, 3-hydroxy-2-(hydroxymethyl)prop-1-yl, oxetan-3-yl, thietan-3-yl, 1,1-dioxidothietan-3-yl, $(C_3-C_6)$cycloalkyl, 3-hydroxycyclobut-1-yl, tetrahydropyran-4-yl or $(C_3-C_6)$cycloalkyl$(C_1-C_3)$alkyl,
$X^{A21}$ and $X^{A22}$ each independently represent H, $(C_1-C_4)$alkyl, $(C_1-C_3)$haloalkyl or hydroxy$(C_1-C_3)$alkyl, and
$X^{A3}$ represents H, $(C_1-C_3)$alkyl or halogen, provided that if $X^{A1}$ represents oxetan-3-yl, at least one of $X^{A21}$, $X^{A22}$ and $X^{A3}$ does not represent H;

$X^{B1}$ represents H, $(C_1-C_4)$alkyl, ω-hydroxy$(C_2-C_3)$alkyl, $(C_3-C_6)$cycloalkyl, oxetan-3-yl or tetrahydropyran-4-yl,
$X^{B21}$ and $X^{B22}$ each independently represent H, $(C_1-C_4)$alkyl, $(C_1-C_3)$haloalkyl or hydroxy$(C_1-C_3)$alkyl, and
$X^{B4}$ represents H, halogen, hydroxy or $(C_1-C_3)$alkyl;
$X^{C1}$ represents H, $(C_1-C_4)$alkyl, $(C_3-C_6)$cycloalkyl, ω-hydroxy$(C_2-C_3)$alkyl, oxetan-3-yl or tetrahydropyran-4-yl,
$X^{C2}$ represents H, $(C_1-C_4)$alkyl, $(C_1-C_3)$haloalkyl or hydroxy$(C_1-C_3)$alkyl,
$X^{C3}$ represents H, halogen (especially fluorine), hydroxy, $(C_1-C_4)$alkyl, $(C_1-C_3)$haloalkyl, hydroxy$(C_1-C_3)$alkyl, and
$X^{C4}$ represents H, $(C_1-C_3)$alkyl, halogen or hydroxy;
$R^{1C}$ represents hydrogen or fluorine;
$R^{3C}$ represents a group Q as defined before; and
$R^1$ represents H, $PO_3H_2$, $SO_3H$, phosphonooxymethyl or the group L represented below

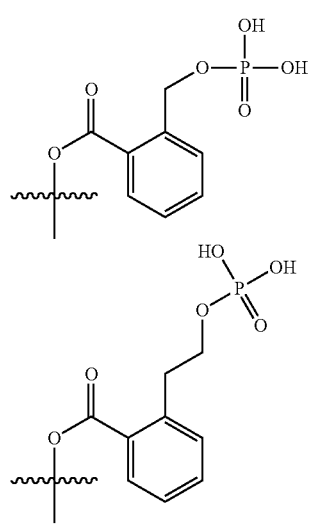

wherein $R^2$ represents $(C_1-C_4)$alkylamino$(C_1-C_4)$alkyl, [di$(C_1-C_4)$alkylamino]$(C_1-C_4)$alkyl, phosphonooxy$(C_1-C_4)$alkyl, phosphonooxymethoxy, 2-(phosphonooxy-$(C_1-C_4)$alkyl)-phenyl, (2-(phosphonooxy)-phenyl)-$(C_1-C_4)$alkyl (especially 2-(2-(phosphonooxy)-phenyl)-ethyl) or [2-(phosphonooxy-$(C_1-C_4)$alkyl)-phenyl]-$(C_1-C_4)$alkyl; and to salts (in particular pharmaceutically acceptable salts) of compounds of formula I.

It is understood that groups —O—$R^1$ in the fragment —CO—NH—O—$R^1$ wherein $R^1$ is not H represent prodrugs of the —CO—NH—OH group. In particular:
- the prodrug group (di$(C_1-C_4)$alkylamino)-$(C_1-C_3)$alkyl-carbonyloxy (occurring when $R^2$ represents [di$(C_1-C_4)$alkylamino]$(C_1-C_4)$alkyl)) notably refers to dimethyl-aminoacetoxy;
- the prodrug group [2-(phosphonooxy-$(C_1-C_4)$alkyl)-phenyl]-carbonyloxy (occurring when $R^2$ represents 2-(phosphonooxy-$(C_1-C_4)$alkyl)-phenyl) notably refers to one of the groups represented below

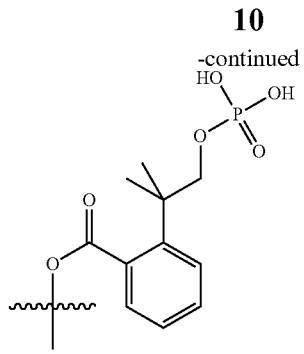

the prodrug group [(2-phosphonooxy-phenyl)-$(C_1-C_4)$alkyl]-carbonyloxy (occurring when $R^2$ represents (2-(phosphonooxy)-phenyl)-$(C_1-C_4)$alkyl) notably refers to one of the groups represented below

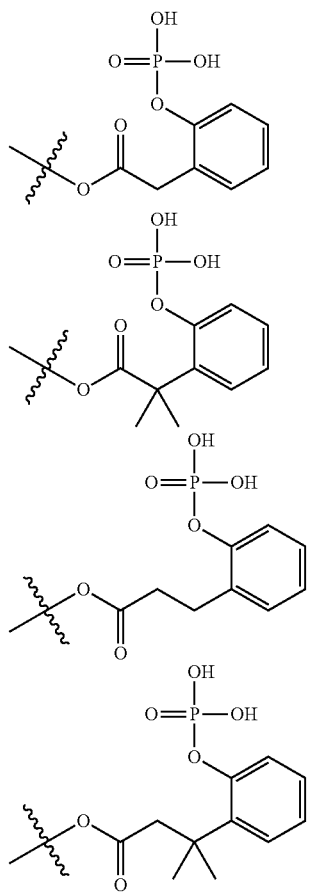

The following paragraphs provide definitions of the various chemical moieties for the compounds according to the invention and are intended to apply uniformly throughout the specification and claims, unless an otherwise expressly set out definition provides a broader or narrower definition:

The term "halogen" refers to fluorine, chlorine, bromine or iodine. It refers preferably to fluorine or chlorine and more preferably to fluorine.

The term "methyl-d", used alone or in combination, refers to a methyl group in which one hydrogen atom has been replaced by a deuterium ($^2$H) atom.

The term "methyl-d2", used alone or in combination, refers to a methyl group in which two hydrogen atoms have been replaced by deuterium ($^2$H) atoms.

The term "alkyl", used alone or in combination, refers to a straight or branched chain alkyl group containing from one to four carbon atoms. The term "$(C_x$-$C_y)$alkyl" (x and y each being an integer) refers to a straight or branched chain alkyl group containing x to y carbon atoms. For example, a $(C_1$-$C_3)$alkyl group contains from one to three carbon atoms. Representative examples of alkyl groups include methyl, ethyl, propyl, iso-propyl, n-butyl, iso-butyl, sec-butyl and tert-butyl. Preferred are methyl and ethyl. Most preferred is methyl.

The term "haloalkyl" refers to an alkyl group as defined before containing one to three carbon atoms in which one or more (and possibly all) hydrogen atoms have been replaced by halogen atoms. The term "$(C_x$-$C_y)$haloalkyl" (x and y each being an integer) refers to a haloalkyl group as defined before containing x to y carbon atoms. In a sub-embodiment, an "ω-$(C_2$-$C_3)$haloalkyl" group refers to an alkyl group of two or three carbon atoms in which one, two or three terminal hydrogen atoms have been replaced by halogen atoms. Representative examples of haloalkyl groups include especially the ω-$(C_2)$fluoroalkyl groups 2-fluoroethyl, 2,2-difluoroethyl and 2,2,2-trifluoroethyl. Preferred ω-$(C_2)$fluoroalkyl groups as used in the definitions of substituent $R^{1B}$ are 2-fluoroethyl and 2,2,2-trifluoroethyl, especially 2-fluoroethyl.

The term "hydroxyalkyl", used alone or in combination, refers to an alkyl group as defined before wherein one hydrogen atom has been replaced by a hydroxy group. The term "hydroxy$(C_x$-$C_y)$alkyl" (x and y each being an integer) refers to a hydroxyalkyl group as defined which contains x to y carbon atoms. For example, a hydroxy$(C_1$-$C_3)$alkyl group is a hydroxyalkyl group as defined before which contains from one to three carbon atoms. Representative examples of hydroxyalkyl groups are hydroxy$(C_1$-$C_3)$alkyl groups such as hydroxymethyl, 2-hydroxyethyl, 2-hydroxypropyl and 3-hydroxypropyl. Preferred are hydroxymethyl and 2-hydroxyethyl. Most preferred is hydroxymethyl. An "ω-hydroxy$(C_2$-$C_4)$alkyl" group as used for substituent $R^{1B}$ is a linear alkyl group which contains from two to four carbon atoms in which one terminal hydrogen atom has been replaced with hydroxy. Examples of ω-hydroxy$(C_2$-$C_3)$alkyl groups are 2-hydroxyethyl, 3-hydroxypropyl and 4-hydroxybutyl. Preferred ω-hydroxy$(C_2$-$C_3)$alkyl groups as used in the definitions of substituent $R^{1B}$ are 2-hydroxyethyl and 3-hydroxypropyl. Most preferred is 2-hydroxyethyl.

The term "alkylamino", used alone or in combination, refers to an amino group wherein one of the two hydrogen atoms has been replaced by an alkyl group as defined before. The term "$(C_x$-$C_y)$alkylamino" (x and y each being an integer) refers to an alkylamino group as defined before wherein the alkyl group contains x to y carbon atoms. For example, a $(C_1$-$C_4)$alkylamino group is an alkylamino group as defined before wherein the alkyl group contains from one to four carbon atoms. Representative examples of alkylamino groups include methylamino, ethylamino and iso-propylamino. Preferred are methylamino and ethylamino. Most preferred is methylamino.

The term "dialkylamino", used alone or in combination, refers to an amino group wherein each hydrogen atom has been replaced by an alkyl group as defined before, whereby the alkyl groups may be the same or different. The term "di$(C_x$-$C_y)$alkylamino" (x and y each being an integer) refers to a dialkylamino group as defined before wherein each alkyl group independently contains x to y carbon atoms. For example, a di$(C_1$-$C_4)$alkylamino group is a dialkylamino group as defined before wherein each alkyl group independently contains from one to four carbon atoms. Representative examples of dialkylamino groups include dimethylamino, diethylamino, N-ethyl-N-methyl-amino and N-iso-propyl-N-methyl-amino. Preferred are dimethylamino and diethylamino. Most preferred is dimethylamino.

The term "$(C_1$-$C_4)$alkylamino-$(C_1$-$C_4)$alkyl" refers to an alkyl group containing from one to four carbon atoms as defined before wherein one of the hydrogen atoms has been replaced by a $(C_1$-$C_4)$alkylamino group as defined before. Representative examples of $(C_1$-$C_4)$alkylamino-$(C_1$-$C_4)$alkyl groups include methylaminomethyl, 2-methylamino-ethyl, 3-methylamino-propyl, 4-methylamino-butyl, ethylaminomethyl, 2-ethylamino-ethyl, 3-ethylamino-propyl, 4-ethylamino-butyl, n-propylaminomethyl, 2-(n-propylamino)-ethyl and 3-(n-propylamino)-propyl; preferred are methylaminomethyl, 2-methylamino-ethyl and 3-methylamino-propyl; most preferred is methylaminomethyl.

The term "[di$(C_1$-$C_4)$alkylamino]-$(C_1$-$C_4)$alkyl" refers to an alkyl group containing from one to four carbon atoms as defined before wherein one of the hydrogen atoms has been replaced by a di$(C_1$-$C_4)$alkylamino group as defined before. Representative examples of [di$(C_1$-$C_4)$alkylamino]-$(C_1$-$C_4)$alkyl groups include dimethylaminomethyl, 2-(dimethylamino)-ethyl, 3-(dimethylamino)-propyl, 4-(dimethylamino)-butyl, diethylaminomethyl, 2-(diethylamino)-ethyl, 3-(diethylamino)-propyl, 4-(diethylamino)-butyl, di(n-propyl)aminomethyl, 2-(di(n-propyl)amino)-ethyl and 3-(di(n-propyl)amino)-propyl; preferred are dimethylaminomethyl, 2-(dimethylamino)-ethyl and 3-(dimethylamino)-propyl; most preferred is dimethylaminomethyl.

The term "cycloalkyl", used alone or in combination, refers to a saturated monocyclic hydrocarbon ring containing three to six carbon atoms. The term "$(C_x$-$C_y)$cycloalkyl" (x and y each being an integer), refers to a cycloalkyl group as defined before containing x to y carbon atoms. For example a $(C_3$-$C_4)$cycloalkyl group contains from three to four carbon atoms. Examples of cycloalkyl groups are cyclopropyl, cyclobutyl, cyclopentyl and cyclohexyl. Examples of $(C_3$-$C_4)$cycloalkyl groups are cyclopropyl and cyclobutyl, especially cyclopropyl.

The term "cycloalkyl-alkyl", used alone or in combination, refers to an alkyl group as defined before wherein one hydrogen atom has been replaced by a cycloalkyl group as defined before. The term "$(C_w$-$C_x)$cycloalkyl$(C_y$-$C_z)$alkyl" (w, x, y and z each being an integer) refers to a cycloalkyl-alkyl group as defined wherein the alkyl group contains y to z carbon atoms and the cycloalkyl group contains w to x carbon atoms. For example, a $(C_3$-$C_6)$cycloalkyl$(C_1$-$C_3)$alkyl group is a cycloalkyl-alkyl group as defined before wherein the alkyl group contains 1 to 3 carbon atoms and the cycloalkyl group contains 3 to 6 carbon atoms. Representative examples of cycloalkyl-alkyl groups are $(C_3$-$C_6)$cycloalkyl$(C_1$-$C_3)$alkyl groups such as (cyclopropyl)methyl, (cyclobutyl)methyl, (cyclopentyl)methyl, (cyclohexyl)methyl, 2-cyclopropyl-ethyl, 2-cyclobutyl-ethyl and 3-cyclopropyl-propyl. Preferred are (cyclopropyl)methyl and 2-cyclopropyl-ethyl. Most preferred is (cyclopropyl)methyl.

The term "quinolone-resistant", when used in this text, refers to a bacterial strain against which ciprofloxacin has a Minimal Inhibitory Concentration of at least 16 mg/L (said Minimal Inhibitory Concentration being measured with the standard method described in "*Methods for Dilution Antimicrobial Susceptibility Tests for Bacteria that Grow Aerobically*", Approved standard, 7$^{th}$ ed., Clinical and Laboratory Standards Institute (CLSI) Document M7-A7, Wayne, Pa., USA (2006)).

The term "carbapenem-resistant", when used in this text, refers to a bacterial strain against which imipenem has a Minimal Inhibitory Concentration of at least 16 mg/L (said Minimal Inhibitory Concentration being measured with the standard method described in "Methods for Dilution Antimicrobial Susceptibility Tests for Bacteria that Grow Aerobically", Approved standard, 7th ed., Clinical and Laboratory Standards Institute (CLSI) Document M7-A7, Wayne, Pa., USA (2006)).

The term "multi-drug resistant", when used in this text, refers to a bacterial strain against which at least three antibiotic compounds selected from three distinct antibiotic categories have Minimal Inhibitory Concentrations (MICs) over their respective clinical breakpoints, whereby said three distinct antibiotic categories are chosen among penicillins, combinations of penicillins with beta-lactamase inhibitors, cephalosporins, carbapenems, monobactams, fluoro-quinolones, aminoglycosides, phosphonic acids, tetracyclins and polymixins. Clinical breakpoints are defined according to the latest available list published by Clinical and Laboratory Standards Institute (Wayne, Pa., USA). Accordingly, clinical breakpoints are the levels of MIC at which, at a given time, a bacterium is deemed either susceptible or resistant to treatment by the corresponding antibiotic or antibiotic combination.

The term "pharmaceutically acceptable salts" refers to salts that retain the desired biological activity of the subject compound and exhibit minimal undesired toxicological effects. Such salts include inorganic or organic acid and/or base addition salts depending on the presence of basic and/or acidic groups in the subject compound. For reference see for example '*Handbook of Pharmaceutical Salts. Properties, Selection and Use.*', P. Heinrich Stahl, Camille G. Wermuth (Eds.), Wiley-VCH (2008) and '*Pharmaceutical Salts and Co-crystals*', Johan Wouters and Luc Quere (Eds.), RSC Publishing (2012).

In this text, a bond interrupted by a wavy line shows a point of attachment of the radical drawn to the rest of the molecule. For example, the radical drawn below

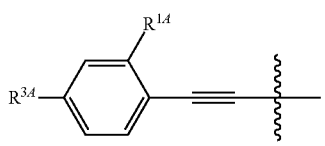

wherein R$^{1A}$ represents H and R$^{3A}$ represents 1-(3-fluoroazetidin-1-yl)methyl is the 4-((3-fluoroazetidin-1-yl)methyl)phenyl)ethynyl group.

Besides, the term "room temperature" as used herein refers to a temperature of 25° C.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C.

2) The invention in particular relates to compounds of formula I according to embodiment 1) which are also compounds of formula I$_{CE}$

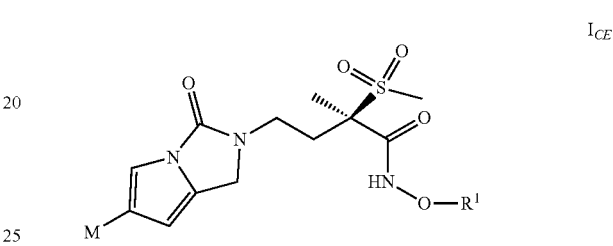

wherein
M is one of the groups M$^A$, M$^B$ and M$^C$ represented below

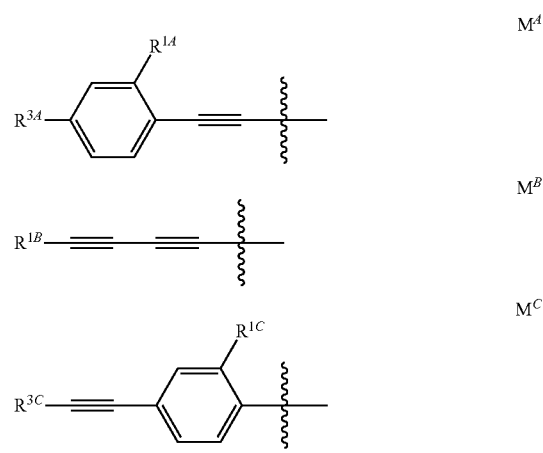

wherein
R$^{1A}$ represents hydrogen or fluorine;
R$^{3A}$ represents 3-fluoroazetidin-3-yl, 3-fluoro-1-methyl-azetidin-3-yl, 1-acetyl-3-hydroxyazetidin-3-yl, 3-fluoro-1-(oxetan-3-yl)azetidin-3-yl, (3-fluoroazetidin-1-yl)methyl, (3-hydroxyazetidin-1-yl)methyl, (5-(hydroxymethyl)-2-oxooxazolidin-3-yl)methyl, (4-hydroxy-3-fluoropiperidin-1-yl)methyl, (4-amino-3-fluoropiperidin-1-yl)methyl, (4-hydroxy-3,3-difluoropiperidin-1-yl)methyl, (4-amino-3,3-difluoropiperidin-1-yl)methyl, (6-amino-3-azabicyclo[3.1.0]hexan-3-yl)methyl, (2-oxa-6-azaspiro[3.3]heptan-6-yl)methyl, 2-morpholino-1-hydroxyethyl, 2-(methylsulfonyl)ethoxy, (3-hydroxyazetidin-1-yl)carbonyloxymethyl, (4-hydroxypiperidin-1-yl)carbonyloxymethyl, (4-methylpiperazin-1-yl)carbonyloxymethyl, N-(2-hydroxyethyl)-N-(methyl)carbamoyloxymethyl, 1-hydroxy-2-[(2-methoxyethyl)(methyl)amino]ethyl, azetidin-3-yloxycarbonylaminomethyl or (N-methylazetidin-3-yl)oxycarbonylaminomethyl;

$R^{1B}$ represents trans-2-(1,2-dihydroxyethyl)cycloprop-1-yl, 1-(methylamino)cycloprop-1-yl, 1-(dimethylamino)cycloprop-1-yl, 2-(dimethylaminomethyl)cycloprop-1-yl, 1-((3-hydroxyazetidinyl)-1-carbonyloxymethyl)cycloprop-1-yl, 2-(morpholinomethyl)cycloprop-1l-yl, 1-((4-methylpiperazinyl)-1-carbonyloxymethyl)cycloprop-1-yl, 4-fluoropyrrolidin-2-yl, (2-oxooxazolidin-3-yl)methyl, 1-(3-hydroxyazetidine)-1-carbonyloxymethyl, (4-hydroxypiperidin-1-yl)carbonyloxymethyl, 1-(4-methylpiperazine)-1-carbonyloxymethyl or N-methylazetidin-3-yl)oxycarbonylaminomethyl, or $R^{1B}$ represents a group Q, Q being one of the groups $Q^A$, $Q^B$ and $Q^C$ represented below

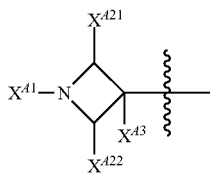
$Q^A$

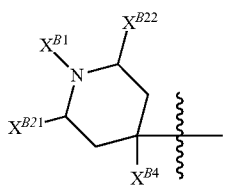
$Q^B$

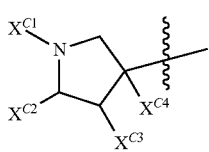
$Q^C$ wherein $X^{A1}$ represents H, methyl-d, methyl-d2, $(C_1-C_4)$alkyl, acetyl, $\omega$-$(C_2-C_3)$haloalkyl, $\omega$-hydroxy$(C_2-C_3)$alkyl, 2,3-dihydroxyprop-1-yl, 3-hydroxy-2-(hydroxymethyl)prop-1-yl, oxetan-3-yl, thietan-3-yl, 1,1-dioxidothietan-3-yl, $(C_3-C_6)$cycloalkyl, 3-hydroxycyclobut-1-yl, tetrahydropyran-4-yl or $(C_3-C_6)$cycloalkyl$(C_1-C_3)$alkyl, $X^{A21}$ and $X^{A22}$ each independently represent H, $(C_1-C_4)$alkyl, $(C_1-C_3)$haloalkyl or hydroxy$(C_1-C_3)$alkyl, and $X^{A3}$ represents represents H, $(C_1-C_3)$alkyl or halogen, provided that if $X^{A1}$ represents oxetan-3-yl, then at least one of $X^{A21}$, $X^{A22}$ and $X^{A3}$ does not represent H;

$X^{B1}$ represents H, $(C_1-C_4)$alkyl or oxetan-3-yl, $X^{B21}$ and $X^{B22}$ each represent H, and $X^{B4}$ represents H, halogen or hydroxy;

$X^{C1}$ represents H, $(C_1-C_4)$alkyl, $(C_3-C_6)$cycloalkyl, $\omega$-hydroxy$(C_2-C_3)$alkyl or oxetan-3-yl, $X^{C2}$ represents H or hydroxy$(C_1-C_3)$alkyl, $X^{C3}$ represents H or hydroxy and $X^{C4}$ represents H, $(C_1-C_3)$alkyl or halogen;

$R^{1C}$ represents hydrogen or fluorine and $R^{3C}$ represents one of the groups $Q^A$ and $Q^B$ represented below

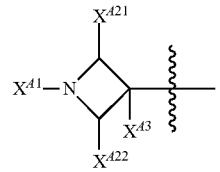
$Q^A$

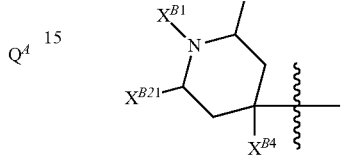
$Q^B$ wherein $X^{A1}$ represents $(C_1-C_4)$alkyl or $\omega$-hydroxy$(C_2-C_3)$alkyl, and $X^{A21}$, $X^{A22}$ and $X^{A3}$ each represent H;

$X^{B1}$ represents $(C_1-C_4)$alkyl, $X^{B21}$ and $X^{B22}$ each represent H, and $X^{B4}$ represents H;

and to salts (in particular pharmaceutically acceptable salts) of compounds of formula $I_{CE}$.

3) The invention in particular relates to compounds of formula I according to embodiment 1) or 2) which are also compounds of formula $I_{CEP}$

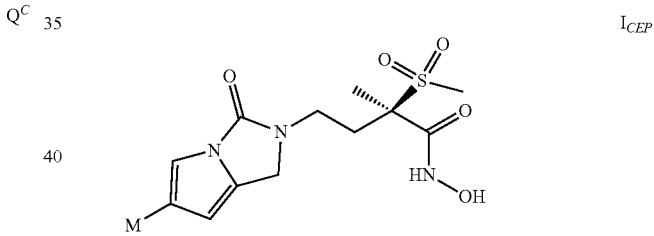
$I_{CEP}$ wherein

M is one of the groups $M^A$ and $M^B$ represented below

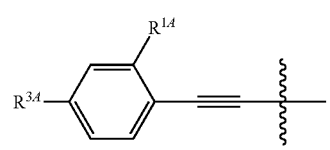
$M^A$

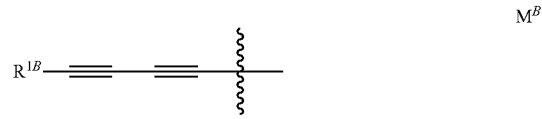
$M^B$ wherein $R^{1A}$ represents hydrogen or fluorine;

$R^{3A}$ represents 3-fluoroazetidin-3-yl, 3-fluoro-1-methyl-azetidin-3-yl, 1-acetyl-3-hydroxyazetidin-3-yl, 3-fluoro-1-(oxetan-3-yl)azetidin-3-yl, (3-fluoroazetidin-1-yl)methyl, (3-hydroxyazetidin-1-yl)methyl, (5-(hydroxymethyl)-2-oxooxazolidin-3-yl)methyl, (4-hydroxy-3-fluoropiperidin- 1-yl)methyl, (4-amino-3-fluoropiperidin-1-yl)methyl, (4-hydroxy-3,3-difluoropiperidin-1-yl)methyl, (4-amino-3,3-difluoropiperidin-1-yl)methyl, (6-amino-3-azabicyclo[3.1.0]hexan-3-yl)methyl, (2-oxa-6-azaspiro[3.3]heptan-6-yl)methyl, 2-morpholino-1-hydroxyethyl, 2-(methylsulfonyl)ethoxy, (3-hydroxyazetidin-1-yl)carbonyloxymethyl, (4-hydroxypiperidin-1-yl)carbonyloxymethyl, (4-methylpiperazin-1-yl)carbonyloxymethyl, N-(2-hydroxyethyl)-N-(methyl)carbamoyloxymethyl, 1-hydroxy-2-[(2-methoxyethyl)(methyl)amino]ethyl, azetidin-3-yloxycarbonylaminomethyl or (N-methylazetidin-3-yl)oxycarbonylaminomethyl;

$R^{1B}$ represents trans-2-(1,2-dihydroxyethyl)cycloprop-1-yl, 1-(methylamino)cycloprop-1-yl, 1-(dimethylamino)cycloprop-1-yl, 2-(dimethylaminomethyl)cycloprop-1-yl, 1-((3-hydroxyazetidinyl)-1-carbonyloxymethyl)cycloprop-1-yl, 2-(morpholinomethyl)cycloprop-1-yl, 1-((4-methylpiperazinyl)-1-carbonyloxymethyl)cycloprop-1-yl, 4-fluoropyrrolidin-2-yl, (2-oxooxazolidin-3-yl)methyl, 1-(3-hydroxyazetidine)-1-carbonyloxymethyl, (4-hydroxypiperidin-1-yl)carbonyloxymethyl, 1-(4-methylpiperazine)-1-carbonyloxymethyl or N-methylazetidin-3-yl)oxycarbonylaminomethyl, or $R^{1B}$ represents a group Q, Q being one of the groups $Q^A$ and $Q^B$ represented below

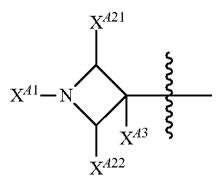

$Q^A$

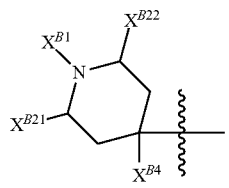

$Q^B$ wherein $X^{A1}$ represents H, methyl-d, methyl-d2, $(C_1-C_4)$alkyl, acetyl, ω-$(C_2-C_3)$haloalkyl, ω-hydroxy$(C_2-C_3)$alkyl, 2,3-dihydroxyprop-1-yl, 3-hydroxy-2-(hydroxymethyl)prop-1-yl, oxetan-3-yl, 1,1-dioxidothietan-3-yl, $(C_3-C_6)$cycloalkyl or $(C_3-C_6)$cycloalkyl$(C_1-C_3)$alkyl, $X^{A21}$ and $X^{A22}$ each represent H, and $X^{A3}$ represents H, $(C_1-C_3)$alkyl or halogen, provided that if $X^{A1}$ represents oxetan-3-yl, then $X^{A3}$ does not represent H;

$X^{B1}$ represents H, $(C_1-C_4)$alkyl or oxetan-3-yl, $X^{B21}$ and $X^{B22}$ each represent H, and $X^{B4}$ represents H, halogen or hydroxy;

and to salts (in particular pharmaceutically acceptable salts) of compounds of formula $I_{CEP}$.

4) One particular sub-embodiment of embodiment 1) or 2) relates to the compounds of formula I as defined in embodiment 1) or 2) wherein $R^1$ represents H.

5) Another sub-embodiment of embodiment 1) or 2) relates to the compounds of formula I as defined in embodiment 1) or 2) wherein $R^1$ does not represent H.

6) According to one main embodiment of this invention, the compounds of formula I as defined in embodiments 1) to 5) will be such that M is the group $M^A$.

7) One sub-embodiment of embodiment 6) relates to the compounds of formula I as defined in embodiment 6) wherein $R^{1A}$ represents hydrogen.

8) Another sub-embodiment of embodiment 6) relates to the compounds of formula I as defined in embodiment 6) wherein $R^{1A}$ represents fluorine.

9) According to one variant of embodiments 6) to 8), the compounds of formula I as defined in embodiments 6) to 8) will be such that $R^{3A}$ represents 3-fluoroazetidin-3-yl, 3-fluoro-1-methyl-azetidin-3-yl, 1-acetyl-3-hydroxyazetidin-3-yl or 3-fluoro-1-(oxetan-3-yl)azetidin-3-yl.

10) According to another variant of embodiments 6) to 8), the compounds of formula I as defined in embodiments 6) to 8) will be such that $R^{3A}$ represents (3-fluoroazetidin-1-yl)methyl, (3-hydroxyazetidin-1-yl)methyl, (5-(hydroxymethyl)-2-oxooxazolidin-3-yl)methyl, (4-hydroxy-3-fluoropiperidin-1-yl)methyl, (4-amino-3-fluoropiperidin-1-yl)methyl, (4-hydroxy-3,3-difluoropiperidin-1-yl)methyl, (4-amino-3,3-difluoropiperidin-1-yl)methyl, (6-amino-3-azabicyclo[3.1.0]hexan-3-yl)methyl or (2-oxa-6-azaspiro[3.3]heptan-6-yl)methyl.

11) According to yet another variant of embodiments 6) to 8), the compounds of formula I as defined in embodiments 6) to 8) will be such that $R^{3A}$ represents 2-morpholino-1-hydroxyethyl, 2-(methylsulfonyl)ethoxy, (3-hydroxyazetidin-1-yl)carbonyloxymethyl, (4-hydroxypiperidin-1-yl)carbonyloxymethyl, (4-methylpiperazin-1-yl)carbonyloxymethyl, N-(2-hydroxyethyl)-N-(methyl)carbamoyloxymethyl, 1-hydroxy-2-[(2-methoxyethyl)(methyl)amino]ethyl, azetidin-3-yloxycarbonylaminomethyl or (N-methylazetidin-3-yl)oxycarbonylaminomethyl.

12) According to another main embodiment of this invention, the compounds of formula I as defined in embodiments 1) to 5) will be such that M is the group $M^B$.

13) According to one variant of embodiment 12), the compounds of formula I as defined in embodiment 12) will be such that $R^{1B}$ represents trans-2-(1,2-dihydroxyethyl)cycloprop-1-yl, 1-(methylamino)cycloprop-1-yl, 1-(dimethylamino)cycloprop-1-yl, 2-(dimethylaminomethyl)cycloprop-1-yl, 1-((3-hydroxyazetidinyl)-1-carbonyloxymethyl)cycloprop-1-yl, 2-(morpholinomethyl)cycloprop-1-yl, 1-((4-methylpiperazinyl)-1-carbonyloxymethyl)cycloprop-1-yl or 4-fluoropyrrolidin-2-yl.

14) According to another variant of embodiment 12), the compounds of formula I as defined in embodiment 12) will be such that $R^{1B}$ represents (2-oxooxazolidin-3-yl)methyl, 1-(3-hydroxyazetidine)-1-carbonyloxymethyl, (4-hydroxypiperidin-1-yl)carbonyloxymethyl, 1-(4-methylpiperazine)-1-carbonyloxymethyl or N-methylazetidin-3-yl)oxycarbonylaminomethyl.

15) According to yet another variant of embodiment 12), the compounds of formula I as defined in embodiment 12) will be such that $R^{1B}$ represents a group Q, Q being one of the groups $Q^A$, $Q^B$ and $Q^C$.

16) Preferably, the compounds of formula I as defined in embodiment 15) will be such that $R^{1B}$ represents one of the groups $Q^A$ and $Q^B$.

17) According to one sub-embodiment of embodiment 16), the compounds of formula I as defined in embodiment 16) will be such that $R^{1B}$ represents the group $Q^A$.

18) Preferably, the compounds of formula I as defined in embodiment 17) will be such that $R^{1B}$ represents the group $Q^A$ wherein:

$X^{A1}$ represents methyl-d, methyl-d2, $(C_1-C_4)$alkyl, ω-$(C_2-C_3)$haloalkyl, ω-hydroxy$(C_2-C_3)$alkyl, 2,3-dihydroxyprop-1-yl, 3-hydroxy-2-(hydroxymethyl)prop-1-yl, oxetan-3-yl, thietan-3-yl, 1,1-dioxidothietan-3-yl, ($C_3$-$C_6$)cycloalkyl, 3-hydroxycyclobut-1-yl, tetrahydropyran-4-yl or ($C_3$-$C_6$)cycloalkyl($C_1$-$C_3$)alkyl;
$X^{A21}$ and $X^{A22}$ each represent H; and
$X^{A3}$ represents H or halogen, provided that if $X^{A1}$ represents oxetan-3-yl, then $X^{A3}$ represents halogen.

19) More preferably, the compounds of formula I as defined in embodiment 17) will be such that $R^{1B}$ represents the group $Q^A$ wherein:
$X^{A1}$ represents methyl-d, methyl-d2, ($C_1$-$C_4$)alkyl, ω-($C_2$-$C_3$)haloalkyl, ω-hydroxy($C_2$-$C_3$)alkyl, ($C_3$-$C_6$)cycloalkyl, 3-hydroxycyclobut-1-yl or ($C_3$-$C_6$)cycloalkyl($C_1$-$C_3$)alkyl;
$X^{A21}$ and $X^{A22}$ each represent H; and
$X^{A3}$ represents H or fluorine.

20) Even more preferably, the compounds of formula I as defined in embodiment 17) will be such that $R^{1B}$ represents the group $Q^A$ wherein:
$X^{A1}$ represents methyl, methyl-d, methyl-d2,2-fluoro-ethyl, 2-hydroxy-ethyl, cycloprop-1-yl, 3-hydroxyprop-1-yl or 3-hydroxycyclobut-1-yl;
$X^{A21}$ and $X^{A22}$ each represent H; and
$X^{A3}$ represents H.

21) Further preferred compounds are compounds of formula I as defined in embodiment 17) which are such that $R^{1B}$ represents the group $Q^A$ wherein:
$X^{A1}$ represents ($C_3$-$C_6$)cycloalkyl, 3-hydroxycyclobut-1-yl or tetrahydropyran-4-yl;
$X^{A21}$ and $X^{A22}$ each represent H; and
$X^{A3}$ represents H.

22) More preferably, the compounds of formula I as defined in embodiment 21) which are such that $R^{1B}$ represents the group $Q^A$ wherein:
$X^{A1}$ represents cycloprop-1-yl, 3-hydroxycyclobut-1-yl or cyclohex-1-yl;
$X^{A21}$ and $X^{A22}$ each represent H; and
$X^{A3}$ represents H.

23) Further preferred compounds are compounds of formula I as defined in embodiment 17) which are such that $R^{1B}$ represents the group $Q^A$ wherein:
$X^{A1}$ represents ($C_1$-$C_4$)alkyl;
one of $X^{A21}$ and $X^{A22}$ represents ($C_1$-$C_4$)alkyl or ($C_1$-$C_3$)haloalkyl and the other represents H; and
$X^{A3}$ represents H or fluorine.

24) More preferably, the compounds of formula I as defined in embodiment 23) which are such that $R^{1B}$ represents the group $Q^A$ wherein:
$X^{A1}$ represents methyl or ethyl (in particular methyl);
one of $X^{A21}$ and $X^{A22}$ represents methyl or fluoromethyl and the other represents H; and
$X^{A3}$ represents H.

25) According to the other sub-embodiment of embodiment 16), the compounds of formula I as defined in embodiment 16) will be such that $R^{1B}$ represents the group $Q^B$.

26) Preferably, the compounds of formula I as defined in embodiment 25) will be such that $R^{1B}$ represents the group $Q^B$ wherein:
$X^{B1}$ represents H, ($C_1$-$C_4$)alkyl, ω-hydroxy($C_2$-$C_3$)alkyl, ($C_3$-$C_6$)cycloalkyl, oxetan-3-yl or tetrahydropyran-4-yl;
$X^{B21}$ and $X^{B22}$ each represent H; and
$X^{B4}$ represents H, halogen, hydroxy or ($C_1$-$C_3$)alkyl.

27) More preferably, the compounds of formula I as defined in embodiment 25) will be such that $R^{1B}$ represents the group $Q^B$ wherein:
$X^{B1}$ represents ($C_1$-$C_3$)alkyl or oxetan-3-yl;
$X^{B21}$ and $X^{B22}$ each represent H; and
$X^{B4}$ represents H, halogen or hydroxy.

28) Even more preferably, the compounds of formula I as defined in embodiment 25) will be such that $R^{1B}$ represents the group $Q^B$ wherein:
$X^{B1}$ represents methyl;
$X^{B21}$ and $X^{B22}$ each represent H; and
$X^{B4}$ represents H or fluorine.

29) According to another sub-embodiment of embodiment 15), the compounds of formula I as defined in embodiment 15) will be such that $R^{1B}$ represents the group $Q^C$.

30) Preferably, the compounds of formula I as defined in embodiment 29) will be such that $X^{C1}$ represents ($C_1$-$C_4$)alkyl and $X^{C2}$ represents hydroxy($C_1$-$C_3$)alkyl.

31) More preferably, the compounds of formula I as defined in embodiment 29) will be such that $X^{C1}$ represents methyl and $X^{C2}$ represents hydroxy($C_1$-$C_3$)alkyl (and in particular such that $X^{C1}$ represents methyl, $X^{C2}$ represents hydroxy($C_1$-$C_3$)alkyl, $X^{C3}$ and $X^{C4}$ each represent H).

32) According to another main embodiment of this invention, the compounds of formula I as defined in embodiment 1), 2), 4) or 5) will be such that M is the group $M^C$.

33) Preferably, the compounds of formula I as defined in embodiment 32) will be such that $R^{3C}$ represents one of the groups $Q^A$ and $Q^B$.

34) According to one sub-embodiment of embodiment 33), the compounds of formula I as defined in embodiment 33) will be such that $R^{3C}$ represents the group $Q^A$.

35) Preferably, the compounds of formula I as defined in embodiment 34) will be such that $R^{3C}$ represents the group $Q^A$ wherein:
$X^{A1}$ represents methyl-d, methyl-d2, ($C_1$-$C_4$)alkyl, ω-($C_2$-$C_3$)haloalkyl, ω-hydroxy($C_2$-$C_3$)alkyl, ($C_3$-$C_6$)cycloalkyl, 3-hydroxycyclobut-1-yl or ($C_3$-$C_6$)cycloalkyl($C_1$-$C_3$)alkyl;
$X^{A21}$ and $X^{A22}$ each represent H; and
$X^{A3}$ represents H or fluorine.

36) More preferably, the compounds of formula I as defined in embodiment 34) will be such that $R^{3C}$ represents H or fluorine and $R^{3C}$ represents the group $Q^A$ wherein:
$X^{A1}$ represents methyl;
$X^{A21}$ and $X^{A22}$ each represent H; and
$X^{A3}$ represents H.

37) According to another sub-embodiment of embodiment 33), the compounds of formula I as defined in embodiment 33) will be such that $R^{3C}$ represents the group $Q^B$.

38) Preferably, the compounds of formula I as defined in embodiment 37) will be such that $R^{3C}$ represents the group $Q^B$ wherein:
$X^{B1}$ represents ($C_1$-$C_3$)alkyl or oxetan-3-yl;
$X^{B21}$ and $X^{B22}$ each represent H; and
$X^{B4}$ represents H, halogen or hydroxy.

39) In a preferred embodiment, the compounds of formula I according to embodiment 1) or 3) will be such that:
M is the group $M^A$ wherein $R^{1A}$ represents hydrogen or fluorine and $R^{3A}$ represents 3-fluoroazetidin-3-yl, 3-fluoro-1-methyl-azetidin-3-yl, 1-acetyl-3-hydroxyazetidin-3-yl, 3-fluoro-1-(oxetan-3-yl)azetidin-3-yl, (3-fluoroazetidin-1-yl)methyl, (3-hydroxyazetidin-1-yl)methyl, (5-(hydroxymethyl)-2-oxooxazolidin-3-yl)methyl, (4-hydroxy-3-fluoropiperidin-1-yl)methyl, (4-amino-3-fluoropiperidin-1-yl)methyl, (4-hydroxy-3,3-difluoropiperidin-1-yl)methyl, (4-amino-3,3-difluoropiperidin-1-yl)methyl, (6-amino-3-azabicyclo[3.1.0]hexan-3-yl)methyl, (2-oxa-6-azaspiro[3.3]heptan-6-yl)methyl, 2-morpholino-1-hydroxyethyl, 2-(methylsulfonyl)ethoxy, (3-hydroxyazetidin-1-yl)carbonyloxymethyl, (4-hydroxypiperidin-1-yl)carbonyloxymethyl, (4-methylpiperazin-1-yl)carbonyloxymethyl, N-(2-hydroxyethyl)-N-(methyl)carbamoyloxymethyl, 1-hydroxy-2-[(2-methoxyethyl)(methyl)amino]ethyl, azetidin-3-yloxycarbonylaminomethyl or (N-methylazetidin-3-yl)oxycarbonylaminomethyl; or M is the group $M^B$ wherein $R^{1B}$ represents trans-2-(1,2-dihydroxyethyl)cycloprop-1-yl, 1-(methylamino)cycloprop-1-yl, 1-(dimethylamino)cycloprop-1-yl, 2-(dimethylaminomethyl)cycloprop-1-yl, 1-((3-hydroxyazetidinyl)-1-carbonyloxymethyl)cycloprop-1-yl, 2-(morpholinomethyl)cycloprop-1-yl, 1-((4-methylpiperazinyl)-1-carbonyloxymethyl)cycloprop-1-yl, 4-fluoropyrrolidin-2-yl, (2-oxooxazolidin-3-yl)methyl, 1-(3-hydroxyazetidine)-1-carbonyloxymethyl, (4-hydroxypiperidin-1-yl)carbonyloxymethyl, 1-(4-methylpiperazine)-1-carbonyloxymethyl or N-methylazetidin-3-yl)oxycarbonylaminomethyl; or M is the group $M^B$ wherein $R^{1B}$ represents the group $Q^A$ wherein $X^{A1}$ represents H, methyl-d, methyl-d2, $(C_1-C_4)$alkyl, acetyl, ω-$(C_2-C_3)$haloalkyl, ω-hydroxy$(C_2-C_3)$alkyl, 2,3-dihydroxyprop-1-yl, 3-hydroxy-2-(hydroxymethyl)prop-1-yl, oxetan-3-yl, 1,1-dioxidothietan-3-yl, $(C_3-C_6)$cycloalkyl or $(C_3-C_6)$cycloalkyl$(C_1-C_3)$alkyl, $X^{A21}$ and $X^{A22}$ each represent H, and $X^{A3}$ represents H, $(C_1-C_3)$alkyl or halogen, provided that if $X^{A1}$ represents oxetan-3-yl, then $X^{A3}$ represents halogen; or M is the group $M^B$ wherein $R^{1B}$ represents the group $Q^B$ wherein $X^{B1}$ represents H, $(C_1-C_4)$alkyl or oxetan-3-yl, $X^{B21}$ and $X^{B22}$ each represent H, and $X^{B4}$ represents H, halogen or hydroxy.

40) In a more preferred embodiment, the compounds of formula I according to embodiment 1) or 3) will be such that:

M is the group $M^A$ wherein $R^{1A}$ represents hydrogen or fluorine and $R^{3A}$ represents 3-fluoroazetidin-3-yl, 3-fluoro-1-methyl-azetidin-3-yl, 3-fluoro-1-(oxetan-3-yl)azetidin-3-yl, (3-fluoroazetidin-1-yl)methyl, (3-hydroxyazetidin-1-yl)methyl, (4-hydroxy-3-fluoropiperidin-1-yl)methyl, (4-amino-3-fluoropiperidin-1-yl)methyl, (4-hydroxy-3,3-difluoropiperidin-1-yl)methyl, (4-amino-3,3-difluoropiperidin-1-yl)methyl, (6-amino-3-azabicyclo[3.1.0]hexan-3-yl)methyl, (2-oxa-6-azaspiro[3.3]heptan-6-yl)methyl, 2-morpholino-1-hydroxyethyl, 2-(methylsulfonyl)ethoxy, (3-hydroxyazetidin-1-yl)carbonyloxymethyl, (4-hydroxypiperidin-1-yl)carbonyloxymethyl, (4-methylpiperazin-1-yl)carbonyloxymethyl, N-(2-hydroxyethyl)-N-(methyl)carbamoyloxymethyl or azetidin-3-yloxycarbonylaminomethyl; or M is the group $M^B$ wherein $R^{1B}$ represents trans-2-(1,2-dihydroxyethyl)cycloprop-1-yl, 1-(methylamino)cycloprop-1-yl, 1-(dimethylamino)cycloprop-1-yl, 1-((3-hydroxyazetidinyl)-1-carbonyloxymethyl)cycloprop-1-yl, 2-(morpholinomethyl)cycloprop-1-yl, 1-(3-hydroxyazetidine)-1-carbonyloxymethyl, (4-hydroxypiperidin-1-yl)carbonyloxymethyl or 1-(4-methylpiperazine)-1-carbonyloxymethyl; or M is the group $M^B$ wherein $R^{1B}$ represents the group $Q^A$ wherein $X^{A1}$ represents H, methyl-d, methyl-d2, $(C_1-C_4)$alkyl, ω-$(C_2-C_3)$haloalkyl, ω-hydroxy$(C_2-C_3)$alkyl, 2,3-dihydroxyprop-1-yl, 3-hydroxy-2-(hydroxymethyl)prop-1-yl, $(C_3-C_6)$cycloalkyl or $(C_3-C_6)$cycloalkyl$(C_1-C_3)$alkyl, $X^{A21}$ and $X^{A22}$ each represent H, and $X^{A3}$ represents H or fluorine; or M is the group $M^B$ wherein $R^{1B}$ represents the group $Q^B$ wherein $X^{B1}$ represents H, $(C_1-C_4)$alkyl or oxetan-3-yl, $X^{B21}$ and $X^{B22}$ each represent H, and $X^{B4}$ represents H or halogen.

41) In an even more preferred embodiment, the compounds of formula I according to embodiment 1) or 3) will be such that:

M is the group $M^A$ wherein $R^{1A}$ represents hydrogen or fluorine and $R^{3A}$ represents 3-fluoro-1-methyl-azetidin-3-yl, 3-fluoro-1-(oxetan-3-yl)azetidin-3-yl, (3-fluoroazetidin-1-yl)methyl, (3-hydroxyazetidin-1-yl)methyl, (4-hydroxy-3-fluoropiperidin-1-yl)methyl, (4-hydroxy-3,3-difluoropiperidin-1-yl)methyl, (6-amino-3-azabicyclo[3.1.0]hexan-3-yl)methyl, (2-oxa-6-azaspiro[3.3]heptan-6-yl)methyl, 2-(methylsulfonyl)ethoxy, (3-hydroxyazetidin-1-yl)carbonyloxymethyl, (4-methylpiperazin-1-yl)carbonyloxymethyl, N-(2-hydroxyethyl)-N-(methyl)carbamoyloxymethyl or azetidin-3-yloxycarbonylaminomethyl; or M is the group $M^B$ wherein $R^{1B}$ represents trans-2-(1,2-dihydroxyethyl)cycloprop-1-yl, 1-(methylamino)cycloprop-1-yl, 1-(dimethylamino)cycloprop-1-yl, 2-(morpholinomethyl)cycloprop-1-yl or 1-(3-hydroxyazetidine)-1-carbonyloxymethyl; or M is the group $M^B$ wherein $R^{1B}$ represents the group $Q^A$ wherein $X^{A1}$ represents H, methyl-d, methyl-d2, $(C_1-C_4)$alkyl, ω-$(C_2-C_3)$haloalkyl, ω-hydroxy$(C_2-C_3)$alkyl, $(C_3-C_6)$cycloalkyl or $(C_3-C_6)$cycloalkyl$(C_1-C_3)$alkyl, $X^{A21}$ and $X^{A22}$ each represent H, and $X^{A3}$ represents H; or M is the group $M^B$ wherein $R^{1B}$ represents the group $Q^B$ wherein $X^{B1}$ represents H or $(C_1-C_3)$alkyl, $X^{B21}$ and $X^{B22}$ each represent H, and $X^{B4}$ represents H or fluorine.

42) According to one variant of embodiment 41), the compounds of embodiment 41) will be such that M is the group $M^A$, $R^{1A}$ represents hydrogen or fluorine and $R^{3A}$ represents 3-fluoro-1-methyl-azetidin-3-yl, 3-fluoro-1-(oxetan-3-yl)azetidin-3-yl, (3-fluoroazetidin-1-yl)methyl, (3-hydroxyazetidin-1-yl)methyl, (4-hydroxy-3-fluoropiperidin-1-yl)methyl, (4-hydroxy-3,3-difluoropiperidin-1-yl)methyl, (6-amino-3-azabicyclo[3.1.0]hexan-3-yl)methyl, (2-oxa-6-azaspiro[3.3]heptan-6-yl)methyl, 2-(methylsulfonyl)ethoxy, (3-hydroxyazetidin-1-yl)carbonyloxymethyl, (4-methylpiperazin-1-yl)carbonyloxymethyl, N-(2-hydroxyethyl)-N-(methyl)carbamoyloxymethyl or azetidin-3-yloxycarbonylaminomethyl.

43) According to another variant of embodiment 41), the compounds of embodiment 41) will be such that M is the group $M^B$ wherein $R^{1B}$ represents trans-2-(1,2-dihydroxyethyl)cycloprop-1-yl, 1-(methylamino)cycloprop-1-yl, 1-(dimethylamino)cycloprop-1-yl, 2-(morpholinomethyl)cycloprop-1-yl or 1-(3-hydroxyazetidine)-1-carbonyloxymethyl.

44) According to yet another variant of embodiment 41), the compounds of embodiment 41) will be such that M is the group $M^B$ wherein $R^{1B}$ represents the group $Q^A$ wherein $X^{A1}$ represents H, methyl-d, methyl-d2, $(C_1-C_4)$alkyl, ω-$(C_2-C_3)$haloalkyl, ω-hydroxy$(C_2-C_3)$alkyl, $(C_3-C_6)$cycloalkyl or $(C_3-C_6)$cycloalkyl$(C_1-C_3)$alkyl, $X^{A21}$ and $X^{A22}$ each represent H, and $X^{A3}$ represents H (especially such that M is the group $M^B$ wherein $R^{1B}$ represents the group $Q^A$ wherein $X^{A1}$ represents methyl, methyl-d, methyl-d2,2-fluoro-ethyl, 2-hydroxy-ethyl, cycloprop-1-yl, 3-hydroxy-prop-1-yl or 3-hydroxycyclobut-1-yl, $X^{A21}$ and $X^{A22}$ each represent H, and $X^{A3}$ represents H).

45) According to a further variant of embodiment 41), the compounds of embodiment 41) will be such that M is the group $M^B$ wherein $R^{1B}$ represents the group $Q^B$ wherein $X^{B1}$ represents H or (C$_1$-C$_3$)alkyl, $X^{B21}$ and $X^{B22}$ each represent H, and $X^{B4}$ represents H or fluorine (especially such that M is the group $M^B$ wherein $R^{1B}$ represents the group $Q^B$ wherein $X^{B1}$ represents H or methyl, $X^{B21}$ and $X^{B22}$ each represent H, and $X^{B4}$ represents H or fluorine).

46) Another embodiment of this invention relates to compounds of formula I as defined in one of embodiments 1) to 45) as well as to isotopically labelled, especially $^2$H (deuterium) labelled compounds of formula I as defined in one of embodiments 1) to 45), which compounds are identical to the compounds of formula I as defined in one of embodiments 1) to 45) except that one or more (possibly additional) atoms has or have each been replaced by an atom having the same atomic number but an atomic mass different from the atomic mass usually found in nature. Isotopically labelled, especially $^2$H (deuterium) labelled compounds of formula I and salts (in particular pharmaceutically acceptable salts) thereof are thus within the scope of the present invention. Substitution of hydrogen with the heavier isotope $^2$H (deuterium) may lead to greater metabolic stability, resulting e.g. in an increased in-vivo half-life, reduced dosage requirements, or an improved safety profile. In one variant of the invention, the compounds of formula I are not isotopically labelled, or they are labelled only with one or more deuterium atoms. Isotopically labelled compounds of formula I may be prepared in analogy to the methods described hereinafter, but using the appropriate isotopic variation of suitable reagents or starting materials.

47) Thus the invention notably also relates to the following isotopically labelled compounds according to embodiment 46):

(2R)—N-hydroxy-2-methyl-2-((methyl-d$_2$)sulfonyl)-4-(6-((1-methylazetidin-3-yl)buta-1,3-diyn-1-yl)-3-oxo-1H-pyrrolo[1,2-c]imidazol-2(3H)-yl)butanamide; and (2R)—N-hydroxy-4-(6-((1-(2-hydroxyethyl)azetidin-3-yl)buta-1,3-diyn-1-yl)-3-oxo-1H-pyrrolo[1,2-c]imidazol-2(3H)-yl)-2-methyl-2-((methyl-d$_3$)sulfonyl)butanamide;

as well as the salts (in particular the pharmaceutically acceptable salts) thereof.

48) Particularly preferred are the following compounds of formula I as defined in one of embodiments 1) to 3):

(2R)—N-hydroxy-4-(6-((4-((1R)-1-hydroxy-2-morpholinoethyl)phenyl)ethynyl)-3-oxo-1H-pyrrolo[1,2-c]imidazol-2(3H)-yl)-2-methyl-2-(methylsulfonyl)butanamide;

(2R)—N-hydroxy-4-(6-((4-((1S)-1-hydroxy-2-morpholinoethyl)phenyl)ethynyl)-3-oxo-1H-pyrrolo[1,2-c]imidazol-2(3H)-yl)-2-methyl-2-(methylsulfonyl)butanamide;

(2R)-4-(6-((4-((2-oxa-6-azaspiro[3.3]heptan-6-yl)methyl)phenyl)ethynyl)-3-oxo-1H-pyrrolo[1,2-c]imidazol-2(3H)-yl)-N-hydroxy-2-methyl-2-(methylsulfonyl)butanamide;

(2R)-4-(6-((4-((6-amino-3-azabicyclo[3.1.0]hexan-3-yl)methyl)phenyl)ethynyl)-3-oxo-1H-pyrrolo[1,2-c]imidazol-2(3R)-yl)-N-hydroxy-2-methyl-2-(methylsulfonyl)butanamide;

(3R)-4-((2-(4-(hydroxyamino)-3-methyl-3-(methylsulfonyl)-4-oxobutyl)-3-oxo-2,3-dihydro-1H-pyrrolo[1,2-c]imidazol-6-yl)ethynyl)benzyl 4-hydroxypiperidine-1-carboxylate;

(2R)-4-(6-((4-(1-acetyl-3-hydroxyazetidin-3-yl)phenyl)ethynyl)-3-oxo-1H-pyrrolo[1,2-c]imidazol-2(3R)-yl)-N-hydroxy-2-methyl-2-(methylsulfonyl)butanamide;

(2R)-4-(6-(((1R,2R)-2-((S)-1,2-dihydroxyethyl)cyclopropyl)buta-1,3-diyn-1-yl)-3-oxo-1H-pyrrolo[1,2-c]imidazol-2(3R)-yl)-N-hydroxy-2-methyl-2-(methylsulfonyl)butanamide;

(3R)-5-(2-(4-(hydroxyamino)-3-methyl-3-(methylsulfonyl)-4-oxobutyl)-3-oxo-2,3-dihydro-1H-pyrrolo[1,2-c]imidazol-6-yl)penta-2,4-diyn-1-yl 4-hydroxypiperidine-1-carboxylate;

(2R)—N-hydroxy-2-methyl-2-(methylsulfonyl)-4-(3-oxo-6-(5-(2-oxooxazolidin-3-yl)penta-1,3-diyn-1-yl)-1H-pyrrolo[1,2-c]imidazol-2(3H)-yl)butanamide;

(3R)-4-((2-(4-(hydroxyamino)-3-methyl-3-(methylsulfonyl)-4-oxobutyl)-3-oxo-2,3-dihydro-1H-pyrrolo[1,2-c]imidazol-6-yl)ethynyl)benzyl 3-hydroxyazetidine-1-carboxylate;

(3R)-4-((2-(4-(hydroxyamino)-3-methyl-3-(methylsulfonyl)-4-oxobutyl)-3-oxo-2,3-dihydro-1H-pyrrolo[1,2-c]imidazol-6-yl)ethynyl)benzyl (2-hydroxyethyl)(methyl)carbamate;

(2R)—N-hydroxy-4-(6-((4-((5-(hydroxymethyl)-2-oxooxazolidin-3-yl)methyl)phenyl)ethynyl)-3-oxo-1H-pyrrolo[1,2-c]imidazol-2(3H)-yl)-2-methyl-2-(methylsulfonyl)butanamide;

(2R)-4-(6-((4-(((3S*,4S*)-4-amino-3-fluoropiperidin-1-yl)methyl)phenyl)ethynyl)-3-oxo-1H-pyrrolo[1,2-c]imidazol-2(3R)-yl)-N-hydroxy-2-methyl-2-(methylsulfonyl)butanamide;

(2R)-4-(6-((4-((4-amino-3,3-difluoropiperidin-1-yl)methyl)phenyl)ethynyl)-3-oxo-1H-pyrrolo[1,2-c]imidazol-2(3R)-yl)-N-hydroxy-2-methyl-2-(methylsulfonyl)butanamide;

(2R)-4-(6-((4-(3-fluoroazetidin-3-yl)phenyl)ethynyl)-3-oxo-1H-pyrrolo[1,2-c]imidazol-2(3R)-yl)-N-hydroxy-2-methyl-2-(methylsulfonyl)butanamide;

(2R)-4-(6-((4-(3-fluoro-1-(oxetan-3-yl)azetidin-3-yl)phenyl)ethynyl)-3-oxo-1H-pyrrolo[1,2-c]imidazol-2(3H)-yl)-N-hydroxy-2-methyl-2-(methylsulfonyl)butanamide;

(3R)-4-((2-(4-(hydroxyamino)-3-methyl-3-(methylsulfonyl)-4-oxobutyl)-3-oxo-2,3-dihydro-1H-pyrrolo[1,2-c]imidazol-6-yl)ethynyl)benzyl 4-methylpiperazine-1-carboxylate;

(2R)-4-(6-((3-fluoroazetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide;

(2R)-4-(6-((3-fluoro-1-(oxetan-3-yl)azetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide;

(2R)-4-(6-((4-(3-fluoro-1-methylazetidin-3-yl)phenyl)ethynyl)-3-oxo-1H-pyrrolo[1,2-c]imidazol-2(3H)-yl)-N-hydroxy-2-methyl-2-(methylsulfonyl)butanamide;

(2R)-4-(6-((1-(dimethylamino)cyclopropyl)buta-1,3-diyn-1-yl)-3-oxo-1H-pyrrolo[1,2-c]imidazol-2(3H)-yl)-N-hydroxy-2-methyl-2-(methylsulfonyl)butanamide;

(3R)-(1-((2-(4-(hydroxyamino)-3-methyl-3-(methylsulfonyl)-4-oxobutyl)-3-oxo-2,3-dihydro-1H-pyrrolo[1,2-c]imidazol-6-yl)buta-1,3-diyn-1-yl)cyclopropyl)methyl 3-hydroxyazetidine-1-carboxylate;

(3R)-(1-((2-(4-(hydroxyamino)-3-methyl-3-(methylsulfonyl)-4-oxobutyl)-3-oxo-2,3-dihydro-1H-pyrrolo[1,2-c]imidazol-6-yl)buta-1,3-diyn-1-yl)cyclopropyl)methyl 4-methylpiperazine-1-carboxylate;

(3R)-5-(2-(4-(hydroxyamino)-3-methyl-3-(methylsulfonyl)-4-oxobutyl)-3-oxo-2,3-dihydro-1H-pyrrolo[1,2-c]imidazol-6-yl)penta-2,4-diyn-1-yl 3-hydroxyazetidine-1-carboxylate;

(2R)—N-hydroxy-2-methyl-2-(methylsulfonyl)-4-(6-((4-(2-(methylsulfonyl)ethoxy)phenyl)ethynyl)-3-oxo-1H-pyrrolo[1,2-c]imidazol-2(3H)-yl)butanamide;

azetidin-3-yl (3R)-(4-((2-(4-(hydroxyamino)-3-methyl-3-(methylsulfonyl)-4-oxobutyl)-3-oxo-2,3-dihydro-1H-pyrrolo[1,2-c]imidazol-6-yl)ethynyl)benzyl)carbamate;

1-methylazetidin-3-yl (3R)-(4-((2-(4-(hydroxyamino)-3-methyl-3-(methylsulfonyl)-4-oxobutyl)-3-oxo-2,3-dihydro-1H-pyrrolo[1,2-c]imidazol-6-yl)ethynyl)benzyl)carbamate;

(2R)—N-hydroxy-4-(6-((4-(1-hydroxy-2-((2-methoxyethyl)(methyl)amino)ethyl)phenyl)ethynyl)-3-oxo-1H-pyrrolo[1,2-c]imidazol-2(3H)-yl)-2-methyl-2-(methylsulfonyl)butanamide;

(2R)—N-hydroxy-2-methyl-2-(methylsulfonyl)-4-(6-(((1R,2R)-2-(morpholinomethyl)cyclopropyl)buta-1,3-diyn-1-yl)-3-oxo-1H-pyrrolo[1,2-c]imidazol-2(3H)-yl)butanamide;

(2R)—N-hydroxy-2-methyl-4-(6-((1-methylazetidin-3-yl)buta-1,3-diyn-1-yl)-3-oxo-1H-pyrrolo[1,2-c]imidazol-2(3H)-yl)-2-(methylsulfonyl)butanamide;

(2R)-4-(6-(azetidin-3-ylbuta-1,3-diyn-1l-yl)-3-oxo-1H-pyrrolo[1,2-c]imidazol-2(3H)-yl)-2-methyl-2-(methylsulfonyl)-N-((tetrahydro-2H-pyran-2-yl)oxy)butanamide;

(2R)-4-(6-((1-acetylazetidin-3-yl)buta-1,3-diyn-1-yl)-3-oxo-1H-pyrrolo[1,2-c]imidazol-2(3R)-yl)-N-hydroxy-2-methyl-2-(methylsulfonyl)butanamide;

(2R)-4-(6-((3-fluoro-1-methylazetidin-3-yl)buta-1,3-diyn-1-yl)-3-oxo-1H-pyrrolo[1,2-c]imidazol-2(3R)-yl)-N-hydroxy-2-methyl-2-(methylsulfonyl)butanamide;

(2R)—N-hydroxy-2-methyl-4-(6-((1-methylpiperidin-4-yl)buta-1,3-diyn-1-yl)-3-oxo-1H-pyrrolo[1,2-c]imidazol-2(3H)-yl)-2-(methylsulfonyl)butanamide;

(2R)—N-hydroxy-2-methyl-2-(methylsulfonyl)-4-(6-((1-(oxetan-3-yl)piperidin-4-yl)buta-1,3-diyn-1-yl)-3-oxo-1H-pyrrolo[1,2-c]imidazol-2(3H)-yl)butanamide;

(2R)-4-(6-((4-(((3S*,4S)-3-fluoro-4-hydroxypiperidin-1-yl)methyl)phenyl)ethynyl)-3-oxo-1H-pyrrolo[1,2-c]imidazol-2(3R)-yl)-N-hydroxy-2-methyl-2-(methylsulfonyl)butanamide;

(2R)-4-(6-((4-(((S)-3,3-difluoro-4-hydroxypiperidin-1l-yl)methyl)phenyl)ethynyl)-3-oxo-1H-pyrrolo[1,2-c]imidazol-2(3H)-yl)-N-hydroxy-2-methyl-2-(methylsulfonyl)butanamide;

(2R)—N-hydroxy-2-methyl-4-(6-((1-(methylamino)cyclopropyl)buta-1,3-diyn-1-yl)-3-oxo-1H-pyrrolo[1,2-c]imidazol-2(3H)-yl)-2-(methylsulfonyl)butanamide;

1-methylazetidin-3-yl (3R)-(5-(2-(4-(hydroxyamino)-3-methyl-3-(methylsulfonyl)-4-oxobutyl)-3-oxo-2,3-dihydro-1H-pyrrolo[1,2-c]imidazol-6-yl)penta-2,4-diyn-1-yl)carbamate;

(2R)—N-hydroxy-4-(6-(5-(4-hydroxypiperidin-1-yl)penta-1,3-diyn-1-yl)-3-oxo-1H-pyrrolo[1,2-c]imidazol-2(3H)-yl)-2-methyl-2-(methylsulfonyl)butanamide;

(2R)—N-hydroxy-4-(6-((1-(2-hydroxyethyl)azetidin-3-yl)buta-1,3-diyn-1-yl)-3-oxo-1H-pyrrolo[1,2-c]imidazol-2(3H)-yl)-2-methyl-2-(methylsulfonyl)butanamide;

(2R)-4-(6-((4-(((3R*,4S)-3-fluoro-4-hydroxypiperidin-1-yl)methyl)phenyl)ethynyl)-3-oxo-1H-pyrrolo[1,2-c]imidazol-2(3R)-yl)-N-hydroxy-2-methyl-2-(methylsulfonyl)butanamide;

(2R)—N-hydroxy-4-(6-((4-((3-hydroxyazetidin-1-yl)methyl)phenyl)ethynyl)-3-oxo-1H-pyrrolo[1,2-c]imidazol-2(3H)-yl)-2-methyl-2-(methylsulfonyl)butanamide;

(2R)-4-(6-(((1R,2R)-2-((dimethylamino)methyl)cyclopropyl)buta-1,3-diyn-1-yl)-3-oxo-1H-pyrrolo[1,2-c]imidazol-2(3H)-yl)-N-hydroxy-2-methyl-2-(methylsulfonyl)butanamide;

(2R)—N-hydroxy-4-(6-((4-hydroxy-1-(oxetan-3-yl)piperidin-4-yl)buta-1,3-diyn-1-yl)-3-oxo-1H-pyrrolo[1,2-c]imidazol-2(3H)-yl)-2-methyl-2-(methylsulfonyl)butanamide;

(2R)-4-(6-((4-fluoro-1-methylpiperidin-4-yl)buta-1,3-diyn-1-yl)-3-oxo-1H-pyrrolo[1,2-c]imidazol-2(3H)-yl)-N-hydroxy-2-methyl-2-(methylsulfonyl)butanamide;

(2R)-4-(6-((4-fluoro-1-(oxetan-3-yl)piperidin-4-yl)buta-1,3-diyn-1-yl)-3-oxo-1H-pyrrolo[1,2-c]imidazol-2(3H)-yl)-N-hydroxy-2-methyl-2-(methylsulfonyl)butanamide;

(2R)—N-hydroxy-4-(6-((4-hydroxy-1-methylpiperidin-4-yl)buta-1,3-diyn-1-yl)-3-oxo-1H-pyrrolo[1,2-c]imidazol-2(3H)-yl)-2-methyl-2-(methylsulfonyl)butanamide;

(2R)-4-(6-((4-((3-fluoroazetidin-1-yl)methyl)phenyl)ethynyl)-3-oxo-1H-pyrrolo[1,2-c]imidazol-2(3H)-yl)-N-hydroxy-2-methyl-2-(methylsulfonyl)butanamide;

(3R)-5-(2-(4-(hydroxyamino)-3-methyl-3-(methylsulfonyl)-4-oxobutyl)-3-oxo-2,3-dihydro-1H-pyrrolo[1,2-c]imidazol-6-yl)penta-2,4-diyn-1-yl 4-methylpiperazine-1-carboxylate;

(2R)-4-(6-((1-((R)-2,3-dihydroxypropyl)azetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide;

(2R)—N-hydroxy-2-methyl-4-(6-((1-(methyl-d2)azetidin-3-yl)buta-1,3-diyn-1-yl)-3-oxo-1H-pyrrolo[1,2-c]imidazol-2(3H)-yl)-2-(methylsulfonyl)butanamide;

(2R)-4-(6-(((2S,4S)-4-fluoropyrrolidin-2-yl)buta-1,3-diyn-1-yl)-3-oxo-1H-pyrrolo[1,2-c]imidazol-2(3H)-yl)-N-hydroxy-2-methyl-2-(methylsulfonyl)butanamide;

(2R)-4-(6-((1-ethylazetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide;

(2R)-4-(6-((1-(cyclopropylmethyl)azetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide;

(2R)-4-(6-(((S,2S)-2-((R)-1,2-dihydroxyethyl)cyclopropyl)buta-1,3-diyn-1-yl)-3-oxo-1H-pyrrolo[1,2-c]imidazol-2(3H)-yl)-N-hydroxy-2-methyl-2-(methylsulfonyl)butanamide;

(2R)-4-(6-((1-cyclopropylazetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide;

(2R)—N-hydroxy-2-methyl-2-(methylsulfonyl)-4-(3-oxo-6-((1-(2,2,2-trifluoroethyl)azetidin-3-yl)buta-1,3-diyn-1-yl)-1H-pyrrolo[1,2-c]imidazol-2(3H)-yl)butanamide;

(2R)-4-(6-((1-isopropylazetidin-3-yl)buta-1,3-diyn-1-yl)-3-oxo-1H-pyrrolo[1,2-c]imidazol-2(3H)-yl)-2-methyl-2-(methylsulfonyl)-N-((tetrahydro-2H-pyran-2-yl)oxy)butanamide;

(2R)—N-hydroxy-2-methyl-4-(6-((1-(methyl-d)azetidin-3-yl)buta-1,3-diyn-1-yl)-3-oxo-1H-pyrrolo[1,2-c]imidazol-2(3H)-yl)-2-(methylsulfonyl)butanamide;

(2R)-4-(6-((1-(2-fluoroethyl)azetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide;

(2R)-4-(6-((1-cyclobutylazetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide;

(2R)-4-(6-((1-(1,1-dioxidothietan-3-yl)azetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide;
(2R)—N-hydroxy-4-(6-((1-(3-hydroxypropyl)azetidin-3-yl)buta-1,3-diyn-1-yl)-3-oxo-1H-pyrrolo[1,2-c]imidazol-2(3H)-yl)-2-methyl-2-(methylsulfonyl)butanamide;
(2R)-4-(6-((1,3-dimethylazetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide;
(2R)-4-(6-((3-fluoro-1-(2-hydroxyethyl)azetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide;
(2R)—N-hydroxy-4-(6-((1-(3-hydroxy-2-(hydroxymethyl)propyl)azetidin-3-yl)buta-1,3-diyn-1-yl)-3-oxo-1H-pyrrolo[1,2-c]imidazol-2(3H)-yl)-2-methyl-2-(methylsulfonyl)butanamide;
(2R)-4-(6-((1-(2,2-difluoroethyl)azetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide; and
(2R)—N-hydroxy-4-(6-((1-(3-hydroxycyclobutyl)azetidin-3-yl)buta-1,3-diyn-1-yl)-3-oxo-1H-pyrrolo[1,2-c]imidazol-2(3H)-yl)-2-methyl-2-(methylsulfonyl)butanamide;
as well as the salts (in particular the pharmaceutically acceptable salts) thereof.

49) Also preferred are the following compounds of formula I as defined in embodiment 1) or 2):
(2R)-4-(6-((1-cyclohexylazetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide;
(2R)-4-(6-(((3R)-3-fluoro-1-methylpyrrolidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide;
(2R)-4-(6-(((3S)-3-fluoro-1-methylpyrrolidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide;
(2R)-4-(6-((1-cyclopentylazetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide;
(2R)—N-hydroxy-2-methyl-2-(methylsulfonyl)-4-(3-oxo-6-((1-(tetrahydro-2H-pyran-4-yl)azetidin-3-yl)buta-1,3-diyn-1-yl)-1H-pyrrolo[1,2-c]imidazol-2(3H)-yl)butanamide;
(2R)—N-hydroxy-2-methyl-2-(methylsulfonyl)-4-(3-oxo-6-((1-(thietan-3-yl)azetidin-3-yl)buta-1,3-diyn-1l-yl)-1H-pyrrolo[1,2-c]imidazol-2(3H)-yl)butanamide;
(2R)-4-(6-((1-cyclopropyl-3-fluoropyrrolidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide;
(2R)-4-(6-((3-fluoro-1-(2-hydroxyethyl)pyrrolidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide;
(2R)-4-(6-((3-fluoropyrrolidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide;
(2R)-4-(6-((3-ethyl-1-methylazetidin-3-yl)buta-1,3-diyn-1l-yl)-3-oxo-1H-pyrrolo[1,2-c]imidazol-2(3H)-yl)-N-hydroxy-2-methyl-2-(methylsulfonyl)butanamide;
(2R)-4-(6-((1,3-dimethylpyrrolidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide;
(2R)—N-hydroxy-2-methyl-4-(6-((1-methylpyrrolidin-3-yl)buta-1,3-diyn-1-yl)-3-oxo-1H-pyrrolo[1,2-c]imidazol-2(3H)-yl)-2-(methylsulfonyl)butanamide;
(2R)-4-(6-(2-fluoro-4-((1-methylazetidin-3-yl)ethynyl)phenyl)-3-oxo-1H-pyrrolo[1,2-c]imidazol-2(3H)-yl)-N-hydroxy-2-methyl-2-(methylsulfonyl)butanamide;
(2R)—N-hydroxy-2-methyl-4-(6-(4-((1-methylazetidin-3-yl)ethynyl)phenyl)-3-oxo-1H-pyrrolo[1,2-c]imidazol-2(3H)-yl)-2-(methylsulfonyl)butanamide;
(2R)-2-(3-((4-(6-((1-(2-hydroxyethyl)azetidin-3-yl)buta-1,3-diyn-1-yl)-3-oxo-1H-pyrrolo[1,2-c]imidazol-2(3H)-yl)-2-methyl-2-(methylsulfonyl)butanamido)oxy)-3-oxopropyl)phenyl dihydrogen phosphate;
(2R)-4-(6-(2-fluoro-4-((1-methylpiperidin-4-yl)ethynyl)phenyl)-3-oxo-1H-pyrrolo[1,2-c]imidazol-2(3H)-yl)-N-hydroxy-2-methyl-2-(methylsulfonyl)butanamide;
(2R)-4-(6-(2-fluoro-4-((1-(2-hydroxyethyl)azetidin-3-yl)ethynyl)phenyl)-3-oxo-1H-pyrrolo[1,2-c]imidazol-2(3H)-yl)-N-hydroxy-2-methyl-2-(methylsulfonyl)butanamide;
(2R)—N-hydroxy-2-methyl-2-(methylsulfonyl)-4-(6-((1-(oxetan-3-yl)pyrrolidin-3-yl)buta-1,3-diyn-1-yl)-3-oxo-1H-pyrrolo[1,2-c]imidazol-2(3H)-yl)butanamide;
(2R)—N-hydroxy-4-(6-((1-((1r,3r)-3-hydroxycyclobutyl)azetidin-3-yl)buta-1,3-diyn-1-yl)-3-oxo-1H-pyrrolo[1,2-c]imidazol-2(3H)-yl)-2-methyl-2-(methylsulfonyl)butanamide;
(2R)—N-hydroxy-4-(6-((1-((1s,3s)-3-hydroxycyclobutyl)azetidin-3-yl)buta-1,3-diyn-1-yl)-3-oxo-1H-pyrrolo[1,2-c]imidazol-2(3H)-yl)-2-methyl-2-(methylsulfonyl)butanamide;
(2R)-4-(6-(((2S,3R)-1,2-dimethylazetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide;
(2R)-4-(6-(((2R,3S)-1,2-dimethylazetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide;
(2R)—N-hydroxy-4-(6-(((3R,5R)-5-(hydroxymethyl)-1-methylpyrrolidin-3-yl)buta-1,3-diyn-1-yl)-3-oxo-1H-pyrrolo[1,2-c]imidazol-2(3H)-yl)-2-methyl-2-(methylsulfonyl)butanamide;
(2R)—N-hydroxy-4-(6-(((2R,3R)-2-(hydroxymethyl)-1-methylazetidin-3-yl)buta-1,3-diyn-1-yl)-3-oxo-1H-pyrrolo[1,2-c]imidazol-2(3H)-yl)-2-methyl-2-(methylsulfonyl)butanamide;
(2R)-4-(6-(((2R,3R)-1,2-dimethylazetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide;
(2R)—N-hydroxy-4-(6-(((2S,3S)-2-(hydroxymethyl)-1-methylazetidin-3-yl)buta-1,3-diyn-1-yl)-3-oxo-1H-pyrrolo[1,2-c]imidazol-2(3H)-yl)-2-methyl-2-(methylsulfonyl)butanamide;
(2R)—N-hydroxy-4-(6-(((2S,3S)-2-(fluoromethyl)-1-methylazetidin-3-yl)buta-1,3-diyn-1-yl)-3-oxo-1H-pyrrolo[1,2-c]imidazol-2(3H)-yl)-2-methyl-2-(methylsulfonyl)butanamide;
(2R)—N-hydroxy-4-(6-(((3S*,4R*)-4-hydroxy-1-methylpyrrolidin-3-yl)buta-1,3-diyn-1-yl)-3-oxo-1H-pyrrolo[1,2-c]imidazol-2(3H)-yl)-2-methyl-2-(methylsulfonyl)butanamide; and
(2R)—N-hydroxy-4-(6-(((3R,5R)-5-(hydroxymethyl)-1-(oxetan-3-yl)pyrrolidin-3-yl)buta-1,3-diyn-1-yl)-3-oxo-1H-pyrrolo[1,2-c]imidazol-2(3H)-yl)-2-methyl-2-(methylsulfonyl)butanamide;
as well as the salts (in particular the pharmaceutically acceptable salts) thereof.

50) The invention further relates to the the groups of compounds of formula I selected from the group consisting of the compounds listed either in embodiment 48) or in embodiment 49), which groups of compounds furthermore correspond to one of embodiments 4) to 45), as well as to the salts (in particular the pharmaceutically acceptable salts) of such compounds (and notably to the groups of compounds of formula I selected from the group consisting of the compounds listed in embodiment 48), which groups of compounds furthermore correspond to one of embodiments 4) to 45), as well as to the salts (in particular the pharmaceutically acceptable salts) of such compounds). The invention moreover relates to any individual compound of formula I selected from the group consisting of the compounds listed in embodiment 47), and to the salts (in particular the pharmaceutically acceptable salts) of such individual compound; the invention also relates to any individual compound of formula I selected from the group consisting of the compounds listed in embodiment 48), and to the salts (in particular the pharmaceutically acceptable salts) of such individual compound; likewise, the invention relates to any individual compound of formula I selected from the group consisting of the compounds listed in embodiment 49), and to the salts (in particular the pharmaceutically acceptable salts) of such individual compound.

The compounds of formula I according to this invention, i.e. according to one of embodiments 1) to 50) above, exhibit antibacterial activity, especially against Gram-negative organisms and are therefore suitable to treat bacterial infections in mammals, especially humans. Said compounds may also be used for veterinary applications, such as treating infections in livestock and companion animals. They may further constitute substances for preserving inorganic and organic materials in particular all types of organic materials for example polymers, lubricants, paints, fibres, leather, paper and wood.

They may therefore be used for the treatment or prevention of infectious disorders caused by fermentative or non-fermentative gram negative bacteria, especially those caused by susceptible and multi-drug resistant Gram-negative bacteria. Examples of such Gram-negative bacteria include *Acinetobacter* spp. such as *Acinetobacter baumannii* or *Acinetobacter haemolyticus*, *Actinobacillus actinomycetemcomitans*, *Achromobacter* spp. such as *Achromobacter xylosoxidans* or *Achromobacter faecalis*, *Aeromonas* spp. such as *Aeromonas hydrophila*, *Bacteroides* spp. such as *Bacteroides fragilis*, *Bacteroides theataioatamicron*, *Bacteroides distasonis*, *Bacteroides ovatus* or *Bacteroides vulgatus*, *Bartonella hensenae*, *Bordetella* spp. such as *Bordetella pertussis*, *Borrelia* spp. *such as Borrelia Burgdorferi*, *Brucella* spp. such as *Brucella melitensis*, *Burkholderia* spp. such as *Burkholderia cepacia*, *Burkholderia pseudomallei* or *Burkholderia mallei*, *Campylobacter* spp. such as *Campylobacter jejuni*, *Campylobacter fetus* or *Campylobacter coli*, *Cedecea*, *Chlamydia* spp. such as *Chlamydia pneumoniae*, *Chlamydia trachomatis*, *Citrobacter* spp. such as *Citrobacter diversus* (*koseri*) or *Citrobacter freundii*, *Coxiella burnetii*, *Edwardsiella* spp. such as *Edwarsiella tarda*, *Ehrlichia chafeensis*, *Eikenella corrodens*, *Enterobacter* spp. such as *Enterobacter cloacae*, *Enterobacter aerogenes*, *Enterobacter agglomerans*, *Escherichia coli*, *Francisella tularensis*, *Fusobacterium* spp., *Haemophilus* spp. such as *Haemophilus influenzae* (beta-lactamase positive and negative) or *Haemophilus ducreyi*, *Helicobacter pylori*, *Kingella kingae*, *Klebsiella* spp. such as *Klebsiella oxytoca*, *Klebsiella pneumoniae* (including those encoding extended-spectrum beta-lactamases (hereinafter "ESBLs"), carbapenemases (KPCs), cefotaximase-Munich (CTX-M), metallo-beta-lactamases, and AmpC-type beta-lactamases that confer resistance to currently available cephalosporins, cephamycins, carbapenems, beta-lactams, and beta-lactam/beta-lactamase inhibitor combinations), *Klebsiella rhinoscleromatis* or *Klebsiella ozaenae*, *Legionella pneumophila*, *Mannheimia haemolyticus*, *Moraxella catarrhalis* (beta-lactamase positive and negative), *Morganella morganii*, *Neisseria* spp. such as *Neisseria gonorrhoeae* or *Neisseria meningitidis*, *Pasteurella* spp. such as *Pasteurella multocida*, *Plesiomonas shigelloides*, *Porphyromonas* spp. such as *Porphyromonas asaccharolytica*, *Prevotella* spp. such as *Prevotella corporis*, *Prevotella intermedia* or *Prevotella endodontalis*, *Proteus* spp. such as *Proteus mirabilis*, *Proteus vulgaris*, *Proteus penneri* or *Proteus myxofaciens*, *Porphyromonas asaccharolytica*, *Plesiomonas shigelloides*, *Providencia* spp. such as *Providencia stuartii*, *Providencia rettgeri* or *Providencia alcalifaciens*, *Pseudomonas* spp. such as *Pseudomonas aeruginosa* (including ceftazidime-, cefpirome- and cefepime-resistant *P. aeruginosa*, carbapenem-resistant *P. aeruginosa* or quinolone-resistant *P. aeruginosa*) or *Pseudomonas fluorescens*, *Ricketsia prowazekii*, *Salmonella* spp. such as *Salmonella typhi* or *Salmonella paratyphi*, *Serratia marcescens*, *Shigella* spp. such as *Shigella flexneri*, *Shigella boydii*, *Shigella sonnei* or *Shigella dysenteriae*, *Streptobacillus moniliformis*, *Stenotrophomonas maltophilia*, *Treponema* spp., *Vibrio* spp. such as *Vibrio cholerae*, *Vibrio parahaemolyticus*, *Vibrio vulnificus*, *Vibrio alginolyticus*, *Yersinia* spp. such as *Yersinia enterocolitica*, *Yersinia pestis* or *Yersinia pseudotuberculosis*.

The compounds of formula I according to this invention may thus be useful for treating a variety of infections caused by fermentative or non-fermentative Gram-negative bacteria, especially infections such as: nosocomial pneumonia (related to infection by *Legionella pneumophila*, *Haemophilus influenzae*, or *Chlamydia pneumoniae*); urinary tract infections; systemic infections (bacteraemia and sepsis); skin and soft tissue infections (including burn patients); surgical infections; intraabdominal infections; lung infections (including those in patients with cystic fibrosis); *Helicobacter pylori* (and relief of associated gastric complications such as peptic ulcer disease, gastric carcinogenesis, etc.); endocarditis; diabetic foot infections; osteomyelitis; otitis media, sinusitus, bronchitis, tonsillitis, and mastoiditis related to infection by *Haemophilus influenzae* or *Moraxella catarrhalis*; pharynigitis, rheumatic fever, and glomerulonephritis related to infection by *Actinobacillus haemolyticum*; sexually transmitted diseases related to infection by *Chlamydia* trachormatis, *Haemophilus ducreyi*, *Treponema pallidum*, *Ureaplasma urealyticum*, or *Neisseria gonorrheae*; systemic febrile syndromes related to infection by *Borrelia recurrentis*; Lyme disease related to infection by *Borrelia burgdorferi*; conjunctivitis, keratitis, and dacrocystitis related to infection by *Chlamydia trachomatis*, *Neisseria gonorrhoeae* or *H. influenzae*; gastroenteritis related to infection by *Campylobacter jejuni*; persistent cough related to infection by *Bordetella pertussis* and gas gangrene related to infection by *Bacteroides* spp. Other bacterial infections and disorders related to such infections that may be treated or prevented in accord with the method of the present invention are referred to in J. P. Sanford et al., "*The Sanford Guide to Antimicrobial Therapy*", 26th Edition, (Antimicrobial Therapy, Inc., 1996).

The preceding lists of infections and pathogens are to be interpreted merely as examples and in no way as limiting.

The compounds of formula I according to this invention, or the pharmaceutically acceptable salts thereof, may therefore be used for the preparation of a medicament, and are suitable, for the prevention or treatment of a bacterial infection, in particular for the prevention or treatment of a bacterial infection caused by Gram-negative bacteria, especially by multi-drug resistant Gram-negative bacteria.

The compounds of formula I according to this invention, or the pharmaceutically acceptable salts thereof, may thus especially be used for the preparation of a medicament, and are suitable, for the prevention or treatment of a bacterial infection caused by Gram-negative bacteria selected from the group consisting of *Burkholderia* spp. (e.g. *Burkholderia cepacia*), *Citrobacter* spp., *Enterobacter aerogenes, Enterobacter cloacae, Escherichia coli, Klebsiella oxytoca, Klebsiella pneumoniae, Serratia marcescens, Stenotrophomonas maltophilia* and *Pseudomonas aeruginosa* (notably for the prevention or treatment of a bacterial infection caused by *Escherichia coli* bacteria, *Klebsiella pneumoniae* bacteria or *Pseudomonas aeruginosa* bacteria, and in particular for the prevention or treatment of a bacterial infection mediated by quinolone-resistant, carbapenem-resistant or multi-drug resistant *Klebsiella pneumoniae* bacteria).

The compounds of formula I according to this invention, or the pharmaceutically acceptable salts thereof, may more especially be used for the preparation of a medicament, and are suitable, for the prevention or treatment of a bacterial infection caused by Gram-negative bacteria selected from the group consisting of *Citrobacter* spp., *Enterobacter aerogenes, Enterobacter cloacae, Escherichia coli, Klebsiella oxytoca, Klebsiella pneumoniae, Serratia marcescens, Stenotrophomonas maltophilia* and *Pseudomonas aeruginosa* bacteria (notably of a bacterial infection caused by Gram-negative bacteria selected from the group consisting of *Klebsiella pneumoniae* and *Pseudomonas aeruginosa* bacteria, and in particular of a bacterial infection caused by *Pseudomonas aeruginosa* bacteria).

The compounds of formula I according to this invention, or the pharmaceutically acceptable salts thereof, may thus especially be used for the preparation of a medicament, and are suitable, for the prevention or treatment of a bacterial infection selected from urinary tract infections, systemic infections (such as bacteraemia and sepsis), skin and soft tissue infections (including burn patients), surgical infections; intraabdominal infections and lung infections (including those in patients with cystic fibrosis).

The compounds of formula I according to this invention, or the pharmaceutically acceptable salts thereof, may more especially be used for the preparation of a medicament, and are suitable, for the prevention or treatment of a bacterial infection selected from urinary tract infections, intraabdominal infections and lung infections (including those in patients with cystic fibrosis), and in particular for the prevention or treatment of a bacterial infection selected from urinary tract infections and intraabdominal infections.

Besides, the compounds of formula I according to this invention display intrinsic antibacterial properties and have the ability to improve permeability of the outer membrane of Gram-negative bacteria to other antibacterial agents. Their use in combination with another antibacterial agent might offer some further advantages such as lowered side-effects of drugs due to lower doses used or shorter time of treatment, more rapid cure of infection shortening hospital stays, increasing spectrum of pathogens controlled, and decreasing incidence of development of resistance to antibiotics. The antibacterial agent for use in combination with a compound of formula I according to this invention will be selected from the group consisting of a penicillin antibiotic (such as ampicillin, piperacillin, penicillin G, amoxicillin, or ticarcillin), a cephalosporin antibiotic (such as ceftriaxone, ceftazidime, cefepime, cefotaxime) a carbapenem antibiotic (such as imipenem, or meropenem), a monobactam antibiotic (such as aztreonam or carumonam), a fluoroquinolone antibiotic (such as ciprofloxacin, moxifloxacin or levofloxacin), a macrolide antibiotic (such as erythromycin or azithromycin), an aminoglycoside antibiotic (such as amikacin, gentamycin or tobramycin), a glycopeptide antibiotic (such as vancomycin or teicoplanin), a tetracycline antibiotic (such as tetracycline, oxytetracycline, doxycycline, minocycline or tigecycline), and linezolid, clindamycin, telavancin, daptomycin, novobiocin, rifampicin and polymyxin. Preferably, the antibacterial agent for use in combination with a compound of formula I according to this invention will be selected from the group consisting of vancomycin, tigecycline and rifampicin.

The compounds of formula I according to this invention, or the pharmaceutically acceptable salt thereof, may moreover be used for the preparation of a medicament, and are suitable, for the prevention or treatment (and especially the treatment) of infections caused by biothreat Gram negative bacterial pathogens as listed by the US Center for Disease Control (the list of such biothreat bacterial pathogens can be found at the web page http://www.selectagents.gov/SelectAgentsandToxinsList.html), and in particular by Gram negative pathogens selected from the group consisting of *Yersinia pestis, Francisella tularensis* (tularemia), *Burkholderia pseudomallei* and *Burkholderia mallei.*

One aspect of this invention therefore relates to the use of a compound of formula I according to one of embodiments 1) to 50), or of a pharmaceutically acceptable salt thereof, for the manufacture of a medicament for the prevention or treatment of a bacterial infection (in particular one of the previously mentioned infections caused by Gram-negative bacteria, especially by multi-drug resistant Gram-negative bacteria). Another aspect of this invention relates to a compound of formula I according to one of embodiments 1) to 50), or a pharmaceutically acceptable salt thereof, for the prevention or treatment of a bacterial infection (in particular for the prevention or treatment of one of the previously mentioned infections caused by Gram-negative bacteria, especially by multi-drug resistant Gram-negative bacteria). Yet another aspect of this invention relates to a compound of formula I according to one of embodiments 1) to 50), or a pharmaceutically acceptable salt thereof, as a medicament. Yet a further aspect of this invention relates to a pharmaceutical composition containing, as active principle, a compound of formula I according to one of embodiments 1) to 50), or a pharmaceutically acceptable salt thereof, and at least one therapeutically inert excipient.

As well as in humans, bacterial infections can also be treated using compounds of formula I (or pharmaceutically acceptable salts thereof) in other species like pigs, ruminants, horses, dogs, cats and poultry.

The present invention also relates to pharmacologically acceptable salts and to compositions and formulations of compounds of formula I, $I_{CE}$ or $I_{CEP}$.

Any reference to a compound of formula I, $I_{CE}$ or $I_{CEP}$ in this text is to be understood as referring also to the salts (and especially the pharmaceutically acceptable salts) of such compounds, as appropriate and expedient.

A pharmaceutical composition according to the present invention contains at least one compound of formula I (or a pharmaceutically acceptable salt thereof) as the active agent and optionally carriers and/or diluents and/or adjuvants, and may also contain additional known antibiotics.

The compounds of formula I and their pharmaceutically acceptable salts can be used as medicaments, e.g. in the form of pharmaceutical compositions for enteral or parenteral administration.

The production of the pharmaceutical compositions can be effected in a manner which will be familiar to any person skilled in the art (see for example Remington, *The Science and Practice of Pharmacy,* 21st Edition (2005), Part 5, "Pharmaceutical Manufacturing" [published by Lippincott Williams & Wilkins]) by bringing the described compounds of formula I or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Another aspect of the invention concerns a method for the prevention or the treatment of a Gram-negative bacterial infection in a patient, comprising the administration to said patient of a pharmaceutically active amount of a compound of formula I according to one of embodiments 1) to 50) or a pharmaceutically acceptable salt thereof. Accordingly, the invention provides a method for the prevention or the treatment of a bacterial infection caused by Gram-negative bacteria (notably for the prevention or treatment of a bacterial infection caused by *Escherichia coli* bacteria, *Klebsiella pneumoniae* bacteria or *Pseudomonas aeruginosa* bacteria, and in particular for the prevention or treatment of a bacterial infection caused by quinolone-resistant, carbapenem-resistant or multi-drug resistant *Klebsiella pneumoniae* bacteria) in a patient, comprising the administration to said patient of a pharmaceutically active amount of a compound of formula I according to one of embodiments 1) to 50) or a pharmaceutically acceptable salt thereof.

Moreover, the compounds of formula I according to this invention may also be used for cleaning purposes, e.g. to remove pathogenic microbes and bacteria from surgical instruments, catheters and artificial implants or to make a room or an area aseptic. For such purposes, the compounds of formula I could be contained in a solution or in a spray formulation.

This invention, thus, relates to the compounds of formula I as defined in embodiment 1), or further limited under consideration of their respective dependencies by the characteristics of any one of embodiments 2) to 50), and to pharmaceutically acceptable salts thereof. It relates furthermore to the use of such compounds as medicaments, especially for the prevention or treatment of a bacterial infection, in particular for the prevention or treatment of a bacterial infection caused by Gram-negative bacteria (notably for the prevention or treatment of a bacterial infection caused by *Escherichia coli* bacteria, *Klebsiella pneumoniae* bacteria or *Pseudomonas aeruginosa* bacteria, and in particular for the prevention or treatment of a bacterial infection caused by *Klebsiella pneumoniae* quinolone-resistant, carbapenem-resistant or multi-drug resistant bacteria). The following embodiments relating to the compounds of formula I according to embodiment 1) are thus possible and intended and herewith specifically disclosed in individualised form:

1, 2+1, 3+1, 3+2+1, 4+1, 4+2+1, 5+1, 5+2+1, 6+1, 6+2+1, 6+3+1, 6+3+2+1, 6+4+1, 6+4+2+1, 6+5+1, 6+5+2+1, 7+6+1, 7+6+2+1, 7+6+3+1, 7+6+3+2+1, 7+6+4+1, 7+6+4+2+1, 7+6+5+1, 7+6+5+2+1, 8+5+1, 8+5+2+1, 8+6+1, 8+6+2+1, 8+6+3+1, 8+6+3+2+1, 8+6+4+1, 8+6+4+2+1, 8+6+5+1, 8+6+5+2+1, 8+7+6+1, 8+7+6+2+1, 8+7+6+3+1, 8+7+6+3+2+1, 8+7+6+4+1, 8+7+6+4+2+1, 8+7+6+5+1, 8+7+6+5+2+1, 9+6+1, 9+6+2+1, 9+6+3+1, 9+6+3+2+1, 9+6+4+1, 9+6+4+2+1, 9+6+5+1, 9+6+5+2+1, 9+7+6+1, 9+7+6+2+1, 9+7+6+3+1, 9+7+6+3+2+1, 9+7+6+4+1, 9+7+6+4+2+1, 9+7+6+5+1, 9+7+6+5+2+1, 9+8+5+1, 9+8+5+2+1, 9+8+6+1, 9+8+6+2+1, 9+8+6+3+1, 9+8+6+3+2+1, 9+8+6+4+1, 9+8+6+4+2+1, 9+8+6+5+1, 9+8+6+5+2+1, 9+8+7+6+1, 9+8+7+6+2+1, 9+8+7+6+3+1, 9+8+7+6+3+2+1, 9+8+7+6+4+1, 9+8+7+6+4+2+1, 9+8+7+6+5+1, 9+8+7+6+5+2+1, 10+6+1, 10+6+2+1, 10+6+3+1, 10+6+3+2+1, 10+6+4+1, 10+6+4+2+1, 10+6+5+1, 10+6+5+2+1, 10+7+6+1, 10+7+6+2+1, 10+7+6+3+1, 10+7+6+3+2+1, 10+7+6+4+1, 10+7+6+4+2+1, 10+7+6+5+1, 10+7+6+5+2+1, 10+8+5+1, 10+8+5+2+1, 10+8+6+1, 10+8+6+2+1, 10+8+6+3+1, 10+8+6+3+2+1, 10+8+6+4+1, 10+8+6+4+2+1, 10+8+6+5+1, 10+8+6+5+2+1, 10+8+7+6+1, 10+8+7+6+2+1, 10+8+7+6+3+1, 10+8+7+6+3+2+1, 10+8+7+6+4+1, 10+8+7+6+4+2+1, 10+8+7+6+5+1, 10+8+7+6+5+2+1, 11+6+1, 11+6+2+1, 11+6+3+1, 11+6+3+2+1, 11+6+4+1, 11+6+4+2+1, 11+6+5+1, 11+6+5+2+1, 11+7+6+1, 11+7+6+2+1, 11+7+6+3+1, 11+7+6+3+2+1, 11+7+6+4+1, 11+7+6+4+2+1, 11+7+6+5+1, 11+7+6+5+2+1, 11+8+5+1, 11+8+5+2+1, 11+8+6+1, 11+8+6+2+1, 11+8+6+3+1, 11+8+6+3+2+1, 11+8+6+4+1, 11+8+6+4+2+1, 11+8+6+5+1, 11+8+6+5+2+1, 11+8+7+6+1, 11+8+7+6+2+1, 11+8+7+6+3+1, 11+8+7+6+3+2+1, 11+8+7+6+4+1, 11+8+7+6+4+2+1, 11+8+7+6+5+1, 11+8+7+6+5+2+1, 12+1, 12+2+1, 12+3+1, 12+3+2+1, 12+4+1, 12+4+2+1, 12+5+1, 12+5+2+1, 13+12+1, 13+12+2+1, 13+12+3+1, 13+12+3+2+1, 13+12+4+1, 13+12+4+2+1, 13+12+5+1, 13+12+5+2+1, 14+12+1, 14+12+2+1, 14+12+3+1, 14+12+3+2+1, 14+12+4+1, 14+12+4+2+1, 14+12+5+1, 14+12+5+2+1, 15+12+1, 15+12+2+1, 15+12+3+1, 15+12+3+2+1, 15+12+4+1, 15+12+4+2+1, 15+12+5+1, 15+12+5+2+1, 16+15+12+1, 16+15+12+2+1, 16+15+12+3+1, 16+15+12+3+2+1, 16+15+12+4+1, 16+15+12+4+2+1, 16+15+12+5+1, 16+15+12+5+2+1, 17+16+15+12+1, 17+16+15+12+2+1, 17+16+15+12+3+1, 17+16+15+12+3+2+1, 17+16+15+12+4+1, 17+16+15+12+4+2+1, 17+16+15+12+5+1, 17+16+15+12+5+2+1, 22+21, 23+17+16+15+12+1, 23+17+16+15+12+2+1, 23+17+16+15+12+3+1, 23+17+16+15+12+3+2+1, 23+17+16+15+12+4+1, 23+17+16+15+12+4+2+1, 23+17+16+15+12+5+1, 23+17+16+15+12+5+2+1, 24+23+17+16+15+12+1, 24+23+17+16+15+12+2+1, 24+23+17+16+15+12+3+1, 24+23+17+16+15+12+3+2+1, 24+23+17+16+15+12+4+1, 24+23+17+16+15+12+4+2+1, 24+23+17+16+15+12+5+1, 24+23+17+16+15+12+5+2+1, 25+16+15+12+1, 25+16+15+12+2+1, 25+16+15+12+3+1, 25+16+15+12+3+2+1, 25+16+15+12+4+1, 25+16+15+12+4+2+1, 25+16+15+12+5+1, 25+16+15+12+5+2+1, 26+25+16+15+12+1, 26+25+16+15+12+2+1, 26+25+16+15+12+3+1, 26+25+16+15+12+3+2+1, 26+25+16+15+12+4+1, 26+25+16+15+12+4+2+1, 26+25+16+15+12+5+1, 26+25+16+15+12+5+2+1, 27+25+16+15+12+1, 27+25+16+15+12+2+1, 27+25+16+15+12+3+1, 27+25+16+15+12+3+2+1, 27+25+16+15+12+4+1, 27+25+16+15+12+4+2+1, 27+25+16+15+12+5+1, 27+25+16+15+12+5+2+1, 28+25+16+15+12+1, 28+25+16+15+12+2+1, 28+25+16+15+12+3+1, 28+25+16+15+12+3+2+1, 28+25+16+15+12+4+1, 28+25+16+15+12+4+2+1, 28+25+16+15+12+5+1, 28+25+16+15+12+5+2+1, 29+15+12+1, 29+15+12+2+1, 29+15+12+3+1, 29+15+12+3+2+1, 29+15+12+4+1, 29+15+12+4+2+1, 29+15+12+5+1, 29+15+12+5+2+1, 30+29+15+12+1, 30+29+15+12+2+1, 30+29+15+12+3+1, 30+29+15+12+3+2+1, 30+29+15+12+4+1, 30+29+15+12+4+2+1, 30+29+15+12+5+1, 30+29+15+12+5+2+1, 31+29+15+12+1, 31+29+15+12+2+1, 31+29+15+12+3+1, 31+29+15+12+3+2+1, 31+29+15+12+4+1, 31+29+15+12+4+2+1, 31+29+15+12+5+1, 31+29+15+12+5+2+1, 32+1, 32+2+1, 32+4+1, 32+4+2+1, 32+5+1, 32+5+2+1, 33+32+1, 33+32+2+1, 33+32+4+1, 33+32+4+2+1, 33+32+5+1, 33+32+5+2+1, 34+33+32+1, 34+33+32+2+1, 34+33+32+4+1, 34+33+32+4+2+1, 34+33+32+5+1, 34+33+32+5+2+1, 35+34+33+32+1, 35+34+33+32+2+1, 35+34+33+32+4+1, 35+34+33+32+4+2+1, 35+34+33+32+5+1, 35+34+33+32+5+2+1, 36+34+33+32+1, 36+34+33+32+2+1, 36+34+33+32+4+1, 36+34+33+32+4+2+1, 36+34+33+32+5+1, 36+34+33+32+5+2+1, 37+33+32+1, 37+33+32+2+1, 37+33+32+4+1, 37+33+32+

4+2+1, 37+33+32+5+1, 37+33+32+5+2+1, 38+37+33+32+1, 38+37+33+32+2+1, 38+37+33+32+4+1, 38+37+33+32+4+2+1, 38+37+33+32+5+1, 38+37+33+32+5+2+1, 39+1, 39+3+1, 39+3+2+1, 40+1, 40+3+1, 40+3+2+1, 41+1, 41+3+1, 41+3+2+1, 42+41+1, 42+41+3+1, 42+41+3+2+1, 43+41+1, 43+41+3+1, 43+41+3+2+1, 44+41+1, 44+41+3+1, 44+41+3+2+1, 45+41+1, 45+41+3+1, 45+41+3+2+1, 46, 47+46, 48, 49 and 50.

In the list above, the numbers refer to the embodiments according to their numbering provided hereinabove whereas "+" indicates the dependency from another embodiment.

The different individualised embodiments are separated by commas. In other words, "5+3+1" for example refers to embodiment 5) depending on embodiment 3), depending on embodiment 1), i.e. embodiment "5+3+1" corresponds to embodiment 1) further limited by the features of embodiments 3) and 5). Likewise, "9+5+4+1" refers to embodiment 9) depending mutatis mutandis on embodiments 5) and 4), depending on embodiment 1), i.e. embodiment "9+5+4+1" corresponds to embodiment 1) further limited by the features of embodiments 4) and 5), further limited by the features of embodiment 9).

The compounds of formula I can be manufactured in accordance with the present invention using the procedures described hereafter.

Preparation of the Compounds of Formula I

Abbreviations

The following abbreviations are used throughout the specification and the examples:
Ac acetyl
AcOH acetic acid
aq. aqueous
Boc tert-butoxycarbonyl
Bu n-butyl
BuLi n-butyl lithium
CC column chromatography over silica gel
CDI 1,1'-carbonyldiimidazole
Cipro ciprofloxacin
Cy cyclohexyl
DAD diode array detection
DAST (N,N-diethylamino)sulfur trifluoride
dba dibenzylideneacetone
DCC dicyclohexylcarbodiimide
DCE 1,2-dichloroethane
DCM dichloromethane
DEA diethylamine
DIBAH diisobutylaluminium hydride
DIPEA N,N-diisopropylethylamine
DME 1,2-dimethoxyethane
DMF N,N-dimethylformamide
DMSO dimethylsulfoxide
DPPA diphenyl phosphoryl azide
DSC N,N'-disuccinimidyl carbonate
EA ethyl acetate
EDC N-(3-dimethylaminopropyl)-N'-ethylcarbodiimide hydrochloride
ELSD evaporative light scattering detector
ESI electron spray ionisation
eq. equivalent
Et ethyl
$Et_2O$ diethyl ether
EtOH ethanol
Gly glycine
HATU O-(7-azabenzotriazol-1-yl)-N,N,N',N'-tetramethyluronium hexafluorophosphate
Hept heptane
Hex hexane
HMPA hexamethylphosphoramide
HOBT hydroxybenzotriazole
HPLC high pressure liquid chromatography
iPr iso-propyl
iPrOH iso-propanol
IT internal temperature
LC liquid chromatography
LDA lithium diisopropylamide
LiHMDS lithium hexamethyldisilazide
MCPBA meta-chloro perbenzoic acid
Me methyl
MeCN acetonitrile
MeOH methanol
Ms methanesulfonyl (mesyl)
MS mass spectroscopy
NBS N-bromosuccinimide
NMP N-methyl-2-pyrrolidone
NMR Nuclear Magnetic Resonance
org. organic
Pd/C palladium on carbon
PE petroleum ether
PEPPSI™-IPr [1,3-bis(2,6-diisopropylphenyl)imidazol-2-ylidene](3-chloropyridyl)palladium(II) dichloride
Ph phenyl
PPTS para-toluenesulfonic acid pyridinium salt
prep-HPLC preparative HPLC
Pyr pyridine
Q-phos 1,2,3,4,5-pentaphenyl-1'-(di-tert-butylphosphino) ferrocene
rt room temperature
sat. saturated
SK-CC01-A 2'-(dimethylamino)-2-biphenylyl-palladium(II) chloride dinorbomylphosphine complex
S-Phos 2-dicyclohexylphosphino-2',6'-dimethoxybiphenyl
T3P propylphosphonic anhydride
TBAF tetra-n-butylammonium fluoride
TBME tert-butyl methyl ether
tBu tert-butyl
tBuOH tert-butanol
TEA triethylamine
Tf trifluoromethanesulfonyl
TFA trifluoroacetic acid
THF tetrahydrofuran
THP tetrahydropyranyl
TLC thin layer chromatography
TMS trimethylsilyl
TMSE 2-(trimethylsilyl)ethyl
$t_R$ retention time
$T_S$ para-toluenesulfonyl
wt % percent in weight
General Reaction Techniques:
General Reaction Technique 1 (Protecting Group Removal):
The protecting groups of hydroxamic acid ester derivatives (CONHOPG) and the protecting groups of phosphonic acid ester derivatives $(P(O)(OPG')_2$ are removed as follows:
When PG or PG' is THP, (2-methylpropoxy)ethyl, methoxymethyl, tBu, COOtBu or COtBu: by acidic treatment with e.g. TFA or HCl in an org. solvent such as DCM, dioxane, $Et_2O$ or MeOH between 0° C. and rt or by treatment with pyridinium para-toluenesulfonate in EtOH between rt and about +80° C.;

When PG, or PG' is trityl: by treatment with diluted acid such as citric acid or HCl in an org. solvent such as MeOH or DCM;

When PG or PG' is TMSE: by using fluoride anion sources such as BF₃.etherate complex in MeCN at 0° C., TBAF in THF between 0° C. and about +40° C. or HF in MeCN or water between 0° C. and +40° C., or using acidic conditions such as AcOH in THF/MeOH or HCl in MeOH;

When PG or PG' is allyl: by treatment with Pd(PPh₃)₄ in a solvent such as MeOH in presence of K₂CO₃ or a scavenger such as dimedone, morpholine or tributyltin hydride;

Further general methods to remove hydroxamic acid protecting groups have been described in T. W. Greene & P. G. M. Wuts, *Protecting Groups in Organic Synthesis*, 3$^{rd}$ Ed (1999), 23-147 (Publisher: John Wiley and Sons, Inc., New York, N.Y.).

General Reaction Technique 2 (Peptide-Type Coupling):

The carboxylic acid is reacted respectively with the hydroxylamine derivative or an hydroxamic acid in the presence of an activating agent such as DCC, EDC, HOBT, n-propylphosphonic cyclic anhydride, HATU or di-(N-succinimidyl)-carbonate, in a dry aprotic solvent such as DCM, MeCN or DMF between −20° C. and +60° C. (see G. Benz in *Comprehensive Organic Synthesis*, B. M. Trost, I. Fleming, Eds; Pergamon Press: New York (1991), vol. 6, p. 381). Alternatively, the carboxylic acid can be activated by conversion into its corresponding acid chloride by reaction with oxalyl chloride or thionyl chloride neat or in a solvent like DCM between −20° and +60° C. Further activating agents can be found in R. C. Larock, *Comprehensive Organic Transformations. A guide to Functional Group Preparations*, 2$^{nd}$ Edition (1999), section nitriles, carboxylic acids and derivatives, p. 1941-1949 (Wiley-VC; New York, Chichester, Weinheim, Brisbane, Singapore, Toronto).

General Reaction Technique 3 (Alkyne-Alkyne Cross Coupling, Haloaryl-Alkyne or Alkyne-Haloalkyne Cross Coupling):

An alkyne derivative is coupled with a second alkyne, an haloaryl such as a bromo- or an iodoaryl, or a haloalkyne derivative, using a catalytic amount of a palladium salt, an org. base such as TEA and a catalytic amount of a copper derivative (usually copper iodide) in a solvent such as DMF at a temperature from 20 to 100° C. (see Sonogashira, K. in *Metal-Catalyzed Reactions*, Diederich, F., Stang, P. J., Eds.; Wiley-VCH: New York (1998)). Alternatively, the alkyne-haloalkyne cross coupling reaction can be performed using only a catalytic amount of copper derivative in the presence of aqueous hydroxylamine and a base such as piperidine or pyrrolidine (see Chodkiewicz and Cadiot, C. R. *Hebd. Seances Acad. Sci.* (1955), 241, 1055-1057), or in the presence of a ligand such as PPh₃ and a base such as K₂CO₃ in EtOH at reflux (see Wand et al., *Synthesis* (2011), 10, 1541).

General Reaction Technique 4 (Transformation of an Ester into an Acid):

When the ester side chain is a linear alkyl, the hydrolysis is usually performed by treatment with an alkali hydroxide such as LiOH, KOH or NaOH in a water-dioxan or water-THF mixture between 0° C. and 80° C. When the ester side chain is tBu, the release of the corresponding acid can also be performed in neat TFA or diluted TFA or HCl in an org. solvent such as ether or THF. When the ester side chain is the allyl group, the reaction is performed in the presence of tetrakis(triphenylphosphine)palladium(0) in the presence of an allyl cation scavenger such as morpholine, dimedone or tributyltin hydride between 0° C. and 50° C. in a solvent such as THF. When the ester side chain is benzyl, the reaction is performed under hydrogen in the presence of a noble metal catalyst such as Pd/C in a solvent such as MeOH, THF or EA. Further strategies to introduce other acid protecting groups and general methods to remove them have been described in T. W. Greene & P. G. M. Wuts, *Protecting Groups in Organic Synthesis*, 3$^{rd}$ Ed. (1999), 369-441 (Publisher: John Wiley and Sons, Inc., New York, N.Y.).

General Reaction Technique 5 (Suzuki Coupling):

The aromatic halide (typically a bromide) is reacted with the required boronic acid derivative or its boronate ester equivalent (e.g. pinacol ester) in the presence of a palladium catalyst and a base such as K₂CO₃, Cs₂CO₃, K₃PO₄, tBuONa or tBuOK between 20 and 120° C. in a solvent such as toluene, THF, dioxane, DME or DMF, usually in the presence of water (20 to 50%). Examples of typical palladium catalysts are triarylphosphine palladium complexes such as Pd(PPh₃)₄. These catalysts can also be prepared in situ from a common palladium source such as Pd(OAc)₂ or Pd₂(dba)₃ and a ligand such as trialkylphosphines (e.g. PCy₃ or P(tBu)₃), dialkylphosphinobiphenyls (e.g. S-Phos) or ferrocenylphosphines (e.g. Q-phos). Alternatively, one can use a commercially available precatalyst based on palladacycle (e.g. SK-CC01-A) or N-heterocyclic carbene complexes (e.g. PEPPSI™-IPr). The reaction can also be performed by using the corresponding aromatic triflate. Further variations of the reaction are described in Miyaura and Suzuki, *Chem. Rev.* (1995), 95, 2457-2483, Bellina et al., *Synthesis* (2004), 2419-2440, Mauger and Mignani, *Aldrichimica Acta* (2006), 39, 17-24, Kantchev et al., *Aldrichimica Acta* (2006), 39, 97-111, Fu, *Acc. Chem. Res.* (2008), 41, 1555-1564, and references cited therein.

General Preparation Methods:

Preparation of the Compounds of Formula I:

The compounds of formula I can be manufactured by the methods given below, by the methods given in the examples or by analogous methods. Optimum reaction conditions may vary with the particular reactants or solvents used, but such conditions can be determined by a person skilled in the art by routine optimisation procedures.

The sections hereafter describe general methods for preparing compounds of formula I. If not indicated otherwise, the generic groups $R^1$, $R^2$, L, M, $M^A$, $M^B$, $M^C$, $R^{1A}$, $R^{3A}$, $R^{1B}$, $R^{1C}$ and $R^{3C}$ are as defined for formula I. General synthetic methods used repeatedly throughout the text below are referenced to and described in the above section entitled "General reaction techniques". In some instances certain generic groups might be incompatible with the assembly illustrated in the procedures and schemes below and so will require the use of protecting groups. The use of protecting groups is well known in the art (see for example T. W. Greene and P. G. M. Wuts, *Protective Groups in Organic Synthesis*, 3$^{rd}$ Ed. (1999), Wiley-Interscience).

The compounds of formula I wherein $R^1$ is H can be obtained by deprotecting a compound of formula II

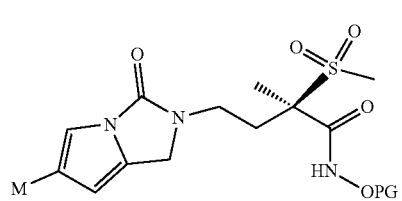

II wherein M is as defined in formula I and PG represents THP, TMSE, benzyl, trityl, (2-methylpropoxy)ethyl, methoxymethyl, allyl, tBu, COOtBu or COtBu using general reaction technique 1. The reaction can also be performed with racemic material and the (R) enantiomer can be obtained by chiral HPLC separation.

The compounds of formula I wherein $R^1$ is not H can be obtained by:

i) reacting a compound of formula I wherein $R^1$ is H and M is as defined in formula I with a compound of formula III

$(PG^4O)_2P-N(iPr)_2$      III wherein $PG^4$ represents tert-butyl, the reaction being performed in the presence of a base such as tetrazole in a solvent such as acetonitrile at a temperature in the vicinity of 0° C., an oxidation reaction being subsequently performed adding an oxidizing agent such as hydrogen peroxide in water or MCPBA and subsequent cleavage of $PG^4$ being performed using general reaction technique 1 (this reaction sequence can also be performed with racemic compound of formula I wherein $R^1$ is H and the (R)-enantiomer can then be obtained by chiral HPLC separation of the reaction products), whereby functional groups (e.g. amino or hydroxy) present on M that would be incompatible with the reaction conditions abovementioned can be protected (as carbamates or THP/silyl/tert-butyl ethers respectively) before performing said reaction and deprotected after performing said reaction, yielding compounds of formula I wherein $R^1$ is $PO_3H_2$; or ii) reacting a compound of formula I wherein $R^1$ is H and M is as defined in formula I with a compound of formula IV

$HO(O)CR^2$      IV wherein $R^2$ is as defined in formula I, the reaction being performed using general reaction technique 2 (this reaction sequence can also be performed with racemic compound of formula I wherein $R^1$ is H and the (R)-enantiomer can then be obtained by chiral HPLC separation of the reaction product), whereby functional groups (e.g. amino or hydroxy) present on M that would be incompatible with the abovementioned reaction conditions can be protected (as carbamates or THP/silyl/tert-butyl ethers respectively) before performing said reaction and deprotected after performing said reaction, yielding compounds of formula I wherein $R^1$ is $C(O)R^2$; or iii) reacting a compound of formula I wherein $R^1$ is H and M is as defined in formula I with a compound of formula V $X^a-(CH_2)-O-P(O)(OPG^4)_2$      V wherein $X^a$ represents iodine, bromine or chlorine and $PG^4$ is as defined in formula III, the reaction being performed in the presence of a mineral base such as NaH or $K_2CO_3$ or in the presence of an organic base such as TEA or DIPEA in a solvent such as THF at a temperature ranging between -50° C. and rt and subsequent cleavage of $PG^4$ being performed using general reaction technique 1 (this reaction sequence can also be performed with racemic compound of formula I wherein $R^1$ is H and the (R)-enantiomer can then be obtained by chiral HPLC separation of the reaction products), whereby functional groups (e.g. amino or hydroxy) present on M that would be incompatible with the abovementioned reaction conditions can be protected (as carbamates or THP/silyl/tert-butyl ethers respectively) before performing said reaction and deprotected after performing said reaction, yielding compounds of formula I wherein $R^1$ is $CH_2-O-PO_3H_2$; or iv) reacting a compound of formula I wherein $R^1$ is H and M is as defined in formula I with $Pyr.SO_3$ complex or $Me_2NCHO.SO_3$ complex in a solvent such as DMF or Pyr (this reaction sequence can also be performed with racemic compound of formula I wherein $R^1$ is H and the (R)-enantiomer can then be obtained by chiral HPLC separation of the reaction product), whereby functional groups (e.g. amino or hydroxy) present on M that would be incompatible with the abovementioned reaction conditions can be protected (as carbamates or THP/silyl/tert-butyl ethers respectively) before performing said reaction and deprotected after performing said reaction, yielding compounds of formula I wherein $R^1$ is $SO_3H$.

If desired, the compounds of formula I thus obtained may be converted into their salts, and notably into their pharmaceutically acceptable salts using standard methods.

Besides, whenever the compounds of formula I are obtained in the form of mixtures of enantiomers, the enantiomers can be separated using methods known to one skilled in the art, e.g. by formation and separation of diastereomeric salts or by HPLC over a chiral stationary phase such as a Regis Whelk-O1(R,R) (10 µm) column, a Daicel ChiralCel OD-H (5-10 µm) column, or a Daicel ChiralPak IA (10 µm) or AD-H (5 µm) column. Typical conditions of chiral HPLC are an isocratic mixture of eluent A (EtOH, in the presence or absence of an amine such as TEA or diethylamine) and eluent B (Hex), at a flow rate of 0.8 to 150 mL/min.

Preparation of the Compounds of Formula II:

The compounds of formula II can be obtained by:

a) reacting a compound of formula VI

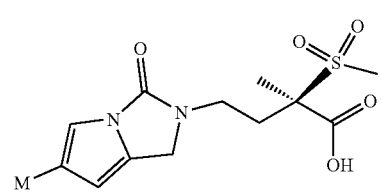

VI

wherein M is as defined in formula I with a compound of formula VII

$H_2N-OPG$      VII wherein PG has the same meaning as in formula II using general reaction technique 2 (this reaction sequence can also be performed with racemic compound of formula VI and the (R)-enantiomer can then be obtained by chiral HPLC separation of the reaction products), whereby functional groups (e.g. amino or hydroxy) present on M that would be incompatible with the coupling conditions mentioned in general reaction technique 2 can be protected (as carbamates or THP/silyl ethers respectively) before performing said reaction and deprotected after performing said reaction; or b) reacting a compound of formula VIII

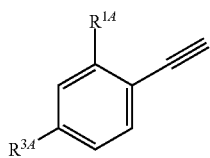
VIII wherein $R^{1A}$ and $R^{3A}$ have the same respective meanings as in formula I, with a compound of formula IX

IX wherein $X^b$ represents iodine, using general reaction technique 3 (this reaction can also be performed with racemic compound of formula IX and the (R)-enantiomer can then be obtained by chiral HPLC separation of the reaction products); or c) reacting a compound of formula X

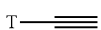
X wherein $R^{1A}$ and $R^{3A}$ have the same respective meanings as in formula I and $X^c$ represents iodine or bromine (and preferably iodine), with a compound of formula IXa

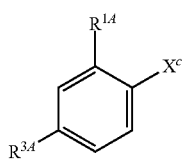
IXa wherein $X^b$ represents ethynyl and PG has the same meaning as in formula II, using general reaction technique 3 (this reaction can also be performed with racemic compound of formula IXa and the (R)-enantiomer can then be obtained by chiral HPLC separation of the reaction products); or d) reacting a compound of formula XI $$T\!\!-\!\!\equiv\!\!-\!\!X^d \qquad XI$$

wherein T represents $R^{1B}$ and $X^d$ represents iodine or bromine, with a compound of formula IXa as defined in section c) above, using general reaction technique 3 (this reaction can also be performed with racemic compound of formula IXa and the (R)-enantiomer can then be obtained by chiral HPLC separation of the reaction products); or e) reacting a compound of formula XII $$T\!\!-\!\!\equiv \qquad XII$$

wherein T represents $R^{3C}$, with a compound of formula XIII

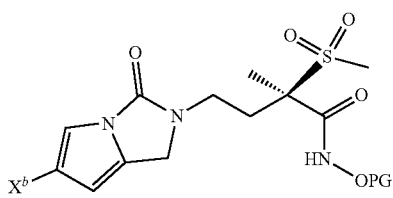
XIII wherein $X^e$ represents halogen or triflate, $R^{1C}$ is as defined in formula I and PG has the same meaning as in formula II using general reaction technique 3 (this reaction can also be performed with racemic compound of formula XIII and the (R)-enantiomer can then be obtained by chiral HPLC separation of the reaction products).

Preparation of the Synthesis Intermediates of Formulae VI, VII, VIII, IX, IXa, X, XI, XII, and XIII:

Compounds of Formula VI:

The compounds of formula VI can be prepared as summarised in Scheme 1 hereafter.

Scheme 1

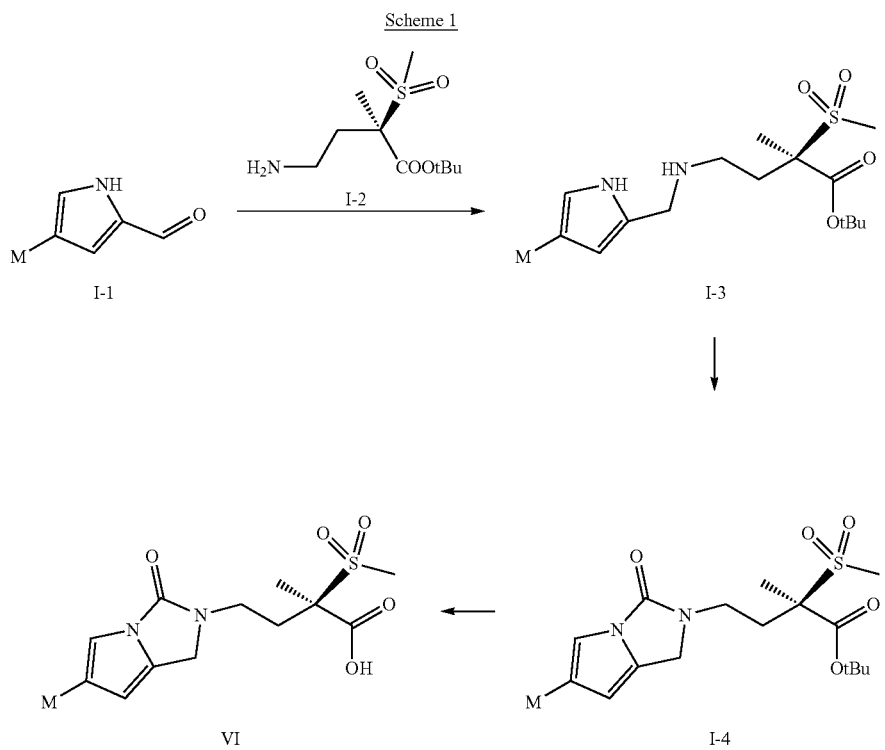

In Scheme 1, M is as defined in formula I.

The derivatives of formula I-3 can be obtained (Scheme 1) by reaction of the pyrrole aldehydes of formula I-1 with the amine of formula I-2 using general reaction technique 6.

The derivatives of formula I-4 can be obtained from the derivatives of formula I-3 by treatment with CDI in a solvent such as THF in the presence of a base such as NaH; this reaction can be performed at a temperature ranging from 0 to 50° C., and ideally at rt. The compounds of formula I-4 can be transformed into the compounds of formula VI using general reaction technique 4. These reactions can also be performed with racemic material and the (R)-enantiomer can be obtained by chiral HPLC separation at any step when suitable.

The compounds of formula VI can also be prepared as summarised in Scheme 1a hereafter.

Scheme 1a

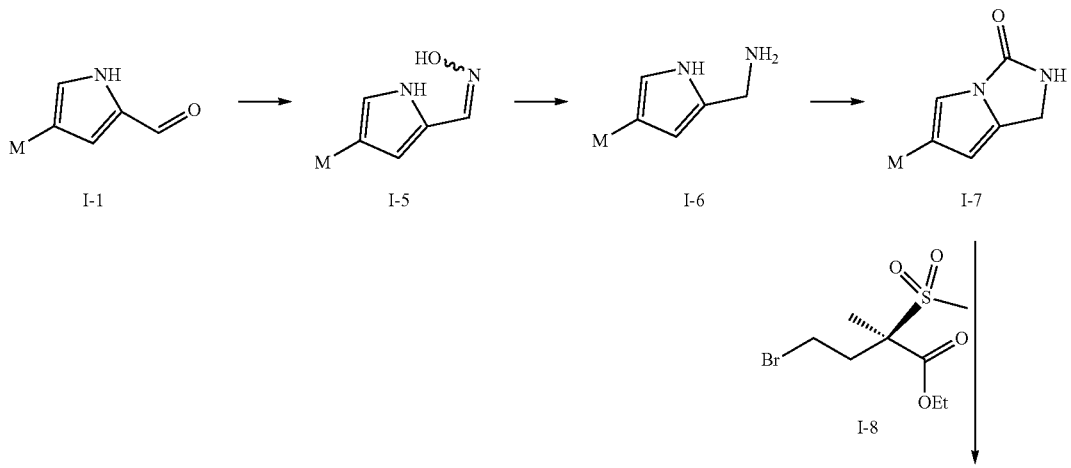

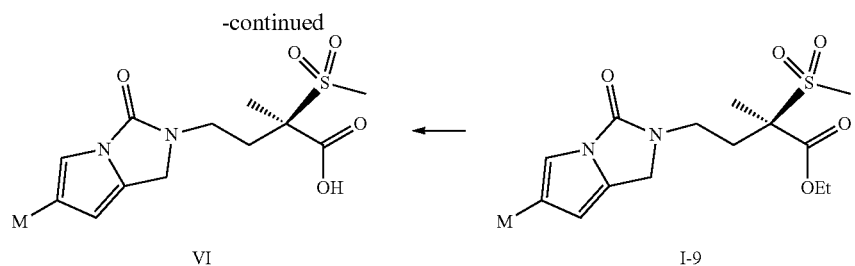

In Scheme 1a, M is as defined in formula I.

The oxime derivatives of formula I-5 can be obtained (Scheme 1a) by reaction of the pyrrole aldehydes of formula I-1 with hydroxylamine in AcOH in the presence of NaOAc. The oxime derivatives of formula I-5 can be reduced into the amine derivatives of formula I-6 by treatment with Zn in a solvent such as AcOH. The derivatives of formula I-7 can be obtained from the derivatives of formula I-6 by treatment with CDI in a solvent such as THF in the presence of a base such as NaH. This reaction can be performed at a temperature ranging from 0 to 50° C., and ideally at rt. The compounds of formula I-7 can be transformed into the compounds of formula I-9 by treatment with the bromide of formula I-8 in the presence of a base such as NaH and in a solvent such as THF or DMF. The compounds of formula I-9 can then be transformed into the compounds of formula VI using general reaction technique 4.

Compounds of Formula VII:

The compounds of formula VII are commercially available (PG=THP, tBu, COOtBu or allyl) or can be prepared according to WO 2010/060785 (PG=(2-methylpropoxy)ethyl) or Marmer and Maerker, *J. Org. Chem.* (1972), 37, 3520-3523 (PG=COtBu).

Compounds of Formula VIII:

The compounds of formula VIII can be obtained as summarised in Scheme 2 hereafter.

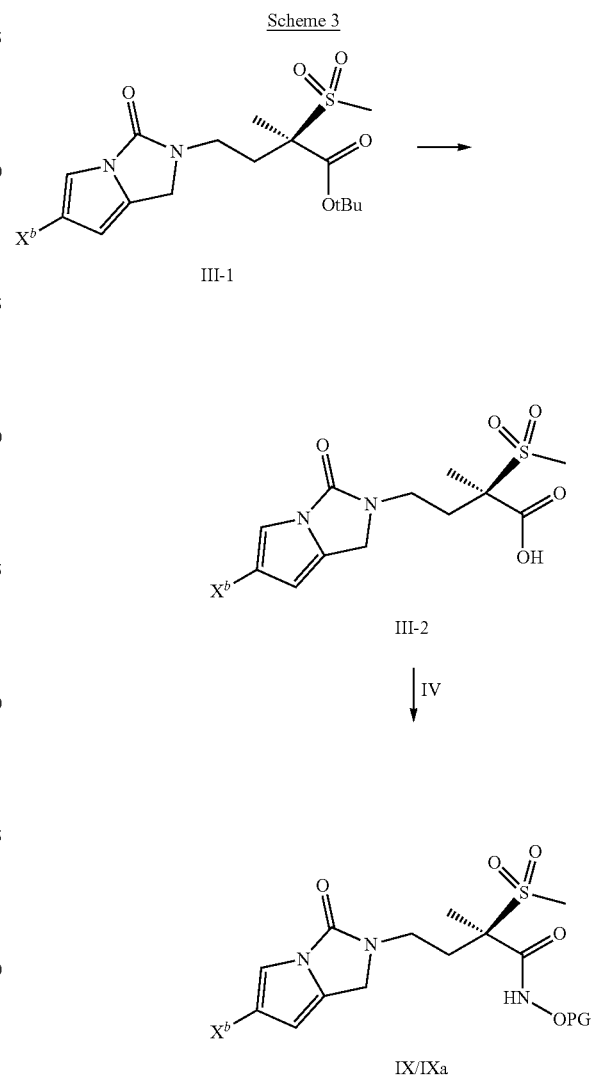

In Scheme 2, $R^{1A}$ and $R^{3A}$ have the same respective meanings as in formula I.

The compounds of formula X wherein $X^c$ represents iodine can be reacted (Scheme 3) with trimethylsilylacetylene (II-1) using general reaction technique 3 followed by treatment with TBAF in THF, affording the derivatives of formula VIII.

Compounds of Formulae IX and IXa:

The compounds of formulae IX and IXa can be prepared as summarised in Scheme 3 hereafter.

In Scheme 3, $X^b$ represents halogen or ethynyl.

The derivatives of formula III-1 can be transformed (Scheme 2) into the carboxylic acid derivatives of formula III-2 using general reaction technique 4 and further reacted with the compounds of formula IV using general reaction technique 2, thus affording the compounds of formula IX ($X^b$=halogen) or IXa ($X^b$=ethynyl). The reactions can also be performed with racemic material and the (R)-enantiomer can be obtained by chiral HPLC separation at any step when suitable.

Alternatively, the compounds of formula III-2 can be prepared as summarised in Scheme 3a hereafter.

Scheme 3a

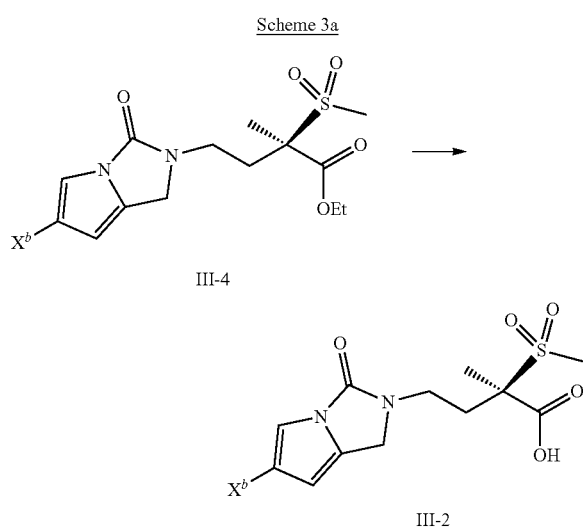

In Scheme 3a, $X^b$ represents iodine or ethynyl.

compounds of formula X wherein $X^c$ represents iodine can be obtained from the corresponding bromine derivatives by reaction with NaI in the presence of a copper (I) salt and a ligand such as trans-N,N'-dimethylcyclohexa-1,2-diamine in a solvent such as dioxane at a temperature ranging between rt and 100° C., or in a microwave oven at about 150° C.

Compounds of Formula XI:

The compounds of formula XI wherein $X^d$ represents iodine can be prepared by iodination of the compounds of formula XII with iodine in the presence of an inorganic base such as KOH. The compounds of formula XI wherein $X^d$ represents bromine can be prepared from the compounds of formula XII by treatment with NBS in the presence of $AgNO_3$ in a solvent such as acetone or MeCN.

Compounds of Formula XII:

The compounds of formula XII are commercially available or can be prepared by standard methods known to one skilled in the art.

Compounds of Formula XIII:

The compounds of formula XIII can be prepared as summarised in Scheme 4 hereafter.

Scheme 4

The derivatives of formula II-4 can be transformed (Scheme 2a) into the carboxylic acid derivatives of formula II-2 using general reaction technique 4. The reaction can also be performed with racemic material and the (R)-enantiomer can then be obtained by chiral HPLC separation.

Compounds of Formula X:

The compounds of formula X wherein $X^c$ represents bromine are commercially available or can be prepared by standard methods known to one skilled in the art. The In Scheme 4, $R^{1C}$ has the same meaning as in formula I, $X^b$ represents bromine and $X^e$ represents iodine, hydroxy or —OTf.

The derivatives of formula IX wherein $X^b$=Br can be transformed to the compounds of formula XIII using a boron compound of formula IV-1 wherein $X^e$ represents either iodine of hydroxy, and applying general reaction technique 5. The compounds of formula XIII wherein $X^e$ is Tf can be obtained from the compounds of formula XIII wherein $X^e$ is hydroxy by treatment with Tf$_2$O in presence of a base such as pyridine or 2,6-lutidine in a solvent such as DCM or pyridine between −30° C. and 50° C. The reactions can also be performed with racemic material and the (R)-enantiomer can be obtained by chiral HPLC separation when suitable.

Other Synthesis Intermediates and Starting Materials:

The compounds of formula I-1 are commercially available or can be prepared by standard methods known to one skilled in the art.

The compound of formula I-2 can be prepared in analogy to the methods described in the section entitled "EXAMPLES" hereafter (see Preparations A and B), or by standard methods known to one skilled in the art.

The compounds of formula III-1 wherein $X^b$ represents iodine or ethynyl can be prepared as summarised in Scheme 5 hereafter.

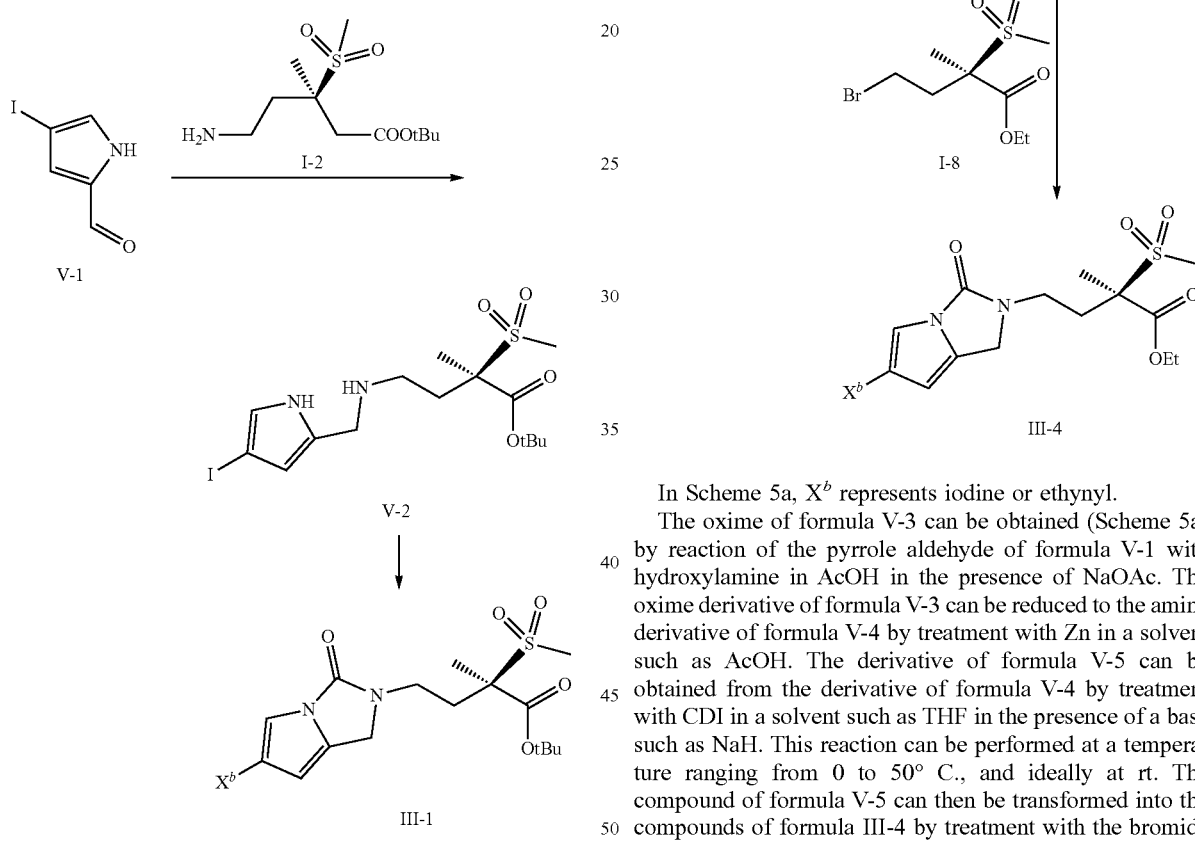

In Scheme 5, $X^b$ represents iodine or ethynyl.

The derivative of formula V-2 can be obtained (Scheme 5) by reaction of the pyrrole aldehyde of formula V-1 with the amine of formula I-2 using general reaction technique 6. The derivative of formula III-1 can then be obtained from the derivatives of formula V-2 by treatment with CDI in the presence of a base such as NaH in a solvent such as THF; this reaction can be performed at a temperature ranging from 0° C. to 50° C., and ideally at rt.

The compound of formula III-1 wherein $X^b$ is iodine can be transformed to the derivative of formula III-1 wherein $X^b$ is ethynyl using the protocol described for the formation of the compounds of formula VIII.

The compounds of formula III-4 wherein $X^b$ represents iodine or ethynyl can be prepared as summarised in Scheme 5a hereafter.

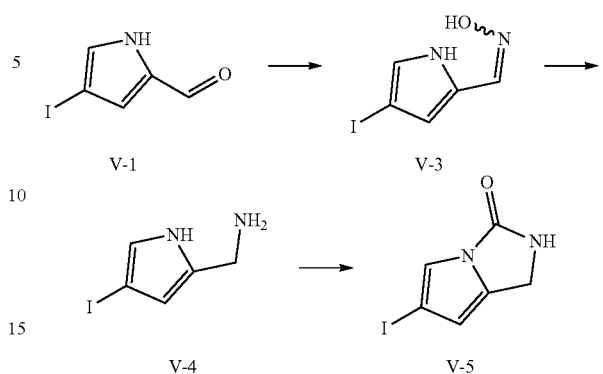

In Scheme 5a, $X^b$ represents iodine or ethynyl.

The oxime of formula V-3 can be obtained (Scheme 5a) by reaction of the pyrrole aldehyde of formula V-1 with hydroxylamine in AcOH in the presence of NaOAc. The oxime derivative of formula V-3 can be reduced to the amine derivative of formula V-4 by treatment with Zn in a solvent such as AcOH. The derivative of formula V-5 can be obtained from the derivative of formula V-4 by treatment with CDI in a solvent such as THF in the presence of a base such as NaH. This reaction can be performed at a temperature ranging from 0 to 50° C., and ideally at rt. The compound of formula V-5 can then be transformed into the compounds of formula III-4 by treatment with the bromide of formula I-8 in the presence of a base such as NaH and in a solvent such as THF or DMF. The compound of formula III-4 wherein $X^b$ is iodine can be transformed to the derivative of formula III-4 wherein $X^b$ is ethynyl using the protocol described for the formation of the compounds of formula VIII.

The compounds of formula IV-1 wherein $D^1$ and $D^2$ each represent H or (C$_1$-C$_2$)alkyl are commercially available or can be prepared according to Sleveland et al., *Organic Process Research & Development* (2012), 16, 1121-1130 starting from tri((C$_1$-C$_2$)alkyl)borate and the corresponding commercially available bromo derivatives (optionally followed by acidic hydrolysis). The compounds of formula IV-1 wherein $D^1$ and $D^2$ together represent CH$_2$C(Me)$_2$CH$_2$ or C(Me)$_2$C(Me)$_2$ are commercially available or can be prepared according to WO 2012/093809, starting from bis(pinacolato)diborane or 5,5-dimethyl-1,3,2-dioxaborinane (both commercially available) with the corresponding commercially available bromo derivatives.

The compound of formula V-1 is commercially available or can be prepared by standard methods known to one skilled in the art.

Particular embodiments of the invention are described in the following Examples, which serve to illustrate the invention in more detail without limiting its scope in any way.

EXAMPLES

All temperatures are stated in ° C. Unless otherwise indicated, the reactions take place at rt. The combined org. layers resulting from the workup of an aq. layer are, unless otherwise indicated, washed with a minimal volume of brine, dried over $MgSO_4$, filtered and evaporated to dryness to provide a so-called evaporation residue.

Analytical TLC characterisations were performed with 0.2 mm plates: Merck, Silica gel 60 $F_{254}$. Elution is performed with EA, Hept, DCM, MeOH or mixtures thereof. Detection was done with UV or with a solution of $KMnO_4$ (3 g), $K_2CO_3$ (20 g), 5% NaOH (3 mL) and $H_2O$ (300 mL) with subsequent heating.

CCs were performed using Brunschwig 60A silica gel (0.032-0.63 mm) or using an ISCO CombiFlash system and prepacked $SiO_2$ cartridges, elution being carried out with either Hept-EA or DCM-MeOH mixtures with an appropriate gradient. When the compounds contained an acid function, 1% of AcOH was added to the eluent(s). When the compounds contained a basic function, 25% aq. $NH_4OH$ was added to the eluents.

The compounds were characterized by $^1$H-NMR (300 MHz, Varian Oxford; 400 MHz, Bruker Avance 400 or 500 MHz, Bruker Avance 500 Cryoprobe). Chemical shifts δ are given in ppm relative to the solvent used; multiplicities: s=singlet, d=doublet, t=triplet, q=quartet, p=pentet, hex=hexet, hep=heptet, m=multiplet, br.=broad; coupling constants J are given in Hz. Alternatively compounds were characterized by LC-MS (Sciex API 2000 with Agilent 1100 Binary Pump with DAD and ELSD or an Agilent quadrupole MS 6140 with Agilent 1200 Binary Pump, DAD and ELSD); by TLC (TLC plates from Merck, Silica gel 60 $F_{254}$); or by melting point.

The analytical LC-MS data have been obtained using the following respective conditions:
  Column: Zorbax SB-Aq, 30.5 µm, 4.6×50 mm;
  Injection volume: 1 µL;
  Column oven temperature: 40° C.;
  Detection: UV 210 nm, ELSD and MS;
  MS ionization mode: ESI+;
  Eluents: A: $H_2O$+0.04% TFA; and B: MeCN;
  Flow rate: 40.5 mL/min;
  Gradient: 5% B to 95% B (0.0 min-1.0 min), 95% B (1.0 min-1.45 min).

The number of decimals given for the corresponding [M+H$^+$] peak(s) of each tested compound depends upon the accuracy of the LC-MS device actually used.

The prep-HPLC purifications were performed on a Gilson HPLC system, equipped with a Gilson 215 autosampler, Gilson 333/334 pumps, Dionex MSQ Plus detector system, and a Dionex UVD340U (or Dionex DAD-3000) UV detector, using the following respective conditions:
  Method 1:
    Column: Waters XBridge C18, 10 µm, 30×75 mm;
    Flow rate: 75 mL/min;
    Eluents: A: $H_2O$+0.5% $NH_4OH$ solution (25%); B: MeCN;
    Gradient: 90% A to 5% A (0.0 min-4.0 min), 5% A (4.0 min-6.0 min).
  Method 2:
    Column: Waters Atlantis T3 OBD, 10 µm, 30×75 mm;
    Flow rate: 75 mL/min;
    Eluents: A: $H_2O$+0.1% HCOOH; B: MeCN+0.1% HCOOH;
    Gradient: 90% A to 5% A (0.0 min-4.0 min), 5% A (4.0 min-6.0 min).
  Method 3:
    Column: Waters XBridge C18, 10 µm, 30×75 mm;
    Flow rate: 75 mL/min;
    Eluents: A: $H_2O$+0.5% HCOOH; B: MeCN;
    Gradient: 90% A to 5% A (0.0 min-4.0 min), 5% A (4.0 min-6.0 min).

Besides, semi-preparative chiral HPLCs were performed using the conditions herafter.

Semi-Preparative Chiral HPLC Method A:

The semi-preparative chiral HPLC is performed on a Daicel ChiralPak ASV column (250×110 mm, 20 µm) using the eluent mixture, flow rate and detection conditions indicated between brackets in the corresponding experimental protocol. The retention times are obtained by elution of analytical samples on a Daicel ChiralPak AS-H column (250×4.6 mm, 5 µm) using the same eluent mixture with the flow rate indicated between brackets in the corresponding experimental protocol.

Semi-Preparative Chiral HPLC Method B:

The semi-preparative chiral HPLC is performed on a Daicel ChiralPak IA column (20×250 mm; 5 µm) using the eluent mixture, flow rate and detection conditions indicated between brackets in the corresponding experimental protocol. The retention times are obtained by elution of analytical samples on a Daicel ChiralPak IA column (4.6×250 mm; 5 µm) using the same eluent mixture with the flow rate indicated between brackets in the corresponding experimental protocol.

Semi-Preparative Chiral HPLC Method C:

The semi-preparative chiral HPLC is performed on a Daicel ChiralPak AD-H column (30×250 mm, 5 µm) using the eluent mixture, flow rate and detection conditions indicated between brackets in the corresponding experimental protocol. The retention times are obtained by elution of analytical samples on a Daicel ChiralPak AD-H column (4.6×250 mm, 5 µm) using the same eluent mixture with the flow rate indicated between brackets in the corresponding experimental protocol.

Semi-Preparative Chiral HPLC Method D:

The semi-preparative chiral HPLC is performed on a Daicel ChiralPak AY-H column (20×250 mm, 5 µm) using the eluent mixture, flow rate and detection conditions indicated between brackets in the corresponding experimental protocol. The retention times are obtained by elution of analytical samples on a Daicel ChiralPak AY-H column (4.6×250 mm, 5 µm) using the same eluent mixture with the flow rate indicated between brackets in the corresponding experimental protocol.

Semi-Preparative Chiral HPLC Method E:

The semi-preparative chiral HPLC is performed on a Daicel ChiralPak IE column (20×250 mm, 5 µm) using the eluent mixture, flow rate and detection conditions indicated between brackets in the corresponding experimental protocol. The retention times are obtained by elution of analytical samples on a Daicel ChiralPak AD-H column (4.6×250 mm, 5 µm) using the same eluent mixture with the flow rate indicated between brackets in the corresponding experimental protocol.

Procedures:
Procedure A:

CuI (0.2 mmol), PdCl$_2$(PPh$_3$)$_2$(0.1 mmol), the terminal alkyne derivative (1 mmol) and the iodo derivative (1.2 mmol) are introduced in a two necked round flask. The atmosphere is flushed with nitrogen during 30 min, then degassed THF (5 mL) and degassed TEA (2.5 mmol) are added. The suspension is stirred under nitrogen atmosphere at 50° C. for 45 min. After concentration to dryness, the residue is then purified by CC (Hept-EA).

Procedure B

To a solution of the THP-protected hydroxamic acid derivative (0.15 mmol) in MeOH (1.2 mL) and water (0.4 mL) is added 2M aq. HCl (0.6 mL; 1.2 mmol). The reaction mixture is stirred at rt until completion. The reaction mixture, after neutralization with sat. aq. NaHCO$_3$ is extracted with DCM-MeOH (9-1, 3×20 mL). The evaporation residue is then purified by CC (DCM-MeOH) or by prep-HPLC using a suitable method.

Procedure C:

To the THP-protected hydroxamic acid derivative (0.02 mmol) in EtOH (3 mL) is added PPTS (0.025 g; 0.03 mmol). The mixture is stirred at 80° C. for 2 h, cooled to rt and directly purified by CC (DCM-MeOH) or by prep-HPLC using a suitable method.

Procedure D:

A solution of the THP-protected hydroxamic acid derivative (0.070 g, 0.119 mmol) in 4M HCl in dioxane (1 mL) was stirred 10 min at rt. The mixture was directly purified by prep-HPLC using a suitable method.

Procedure E:

CuCl (0.0117 g, 0.118 mmol) and NH$_2$OH.HCl (0.0833 g, 1.2 mmol) are dissolved in BuNH$_2$ (30% in water, 0.75 mL). The terminal alkyne (0.250 g; 0.59 mmol) and BuNH$_2$ (0.288 mL, 2.32 mmol) is added. The reaction mixture is ice-chilled and halo-alkyne (0.157 g; 0.768 mmol) in dioxane (0.1 mL) is added at 0° C. The reaction proceeds 1 h at that temperature. The reaction mixture is then allowed to warm up to rt over 1 h. Water (5 mL) and EA (30 mL) are added and two phases are separated. The aq. layer is extracted with EA (10 mL). The evaporation residue is then purified by CC or by prep-HPLC using a suitable method to afford the bis-alkyne product.

Procedure F:

A mixture of alkyne (0.236 mmol), iodoalkyne (0.26 mmol), CuI (0.0472 mmol) and PdCl$_2$(PPh$_3$)$_2$(0.0236 mmol) in degassed THF (1.6 mL) and TEA (0.826 mmol) is stirred at 40° C. for 40 min. The reaction mixture is concentrated in vacuo and the residue is purified by CC using a suitable eluent or by prep-HPLC using a suitable method to afford the bis-alkyne product.

PREPARATIONS

Preparation A: (2RS)-tert-butyl 4-amino-2-methyl-2-(methylsulfonyl)butanoate

A.i. (2RS)-tert-butyl 2-(methylsulfonyl)propanoate

To a suspension of sodium methanesulfinate (100 g; 929 mmol) in tBuOH (350 mL) was added tert-butyl 2-bromopropionate (150 mL; 877 mmol). The reaction mixture was stirred at 90° C. for 24 h under nitrogen atmosphere, then cooled to rt and concentrated to dryness. The residue was partitioned between water (750 mL) and EA (600 mL). The aq. layer was extracted with EA (2×500 mL). The evaporation residue afforded the title compound as a yellowish solid (175 g, 96% yield).

$^1$H NMR (d6-DMSO) δ: 4.24 (q, J=7.2 Hz, 1H); 3.11 (s, 3H); 1.45 (s, 9H); 1.40 (d, J=7.2 Hz, 3H).

A.ii. (2RS)-tert-butyl 4-bromo-2-methyl-2-(methylsulfonyl)butanoate

To an ice-chilled suspension of intermediate A.i (130 g; 626 mmol) in DMF (750 mL) was added portionwise NaH (60% in mineral oil; 32.1 g; 802 mmol) over 1.5 h, keeping IT below 7° C. The mixture was stirred at 0° C. for 1.5 h, allowed to reach rt and stirred at rt for 0.5 h. The mixture was cooled down to 12° C. with an ice bath and 1,2-dibromoethane (166 mL; 1.9 mol) was then added dropwise, keeping IT below 22° C. The reaction mixture was stirred at rt for 2 h. The mixture was poured into cold water (1 L) and Et$_2$O (1 L) and the aq. layer was extracted with Et$_2$O (2×750 mL). The org. layer was washed with cold water (2×500 mL). The evaporation residue was purified by CC (Hept-EA) to afford the title compound as a pale yellowish oil (116.8 g; 59% yield).

$^1$H NMR (d$_6$-DMSO) δ: 3.71-3.63 (m, 1H); 3.45-3.37 (m, 1H); 3.12 (s, 3H); 2.72-2.62 (m, 1H); 2.43-2.33 (m, 1H); 1.49 (s, 3H); 1.46 (s, 9H).

A.iii. (2RS)-tert-butyl 4-azido-2-methyl-2-(methylsulfonyl)butanoate

To a solution of intermediate A.ii (70.3 g; 223 mmol) in DMF (400 mL) was added NaN$_3$ (54.6 g; 831 mmol). The reaction mixture was stirred at 80° C. overnight, before being cooled to rt. Water (500 mL) and EA (500 mL) were added. The aq. layer was extracted with EA (2×500 mL) and the org. layer was washed with water (2×500 mL). The evaporation residue was triturated in Hept, filtered and washed with Hept to afford the title compound as a white solid (59.6 g; 96% yield).

$^1$H NMR (d6-DMSO) δ: 3.66-3.60 (m, 1H); 3.35-3.29 (overlapped m, 1H); 3.11 (s, 3H); 2.49-2.43 (m, 1H); 2.04-1.96 (m, 1H); 1.46 (s, 9H); 1.44 (s, 3H).

MS (ESI, m/z): 278.95 [M+H$^+$] for C$_{10}$H$_{19}$N$_3$O$_4$S; t$_R$=0.80 min.

A.iv. (2RS)-tert-butyl 4-amino-2-methyl-2-(methylsulfonyl)butanoate

A solution of intermediate A.iii (45 g; 162 mmol) in a mixture of tBuOH-EA (1-1, 900 mL) was treated with 10% Pd/C (2.3 g). The suspension was stirred at rt under hydrogen for 4 h. Then 10% Pd/C (0.5 g) was added to the suspension and the reaction was stirred under hydrogen for 2 days. The catalyst was filtered off and the filtrate concentrated to dryness to afford the crude material which crystallized on standing (grey solid; 40.6 g; 99% yield).

$^1$H NMR (d6-DMSO) δ: 3.06 (s, 3H); 2.75-2.63 (m, 1H); 2.53-2.40 (overlapped m, 1H); 2.28-2.16 (m, 1H); 1.85-1.74 (m, 1H); 1.44 (s, 9H); 1.40 (s, 3H).

MS (ESI, m/z): 252.03 [M+H$^+$] for C$_{10}$H$_{21}$NO$_4$S; t$_R$=0.45 min.

Preparation B: (2R)-tert-butyl 4-amino-2-methyl-2-(methylsulfonyl)butanoate

B.i. (2R)-tert-butyl 4-azido-2-methyl-2-(methylsulfonyl)butanoate

Intermediate A.iii (184 g) was separated by semi-preparative chiral HPLC Method A (Hept-iPrOH 4-1; flow rate: 570 mL/min; UV detection at 235 nm); the respective retention times were 8.3 and 10.7 min. The title (R)-enantiomer, identified as the second eluting compound, was obtained as a light orange oil (90.7 g).

$^1$H NMR (d$_6$-DMSO) δ: 3.66-3.60 (m, 1H); 3.35-3.29 (overlapped m, 1H); 3.11 (s, 3H); 2.50-2.43 (overlapped m, 1H); 2.04-1.97 (m, 1H); 1.46 (s, 9H); 1.44 (s, 3H).

B.ii. (2R)-tert-butyl 4-amino-2-methyl-2-(methylsulfonyl)butanoate

Starting from intermediate B.i (45 g; 162 mmol) and proceeding in analogy to Preparation A, step A.iv, the title compound was obtained as a grey solid (40.6 g; 99% yield).

$^1$H NMR (d$_6$-DMSO) δ: 3.06 (s, 3H); 2.75-2.63 (m, 11H); 2.53-2.40 (overlapped m, 1H); 2.28-2.16 (m, 1H); 1.85-1.74 (m, 1H); 1.44 (s, 9H); 1.40 (s, 3H).

MS (ESI, m/z): 252.03 [M+H$^+$] for C$_{10}$H$_{21}$NO$_4$S; t$_R$=0.45 min.

Preparation C: tert-butyl (2R)-4-(6-iodo-3-oxo-1H-pyrrolo[1,2-c]imidazol-2(3H)-yl)-2-methyl-2-(methylsulfonyl)butanoate First Method C.i. (2RS)-tert-butyl 4-(((4-iodo-1H-pyrrol-2-yl)methyl)amino)-2-methyl-2-(methylsulfonyl)butanoate To a solution of the compound of Preparation A (24.631 g; 98 mmol) in dry THF (470 mL) was added 4-iodo-1H-pyrrole-2-carbaldhehyde (20.625 g; 93.3 mmol, commercial). The reaction mixture was stirred 2 h. MeOH (144 mL) was added and the resulting mixture was cooled to −20° C. NaBH$_4$ (3.578 g, 94.6 mmol) was added portionwise. Once the addition completed, the reaction proceeded at 0° C. for 1 h. Ice-water (330 mL) was added portionwise, keeping IT below 10° C. DCM (600 mL) was added. The two layers were separated and the the aq. layer was extracted twice with DCM (2×250 mL). The combined org. layers were washed with sat. aq. NaHCO$_3$ (300 mL). The evaporation residue was further co-evaporated twice with toluene (2×150 mL) to afford, after drying under high vacuum, of the crude title product as a brown oil (43.87 g; >95% yield).

$^1$H NMR (d$_6$-DMSO) δ: 10.88 (br. s, 1H); 6.77 (s, 1H); 5.97 (s, 1H); 3.63-3.49 (m, 2H); 3.06 (s, 3H); 2.60-2.55 (overlapped m, 1H); 2.42-2.34 (m, 1H); 2.32-2.24 (m, 1H); 2.05-1.95 (overlapped, m, 1H); 1.84-1.76 (m, 1H); 1.40 (s, 9H); 1.38 (s, 3H).

MS (ESI, m/z): 456.67 [M+H$^+$] for C$_{15}$H$_{25}$N$_2$O$_4$IS; t$_R$=0.63 min.

C.ii. (2RS)-tert-butyl 4-(6-bromo-3-oxo-1H-pyrrolo[1,2-c]imidazol-2(3H)-yl)-2-methyl-2-(methylsulfonyl)butanoate To a solution of intermediate C.i (60.88 g; 124 mmol) in dry THF (329 mL) was added, at 0° C., CDI (21.12 g; 130 mmol). The reaction mixture was then stirred at rt for 3 h. After cooling to 0° C., NaH (60% dispersion in oil, 0.758 g; 17.4 mmol) was added portionwise. After 2 h stirring, a second portion of NaH (60% dispersion in oil, 0.758 g; 17.4 mmol) was added. The reaction proceeded 2 h and sat. aq. NH$_4$Cl (300 mL) was carefully added. The mixture was further diluted with water (200 mL) and EA (1 L). The two phases were separated and the aq. phase was extracted twice with EA (2×500 mL). The evaporation residue was purified by CC (DCM-EA) to afford the title compound as a white solid (40.2 g, 67% yield).

$^1$H NMR (CDCl$_3$) δ: 7.20 (d, J=0.9 Hz, 1H); 6.16 (q, J=1.4 Hz, 1H); 4.43 (m, 1H); 4.29 (m, 1H); 3.80 (m, 1H); 3.57 (m, 1H); 3.05 (s, 3H); 2.58 (m, 1H); 2.18 (m, 1H); 1.71 (s, 3H); 1.43 (s, 9H).

MS (ESI, m/z): 482.85 [M+H$^+$] for C$_{16}$H$_{23}$N$_2$O$_5$IS; t$_R$=0.89 min.

C.iii. Tert-butyl (2R)-4-(6-iodo-3-oxo-1H-pyrrolo[1,2-c]imidazol-2(3H)-yl)-2-methyl-2-(methylsulfonyl)butanoate Intermediate C.ii (22.8 g) was separated by semi-preparative chiral HPLC Method B (MeOH-EtOH 1-1; flow rate: 100 mL/min; UV detection at 243 nM); the respective retention times were 6.2 and 6.8 min. The title (R)-enantiomer, identified as the second eluting compound, was obtained as a white solid (9.5 g).

$^1$H NMR (CDCl$_3$) δ: 7.20 (d, J=0.9 Hz, 1H); 6.16 (q, J=1.4 Hz, 1H); 4.43 (m, 1H); 4.29 (m, 1H); 3.80 (m, 1H); 3.57 (m, 1H); 3.05 (s, 3H); 2.58 (m, 1H); 2.18 (m, 1H); 1.71 (s, 3H); 1.43 (s, 9H).

MS (ESI, m/z): 482.85 [M+H$^+$] for C$_{16}$H$_{23}$N$_2$O$_5$IS; t$_R$=0.89 min.

Second Method

Alternatively, starting from the compound of Preparation B (3.8 g; 15 mmol) and 4-iodo-1H-pyrrole-2-carbaldehyde (3.5 g; 15.8 mmol) and proceeding as described in steps C.i (55% yield) and C.ii (75% yield), the title compound was obtained as a white solid (3.15 g).

The product obtained by the SECOND METHOD had NMR data equivalent to those reported for the compound obtained by the FIRST METHOD.

Preparation D: (2R)-4-(6-ethynyl-3-oxo-1H-pyrrolo[1,2-c]imidazol-2(3H)-yl)-2-methyl-2-(methylsulfonyl)-N-((2RS)-(tetrahydro-2H-pyran-2-yl)oxy)butanamide D.i. (2R)-4-(6-iodo-3-oxo-1H-pyrrolo[1,2-c]imidazol-2(3H)-yl)-2-methyl-2-(methylsulfonyl)butanoic Acid To an ice-chilled solution of the compound of Preparation C (40 g; 85.2 mmol) in DCM (238 mL) was added Et$_3$SiH (14.6 mL; 91.4 mmol) and TFA (182 mL, 2.3 mol) over 15 min. The resulting solution was stirred at rt for 5 h. The reaction mixture was cooled to 0° C. and dry Et$_2$O (450 mL) was added dropwise over 1 h. The resulting suspension was stirred 1 h, filtered and washed with Et$_2$O (3×100 mL). The solid was dried to afford the title compound as an off-white solid (33.56 g; 95% yield).

$^1$H NMR (d6-DMSO) δ: 13.81 (m, 1H); 7.32 (d, J=0.9 Hz, 1H); 6.23 (m, 1H); 4.47-4.35 (m, 2H); 3.59 (m, 1H); 3.53-3.40 (overlapped m, 1H); 3.12 (s, 3H); 2.59-2.48 (overlapped m, 1H); 2.04 (m, 1H); 1.53 (s, 3H).

MS (ESI, m/z): 426.9 [M+H$^+$] for C$_{12}$H$_{15}$N$_2$O$_5$IS; t$_R$=0.69 min.

D.ii. (2R)-4-(6-iodo-3-oxo-1H-pyrrolo[1,2-c]imidazol-2(3H)-yl)-2-methyl-2-(methylsulfonyl)-N-((2RS)-(tetrahydro-2H-pyran-2-yl)oxy)butanamide To a suspension of intermediate D.i (33.56 g; 78.7 mmol) in THF (380 mL) were added DIPEA (74 mL; 433 mmol)

and THPO-NH$_2$ (14.56 g; 118 mmol). The mixture was cooled down to 0° C. and T3P (50% in EA, 72 mL; 181 mmol) was added over 30 min. After 1 h at 0° C., DIPEA (12 mL; 70 mmol) and T3P (50% in EA, 30 mL, 75 mmol) were added. The reaction proceeded further 1 h and sat. aq. NaHCO$_3$ (200 mL) was added at 0° C. The mixture was diluted with water (100 mL) and EA (200 mL). The two layers were separated and the aq. layer was extracted with EA (200 mL). The evaporation residue was purified by CC (Hept-EA gradient) to afford the title compound as a white solid (32.46 g; 78% yield).

$^1$H NMR (d6-DMSO) (mixture of steroisomers) δ: 11.37 (m, 0.5H); 11.34 (m, 0.5H); 7.32 (d, J=7.9 Hz, 1H); 6.21 (dd, J=1.3, 3.0 Hz, 1H); 4.86 (s, 0.5H); 4.48-4.38 (m, 2.5H); 4.05-4.00 (m, 0.5H); 3.98-3.92 (m, 0.5H); 3.55-3.42 (overlapped m, 3H); 3.07 (s, 1.5H); 3.04 (s, 1.5H); 2.70-2.55 (overlapped m, 1H); 2.01-1.92 (m, 1H); 1.70-1.61 (m, 2H); 1.57-1.45 (m, 7H).

MS (ESI, m/z): 525.9 [M+H$^+$] for C$_{17}$H$_{24}$N$_3$O$_6$IS; t$_R$=0.78 min.

D.iii. (2R)-2-methyl-2-(methylsulfonyl)-4-(3-oxo-6-((trimethylsilyl)ethynyl)-1H-pyrrolo[1,2-c]imidazol-2(3H)-yl)-N-(((2RS)-tetrahydro-2H-pyran-2-yl)oxy)butanamide CuI (1.4 g; 7.29 mmol) and PdCl$_2$(PPh$_3$)$_2$(2.36 g; 3.5 mmol) were introduced in a two-necked round-bottom flask. After flushing with nitrogen for 30 min, a solution of intermediate D.ii (19.16 g; 36.5 mmol) in degassed THF (270 mL) was added, followed by trimethylsilylacetylene (7.8 mL, 54.7 mmol). Degassed TEA (15.3 mL, 109 mmol) was added and the reaction proceeded at 50° C. for 2 h. The mixture was concentrated to dryness and the residue was purified by CC (Hept-EA) to afford the title compound as a yellow foam (16.25 g, 90% yield).

$^1$H NMR (d$_6$-DMSO) δ (mixture of stereoisomers): 11.40-11.25 (m, 1H); 7.39-7.29 (m, 1H); 6.21-6.12 (m, 1H); 4.91-4.80 (m, 0.5H); 4.53-4.45 (m, 0.5H); 4.44-4.32 (m, 2H); 4.05-3.96 (m, 1H); 3.51-3.34 (m, 3H); 3.06 (s, 1.5H); 3.03 (s, 1.5H); 2.72-2.53 (m, 1H); 2.04-1.88 (m, 1H); 1.68-1.60 (overlapped m, 2H); 1.56 (s, 1.5H); 1.54 (s, 1.5H); 1.54-1.44 (overlapped m, 4H); 0.17 (s, 9H).

MS (ESI, m/z): 496.01 [M+H$^+$] for C$_{22}$H$_{33}$N$_3$O$_6$SSi; t$_R$=0.90 min.

D.iv. (2R)-4-(6-ethynyl-3-oxo-1H-pyrrolo[1,2-c]imidazol-2(3H)-yl)-2-methyl-2-(methylsulfonyl)-N-(((2RS)-tetrahydro-2H-pyran-2-yl)oxy)butanamide To a solution of intermediate D.iii (14.1 g; 28.5 mmol) in THF (62 mL) was added TBAF (1M in THF, 29.2 mL; 29.2 mmol). The mixture was stirred for 20 min. Cold water was added (100 mL) and the mixture was concentrated to a minimal volume. EA was added (100 mL) and the 2 phases were separated. The water phase was extracted with EA (3×100 mL). The evaporation residue was purified by CC (DCM-MeOH) to afford the title compound as a yellow foam (11.74 g; 97% yield).

$^1$H NMR (d$_6$-DMSO) δ (mixture of stereoisomers): 11.36-11.32 (br. s, 0.5H); 11.32-11.28 (br. s, 0.5H); 7.40-7.35 (m, 1H); 6.20-6.16 (m, 1H); 4.88-4.83 (m, 0.5H); 4.52-4.46 (m, 0.5H) 4.44-4.38 (m, 2H); 4.08-3.89 (overlapped m, 1H); 3.94 (s, 1H); 3.54-3.38 (m, 3H); 3.05 (s, 1.5H); 3.03 (s, 1.5H); 2.50-2.40 (overlapped m, 1H); 2.04-1.86 (m, 1H); 1.69-1.61 (m, 2H); 1.56 (s, 1.5H); 1.54 (s, 1.5H); 1.52-1.42 (overlapped m, 4H).

MS (ESI, m/z): 423.98 [M+H$^+$] for C$_{19}$H$_{25}$N$_3$O$_6$S; t$_R$=0.74 min.

Preparation E: (1S)-1-(4-iodophenyl)-2-morpholinoethan-1-ol and (1R)-1-(4-iodophenyl)-2-morpholinoethan-1-ol E.i. 1-(4-iodophenyl)-2-morpholinoethan-1-one 2-bromo-1-(4-iodo-phenyl)-ethanone (3.8 g; 11.7 mmol) was dissolved in DCM (100 mL). Morpholine (2.02 mL; 23.4 mmol) was added and the reaction mixture was stirred for 2 h. The reaction mixture was washed with water (50 mL). The evaporation residue was purified by CC (Hept-EA) to give the title product as a light yellow solid (3.3 g; 85% yield).

$^1$H NMR (d6-DMSO) δ: 7.93-7.90 (m, 2H); 7.76-7.73 (m, 2H); 3.81 (s, 2H); 3.58-3.55 (m, 4H); 2.52-2.47 (m, 4H).

MS (ESI, m/z): 331.87 [M+H$^+$] for C$_{12}$H$_{14}$NO$_4$I; t$_R$=0.53 min.

E.ii. (1RS)-1-(4-iodophenyl)-2-morpholinoethan-1-ol

To a solution of intermediate E.i (1.3 g; 3.96 mmol) in MeOH (20 mL), cooled at 15° C., was added NaBH$_4$ (0.15 g; 3.96 mmol). The mixture was stirred at that temperature for 30 min, then DCM (100 mL) was added and the mixture was washed with 0.5M aq. NaOH (3×50 mL). The evaporation residue provided the title compound as a white solid (1.1 g; 94% yield).

$^1$H NMR (d$_6$-DMSO) δ: 7.68-7.64 (m, 2H); 7.18-7.14 (m, 2H); 5.13 (d, J=4.1 Hz, 1H); 4.67 (m, 1H); 3.54 (t, J=4.6 Hz, 4H); 2.47-2.41 (m, 6H).

MS (ESI, m/z): 333.91 [M+H$^+$] for C$_{12}$H$_{16}$NO$_2$I; t$_R$=0.54 min.

E.iii. (1S)-1-(4-iodophenyl)-2-morpholinoethan-1-ol and (1R)-1-(4-iodophenyl)-2-morpholinoethan-1-ol Intermediate E.ii (1 g; 3 mmol) was separated by semi-preparative chiral HPLC Method C (Hept-EtOH 1-9; flow rate: 43 mL/min; UV detection at 230 nM); the respective retention times were 6.5 and 8.7 min. Both enantiomers, respectively first-eluting enantiomer (0.48 g) and second-eluting enantiomer (0.46 g) were obtained as yellowish solids (the absolute configuration of each enantiomer was not assigned).

$^1$H NMR (d$_6$-DMSO) δ: 7.68-7.64 (m, 2H); 7.18-7.14 (m, 2H); 5.13 (d, J=4.1 Hz, 1H); 4.67 (m, 1H); 3.54 (t, J=4.6 Hz, 4H); 2.47-2.41 (m, 6H).

MS (ESI, m/z): 333.91 [M+H$^+$] for C$_{12}$H$_{16}$NO$_2$I; t$_R$=0.54 min.

Preparation F: 6-(4-iodobenzyl)-2-oxa-6-azaspiro[3.3]heptane

A mixture of 2-oxa-6-azaspiro[3.3]heptane oxalate (0.637 g; 3.37 mmol), 4-iodobenzyl bromide (0.500 g; 1.68 mmol), K$_2$CO$_3$ (0.698 g; 5.05 mmol) and NaI (0.012 g; 0.0842 mmol) in THF (12 mL) was stirred at rt for 16 h. The solids were removed by filtration, washed with THF and the combined filtrate was evaporated. The resultant residue was purified by CC (DCM-MeOH containing 1% aq. NH$_4$OH) to afford the title compound as a viscous oil (0.350 g, 66% yield).

¹H NMR (d₆-DMSO) δ: 7.65 (d, J=8.3 Hz, 2H); 7.05 (d, J=8.3 Hz, 2H); 4.59 (s, 4H); 3.43 (s, 2H); 3.26 (s, 4H).
MS (ESI, m/z): 315.88 [M+H⁺] for $C_{12}H_{14}NOI$; $t_R$=0.50 min.

Preparation G: tert-butyl (3-(4-iodobenzyl)-3-azabicyclo[3.1.0]hexan-6-yl)carbamate To a stirred solution of 6-(Boc-amino)-3-azabicyclo[3.1.0]hexane (0.250 g, 1.26 mmol) in MeCN (10 mL) were added K₂CO₃ (0.52 g, 3.78 mmol), 4-iodobenzyl bromide (0.449 g, 1.51 mmol) and KI (0.006 g, 0.0378 mmol). The resulting reaction mixture was heated at 80 C for 1 h. The solvent was removed under reduced pressure and the residue was partitioned between DCM (100 mL) and water (25 mL). The org. layer was separated and the aq. layer was extracted with DCM (2×25 mL). The combined org. layers were washed with water (2×25 mL). The evaporation residue was purified by CC (DCM-MeOH) to afford the title compound as a beige solid (0.32 g, 61% yield).
¹H NMR (d₆-DMSO) δ: 7.66 (d, J=8.3 Hz, 2H); 7.06 (d, J=8.3 Hz, 2H); 6.90 (m, 1H); 3.48 (s, 2H); 2.88 (d, J=8.8 Hz, 2H); 2.68 (d, J=0.3 Hz, 1H); 2.30 (d, J=8.4 Hz, 2H); 1.37 (s, 9H).
MS (ESI, m/z): 414.96 [M+H⁺] for $C_{17}H_{17}N_2O_2I$; $t_R$=0.68 min.

Preparation H: 4-iodobenzyl 4-hydroxypiperidine-1-carboxylate

H.i. 2,5-dioxopyrrolidin-1-yl (4-iodobenzyl) carbonate

To a solution of 4-iodobenzylalcohol (1 g; 4.27 mmol) in MeCN (50 mL) was added TEA (1.2 mL; 8.5 mmol) and DSC (6.9 g; 25.6 mmol). The reaction mixture was stirred for 15 min. The reaction mixture was diluted with EA (100 mL), washed with 5% aq. citric acid (3×50 mL). The evaporation residue was purified by CC (Hept-EA) to afford the title product as a white solid (1.21 g; 75% yield).
¹H NMR (d6-DMSO) δ: 7.80-7.83 (m, 2H); 7.29-7.25 (m, 2H); 5.36 (s, 2H); 2.81 (s, 4H).

H.ii. 4-iodobenzyl 4-hydroxypiperidine-1-carboxylate

To a solution of intermediate H.i (1.21 g; 3.23 mmol) in DCM (43 mL) were added 4-hydroxypiperidine (0.33 g, 3.23 mmol) and TEA (0.45 mL, 3.23 mmol) and the reaction mixture was stirred for 1 h. The reaction mixture was concentrated to dryness and purified by CC (Hept-EA-MeOH) to afford the title product as a white solid (1.12 g; 96% yield).
¹H NMR (d6-DMSO) δ: 7.76-7.72 (m, 2H); 7.18-7.15 (m, 2H); 5.02 (s, 2H); 4.74 (d, J=4.1 Hz, 1H); 3.73-3.70 (m, 2H); 3.64 (m, 1H); 3.13-3.00 (m, 2H); 1.74-1.66 (m, 2H); 1.32-1.22 (m, 2H).
MS (ESI, m/z): 361.8 [M+H⁺] for $C_{13}H_{16}NO_3I$; $t_R$=0.77 min.

Preparation I: 1-(3-hydroxy-3-(4-iodophenyl)azetidin-1-yl)ethan-1-one

I.i. Tert-butyl 3-hydroxy-3-(4-iodophenyl)azetidine-1-carboxylate

To a solution of 1,4-diiodobenzene (2.14 g, 6.5 mmol) in dry THF (20 mL); cooled to −78° C., was added dropwise over 5 min BuLi (1.35M in hexanes; 3.7 mL; 5 mmol) keeping IT below −65° C. The resulting mixture was stirred at that temperature for 30 min. A solution of tert-butyl 3-oxoazetidine-1-carboxylate (1 g; 5.84 mmol) in THF (5 mL) was quickly added. The reaction mixture was allowed to reach rt over 1 h. Sat. aq. NaHCO₃ (15 mL), EA (30 mL) and water (10 mL) were added. The two layers were separated and the aq layer was extracted twice with EA (2×30 mL). The evaporation residue was purified by CC (Hept-EA) to afford the title alcohol as a white solid (1.29 g; 69% yield).
¹H NMR (d6-DMSO) δ: 7.74 (d, J=8.5 Hz, 2H); 7.31 (d, J=8.5 Hz, 2H); 6.42 (s, 1H); 4.08-3.94 (m, 4H); 1.41 (s, 9H).
MS (ESI, m/z): 375.8 [M+H⁺] for $C_{14}H_{18}NO_3I$; $t_R$=0.87 min.

I.ii. 3-(4-iodophenyl)azetidin-3-ol trifluoroacetate

To a solution of intermediate I.i (1.9 g; 2.91 mmol) in DCM (65 mL) at 0° C. was added TFA (13 mL, 170 mmol). The reaction mixture was stirred at 0° C. for 15 min and at rt for 30 min. The solvent was removed in vacuo and the residue triturated in Et₂O, and the solid was filtered off, scarcely washed with Et₂O and dried under HV to afford pure title product as a beige solid (1.01 g, 90% yield).
¹H NMR (d6-DMSO) δ: 7.81 (d, J=8.5 Hz, 2H); 7.37 (d, J=8.5 Hz, 2H); 4.31 (d, J=11.4 Hz, 2H); 4.06 (d, J=11.4 Hz, 2H).
MS (ESI, m/z): 275.86 [M+H⁺] for $C_9H_{10}NOI$; $t_R$=0.50 min.

I.iii. 1-(3-hydroxy-3-(4-iodophenyl)azetidin-1-yl)ethan-1-one

To a mixture of intermediate I.ii (0.47 g; 1.23 mmol); EDC (0.4 g; 2.08 mmol) and HOBT (0.342 g; 2.45 mmol) in DMF (6 mL) were added TEA (0.6 mL, 4.31 mmol) and AcOH (0.077 mL; 1.35 mmol). The reaction mixture was then stirred at 60° C. for 2 h. The residue was partitioned between brine (20 mL) and DCM (30 mL). The aq. layer was extracted twice with DCM (2×20 mL). The evaporation residue was purified by CC (DCM-MeOH) to afford the title compound (0.15 g; 40% yield) as a white solid.
¹H NMR (d6-DMSO) δ: 7.82-7.68 (m, 2H); 7.38-7.28 (m, 2H); 6.46 (s, 1H); 4.32 (d, J=9.0 Hz, 1H); 4.23 (d, J=9.0 Hz, 1H); 4.00 (d, J=10.0 Hz, 1H); 3.97 (d, J=10.0 Hz, 1H); 1.84 (s, 3H).
MS (ESI, m/z): 317.8 [M+H⁺] for $C_{11}H_{12}NO_2I$; $t_R$=0.67 min.

Preparation J: (S)-1-((1R,2R)-2-(bromoethynyl)cyclopropyl)ethane-1,2-diol

J.i. ((1R,2R)-2-((S)-2,2-dimethyl-1,3-dioxolan-4-yl)cyclopropyl)methyl Acetate

To a mechanically stirred solution of (S,E)-3-(2,2-dimethyl-1,3-dioxolan-4-yl)allyl acetate (prepared as described in Sugisaki et al., *Eur. J Org. Chem.* (2003), 672-688; 2.5 g; 12.5 mmol) in toluene (170 mL); cooled at −25° C., was added ZnEt₂ (15% in toluene; 56 mL; 62.2 mmol) keeping IT below −20° C. Upon the addition, diiodomethane (10.2 mL; 130 mmol) was added dropwise over 10 min. The reaction mixture was allowed to warm up to rt and stirred overnight. Sat. aq. NH₄Cl (55 mL) was added. The two layers were separated and the aq. layer was extracted with Et₂O (4×50 mL). The evaporation residue was purified by CC (PE-EA) to afford the title compound as a yellow oil (2.33 g; 87% yield).

¹H NMR (CDCl₃) δ: 4.08 (dd, J=6.0, 8.0 Hz, 1H); 3.98 (dd, J=6.9, 11.5 Hz, 1H); 3.86 (dd, J=7.6, 11.5 Hz, 1H); 3.68 (dd, J=7.2, 7.9 Hz, 1H); 3.56-3.61 (m, 1H); 2.06 (s, 3H); 1.43 (s, 3H); 1.34 (s, 3H); 1.04-1.11 (m, 1H); 0.91-0.97 (m, 1H); 0.71-0.75 (m, 1H); 0.60-0.65 (m, 1H).

J.ii. ((1R,2R)-2-((S)-2,2-dimethyl-1,3-dioxolan-4-yl)cyclopropyl)methanol

To a solution of intermediate J.i (3.1 g; 14.5 mmol) in MeOH (117 mL) was added K₂CO₃ (4 g; 29 mmol). The suspension was stirred for 45 min. The solids were removed by filtration and the filtrate was carefully concentrated down. The residue was diluted with DCM (500 mL) and washed with brine (50 mL). The org. layer was dried over MgSO₄, filtered and concentrated to dryness to afford the title compound as a yellow oil (2.25 g; 90% yield).

¹H NMR (CDCl₃) δ: 4.09 (dd, J=6.0, 8.0 Hz, 1H); 3.69 (m, 1H); 3.61 (td, J=6.0, 7.6 Hz, 1H); 3.53-3.45 (m, 2H); 1.43 (s, 3H); 1.34 (s, 3H); 1.05 (m, 1H); 0.89 (m, 1H); 0.68 (dt, J=5.0, 8.5 Hz, 1H); 0.58 (dt, J=5.1, 8.4 Hz, 1H).

J.iii. (1R,2R)-2-((S)-2,2-dimethyl-1,3-dioxolan-4-yl)cyclopropane-1-carbaldehyde To a solution of intermediate J.ii (2.52 g; 14.6 mmol) in DCM (34 mL), cooled to −10° C., was added DIPEA (7.83 mL; 45.7 mmol) over 5 min. A solution of Pyr.SO₃ complex (6.35 g; 20 mmol) in DMSO (18 mL) was added dropwise over 20 min. The reaction mixture was stirred for 1 h at 0° C. and then at rt for 1 h. The reaction mixture was partitioned between water (50 mL) and DCM (50 mL). The org. layer was washed with water (20 mL). The evaporation residue was purified by CC (PE-EA) to afford the title compound as a yellowish oil (1.78 g; 71% yield).

¹H NMR (CDCl₃) δ: 9.12 (d, J=5.1 Hz, 1H); 4.11 (dd, J=6.1, 8.2 Hz, 1H); 3.81 (q, J=6.6 Hz, 1H); 3.70 (dd, J=6.8, 8.2 Hz, 1H); 1.90-1.84 (m, 1H); 1.73-1.67 (m, 1H); 1.43 (s, 3H); 1.34 (s, 3H); 1.21-1.27 (m, 2H).

J.iv. (S)-4-((1R,2R)-2-ethynylcyclopropyl)-2,2-dimethyl-1,3-dioxolane

A suspension of intermediate J.iii (2.32 g; 13.6 mmol) and K₂CO₃ (3.767 g; 27.3 mmol) in MeOH (12.5 mL) was treated drop wise with dimethyl (1-diazo-2-oxopropyl)phosphonate (2.88 g; 15 mmol). The reaction mixture was stirred for 2 h. The solvent was evaporated and the residue was dissolved in DCM (20 mL) and water (15 mL). The aq. layer was extracted once with DCM (15 mL). The evaporation residue afforded the title compound as a yellow oil (1.74 g; 77% yield).

¹H NMR (CDCl₃) δ: 4.13 (dd, J=6.0, 8.1 Hz, 1H); 3.77 (m, 1H); 3.68 (m, 1H); 1.83 (d, J=2.1 Hz, 1H); 1.44 (s, 3H); 1.34 (m, 1H); 1.35 (s, 3H); 1.27-1.22 (m, 1H); 1.02-0.92 (m, 2H).

J.v. (S)-4-((1R,2R)-2-(bromoethynyl)cyclopropyl)-2,2-dimethyl-1,3-dioxolane

To a stirring solution of intermediate J.iv (1.740 g; 10.5 mmol) and NBS (2.23 g; 12.6 mmol) in acetone (45 mL) was added AgNO₃ (0.185 g; 1.09 mmol). The mixture was stirred for 2 h. The solids were filtered off and the filtrate was concentrated to dryness. The residue was purified by CC (Hex-DCM) to afford the title compound as a yellow oil (0.7 g; 27% yield).

¹H NMR (CDCl₃) δ: 4.10 (m, 1H); 3.74 (m, 1H); 3.65 (m, 1H); 1.41 (s, 1H); 1.43 (s, 3H); 1.35 (s, 3H); 1.36-1.20 (overlapped m, 2H); 1.00-0.83 (m, 2H).

J.vi. (S)-1-((1R,2R)-2-(bromoethynyl)cyclopropyl)ethane-1,2-diol

A solution of intermediate J.v (0.663 g; 2.7 mmol) in 1M HCl (3.26 mL) and THF (0.6 mL) was stirred at 50° C. for 1 h. After cooling, EA (15 mL) was added and the two layers were separated. The aq. layer was extracted with EA (2×15 mL). The evaporation residue afforded the title compound as a yellowish oil (0.492 g; 90% yield).

¹H NMR (CDCl₃) δ: 3.80 (dd, J=3.2, 11.2 Hz, 1H); 3.63 (dd, J=7.4, 11.1 Hz, 1H); 3.30 (td, J=3.2, 7.0 Hz, 1H); 1.33-1.26 (m, 3H); 0.94-0.88 (m, 2H).

Preparation K: 3-iodoprop-2-yn-1-yl 4-hydroxypiperidine-1-carboxylate

K.i. Prop-2-yn-1-yl 4-hydroxypiperidine-1-carboxylate

To a solution of propargyl chloroformate (commercial; 2.47 mL; 24.3 mmol) in DCM (50 mL), cooled to 0° C., were added dropwise 4-hydroxypiperidine (2.5 g; 24.3 mmol) and TEA (6.76 mL; 48.6 mmol). The reaction mixture was allowed to warm up to rt and stirred overnight. Sat. aq. NaHCO₃ (100 mL) was added. The two layers were separated. The evaporation residue was purified by CC (DCM-TBME) to afford the title compound as a beige oil (3.17 g; 71% yield).

¹H NMR (d6-DMSO) δ: 4.75 (d, J=4.1 Hz, 1H); 4.65 (d, J=2.4 Hz, 2H); 3.70-3.62 (m, 3H); 3.50 (m, 1H); 3.08-3.06 (m, 2H); 1.74-1.67 (m, 2H); 1.33-1.25 (m, 2H).

K.ii. 3-iodoprop-2-yn-1-yl 4-hydroxypiperidine-1-carboxylate

To a solution of intermediate K.i (2.02 g; 11 mmol) in MeOH (49 mL) and 1M KOH (55.1 mL; 55.1 mmol) was added in one portion iodine (3.6 g; 14.3 mmol). The reaction mixture was stirred overnight at rt. The solvent was evaporated and the residue was diluted with water (400 mL) and extracted with DCM (2×500 mL). The evaporation residue was purified by CC (Hept-EA-MeOH) to afford the title compound as a white solid (2.32 g; 68% yield).

¹H NMR (d6-DMSO) δ: 4.77 (s, 2H); 4.75 (d, J=4.1 Hz, 1H); 3.75-3.61 (m, 3H); 3.13-2.97 (m, 2H); 1.74-1.64 (m, 2H); 1.36-1.21 (m, 2H).

MS (ESI, m/z): 309.9 [M+H⁺] for C₉H₁₁NO₃I; $t_R$=0.63 min.

Preparation L: 3-(3-bromoprop-2-yn-1-yl)oxazolidin-2-one

Starting from 3-(prop-2-yn-1-yl)oxazolidin-2-one (0.5 g; 4 mmol) and proceeding in analogy to Preparation J, step J.v, the title compound was obtained, after purification by CC (Hept-EA-MeOH), as a beige oil (0.68 g; 84% yield).

¹H NMR (d6-DMSO) δ: 4.38-4.25 (m, 2H); 4.09 (s, 2H); 3.64-3.53 (m, 2H).

Preparation M: 4-iodobenzyl 3-hydroxyazetidine-1-carboxylate

Starting from 3-hydroxyazetidine hydrochloride (0.194 g; 1.73 mmol) and intermediate H.i (0.65 g; 1.73 mmol) and proceeding in analogy to Preparation H, step H.ii, the title compound was obtained, after purification by CC (Hept-EA-MeOH), as a white solid (0.54 g; 93% yield).

$^1$H NMR (d6-DMSO) δ: 7.74 (m, 2H); 7.16 (m, 2H); 5.71 (d, J=6.5 Hz, 1H); 4.98 (s, 2H); 4.44 (m, 1H); 4.10-4.06 (m, 2H); 3.68-3.65 (m, 2H).

MS (ESI, m/z): 333.8 [M+H$^+$] for $C_{11}H_{12}NO_3I$; $t_R$=0.74 min.

Preparation N: 4-iodobenzyl (2-hydroxyethyl)(methyl)carbamate

Starting from 2-methylamino ethanol (0.137 g; 1.79 mmol) and intermediate H.i (0.67 g; 1.79 mmol) and proceeding in analogy to Preparation H, step H.ii, the title compound was obtained, after purification by CC (Hept-EA-MeOH), as a colourless oil (0.59 g; 98% yield).

$^1$H NMR (d6-DMSO) δ: 7.73 (d, J=7.6 Hz, 2H); 7.17 (d, J=7.4 Hz, 2H); 5.01 (s, 2H); 4.71 (dt, J=5.3, 20.1 Hz, 1H); 3.49 (q, J=5.9 Hz, 2H); 3.32-3.24 (m, 2H); 2.89 (d, J=20.2 Hz, 3H).

MS (ESI, m/z): 335.9 [M+H$^+$] for $C_{11}H_{14}NO_3I$; $t_R$=0.75 min.

Preparation O: (RS)-5-(hydroxymethyl)-3-(4-iodobenzyl)oxazolidin-2-one 4-iodo-benzylamine (1 g; 4.29 mmol), $K_2CO_3$ (2.96 g; 21.5 mmol), TEA (2.99 mL; 21.5 mmol) and epibromohydrin (1.84 mL; 21.5 mmol) in MeOH (20 mL) were stirred at reflux for 7 h. After cooling, the solvent was removed in vacuo and the residue was partitioned between water (50 mL) and EA (100 mL). The evaporation residue was purified by CC (Hept-EA) to afford the title compound as a white solid (0.3 g; 21% yield).

$^1$H NMR (d6-DMSO) δ: 7.73 (m, 2H); 7.10 (d, J=8.3 Hz, 2H); 5.12 (t, J=5.7 Hz, 1H); 4.57-4.49 (m, 1H); 4.30 (d, J=6.7 Hz, 2H); 3.60-3.53 (m, 1H); 3.48-3.41 (m, 2H); 3.27-3.19 (m, 1H).

MS (ESI, m/z): 333.8 [M+H$^+$] for $C_{11}H_{12}NO_3I$; $t_R$=0.68 min.

Preparation P: (3S*,4S*)-3-fluoro-1-(4-iodobenzyl)piperidin-4-amine trifluoroacetate

P.i. Tert-butyl ((3S,4S)-3-fluoro-1-(4-iodobenzyl)piperidin-4-yl)carbamate

Starting from tert-butyl ((3S*,4S*)-3-fluoropiperidin-4-yl)carbamate (0.4 g; 1.83 mmol) and 4-iodobenzyl bromide (0.5 g; 1.68 mmol) and proceeding in analogy to Preparation G, the title compound was obtained, after purification by CC (Hept-EA), as a yellowish solid (0.5 g; 68% yield).

MS (ESI, m/z): 434.98 [M+H$^+$] for $C_{17}H_{24}N_2O_2FI$; $t_R$=0.69 min.

P.ii. (3S*,4S*)-3-fluoro-1-(4-iodobenzyl)piperidin-4-amine trifluoroacetate

Starting from intermediate P.i (0.5 g; 1.14 mmol) and proceeding in analogy to Preparation I, step I.ii, the title compound was obtained, after trituration in $Et_2O$, as a beige solid (0.616 g; >95% yield).

$^1$H NMR (d6-DMSO) δ: 8.38 (s, 3H); 7.78 (d, J=7.9 Hz, 2H); 7.18 (d, J=7.7 Hz, 2H); 4.89-4.54 (m, 1H); 4.05-3.62 (m, 2H); 3.45-3.31 (m, 2H); 3.09-2.95 (m, 1H); 2.08-2.06 (m, 1H); 1.67-1.59 (m, 1H).

MS (ESI, m/z): 334.94 [M+H$^+$] for $C_{12}H_{16}N_2FI$; $t_R$=0.45 min.

Preparation Q: 3,3-difluoro-1-(4-iodobenzyl)piperidin-4-amine trifluoroacetate Starting from tert-butyl (3,3-difluoropiperidin-4-yl)carbamate (0.4 g; 1.69 mmol) and 4-iodobenzyl bromide (0.5 g; 1.68 mmol) and proceeding in analogy to Preparation G (77% yield) and Preparation I, step I ii (85% yield), the title compound, was obtained after trituration in $Et_2O$, as a beige solid (0.51 g).

$^1$H NMR (d6-DMSO) δ: 8.57-8.54 (m, 3H); 7.72 (d, J=8.2 Hz, 2H); 7.12 (d, J=8.1 Hz, 2H); 3.74-3.68 (m, 1H); 3.60 (s, 2H); 3.17-3.15 (m, 1H); 2.85-2.82 (m, 1H); 2.25-2.21 (m, 1H); 1.99-1.97 (m, 1H); 1.72-1.64 (m, 1H).

MS (ESI, m/z): 352.89 [M+H$^+$] for $C_{12}H_{15}N_2F_2I$; $t_R$=0.55 min.

Preparation R: 3-fluoro-3-(4-iodophenyl)azetidine hydrochloride

R.i. Tert-butyl 3-fluoro-3-(4-iodophenyl)azetidine-1-carboxylate

To a suspension of intermediate I.i (1.50 g; 4.00 mmol) in DCM (52 mL) was added bis(2-methoxyethyl)aminosulfur trifluoride (50% solution in toluene, 2.60 mL; 6.00 mmol) dropwise at −78° C. The reaction mixture was stirred at −78° C. for 5 h. Sat. aq. $NaHCO_3$ (50 mL) was added. The two layers were separated and the aq. layer was extracted with DCM (3×25 mL). The evaporation residue was purified by CC (PE-EA) to afford the title compound as a yellow oil (1.34 g; 89% yield).

MS (ESI, m/z): 378.2 [M+H$^+$] for $C_{14}H_{17}NO_2FI$; $t_R$=0.71 min.

R.ii. 3-fluoro-3-(4-iodophenyl)azetidine hydrochloride

To a solution of intermediate R.i (1.33 g; 3.52 mmol) in dioxane (10 mL) was added 4M HCl in dioxane (10 mL). The mixture was stirred at 60° C. for 1 h, cooled and concentrated in vacuo. EA (5 mL) was added and the solid was collected by filtration and dried to a constant weight affording the title compound as a white solid (1.07 g; 97% yield).

MS (ESI, m/z): 318.2 [M+MeCN+H$^+$] for $C_9H_9NFI$; $t_R$=0.56 min.

Preparation S: 3-fluoro-3-(4-iodophenyl)-1-(oxetan-3-yl)azetidine

To a suspension of the compound of Preparation R (0.72 g; 2.31 mmol) was added in DCE (30 mL) were added oxetan-3-one (0.333 g; 4.62 mmol), $NaBH(OAc)_3$ (1.47 g; 6.93 mmol) and AcOH (0.06 mL). The resulting mixture was stirred overnight at rt. The reaction mixture was quenched with sat. $NaHCO_3$ (30 mL). the two layers were separated and the aq. layer was extracted with DCM (3×25 mL). The evaporation residue was purified by CC (PE-EA) to afford the title compound as a white solid (0.44 g; 57% yield).

¹H NMR (d6-DMSO) δ: 7.83 (d, J=7.9 Hz, 2H); 7.38 (d, J=8.1 Hz, 2H); 4.60 (t, J=6.6 Hz, 1H); 4.40 (dd, J=5.2, 6.4 Hz, 1H); 3.88 (m, 1H); 3.68 (br. s, 2H); 3.66-3.62 (m, 2H).

MS (ESI, m/z): 333.9 [M+H⁺] for $C_{12}H_{13}NOFI$; $t_R$=0.57 min.

Preparation T: 4-iodobenzyl 4-methylpiperazine-1-carboxylate

Starting from 1-methyl piperazine (0.175 g; 1.73 mmol) and intermediate H.i (0.65 g, 1.73 mmol) and proceeding in analogy to Preparation H, step H.ii, the title compound was obtained, after purification by CC (DCM-MeOH), as a white solid (0.59 g; 84% yield).

¹H NMR (d6-DMSO) δ: 7.74 (d, J=8.2 Hz, 2H); 7.17 (d, J=8.2 Hz, 2H); 5.03 (s, 2H); 3.35 (overlapped m, 4H); 2.26 (t, J=4.8 Hz, 4H); 2.17 (s, 3H).

MS (ESI, m/z): 360.9 [M+H⁺] for $C_{13}H_{17}N_2O_2I$; $t_R$=0.62 min.

Preparation U: 3-(bromoethynyl)-3-fluoroazetidine hydrochloride

U.i. Tert-butyl 3-(bromoethynyl)-3-hydroxyazetidine-1-carboxylate

Starting from tert-butyl 3-ethynyl-3-hydroxyazetidine-1-carboxylate (prepared as described in WO 2014/165075; 1.88 g; 9.53 mmol) and proceeding in analogy to Preparation J, step J.v, the title compound was obtained, after purification by CC (Hex-TBME), as a yellowish thick oil (2.16 g; 82% yield).

¹H NMR (CDCl₃) δ: 4.20 (dd, J=1.0, 9.1 Hz, 2H); 4.01 (dd, J=1.0, 9.1 Hz, 2H); 2.87 (br. s, 1H); 1.44 (s, 9H).

MS (ESI, m/z): 316.9 [M+NeCN+H⁺] for $C_{10}H_{14}NO_3Br$; $t_R$=0.75 min.

U.ii. Tert-butyl 3-(bromoethynyl)-3-fluoroazetidine-1-carboxylate

To a solution of intermediate U.i (2.17 g; 7.85 mmol) in DCM (75 mL), cooled at −78° C., was added DAST (1.1 mL; 8.33 mmol) dropwise over 5 min. The reaction was stirred at −78° C. for 75 min then allowed to warm to rt for 1 h. The reaction mixture was poured onto sat. aq. NaHCO₃ (80 mL). The two layers were separated and the aq. layer was extracted with DCM (80 mL). The evaporation residue afforded the title compound as a yellow oil (2.15 g; 98% yield).

¹H NMR (CDCl₃) δ: 4.27-4.17 (m, 4H); 1.45 (s, 9H).

U.iii. 3-(bromoethynyl)-3-fluoroazetidine hydrochloride

A solution of intermediate U.ii (2.15 g; 7.72 mmol) in a 4M HCl solution in dioxane (20 mL) was stirred for 75 min. The reaction mixture was concentrated to dryness then co-evaporated with Et₂O (20 mL) to give the title compound as a beige solid (1.63 g; 98% yield).

¹H NMR (d6-DMSO) δ: 9.80-9.46 (m, 2H); 4.47-4.38 (m, 2H); 4.36-4.28 (m, 2H).

Preparation V: 3-(bromoethynyl)-3-fluoro-1-(oxetan-3-yl)azetidine

To a suspension of the compound of Preparation U (0.355 g; 1.66 mmol) in DCM (24 mL) were added oxetan-3-one (0.333 g; 4.63 mmol) and NaBH(OAc)₃ (2.16 g; 9.87 mmol). The reaction mixture was stirred overnight. Sat. aq. NaHCO₃ (40 mL) and DCM (20 mL) were added. The two layers were separated and the aq. layer was extracted with DCM-MeOH (9-1; 2×25 mL). The evaporation residue was purified by CC (DCM-MeOH) to afford the title compound as a yellow oil (0.363 g; 94% yield).

¹H NMR (CDCl₃) δ: 4.77-4.73 (m, 2H); 4.56 (dd, J=5.2, 7.0 Hz, 2H); 3.96 (m, 1H); 3.91-3.84 (m, 2H); 3.72-3.64 (m, 2H).

Preparation W: 3-fluoro-3-(4-iodophenyl)-1-methylazetidine

To a solution of the compound of Preparation R (0.200 g; 0.638 mmol) in DCM (8.4 mL) were added 37% aq. formaldehyde (0.149 mL; 1.91 mmol) and NaBH(OAc)₃ (0.82 g; 3.87 mmol). The reaction mixture was stirred for 2 h. Sat. aq. NaHCO₃ (10 mL) and DCM (10 mL) were added. The aq. layer was extracted with DCM (2×15 mL). The evaporation residue was purified by CC (Hept-EA-MeOH) to afford the title compound as a colourless oil (0.158 g; 85% yield).

¹H NMR (d6-DMSO) δ: 7.81-7.78 (m, 2H); 7.36-7.33 (m, 2H); 3.63-3.57 (m, 2H); 3.52-3.45 (m, 2H); 2.37 (s, 3H).

MS (ESI, m/z): 291.87 [M+H⁺] for $C_{10}H_{11}NFI$; $t_R$=0.55 min.

Preparation X: 1-(bromoethynyl)cyclopropan-1-amine hydrochloride

X.i. Methyl 1-((tert-butoxycarbonyl)amino)cyclopropane-1-carboxylate

To a solution of cyclopropane-1,1-dicarboxylic acid methyl ester (14.55 g; 97.9 mmol) in toluene (400 mL) and tBuOH (150 mL) were added TEA (15.6 mL; 112 mmol) and DPPA (23.4 mL; 106 mmol). The mixture was stirred 5 min at rt before heating to 90° C. The reaction proceeded for 2 h. CuCl (1.44 g; 14.1 mmol) was added. The reaction was left under heating further 2 h. After cooling, sat. aq. NaHCO₃ (300 mL) and EA (200 mL) were added. The two layers were separated and the aq. layer was extracted with EA (3×150 mL). The evaporation residue was purified by CC (DCM-MeOH) to afford the title compound as a white solid (16.78 g; 80% yield).

¹H NMR (d6-DMSO) δ: 7.53 (s, 1H); 3.59 (s, 3H); 1.38 (s, 9H); 1.32-1.28 (m, 2H); 1.03-0.99 (m, 2H).

MS (ESI, m/z): 216.2 [M+H⁺] for $C_{10}H_{17}NO_4$; $t_R$=0.55 min.

X.ii. Tert-butyl (1-(hydroxymethyl)cyclopropyl)carbamate

To a suspension of LiBH₄ (2.58 g; 113 mmol) in THF (55 mL) cooled at 0° C. was added dropwise a solution of intermediate X.i (12.0 g; 56.1 mmol) in THF (60 mL), keeping IT below 5° C. The mixture was allowed to warm to rt. The reaction mixture was heated at reflux for 2 h. After cooling, sat. aq. NaHCO₃ (60 mL) and EA (80 mL) were added. The two layers were decanted and the aq. layer was extracted twice with EA (2×40 mL). The evaporation residue afforded the title compound as a white solid (10.62 g; crude material).

¹H NMR (d6-DMSO) δ: 7.03 (br. s, 1H); 4.56 (t, J=5.8 Hz, 1H); 3.38 (d, J=5.8 Hz, 2H); 1.37 (s, 9H); 0.64-0.60 (m, 2H); 0.54-0.50 (m, 2H).

X.iii. Tert-butyl (1-formylcyclopropyl)carbamate

Starting from intermediate X.ii (5 g; 26.7 mmol) and proceeding in analogy to Preparation J, step J.iii, the title compound was obtained, after purification by CC (Hept-EA), as a bright white solid (4.74 g; 96% yield).

¹H NMR (d6-DMSO) δ: 8.99 (s, 1H); 7.55 (s, 1H); 1.44-1.31 (overlapped m, 2H); 1.39 (s, 9H); 1.19-1.10 (m, 2H).

MS (ESI, m/z): 186.2 [M+H⁺] for $C_9H_{15}NO_3$; $t_R$=0.62 min.

X.iv. Tert-butyl (1-(2,2-dibromovinyl)cyclopropyl)carbamate

To a solution of CBr₄ (18.3 g; 54.8 mmol) in DCM (40 mL) cooled at −20° C., was added dropwise over 1 h a solution of PPh₃ (29.6 g; 107 mmol) in DCM (65 mL). The solution was allowed to slowly warm to 0° C. and then cooled to −78° C. TEA (7.5 mL; 53.9 mmol) was added. A solution of intermediate X.iii (5.0 g, 26.9 mmol) in DCM (50 mL) was added dropwise over 45 min keeping IT under −72° C. The suspension was kept stirring at this temperature for 30 min before warming to 15° C. The mixture was diluted in Et₂O (20 mL), and the solids were filtered off. The filtrate was concentrated to dryness and the residue was purified by CC (EA-Hept) to afford the title compound as a white solid (7.7 g; 84% yield).

¹H NMR (d6-DMSO) δ: 7.46 (s, 1H); 6.48 (s, 1H); 1.37 (s, 9H); 0.97-0.94 (m, 2H); 0.92-0.89 (m, 2H).

X.v. Tert-butyl (1-(bromoethynyl)cyclopropyl)carbamate

A solution of intermediate X.iv (1.5 g; 4.4 mmol) in dry THF (10 mL) cooled at −78° C., was treated dropwise over 1 h with a freshly prepared suspension of tBuOK (2.71 g; 24.2 mmol) in dry THF (24.2 mL). IT was kept under −73° C. The mixture was stirred for 2 h at −75° C. The suspension was slowly allowed to warm to 0° C. and the mixture was stirred at this temperature for 1 h. Brine (50 mL) was added slowly over 2 min. Once the reaction mixture was warmed to rt, Et₂O (60 mL) was added. The aq. layer was separated and extracted with Et₂O (70 mL). The evaporation residue afforded the title compound as a white solid (1.08 g; 95% yield).

¹H NMR (d6-DMSO) δ: 7.61 (s, 1H); 1.38 (s, 9H); 1.07-1.03 (m, 2H); 0.95-0.91 (m, 2H).

X.vi. 1-(bromoethynyl)cyclopropan-1-amine hydrochloride

A solution of intermediate X.v (0.29 g; 1.11 mmol) in a 4N HCl solution in dioxane (2.22 mL, 8.86 mmol) was stirred at rt for 1 h. The reaction mixture was evaporated and the residue was triturated with Et₂O (15 mL), filtered and the solid was dried in vacuo to afford the title compound as a white solid (0.18 g; 84% yield).

¹H NMR (d6-DMSO) δ: 8.94 (s, 2H); 1.34-1.28 (m, 2H); 1.27-1.20 (m, 2H).

Preparation Y: (1-(bromoethynyl)cyclopropyl)methyl 3-hydroxyazetidine-1-carboxylate

Y.i. (1-(bromoethynyl)cyclopropyl)methanol

To a solution of ((1-(bromoethynyl)cyclopropyl) methoxy)(tert-butyl)diphenylsilane (prepared as described in WO 2015/036964, 1 g; 2.42 mmol) in THF (2.4 mL) was added TBAF (1M in THF; 6.05 mL). The resulting solution was stirred for 30 min. The reaction mixture was concentrated in vacuo and the residue was purified by CC (Hept-EA) to afford the title compound as a colourless oil (0.58 g; >95% yield).

¹H NMR (d6-DMSO) δ: 4.90 (t, J=6.0 Hz, 1H); 3.32 (d, J=6.0 Hz, 2H); 0.80-0.77 (m, 2H); 0.76-0.72 (m, 2H).

Y.ii. (1-(bromoethynyl)cyclopropyl)methyl (2,5-dioxopyrrolidin-1-yl)carbonate Starting from intermediate Y.i (0.425 g; 0.242 mmol) and proceeding in analogy to Preparation H, step H.i, the title compound was obtained, after purification by CC (Hept-EA-MeOH), as a white solid (0.58 g; 76% yield).

¹H NMR (d6-DMSO) δ: 4.28 (s, 2H); 2.83 (s, 4H); 1.07-0.98 (m, 4H).

Y.iii. (1-(bromoethynyl)cyclopropyl)methyl 3-hydroxyazetidine-1-carboxylate Starting from intermediate Y.ii (0.29 g; 0.91 mmol) and 3-hydroxyazetidine hydrochloride (0.10 g; 0.92 mmol) and proceeding in analogy to Preparation H, step H.ii, the title compound was obtained, after purification by CC (Hept-EA-MeOH), as a colourless oil (0.18 g; 74% yield).

¹H NMR (d6-DMSO) δ: 5.71 (d, J=6.5 Hz, 1H); 4.45 (m, 1H); 4.16-4.01 (m, 2H); 3.87 (s, 2H); 3.77-3.60 (m, 2H); 0.94-0.91 (m, 2H); 0.89-0.85 (m, 2H).

MS (ESI, m/z): 273.9 [M+H⁺] for $C_{10}H_{12}NO_3Br$; $t_R$=0.67 min.

Preparation Z: (1-(bromoethynyl)cyclopropyl)methyl 4-methylpiperazine-1-carboxylate Starting from intermediate Y.ii (0.28 g; 0.9 mmol) and 1-methylpiperazine (0.10 mL; 0.90 mmol) and proceeding in analogy to Preparation H, step H.ii, the title compound was obtained without purification as a colourless oil (0.18 g; 74% yield).

¹H NMR (d6-DMSO) δ: 3.92 (s, 2H); 3.40-3.35 (m, 4H); 2.28 (t, J=5.0 Hz, 4H); 2.19 (s, 3H); 0.95-0.91 (m, 2H); 0.90-0.86 (m, 2H).

MS (ESI, m/z): 300.95 [M+H⁺] for $C_{12}H_{17}N_2O_2Br$; $t_R$=0.54 min.

Preparation AA: 3-bromoprop-2-yn-1-yl 3-hydroxyazetidine-1-carboxylate

AA.i. 3-bromoprop-2-yn-1-yl (2,5-dioxopyrrolidin-1-yl) carbonate

Starting from 3-bromoprop-2-yn-1-ol (1 g; 7.41 mmol) and proceeding in analogy to Preparation H, step H.i, the title compound was obtained, after purification by CC (Hept-EA), as a beige solid (1.50 g; 73% yield).

¹H NMR (d6-DMSO) δ: 5.13 (s, 2H); 2.83 (s, 4H).

AA.ii. 3-bromoprop-2-yn-1-yl 3-hydroxyazetidine-1-carboxylate

Starting from intermediate AA.i (1.38 g; 5 mmol) and hydroxyazetidine hydrochloride (0.559 g, 5 mmol) and proceeding in analogy to Preparation H, step H.ii, the title compound was obtained, after purification by CC (Hept-EA), as a white solid (0.875 g; 75% yield).

$^1$H NMR (d6-DMSO) δ: 5.73 (d, J=6.6 Hz, 1H); 4.68 (s, 2H); 4.43 (m, 1H); 4.10 (d, J=1.5 Hz, 2H); 3.68-3.66 (m, 2H).

Preparation AB: azetidin-3-yl (4-iodobenzyl)carbamate trifluoroacetate

AB.i. Tert-butyl 3-((((2,5-dioxopyrrolidin-1-yl)oxy)carbonyl)oxy)azetidine-1-carboxylate Starting from tert-butyl 3-hydroxyazetidine-1-carboxylate (2 g; 11.3 mmol) and proceeding in analogy to Preparation H, step H.i, the title compound was obtained as a greyish solid (2.94 g; 83% yield).

$^1$H NMR (d6-DMSO) δ: 5.35 (m, 1H); 4.26-4.22 (m, 2H); 3.88 (d, J=8.4 Hz, 2H); 2.82 (s, 4H); 1.39 (m, 9H).

AB.ii. Tert-butyl 3-(((4-iodobenzyl)carbamoyl)oxy)azetidine-1-carboxylate

Starting from intermediate AB.i (0.5 g; 1.59 mmol) and (4-iodophenyl)methanamine trifluoroacetate (prepared as described in Lee et al., *Bioorg. Med. Chem.* (2004), 12, 371-385; 0.55 g; 1.59 mmol) and proceeding in analogy to Preparation H, step H.ii, the title compound was obtained, after purification by CC (Hept-EA), as a white foam (0.62 g; 91% yield).

$^1$H NMR (d6-DMSO) δ: 7.98 (t, J=6.0 Hz, 1H); 7.68 (d, J=8.2 Hz, 2H); 7.07 (d, J=8.2 Hz, 2H); 5.06-4.95 (m, 1H); 4.21-4.03 (m, 4H); 3.79-3.61 (m, 2H); 1.38 (s, 9H).

MS (ESI, m/z): 432.95 [M+H$^+$] for $C_{16}H_{21}N_2O_4I$; $t_R$=0.90 min.

AB.iii. Azetidin-3-yl (4-iodobenzyl)carbamate trifluoroacetate

Starting from intermediate AB.ii (0.62 g; 1.44 mmol) and proceeding in analogy to Preparation I, step I.ii, the title compound was obtained, after trituration in Et$_2$O, as a white solid (0.67 g; >95% yield).

$^1$H NMR (d6-DMSO) δ: 8.92 (br. s, 1H); 8.70 (br. s, 1H); 8.10 (t, J=6.1 Hz, 1H); 7.69 (d, J=8.3 Hz, 2H); 7.08 (d, J=8.3 Hz, 2H); 5.16-5.08 (m, 1H); 4.31-4.20 (m, 2H); 4.14 (d, J=6.2 Hz, 2H), 3.99-3.89 (m, 2H).

MS (ESI, m/z): 332.86 [M+H$^+$] for $C_{13}H_{14}N_2O_4F_3I$; $t_R$=0.57 min.

Preparation AC: 1-methylazetidin-3-yl (4-iodobenzyl)carbamate

Starting from the compound of Preparation AB (0.2 g; 0.44 mmol) and proceeding in analogy to Preparation W, the title compound was obtained, after purification by CC (DCM-MeOH containing 1% aq. NH$_4$OH), as a white solid (0.104 g; 67% yield).

$^1$H NMR (d6-DMSO) δ: 7.84 (t, J=6.1 Hz, 1H); 7.68 (d, J=8.2 Hz, 2H); 7.06 (d, J=8.2 Hz, 2H); 4.84-4.77 (m, 1H); 4.11 (d, J=6.2 Hz, 2H); 3.56-3.47 (m, 2H); 2.91-2.86 (m, 2H); 2.24 (s, 3H).

MS (ESI, m/z): 346.89 [M+H$^+$] for $C_{12}H_{15}N_2O_2I$; $t_R$=0.58 min.

Preparation AD: (RS)-1-(4-iodophenyl)-2-((2-methoxyethyl)(methyl)amino)ethan-1-ol Starting from 2-methoxy-N-methylethan-1-amine (1.04 g; 11.7 mmol) and proceeding in analogy to Preparation E, steps E.i and E.ii (40% yield over the 2 steps), the title compound was obtained, after purification by CC (DCM-MeOH containing 1% aq. NH$_4$OH), as a colourless oil (1.57 g).

MS (ESI, m/z): 335.9 [M+H$^+$] for $C_{12}H_{18}NO_2I$; $t_R$=0.58 min.

Preparation AE: 4-(((1R,2R)-2-(bromoethynyl)cyclopropyl)methyl)morpholine

AE.i. ((1R,2R)-2-(bromoethynyl)cyclopropyl)methanol

Starting from ((1R,2R)-2-(bromoethynyl)cyclopropyl)methyl acetate (prepared as described in WO 2005/036964; 1.13 g; 5.22 mmol) and proceeding in analogy to Preparation J, step J.ii, the title compound was obtained as a colourless oil (1.07 g; >95% yield).

$^1$H NMR (d6-DMSO) δ: 4.63 (t, J=5.7 Hz, 1H); 3.37 (m, 1H); 3.19 (m, 1H); 1.29-1.20 (m, 2H); 0.76 (m, 1H); 0.70 (ddd, J=4.2, 6.0, 8.5 Hz, 1H).

AE.ii. ((1R,2R)-2-(bromoethynyl)cyclopropyl)methyl 4-methylbenzenesulfonate To a solution of intermediate AE.i (0.543 g; 3.1 mmol) in DCM (5.5 mL), cooled at 0° C., were added TEA (0.87 mL; 6.2 mmol) and TsCl (0.661 g, 3.43 mmol). The solution was stirred overnight to rt. The reaction mixture was diluted with DCM (10 mL) and washed with sat. aq. NaHCO$_3$ (10 mL). The aq. layer was extracted with DCM (10 mL). The evaporation residue was purified by CC (Hept-EA) to afford the title compound as a colourless oil (0.749 g; 73% yield).

$^1$H NMR (CDCl$_3$) δ: 7.80-7.78 (m, 2H); 7.36-7.34 (m, 2H); 3.94 (dd, J=6.8, 10.9 Hz, 1H); 3.85 (dd, J=7.5, 10.9 Hz, 1H); 2.46 (s, 3H); 1.46 (m, 1H); 1.20 (ddd, J=4.4, 5.4, 8.9 Hz, 1H); 0.97 (dt, J=5.2, 8.6 Hz, 1H); 0.74 (m, 1H).

AE.iii. 4-(((1R,2R)-2-(bromoethynyl)cyclopropyl)methyl)morpholine

To a solution of intermediate AE.ii (0.374 g, 1.14 mmol) in MeCN (5 mL) were added morpholine (0.151 mL; 1.71 mmol) and K$_2$CO$_3$ (0.32 g; 2.31 mmol). The reaction mixture was stirred at 80° C. for 2 h. The reaction mixture was cooled to rt, filtered and the filtrate was evaporated under reduced pressure. The residue was purified by CC (DCM-MeOH) to afford the title compound as a yellow oil (0.254 g; 92% yield).

$^1$H NMR (CDCl$_3$) δ: 3.80-3.72 (m, 4H); 2.60-2.47 (m, 4H); 2.43 (dd, J=5.8, 12.8 Hz, 1H); 2.16 (dd, J=7.3, 12.7 Hz, 1H); 1.27 (m, 1H); 1.08 (m, 1H); 0.96 (dt, J=4.8, 8.6 Hz, 1H); 0.64 (m, 1H).

MS (ESI, m/z): 245.85 [M+H⁺] for $C_{10}H_{14}NOBr$; $t_R$=0.44 min.

Preparation AF: 3-(bromoethynyl)azetidine hydrochloride

AF.i. Tert-butyl 3-(bromoethynyl)azetidine-1-carboxylate

Starting from tert-butyl 3-ethynylazetidine-1-carboxylate (0.5 g; 2.76 mmol; prepared as described in WO 2014/165075), and proceeding in analogy to Preparation J, step J.v, the title compound was obtained, after purification by CC (Hex-TBME), as a colourless oil (0.673 g, 94% yield).

¹H NMR (CDCl₃) δ: 4.14 (m, 2H); 3.96 (dd, J=6.3 Hz, 8.4 Hz, 2H); 3.34 (m, 1H); 1.46 (s, 9H).

AF.ii. 3-(bromoethynyl)azetidine hydrochloride

Starting from the intermediate AF.i (0.670 g; 2.7 mmol) and proceeding in analogy to Preparation U, step U.iii, the title compound was obtained, after trituration in Et₂O, as an off-white solid (0.49 g; 97% yield).

¹H NMR (CDCl₃) δ: 9.44-9.10 (m, 2H); 4.15-4.06 (m, 2H); 3.96-3.87 (m, 2H); 3.74 (m, 1H).

MS (ESI, m/z): 162.0 [M+H⁺] for $C_5H_6NBr$; $t_R$=0.23 min.

Preparation AG: 4-(iodoethynyl)-1-methylpiperidine

AG.i. 4-(iodoethynyl)piperidine trifluoroacetate

Starting from tert-butyl 4-(iodoethynyl)piperidine-1-carboxylate (prepared as described in WO 2005/036964; 0.05 g; 0.15 mmol) and proceeding in analogy to Preparation I, step I.ii, the title compound was obtained, after trituration in Et₂O, as a white solid (0.053 g; >95% yield).

¹H NMR (d6-DMSO) δ: 8.43 (br. s, 2H); 3.21-3.11 (m, 2H); 2.99-2.90 (m, 2H); 2.90-2.81 (m, 1H); 1.98-1.87 (m, 2H); 1.71-1.68 (m, 2H).

MS (ESI, m/z): 235.97 [M+H⁺] for $C_7H_{10}NI$; $t_R$=0.41 min.

AG.ii. 4-(iodoethynyl)-1-methylpiperidine

Starting from intermediate AG.i (0.3 g; 0.859 mmol) and proceeding in analogy to Preparation W, the title product was obtained, without further purification, as a white solid (0.175 g; 82% yield).

¹H NMR (d6-DMSO) δ: 2.81-2.65 (m, 2H); 2.61-2.56 (overlapped m, 1H); 2.36-2.13 (m, 5H); 1.87-1.72 (m, 2H); 1.61-1.46 (m, 2H).

MS (ESI, m/z): 249.94 [M+H⁺] for $C_8H_{12}NI$; $t_R$=0.41 min.

Preparation AH: 4-(iodoethynyl)-1-(oxetan-3-yl)piperidine

Starting from intermediate AG.i (0.3 g; 0.859 mmol) and proceeding in analogy to Preparation V, the title product was obtained, without further purification, as a yellowish solid (0.22 g; 90% yield).

¹H NMR (d6-DMSO) δ: 4.50 (t, J=6.5 Hz, 2H); 4.38 (t, J=6.1 Hz, 2H); 3.38-3.30 (overlapped m, 1H); 2.59-2.53 (overlapped m, 1H); 2.48-2.40 (overlapped m, 2H); 1.97-1.84 (m, 2H); 1.80-1.71 (m, 2H); 1.55-1.44 (m, 2H).

MS (ESI, m/z): 291.79 [M+H⁺] for $C_{10}H_{14}NOI$; $t_R$=0.41 min.

Preparation AI: (3S*,4S*)-3-fluoro-1-(4-iodobenzyl)piperidin-4-ol

Starting from (3S*,4S*)-3-fluoropiperidin-4-ol (0.29 g; 1.88 mmol) and 4-iodobenzyl bromide (0.500 g; 1.68 mmol) and proceeding in analogy to Preparation G, the title compound was obtained, after purification by CC (Hept-EA), as a yellowish gum (0.43 g; 77% yield).

¹H NMR (d6-DMSO) δ: 7.70-7.66 (m, 2H); 7.12-7.08 (m, 2H); 5.16 (d, J=4.8 Hz, 1H); 4.28 (m, 0.5H); 4.18 (m, 0.5H); 3.46 (s, 2H); 3.43 (m, 1H); 2.90 (m, 1H); 2.59 (m, 1H); 2.11-1.91 (m, 2H); 1.78 (m, 1H); 1.39 (m, 1H).

MS (ESI, m/z): 335.88 [M+H⁺] for $C_{12}H_{15}NOFI$; $t_R$=0.62 min.

Preparation AJ: (RS)-3,3-difluoro-1-(4-iodobenzyl)piperidin-4-ol

Starting from (RS)-3,3-difluoropiperidin-4-ol (0.5 g; 1.68 mmol) and 4-iodobenzyl bromide (0.32 g; 1.85 mmol) proceeding in analogy to Preparation G, the title compound was obtained, after purification by CC (Hept-EA), as a yellowish gum (0.445 g; 75% yield).

¹H NMR (d6-DMSO) δ: 7.70-7.67 (m, 2H); 7.10 (d, J=8.3 Hz, 2H); 5.49 (d, J=5.3 Hz, 1H); 3.65 (m, 1H); 3.51 (s, 2H); 2.77 (m, 1H); 2.54 (m, 1H); 2.44 (m, 1H); 2.25 (m, 1H); 1.75 (m, 1H); 1.61 (m, 1H).

MS (ESI, m/z): 353.73 [M+H⁺] for $C_{12}H_{14}NOF_2I$; $t_R$=0.54 min.

Preparation AK: 1-(bromoethynyl)-N-methylcyclopropan-1-amine hydrochloride

AK.i. Tert-butyl (1-(((tert-butyldiphenylsilyl)oxy)methyl)cyclopropyl)carbamate To a solution of tert-butyl (1-(hydroxymethyl)cyclopropyl)carbamate (3.5 g; 18.7 mmol) and imidazole (2.54 g; 37.4 mmol) in DCM (40 mL) was added TBDPSCl (4.11 mL; 18.7 mmol). The reaction mixture was stirred for 4 h. Water (50 mL) and DCM (20 mL) were added. The two layers were separated and the aq. phase was extracted twice with DCM (2×25 mL). The evaporation residue was purified by CC (EA-Hept) to afford the title compound as a colourless oil (8.85 g; >95% yield).

¹H NMR (d6-DMSO) δ: 7.64-7.60 (m, 4H); 7.49-7.40 (m, 6H); 7.20 (s, 1H); 3.66 (s, 2H); 1.36 (br. s, 9H); 1.00 (s, 9H); 0.71-0.65 (m, 2H); 0.64-0.60 (m, 2H).

MS (ESI, m/z): 426.1 [M+H⁺] for $C_{25}H_{35}NO_3Si$; $t_R$=1.11 min.

AK.ii. Tert-butyl (1-(((tert-butyldiphenylsilyl)oxy)methyl)cyclopropyl)(methyl)carbamate A suspension of NaH (60% in oil dispersion; 1.33 g; 33.2 mmol) in dry DMF (21 mL) was added dropwise to an ice-chilled solution of intermediate AK.i (7.85 g; 18.4 mmol) in dry DMF (13 mL). The reaction mixture was stirred for 30 min then MeI (1.38 mL; 22.1 mmol) was added dropwise. After 3 h stirring at rt, water (200 mL) was added carefully and the resulting suspension was extracted with EA (2×100 mL). The evaporation residue was purified by CC (Hept-EA) to afford the title compound as a white solid (5.78 g; 71% yield).

MS (ESI, m/z): 440.1 [M+H$^+$] for $C_{26}H_{37}NO_3Si$; $t_R$=1.15 min.

AK.iii.
1-(bromoethynyl)-N-methylcyclopropan-1-amine hydrochloride

Starting from the intermediate AK.ii (6.57 g; 14.9 mmol), and proceeding successively in analogy to Preparation Y, step Y.i (97% yield), Preparation J, step J.iii (91% yield) and Preparation X, steps X.iv (91% yield), X.v (98% yield) and X.vi (98% yield), the title compound was obtained, after final trituration in Et$_2$O, as a white solid (2.4 g).

$^1$H NMR (d6-DMSO) δ: 9.73 (s, 2H); 2.65 (s, 3H); 1.46-1.42 (m, 2H); 1.29-1.24 (m, 2H).

MS (ESI, m/z): 173.99 [M+H$^+$] for $C_6H_5NBr$; $t_R$=0.35 min.

Preparation AL: azetidin-3-yl (3-bromoprop-2-yn-1-yl)carbamate Hydrochloride Starting from intermediate AB.i (0.8 g; 2.55 mmol) and propargylamine (0.14 g; 2.55 mmol) and proceeding in analogy to Preparation H, step H.ii (98% yield), Preparation J, step J.v (80% yield) and Preparation U, step U.iii (88% yield), the title compound was obtained, after trituration in Et$_2$O, as an off-white solid (0.447 g).

$^1$H NMR (d6-DMSO) δ: 9.26-8.86 (m, 2H); 8.04 (m, 1H); 5.13 (m, 1H); 4.24-4.21 (m, 2H); 3.93-3.88 (m, 2H); 3.85 (d, J=5.8 Hz, 2H).

Preparation AM: 1-(3-iodoprop-2-yn-1-yl)piperidin-4-ol

Starting from 1-(prop-2-yn-1-yl)piperidin-4-ol (1 g; 7.18 mmol) and proceeding in analogy to Preparation K, step K.ii (60% yield), the title compound was obtained, after purification by CC (DCM-MeOH), as a white solid (1.14 g).

$^1$H NMR (d6-DMSO) δ: 4.55 (d, J=4.1 Hz, 1H); 3.41 (m, 1H); 3.36 (s, 2H); 2.63 (m, 2H); 2.14 (m, 2H); 1.70 (m, 2H); 1.37 (m, 2H).

MS (ESI, m/z): 265.93 [M+H$^+$] for $C_5H_{12}NOI$.; $t_R$=0.27 min.

Preparation AN: 3-(bromoethynyl)-1-(2-((tert-butyldimethylsilyl)oxy)ethyl)azetidine To a solution of intermediate AF.ii (0.38 g; 1.91 mmol) in DCM (20 mL) were added (tert-butyldimethylsilyloxy)acetaldehyde (1 mL; 5.25 mmol) and NaBH(OAc)$_3$ (2.39 g, 11.3 mmol). The reaction mixture was stirred overnight. Sat. aq. NaHCO$_3$ (30 mL) and DCM (10 mL) were added. The two layers were separated and the aq. layer was extracted with DCM (2×30 mL). The evaporation residue was purified by CC (Hept-EA) to afford the title compound as an orange oil (0.2 g; 33% yield).

$^1$H NMR (d6-DMSO) δ: 3.67-3.63 (m, 4H); 3.27 (t, J=7.7 Hz, 1H); 3.17-3.12 (m, 2H); 2.58 (t, J=5.7 Hz, 2H); 0.91 (s, 9H); 0.07 (s, 6H).

Preparation AO: (3R*,4S*)-3-fluoro-1-(4-iodobenzyl)piperidin-4-ol

Starting from (3R*,4S*)-3-fluoropiperidin-4-ol (0.3 g; 1.88 mmol) and 4-iodobenzyl bromide (0.500 g; 1.68 mmol) and proceeding in analogy to Preparation G, the title compound was obtained, after purification by CC (Hept-EA), as a yellowish oil (0.37 g; 65% yield).

$^1$H NMR (d6-DMSO) δ: 7.68 (d, J=8.3 Hz, 2H); 7.11 (d, J=8.3 Hz, 2H); 4.91 (d, J=4.8 Hz, 1H); 4.59-4.57 (m, 0.5H); 4.48 (m, 0.5H); 3.67-3.62 (m, 1H); 3.45 (s, 2H); 2.76-2.74 (m, 1H); 2.38-2.29 (m, 1H); 2.16-2.13 (m, 1H); 1.72-1.65 (m, 1H); 1.57 (m, 1H).

MS (ESI, m/z): 335.91 [M+H$^+$] for $C_{12}H_{15}NOFI$; $t_R$=0.49 min.

Preparation AP: 1-(4-iodobenzyl)azetidin-3-ol

AP.i. 1-chloro-3-((4-iodobenzyl)amino)propan-2-ol (4-iodophenyl)methanamine (1 g; 4.21 mmol) in water (15 mL), cooled to 5° C., was treated slowly with epichlorhydrin (0.939 mL; 11.9 mmol). The reaction was gradually warmed to rt and stirred for 15 h. The solid that formed was filtered off, washed with Hept and dried to a constant weight to afford the title compound as a white solid (1.29 g).

MS (ESI, m/z): 325.83 [M+H$^+$] for $C_{10}H_{13}NOClI$; $t_R$=0.56 min.

AP.ii. 1-(4-iodobenzyl)azetidin-3-ol

A mixture of intermediate AP.i (0.5 g; 1.34 mmol) and NaHCO$_3$ (0.28 g; 3.34 mmol) in MeCN (5 mL) was refluxed for 4 h. After cooling, the reaction mixture was filtered and the filtrate was concentrated to dryness. The residue was purified by CC (DCM-MeOH) to afford the title compound as a white solid (0.113 g; 29% yield).

MS (ESI, m/z): 289.78 [M+H$^+$] for $C_{10}H_{12}NOI$; $t_R$=0.49 min.

Preparation AQ: ((1R,2R)-2-(iodoethynyl)cyclopropyl)methanamine

Starting from tert-butyl (((1R,2R)-2-(iodoethynyl)cyclopropyl)methyl)carbamate (prepared as described in WO 2005/036964; 0.409 g; 1.27 mmol) and proceeding in analogy to Preparation U, step U.iii, the title compound was obtained, after purification by CC (DCM-MeOH containing 2% aq. NH$_4$OH), as a yellow oil (0.168 g; 60% yield).

$^1$H NMR (CDCl$_3$) δ: 2.91 (m, 1H); 2.79 (m, 1H); 2.09 (m, 1H); 1.63 (m, 1H); 1.25 (m, 1H); 0.93 (m, 1H).

Preparation AR: 4-(bromoethynyl)-1-(oxetan-3-yl)piperidin-4-ol

AR.i. Tert-butyl 4-(bromoethynyl)-4-hydroxypiperidine-1-carboxylate

Starting from tert-butyl 4-ethynyl-4-hydroxypiperidine-1-carboxylate (3.04 g; 13.5 mmol) and proceeding in analogy to Preparation J, step J.v, the title compound was obtained, after purification by CC (Hept-EA), as a colourless oil (4.05 g; 99% yield).

$^1$H NMR (d6-DMSO) δ: 5.76 (s, 1H); 3.54-3.45 (m, 2H); 3.21-3.18 (m, 2H); 1.73-1.69 (m, 2H); 1.57-1.50 (m, 2H); 1.39 (s, 9H).

MS (ESI, m/z): 303.91 [M+H$^+$] for C$_{12}$H$_{18}$NO$_3$Br; t$_R$=0.78 min.

AR.ii. 4-(bromoethynyl)piperidin-4-ol trifluoroacetate

Starting from intermediate AR.i (0.91 g; 3.01 mmol) and proceeding in analogy to Preparation I, step I.ii, the title compound was obtained as a brownish oil (1.0 g; >95% yield).

$^1$H NMR (d6-DMSO) δ: 8.47 (br. s, 2H); 3.57 (s, 1H); 3.19-3.11 (m, 2H); 3.09-3.00 (m, 2H); 1.96-1.89 (m, 2H); 1.88-1.80 (m, 2H).

MS (ESI, m/z): 204.00 [M+H$^+$] for C$_7$H$_{10}$ONBr; t$_R$=0.92 min.

AR.iii. 4-(bromoethynyl)-1-(oxetan-3-yl)piperidin-4-ol

Starting from intermediate AR.ii (0.35 g; 1.1 mmol) and proceeding in analogy to Preparation V, the title compound was obtained, without further purification as a brownish solid (0.144 g; 50% yield).

$^1$H NMR (d6-DMSO) δ: 5.60 (br. s, 1H); 4.51 (t, J=6.3 Hz, 2H); 4.38 (t, J=6.3 Hz, 2H); 3.43-4.33 (overlapped m, 1H); 2.48-2.27 (overlapped m, 2H); 2.20-1.98 (m, 2H); 1.83-1.70 (m, 2H); 1.69-1.56 (m, 2H).

MS (ESI, m/z): 259.95 [M+H$^+$] for C$_{10}$H$_{14}$NO$_2$Br; t$_R$=0.24 min.

Preparation AS: 4-(bromoethynyl)-4-fluoro-1-methylpiperidine

AS.i. 4-(bromoethynyl)-4-fluoropiperidine trifluoroacetate

Starting from tert-butyl 4-ethynyl-4-hydroxypiperidine-1-carboxylate (commercial; 3.09 g; 10.2 mmol) and proceeding successively in analogy to Preparation J, step J.v (>95% yield), Preparation U, step U.ii (75% yield) and Preparation I, step I.ii (>95% yield), the title compound was obtained, without further purification, as a beige solid (2.42 g).

$^1$H NMR (d6-DMSO) δ: 8.66 (br. s, 2H); 3.30-3.02 (m, 4H); 2.29-2.04 (m, 4H).

MS (ESI, m/z): 205.99 [M+H$^+$] for C$_7$H$_{13}$NBrF; t$_R$=0.42 min.

AS.ii. 4-(bromoethynyl)-4-fluoro-1-methylpiperidine

Starting from intermediate AS.i (0.35 g, 1.1 mmol) and proceeding in analogy to Preparation W, the title compound was obtained, without further purification, as a beige solid (0.168 g; 70% yield).

$^1$H NMR (d6-DMSO) δ: 2.52-2.35 (overlapped m, 4H); 2.23 (s, 3H); 2.02-1.88 (m, 4H).

MS (ESI, m/z): 220.01 [M+H$^+$] for C$_5$H$_{11}$NBrF; t$_R$=0.41 min.

Preparation AT: 4-(bromoethynyl)-4-fluoro-1-(oxetan-3-yl)piperidine

Starting from intermediate AS.i (0.35 g, 1.1 mmol) and proceeding in analogy to Preparation V, the title compound was obtained, without further purification, as a beige solid (0.283 g; >95% yield).

$^1$H NMR (d6-DMSO) δ: 4.52 (t, J=6.5 Hz, 2H); 4.41 (t, J=6.1 Hz, 2H); 3.47-3.39 (m, 1H); 2.36-2.21 (m, 4H); 2.02-1.91 (nm, 4H).

MS (ESI, m/z): 261.92 [M+H$^+$] for C$_{10}$H$_{13}$NOBrF; t$_R$=0.41 min.

Preparation AU: 3-fluoro-1-(4-iodobenzyl)azetidine

Starting from 3-fluoroazetidine hydrochloride (0.297 g; 2.53 mmol) and 4-iodobenzyl bromide (0.25 g; 0.842 mmol) and proceeding in analogy to Preparation G, the title compound was obtained as a yellowish oil (0.244 g; 100% yield).

MS (ESI, m/z): 332.91 [M+MeCN+H$^+$] for C$_{10}$H$_{11}$NFI; t$_R$=0.53 min.

Preparation AV: 3-bromoprop-2-yn-1-yl 4-methylpiperazine-1-carboxylate

Starting from intermediate AA.i (1.5 g; 5.43 mmol) and 1-methylpiperazime (0.550 g; 5.43 mmol) and proceeding in analogy to Preparation Y, step Y.iii, the title compound was obtained as a brownish oil (1.39 g; 98% yield).

$^1$H NMR (d6-DMSO) δ: 4.72 (s, 2H); 3.38-3.34 (m, 4H); 2.28-2.25 (m, 4H); 2.18 (s, 3H).

MS (ESI, m/z): 262.92 [M+H$^+$] for C$_9$H$_{13}$N$_2$O$_2$Br; t$_R$=0.42 min.

Preparation AW: tert-butyl (2S,4S)-2-(bromoethynyl)-4-fluoropyrrolidine-1-carboxylate Starting from tert-butyl (2S,4S)-4-fluoro-2-formylpyrrolidine-1-carboxylate (commercial; 0.641 g; 2.95 mmol) and proceeding successively in analogy to Preparation X, steps X.iv (68% yield) and X.v (95% yield), the title compound was obtained, after purification by CC (EA-Hept), as a yellowish oil (0.55 g).

$^1$H NMR (d6-DMSO) δ: 5.23 (m, 1H); 4.66 (m, 1H); 3.77 (m, 1H); 3.58 (m, 1H); 2.42 (m, 1H); 2.25 (m, 1H); 1.49 (s, 9H).

MS (ESI, m/z): 293.94 [M+H$^+$] for C$_{11}$H$_{15}$NO$_2$BrF; t$_R$=0.85 min.

Preparation AX: (R)-1-((1S,2S)-2-(bromoethynyl)cyclopropyl)ethane-1,2-diol

AX.i. ((1S,2S)-2-((R)-2,2-dimethyl-1,3-dioxolan-4-yl)cyclopropyl)methanol

To a mixture of trimethylsulfonium iodide (1.32 g; 6.0 mmol) and NaH (60% dispersion in oil; 0.24 g; 6.0 mmol) was added DMSO (6 mL) dropwise. The reaction mixture was stirred 1 h, and a solution of tert-butyl (R,E)-3-(2,2-dimethyl-1,3-dioxolan-4-yl)acrylate (as prepared in Sugano et al., *Chemistry—A European Journal* (2012), 18(31), 9682-9690; 1.14 g; 5.0 mmol) in THF (6 mL) was added dropwise. The reaction mixture was stirred at rt overnight. Brine (30 mL) was added dropwise and the resulting mixture was extracted with Et$_2$O (3×30 mL). The combined extracts were washed with brine (4×10 mL), dried over Na$_2$SO$_4$, filtered and carefully evaporated to dryness. The crude (1.2 g) was taken up in THF (20 mL) and the solution was cooled to 0° C. LiAlH$_4$ (0.38 g; 10 mmol) was added. The reaction proceeded at 0° C. for 1 h. Water (0.3 mL), 1M NaOH (0.3 mL) and water (1 mL) were added. The resulting mixture was filtered through a pad of celite and washed with THF (50 mL). The filtrate was concentrated to dryness and the residue was purified by CC (Hept-EA) to afford the title compound as a yellowish oil (0.78 g; 75% yield).

$^1$H NMR (CDCl$_3$) δ: 4.09 (dd, J=6.0, 8.0 Hz, 1H); 3.69 (m, 1H); 3.61 (td, J=6.0, 7.6 Hz, 1H); 3.53-3.45 (m, 2H); 1.43 (s, 3H); 1.34 (s, 3H); 1.05 (m, 1H); 0.89 (m, 1H); 0.68 (dt, J=5.0, 8.5 Hz, 1H); 0.58 (dt, J=5.1, 8.4 Hz, 1H).

AX.ii. (R)-4-((1S,2S)-2-ethynylcyclopropyl)-2,2-dimethyl-1,3-dioxolane

Starting from intermediate AX.i (2.52 g; 14.6 mmol) and proceeding as described in Preparation J, steps J.iii and J.iv, the title compound was obtained, after purification by CC (EA-Hept), as a yellowish oil (1.74 g; 71% yield over 2 steps).

$^1$H NMR (CDCl$_3$) δ: 4.13 (dd, J=6.0, 8.1 Hz, 1H); 3.77 (m, 1H); 3.68 (m, 1H); 1.83 (d, J=2.1 Hz, 1H); 1.44 (s, 3H); 1.34 (m, 1H); 1.35 (s, 3H); 1.22-1.27 (m, 1H); 0.92-1.02 (m, 2H).

AX.iii. (R)-1-((1S,2S)-2-(bromoethynyl)cyclopropyl)ethane-1,2-diol

Starting from intermediate AX.ii (0.633 g; 3.81 mmol) and proceeding as described in Preparation J, steps J.v and J.vi, the title compound was obtained, after purification by CC (EA-Hept), as a yellowish oil (0.165 g; 21% yield over 2 steps).

$^1$H NMR (CDCl$_3$) δ: 3.80 (dd, J=3.2, 11.2 Hz, 1H); 3.63 (dd, J=7.4, 11.1 Hz, 1H); 3.30 (td, J=3.2, 7.0 Hz, 1H); 1.26-1.33 (m, 3H); 0.88-0.94 (m, 2H).

Preparation AY: 3-(bromoethynyl)-3-methylazetidine hydrochloride

Starting from tert-butyl 3-(hydroxymethyl)-3-methylazetidine-1-carboxylate (1.83 g; 9.1 mmol) and proceeding successively in analogy to Preparation J, steps J.iii to J.v and Preparation U, step U.iii, the title compound was obtained as a white solid (0.7 g; 37% yield).

$^1$H NMR (d6-DMSO) δ: 9.61 (br. s, 1H); 9.27 (br. s, 1H); 4.06 (d, J=9.7 Hz, 2H); 3.79 (d, J=10.0 Hz, 2H); 1.56 (s, 3H).

MS (ESI, m/z): 174.0 [M+H$^+$] for C$_6$H$_5$NBr; t$_R$=0.34 min.

Preparation AZ: (3RS)-3-(bromoethynyl)-3-fluoro-1-methylpyrrolidine

AZ.i. (3RS)-3-(bromoethynyl)-3-fluoropyrrolidine hydrochloride

Starting from (3RS)-tert-butyl 3-ethynyl-3-hydroxypyrrolidine-1-carboxylate (4.49 g; 21.3 mmol) and proceeding successively as described in Preparation J, steps J.v and Preparation U, steps U.ii and U.iii, the title compound was obtained as a white solid (1.36 g; 57% yield).

$^1$H NMR (d6-DMSO) δ: 9.78 (s, 1H); 3.72 (m, 1H); 3.57-3.44 (m, 2H); 3.27 (m, 1H); 2.55 (m, 1H); 2.37 (m, 1H).

MS (ESI, m/z): 232.97 [M+MeCN+H$^+$] for C$_6$H$_7$NBrF; t$_R$=0.22 min.

AZ.ii. 3-(bromoethynyl)-3-fluoro-1-methylpyrrolidine

To a solution of intermediate AZ.i (0.350 g, 1.53 mmol) in DCM (20 mL) were added 37% aq. formaldehyde (0.359 mL; 4.6 mmol) and NaBH(OAc)$_3$ (1.95 g, 9.19 mmol). The reaction mixture was stirred at rt for 30 min. Sat. aq. NaHCO$_3$ (50 mL) and DCM (60 mL) were added. The aq. layer was extracted with DCM (2×50 mL). The evaporation residue was purified by CC (DCM-MeOH) to afford the title compound as a yellow oil (0.239 g; 76% yield).

$^1$H NMR (d6-DMSO) δ: 2.98 (m, 1H); 2.76 (m, 1H); 2.69 (m, 1H); 2.42 (m, 1H); 2.29-2.21 (overlapped m, 2H); 2.25 (overlapped s, 3H).

MS (ESI, m/z): 205.99 [M+H$^+$] for C$_7$H$_9$NBrF; t$_R$=0.41 min.

Preparation BA: 3-(bromoethynyl)-3-ethylazetidine hydrochloride

Starting from tert-butyl 3-ethyl-3-(hydroxymethyl)azetidine-1-carboxylate (commercial; 1.35 g; 6.31 mmol) and proceeding successively in analogy to Preparation J, steps J.iii to J.v and Preparation U, step U.iii, the title compound was obtained as a white solid (0.8 g, 3.48 mmol).

$^1$H NMR (d6-DMSO) δ: 9.40 (br. s, 2H); 4.02 (d, J=11.1 Hz, 2H); 3.81 (d, J=11.1 Hz, 2H); 1.86 (q, J=7.4 Hz, 2H), 0.92 (t, J=7.3 Hz, 3H).

MS (ESI, m/z): 188.02 [M+H$^+$] for C$_6$H$_{10}$NBr; t$_R$=0.44 min.

Preparation BB: 3-(bromoethynyl)-1-methylazetidine

Starting from the compound of Preparation AF (7.42 g; 37.8 mmol) and proceeding in analogy to Preparation AZ, step AZ.ii, the title compound was obtained, after purification by CC (DCM-MeOH), as a orange oil (6.08 g, 93% yield).

$^1$H NMR (d6-DMSO) δ 3.45-3.41 (m, 2H); 3.16 (m, 1H); 2.93-2.89 (m, 2H); 2.16 (s, 3H).

MS (ESI, m/z): 173.90 [M+H$^+$] for C$_6$H$_{10}$NBr; t$_R$=0.22 min.

Preparation BC: (3RS)-3-(bromoethynyl)-3-methylpyrrolidine hydrochloride

Starting from tert-butyl (3RS)-3-(hydroxymethyl)-3-methylpyrrolidine-1-carboxylate (commercial, 4.20 g; 19.5 mmol) and proceeding successively in analogy to Preparation J, steps J.iii to J.v and Preparation U, step U.iii, the title compound was obtained, after purification by CC (DCM-MeOH), as a white solid (2.02 g; 3.48 mmol).

$^1$H NMR (d6-DMSO) δ: 9.51 (br. s, 1H); 9.33 (br. s, 1H); 3.35-3.25 (m, 3H); 3.04 (m, 1H); 2.15 (m, 1H); 1.91 (m, 1H); 1.37 (s, 3H).

MS (ESI, m/z): 229.0 [M+MeCN+H$^+$] for C$_7$H$_{10}$NBr; t$_R$=0.40 min.

Preparation BD: (3RS)-3-(bromoethynyl)-1-methylpyrrolidine

BD.i. (3RS)-3-(bromoethynyl)pyrrolidine trifluoroacetate

Starting from tert-butyl (3RS)-3-ethynylpyrrolidine-1-carboxylate (commercial; 1.70 g; 8.75 mmol) and proceeding successively in analogy to Preparation J, step J.v and Preparation I, step I.ii, the title compound was obtained as a brown oil (2.11 g; 84% yield).

¹H NMR (d6-DMSO) δ: 9.19-8.98 (m, 2H); 3.45-3.36 (m, 1H); 3.31-3.25 (m, 1H); 3.23 (t, J=7.3 Hz); 3.21-3.15 (m, 1H); 3.10 (m, 1H); 2.26-2.16 (m, 1H); 1.97-1.86 (m, 1H).
MS (ESI, m/z): 173.9 [M+H$^+$] for $C_6H_5NBr$; $t_R$=0.29 min.

BD.ii. (3RS)-3-(bromoethynyl)-1-methylpyrrolidine

Starting from intermediate BC.i (0.2 g; 0.715 mmol) and proceeding in analogy to Preparation AZ, step AZ.ii, the title compound was obtained, after purification by CC (DCM-MeOH), as a beige oil (0.072 g; 54% yield).
¹H NMR (d6-DMSO) δ: 3.01-2.92 (m, 1H); 2.73 (m, 1H); 2.49-2.46 (m, 1H); 2.42 (m, 1H); 2.31 (m, 1H); 2.22 (s, 3H); 2.16-2.06 (m, 1H); 1.76-1.68 (m, 1H).
MS (ESI, m/z): 184.0 [M+H$^+$] for $C_7H_{10}NBr$; $t_R$=0.31 min.

Preparation BE: methyl (2R)-4-(6-(2-fluoro-4-iodophenyl)-3-oxo-1H-pyrrolo[1,2-c]imidazol-2(3H)-yl)-2-methyl-2-(methylsulfonyl)butanoate BE.i. Methyl (2R)-4-(6-bromo-3-oxo-1H-pyrrolo[1,2-c]imidazol-2(3H)-yl)-2-methyl-2-(methylsulfonyl)butanoate To a mixture of (2R)-4-(6-bromo-3-oxo-1H-pyrrolo[1,2-c]imidazol-2(3H)-yl)-2-methyl-2-(methylsulfonyl)butanoic acid (prepared as described in WO 2015/132228; 4.82 g; 12.7 mmol) in DCM (89 mL) and MeOH (89 mL), cooled at 0° C., was added dropwise TMS-diazomethane (2M in hexanes; 15.1 mL; 30.2 mmol) over 5 min. The reaction mixture was stirred at rt for 2.5 h. AcOH (3.3 mL; 57.2 mmol) was added. After concentration to dryness, the residue was co-evaporated with cyclohexane (2×50 mL) to afford the title compound as a light brown solid (5 g; >95% yield).
¹H NMR (d6-DMSO) δ: 7.35 (d, J=0.8 Hz, 1H); 6.22 (m, 1H); 4.39 (s, 2H); 3.61 (m, 1H); 3.51 (s, 3H); 3.47 (m, 1H); 3.12 (s, 3H); 2.61 (m, 1H); 2.06 (m, 1H); 1.58 (s, 3H).
MS (ESI, m/z): 394.86 [M+H$^+$] for $C_{13}H_{17}N_2O_5BrS$; $t_R$=0.76 min.

BE.ii. (2R)-4-(6-(4-((tert-butoxycarbonyl)amino)-2-fluorophenyl)-3-oxo-1H-pyrrolo[1,2-c]imidazol-2(3H)-yl)-2-methyl-2-(methylsulfonyl)butanoic Acid Intermediate BE.i (2.45 g; 6.22 mmol), 4-(Boc-amino)-2-fluorophenylboronic acid (2.64 g, 9.93 mmol), $Na_2CO_3$ (1.71 g, 16.1 mmol) and $Pd(PPh_3)_4$(1.50 g, 1.29 mmol) were dissolved in dioxane (30 mL) and water (9 mL). The reaction was then stirred at 90° C. for 1.5 h. The reaction mixture was diluted with water (50 mL) and EA (60 mL). The phases were separated. The aq. layer was extracted with EA (2×60 mL). The evaporation residue was purified by CC using a Hept/(EA-MeOH 9-1) gradient to afford the title compound as a grey solid (2.86 g, 88% yield).
¹H NMR (d6-DMSO) δ: 9.60 (s, 1H); 7.61 (t, J=8.8 Hz, 1H); 7.43 (m, 1H); 7.39 (m, 1H); 7.22 (dd, J=1.9, 8.6 Hz, 1H); 6.52 (m, 1H); 4.42 (s, 2H); 3.65 (m, 1H); 3.53-3.45 (overlapped m, 1H); 3.51 (s, 3H); 3.13 (s, 3H); 2.64 (m, 1H); 2.08 (m, 1H); 1.60 (s, 3H); 1.48 (s, 9H).
MS (ESI, m/z): 524.1 [M+H$^+$] for $C_{24}H_{30}N_3O_7FS$; $t_R$=0.91 min.

BE.iii. (2R)-4-(6-(4-amino-2-fluorophenyl)-3-oxo-1H-pyrrolo[1,2-c]imidazol-2(3H)-yl)-2-methyl-2-(methylsulfonyl)butanoic Acid To a suspension of intermediate BE.ii (2.86 g, 5.46 mmol) in dioxane (2.1 mL) was added 4M HCl in dioxane (21 mL). The reaction mixture was stirred for 3 h. The reaction mixture was concentrated to dryness. The residue was partitioned between sat. aq. $NaHCO_3$ (100 mL) and DCM-MeOH 9-1 (70 mL). The phases were separated. The aq. layer was extracted with DCM-MeOH 9-1 (2×70 mL). The evaporation residue gave the title crude product as a yellowish foam (2.75 g; >95% yield).
¹H NMR (d6-DMSO) δ: 7.33 (t, J=8.7 Hz, 1H); 7.21 (m, 1H); 6.42-6.34 (m, 3H); 5.43 (s, 2H); 4.38 (s, 2H); 3.65 (m, 1H); 3.50 (s, 3H); 3.50-3.44 (overlapped m, 1H); 3.13 (s, 3H); 2.63 (m, 1H); 2.07 (m, 1H); 1.60 (s, 3H).
MS (ESI, m/z): 424.1 [M+H$^+$] for $C_{19}H_{22}N_3O_5FS$; $t_R$=0.66 min.

BE.iv. Methyl (2R)-4-(6-(2-fluoro-4-iodophenyl)-3-oxo-1H-pyrrolo[1,2-c]imidazol-2(3H)-yl)-2-methyl-2-(methylsulfonyl)butanoate $TsOH.H_2O$ (3.31 g; 17.4 mmol) was suspended in MeCN (15 mL) and a solution of intermediate BE.iii (2.75 g, 5.4 mmol) in MeCN (20 mL) was added. A solution of sodium nitrite (1.05 g, 14.7 mmol) and KI (2.25 g; 13.4 mmol) in water (5.5 mL) was added dropwise keeping IT below 31° C. The reaction mixture was stirred at rt for 1 h. Sat. aq. $NaHCO_3$ (40 mL) and EA (100 mL) were added. The two phases were separated and the aq. layer was extracted with EA (4×50 mL). The evaporation residue was purified by CC (Hept-EA-MeOH) to afford the title compound as an orangeish solid (2.04 g, 70% yield).
¹H NMR (d6-DMSO) δ: 7.68 (dd, J=1.3, 10.8 Hz, 1H); 7.65-7.51 (m, 3H); 6.58 (m, 1H); 4.44 (s, 2H); 3.64 (m, 1H); 3.53-3.46 (overlapped m, 1H); 3.52 (s, 3H); 3.13 (s, 3H); 2.63 (m, 1H); 2.08 (m, 1H); 1.60 (s, 3H).
MS (ESI, m/z): 535.0 [M+H$^+$] for $C_{19}H_{20}N_2O_5FIS$; $t_R$=0.91 min.

Preparation BF: (2R)—N-hydroxy-4-(6-(4-iodophenyl)-3-oxo-1H-pyrrolo[1,2-c]imidazol-2(3H)-yl)-2-methyl-2-(methylsulfonyl)butanamide Starting from intermediate BE.i (2.55 g; 6.48 mmol) and 4-aminophenylboronic acid hydrochloride (1.72 g; 9.64 mmol) and proceeding successively in analogy to Preparation BE, steps BE.ii (49% yield) and BE.iv (33% yield), the title compound was obtained, after purification by CC (Hept-EA-MeOH), as a orange solid (0.54 g).
¹H NMR (d6-DMSO) δ: 7.70-7.67 (m, 3H); 7.49-7.45 (m, 2H); 6.56 (m, 1H); 4.41 (s, 2H); 3.64 (m, 1H); 3.51 (s, 3H); 3.48 (m, 1H); 3.13 (s, 3H); 2.64 (m, 1H); 2.07 (m, 1H); 1.60 (s, 3H).
MS (ESI, m/z): 516.9 [M+H$^+$] for $C_{19}H_{21}N_2O_5IS$; $t_R$=0.90 min.

Preparation BG: (3RS)-3-(bromoethynyl)-1-(oxetan-3-yl)pyrrolidine

Starting from intermediate BD.i (0.224 g; 0.77 mmol) and proceeding in analogy to Preparation S, the title compound was obtained as a beige oil (0.06 g; 3.48 mmol).
¹H NMR (d6-DMSO) δ: 4.55 (td, J=2.0, 6.4 Hz, 2H); 4.43 (m, 2H); 3.59 (m, 1H); 2.99 (m, 1H); 2.80 (t, J=8.3 Hz, 1H); 2.55 (m, 1H); 2.47 (m, 1H); 2.35 (m, 1H); 2.13 (m, 1H); 1.75 (m, 1H).
MS (ESI, m/z): 230.0 [M+H$^+$] for $C_9H_{12}NOBr$; $t_R$=0.29 min.

Preparation BH: (2S,3R)-3-(bromoethynyl)-2-methylazetidine

BH.i. Tert-butyl (2S,3R)-1-benzyl-3-((benzyloxy)methyl)azetidine-2-carboxylate and tert-butyl (2R,3R)-1-benzyl-3-((benzyloxy)methyl)azetidine-2-carboxylate A solution of tert-butyl (2R)—N-benzyl-N-(3-(benzyloxy)-2-chloropropyl)glycinate (11 g, 27.2 mmol) in THF (110 mL) and HMPA (11 mL) was cooled to −78° C. and LiHMDS (1M in THF, 41 mL; 41 mmol) was added slowly over a period of 30 min. The mixture was allowed to warm to 0° C. over a period of 3 h. The reaction was quenched by addition of sat. aq. NH$_4$Cl (150 mL) and the aq. phase was extracted 3 times with EA (100 mL). The evaporation residue was purified by CC (Hept-EA) to afford first the (2S,3R)-isomer (5.9 g, 59% yield) and then the (2R,3R)-isomer (2.1 g; 21% yield).

(2S,3R)-isomer:
$^1$H NMR (CDCl$_3$) δ: 7.37-7.24 (m, 10H); 4.53-4.49 (m, 2H); 3.82 (dd, J=9.2, 6.5 Hz, 1H); 3.78-3.70 (m, 3H); 3.64 (d, J=12.7 Hz, 1H); 3.23 (d, J=6.1 Hz, 1H); 3.03 (t, J=7.4 Hz, 1H); 2.87 (ddt, J=16.8, 10.7, 5.5 Hz, 1H); 1.35 (s, 9H).
MS (ESI, m/z): 368.1 [M+H$^+$] for C$_{23}$H$_{30}$NO$_3$; t$_R$=0.78 min.

BH.ii. ((2R,3R)-1-benzyl-3-((benzyloxy)methyl)azetidin-2-yl)methanol

A solution of the (2R,3R)-isomer of intermediate BH.i (2.0 g; 5.44 mmol) in THF (10 mL) was cooled to 0° C. and a solution of LiAlH$_4$ (2M in THF, 5.5 mL; 10.9 mmol) was slowly added. The mixture was stirred at 0° C. for 1 h and then warmed to ambient temperature. After 2 h the reaction was quenched by careful addition of 1M aq. NaOH (4 mL) and the resulting slurry was stirred for 1 h. The solid was filtered off and the filtrate was concentrated to dryness. The crude product (1.58 g, 93% yield) was used without further purification in the following step.
$^1$H NMR (CDCl$_3$) δ: 7.41-7.26 (m, 10H); 4.57-4.52 (m, 2H); 3.69 (d, J=12.6 Hz, 1H); 3.63 (d, J=12.6 Hz, 1H); 3.54 (dd, J=9.5, 5.4 Hz, 1H); 3.51-3.46 (m, 2H); 3.35 (d, J=3.7 Hz, 2H); 3.26 (dt, J=7.3, 3.6 Hz, 1H); 2.89 (br. s, 1H, OH); 2.83 (dd, J=8.5, 6.7 Hz, 1H); 2.75 (dtd, J=12.7, 8.5, 7.8, 6.2 Hz, 1H).
MS (ESI, m/z): 298.2 [M+H$^+$] for C$_{19}$H$_{24}$NO$_2$; t$_R$=0.65 min.

BH.iii. ((2R,3R)-1-benzyl-3-((benzyloxy)methyl)azetidin-2-yl)methyl Methanesulfonate A solution of intermediate BH.ii (1.4 g; 4.71 mmol) in DCM (30 mL) was cooled to 0° C. and TEA (0.99 mL; 7.06 mmol) was added followed by MsCl (0.44 mL; 5.65 mmol). After 10 min, water (100 mL) was added to the reaction mixture and the two phases were separated. The aq. phase was extracted with DCM (100 mL). The evaporation residue was purified by CC (Hept-EA) to afford the title compound as a colourless oil (1.32 g; 66% yield).
$^1$H NMR (CDCl$_3$) δ: 7.38-7.24 (m, 10H); 4.53-4.49 (m, 2H); 4.15-4.09 (m, 2H); 4.09-4.01 (m, 1H); 3.75 (d, J=12.7 Hz, 1H); 3.59 (d, J=12.7 Hz, 1H); 3.50-3.36 (m, 3H); 2.92 (s, 3H); 2.82 (m, 1H); 2.68-2.61 (m, 1H).
MS (ESI, m/z): 376.0 [M+H$^+$] for C$_{20}$H$_{26}$NO$_4$S; t$_R$=0.69 min.

BH.iv. (2S,3R)-1-benzyl-3-((benzyloxy)methyl)-2-methylazetidine

To a solution of intermediate BH.iii (1.32 g; 3.52 mmol) in THF (10 mL) at 0° C. was added a solution of LiAlH$_4$ (2M in THF, 3.5 mL; 7.03 mmol). After 1 h, the mixture was warmed to rt and stirred for 4 h. The reaction was quenched by careful addition of 1M NaOH (3 mL). The resulting slurry was stirred for 1 h and the filtered. The filtrate was concentrated to dryness and the residue was purified by CC (Hept-EA) to give the title compound as a colourless oil (0.69 g, 70% yield).
$^1$H NMR (CDCl$_3$) δ: 7.40-7.24 (m, 10H); 4.54-4.50 (m, 2H); 3.68 (d, J=12.5 Hz, 1H); 3.55-3.49 (m, 4H); 3.06 (q, J=6.6 Hz, 1H); 2.71 (t, J=7.8 Hz, 1H); 2.43 (m, 1H); 1.11 (d, J=6.1 Hz, 3H).
MS (ESI, m/z): 282.1 [M+H$^+$] for C$_{19}$H$_{24}$N$_2$O; t$_R$=0.68 min.

BH.v. Tert-butyl (2S,3R)-3-(hydroxymethyl)-2-methylazetidine-1-carboxylate

A flask was charged with a solution of intermediate BH.iv (0.69 g; 2.45 mmol) in MeOH (50 mL) and Pd/C (10 wt % Pd; 0.2 g). The mixture was hydrogenated under atmospheric pressure of hydrogen (balloon). After 24 h, the mixture was filtered and the filtrate was concentrated to dryness. The residue was taken up in a THF-H$_2$O mixture (1-1, 40 mL) and Boc$_2$O (0.75 g; 3.43 mmol) was added followed by solid NaHCO$_3$ (0.29 g; 3.43 mmol) and 1M aq. NaOH (10 mL). The solution was stirred for 48 h. The aq. phase was extracted 3 times with EA (100 mL). The evaporation residue was purified by CC (Hept-EA) to afford the title compound as a colourless oil (0.285 g; 58% yield).
$^1$H NMR (CDCl$_3$) δ: 4.05 (p, J=6.1 Hz, 1H); 3.92 (t, J=8.5 Hz, 1H); 3.77 (d, J=6.7 Hz, 2H); 3.60 (dd, J=8.7, 5.9 Hz, 1H); 2.30 (dp, J=8.3, 6.2 Hz, 1H); 1.46 (s, 9H); 1.42 (d, J=6.3 Hz, 3H).
MS (ESI, m/z): 202.2 [M+H$^+$] for C$_{10}$H$_{19}$NO$_3$; t$_R$=0.63 min.

BH.vi. Tert-butyl (2S,3R)-3-formyl-2-methylazetidine-1-carboxylate

Starting from intermediate BH.v (0.285 g; 1.42 mmol) and proceeding successively in analogy to Preparation J. step J.iii, the title compound was obtained, after purification by CC (Hept-EA), as a colourless oil (0.23 g, 82% yield).
$^1$H NMR (CDCl$_3$) δ: 9.83 (d, J=2.3 Hz, 1H); 4.45 (p, J=6.2 Hz, 1H); 4.05 (dd, J=8.8, 6.4 Hz, 1H); 3.99 (t, J=8.8 Hz, 1H); 3.01-2.97 (m, 1H); 1.51 (d, J=6.3 Hz, 3H); 1.47 (s, 9H).

BH.vii. Tert-butyl (2S,3R)-3-(2,2-dibromovinyl)-2-methylazetidine-1-carboxylate A solution of CBr$_4$ (0.78 g, 2.31 mmol) in DCM (2 mL) was cooled to −20° C. and a solution of PPh$_3$ (1.26 g, 4.62 mmol) in DCM (3 mL) was added. The mixture was stirred for 30 min and then cooled to −78° C. TEA (0.322 mL, 2.31 mmol) was added followed by intermediate BH.vi (0.23 g, 1.15 mmol) in DCM (2 mL). After 1 h at −78° C. the mixture was warmed to ambient temperature over 30 min. The mixture was concentrated to half its volume and Et$_2$O was added. The precipitated solid was filtered and the filtrate was concentrated to dryness. The residue was purified by CC (Hept-EA) to afford the title compound as a colourless oil (0.23 g, 56% yield).

$^1$H NMR (CDCl$_3$) δ: 6.63 (d, J=8.5 Hz, 1H); 4.11-4.05 (m, 2H); 3.68 (dd, J=8.6, 6.5 Hz, 1H); 2.99 (m, 1H); 1.48-1.46 (m, 12H).

MS (ESI, m/z): 396.87 [M+MeCN+H$^+$] for C$_{11}$H$_{17}$NO$_2$Br$_2$; t$_R$=0.95 min.

BH.viii. Tert-butyl (2S,3R)-3-(bromoethynyl)-2-methylazetidine-1-carboxylate To a solution of intermediate BH.vii (0.23 g, 0.648 mmol) in THF (1 mL) was added TBAF (1M in THF; 3 mL; 3 mmol) and the mixture was stirred for 18 h. The mixture was concentrated and the residue was purified by CC (Hept-EA) to afford the title compound as a colorless oil (0.2 g; >95% yield).

$^1$H NMR (CDCl$_3$) δ: 4.24 (p, J=6.3 Hz, 1H); 4.01 (ddd, J=8.7, 8.1, 0.6 Hz, 1H); 3.82 (ddd, J=7.9, 7.1, 0.6 Hz, 1H); 2.84 (ddd, J=8.7, 7.1, 6.4 Hz, 1H); 1.46 (s, 9H); 1.44 (d, J=6.3 Hz, 3H).

MS (ESI, m/z): 316.97 [M+MeCN+H$^+$] for C$_{11}$H$_{16}$NO$_2$B$_2$; t$_R$=0.90 min.

BH.ix. (2S,3R)-3-(bromoethynyl)-2-methylazetidine

To a solution of intermediate BH.viii (0.162 g, 0.589 mmol) in MeCN (0.7 mL) was added a solution of concentrated H$_2$SO$_4$ (0.17 mL, 3.16 mmol) in water (1.5 mL). The reaction was stirred at 60° C. for 3 h. The solution was cooled to rt, then 15% aq. NaOH was added until pH=7. The mixture was concentrated to dryness. The residue was taken up in a DCM-MeOH mixture (9-1, 30 mL) and stirred for 40 min. After filtration and evaporation to dryness, the title compound was obtained as a yellowish oil (0.08 g; 78% yield).

$^1$H NMR (d$_6$-DMSO) δ: 4.05 (m, 1H); 3.65-3.53 (m, 2H); 3.14 (m, 1H); 1.27 (d, J=6.4 Hz, 3H).

Preparation BI: (2R,3S)-3-(bromoethynyl)-2-methylazetidine

Starting from tert-butyl (2S)—N-benzyl-N-(3-(benzyloxy)-2-chloropropyl)glycinate (12.3 g; 30.4 mmol) and proceeding in analogy to Preparation BH, the title compound was obtained as a yellowish solid (0.08 g).

$^1$H NMR (d$_6$-DMSO) δ: 4.06 (m, 1H); 3.65-3.55 (m, 2H); 3.15 (m, 1H); 1.27 (d, J=6.4 Hz, 3H).

Preparation BJ: ((2R,4R)-4-(bromoethynyl)-1-methylpyrrolidin-2-yl)methanol

BJ.i. Tert-butyl (2R,4R)-2-(((tert-butyldiphenylsilyl)oxy)methyl)-4-((methylsulfonyl)oxy)pyrrolidine-1-carboxylate To a stirred solution of tert-butyl (2R,4R)-2-(((tert-butyldiphenylsilyl)oxy)methyl)-4-hydroxypyrrolidine-1-carboxylate (prepared as described in WO 2014/078609; 2 g; 4.39 mmol) and TEA (1.22 mL; 8.78 mmol) in DCM (22 mL) at 0° C. was added MsCl (0.35 mL; 4.52 mmol). The reaction mixture was allowed to reach rt over 30 min. Sat. aq. NaHCO$_3$ (15 mL) was added and the phases were separated. The aq. layer was extracted once with DCM (10 mL). The evaporation residue afforded the crude title compound as a yellow gum (2.37 g; >95% yield).

MS (ESI, m/z): 534.2.0 [M+H$^+$] for C$_{27}$H$_{39}$NO$_6$SSi; t$_R$=1.08 min.

BJ.ii. Tert-butyl (2R,4RS)-2-(((tert-butyldiphenylsilyl)oxy)methyl)-4-iodopyrrolidine-1-carboxylate To a solution of intermediate BJ.i (6.63 g, 12.4 mmol) in 2-butanone (47 mL) was added NaI (5.58 g; 37.3 mmol). The reaction mixture was stirred at 80° C. for 24 h. The reaction mixture was cooled to rt, diluted with water (30 mL) and EA (20 mL). The aq. layer was extracted once with EA (20 mL). The evaporation residue was purified by CC (Hept-EA) to afford the title product as a colourless oil (5.83 g; 83% yield).

MS (ESI, m/z): 566.1 [M+H$^+$] for C$_{26}$H$_{36}$NO$_3$IS; t$_R$=1.16 min.

BJ.iii. Tert-butyl (2R,4R)-2-(((tert-butyldiphenylsilyl)oxy)methyl)-4-((trimethylsilyl)ethynyl)pyrrolidine-1-carboxylate EtMgBr (1M in THF; 15.4 mL; 15.4 mmol) was added dropwise to a solution of TMS-acetylene (2.2 mL; 15.4 mmol) dissolved in THF (15 mL). The mixture was stirred 15 min at rt then 1 h at 50° C. In a separated flask, FeBr$_2$ (0.33 g; 1.54 mmol) and intermediate BJ.ii (5.8 g; 10.3 mmol) were dissolved in THF (35 mL) and NMP (3 mL). The previous warmed Grignard reagent solution was added dropwise over 8 min. The resulting dark mixture was stirred at rt for 3 h. EA (150 mL) and water (120 mL). The two layers were separated. The evaporation residue was purified by CC (Hept-EA) to afford the title compound as an orange gum (2.49 g; 45% yield).

MS (ESI, m/z): 536.2 [M+H$^+$] for C$_{31}$H$_{45}$NO$_3$Si$_2$; t$_R$=1.20 min.

BJ.iv. Tert-butyl (2R,4RS)-2-(((tert-butyldiphenylsilyl)oxy)methyl)-4-ethynylpyrrolidine-1-carboxylate A solution of intermediate BJ.iii (2.49 g; 4.65 mmol) in MeOH (16 mL) was treated by K$_2$CO$_3$ (0.84 g, 6.06 mmol). The mixture was stirred at rt for 1 h. The reaction mixture was diluted in DCM (150 mL) and water (50 mL). The two layers were separated then the aq. layer was extracted with DCM-MeOH mixture (9-1, 80 mL). The evaporation residue afforded the crude title product as a yellow oil (2.23 g; >95% yield).

MS (ESI, m/z): 464.2 [M+H$^+$] for C$_{28}$H$_{37}$NO$_3$Si; t$_R$=1.13 min.

BJ.v. ((2R,4R)-4-(bromoethynyl)pyrrolidin-2-yl)methanol hydrochloride

Starting from intermediate BJ.iv (2.04 g; 3.77 mmol), and proceeding in analogy to Preparation J. steps J.v and J.vi (81% and >95% yield), the crude hydrochloride was obtained, without further purification, as an off-white solid (0.905 g).

MS (ESI, m/z): 204.1 [M+H$^+$] for C$_5$H$_{12}$NOBr; t$_R$=0.28 min.

BJ.vi. ((2R,4R)-4-(bromoethynyl)-1-methylpyrrolidin-2-yl)methanol

Starting from intermediate BJ.v (0.45 g; 1.87 mmol) and proceeding as described in Preparation W (93% yield), the title compound was obtained, after purification by CC (DCM-MeOH), as a yellowish oil (0.385 g).

$^1$H NMR (d$_6$-DMSO) δ: 4.44 (m, 1H); 3.36 (m, 1H); 3.22 (m, 1H); 3.12 (dd, J=6.9 Hz, 8.3 Hz, 1H); 2.85 (m, 1H); 2.36 (m, 1H); 2.26 (s, 3H); 2.16 (dd, J=8.6 Hz, 10.0 Hz, 1H); 1.91 (m, 1H); 1.83 (m, 1H).

MS (ESI, m/z): 218.0 [M+H$^+$] for C$_5$H$_{12}$NOBr; t$_R$=0.31 min.

Preparation BK:
((2R,3R)-3-(bromoethynyl)azetidin-2-yl)methanol

BK.i. Tert-butyl (2R)—N-allyl-N-(3-(benzyloxy)-2-hydroxypropyl)glycinate

A flask was charged with (R)-benzyl glycidyl ether (40.0 g; 244 mmol) and allylamine (183 mL; 2436 mmol). Water (1 mL) was added to the mixture and the reaction was warmed to 55° C. and stirred overnight. After removal of the solvent, the crude product was obtained as a yellowish oil (54 g; 100% yield). The latter (54.0 g; 244 mmol) was taken up in THF (500 mL) and tert-butyl bromoacetate (54 mL, 366 mmol) and TEA (68 mL, 488 mmol) were added. The mixture was allowed to stir at rt for 1 h. The reaction mixture was partitioned between water (500 mL) and Et$_2$O (500 mL). The two phases were separated and the aq. phase was extracted twice with Et$_2$O (500 mL). The evaporation residue was purified by CC (Hept-EA) to give the product as a colourless oil (68 g; 83% yield).

$^1$H NMR (CDCl$_3$) δ: 7.38-7.29 (m, 5H); 5.84 (m, 1H); 5.23-5.14 (m, 2H); 4.61-4.57 (m, 2H); 3.89 (m, 1H); 3.73 (s, 1H); 3.51 (m, 2H); 3.37 (m, 1H); 3.29-3.22 (m, 3H); 2.82 (m, 1H); 2.60 (m, 1H); 1.51-1.46 (m, 9H).

MS (ESI, m/z): 336.1 [M+H$^+$] for C$_{19}$H$_{30}$NO$_4$; t$_R$=0.71 min.

BK.ii. Tert-butyl (2R)—N-allyl-N-(3-(benzyloxy)-2-chloropropyl)glycinate

To a solution of intermediate BK.i (68.0 g; 203 mmol) in DCM (500 mL) was added thionyl chloride (30.3 mL; 416 mmol) and the mixture was heated to reflux for 1 h. The mixture was partitioned between DCM (100 mL) and sat. NaHCO$_3$ (500 mL). The two phases were separated and the aq. phase was extracted with DCM (500 mL). The evaporation residue was taken up in DMF (500 mL) and the mixture was heated to 65° C. for 2 days. The mixture was diluted with water (500 mL) and Et$_2$O (500 mL) and the phases were separated. The aq. phase was extracted twice with Et$_2$O (500 mL). The evaporation residue was purified by CC (Hept-EA) to give the product as a colourless oil (60 g; 84% yield).

$^1$H NMR (CDCl$_3$) δ: 7.41-7.30 (m, 5H); 5.81 (m, 1H); 5.26-5.11 (m, 2H); 4.68-4.57 (m, 2H); 4.10 (m, 1H); 3.79 (m, 1H); 3.72 (m, 1H); 3.40-3.34 (m, 4H); 3.13 (m, 1H); 2.97 (m, 1H); 1.51-1.47 (m, 9H).

MS (ESI, m/z): 353.9 [M+H$^+$] for C$_{19}$H$_{29}$NO$_3$Cl; t$_R$=0.84 min.

BK.iii. Tert-butyl (2S,3R)-1-allyl-3-((benzyloxy)methyl)azetidine-2-carboxylate and tert-butyl (2R,3R)-1-allyl-3-((benzyloxy)methyl)azetidine-2-carboxylate A solution of intermediate BK.ii (58.7 g, 166 mmol) in a mixture of THF (600 mL) and HMPA (60 mL) was cooled to −78° C. and a solution of LiHMDS (1M in THF; 250 mL; 250 mmol) was added slowly. The mixture was allowed to warm to 0° C. over 3 h. The reaction was quenched by addition of sat. aq. NH$_4$Cl. The aq. phase was extracted twice with EA (500 mL). The evaporation residue was purified by CC (Hept-EA) to both diastereomers of the product as colourless oils ((2S,3R): 35.3 g, 67% yield; (2R,3R): 7.8 g, 15% yield).

(2S,3R)-isomer:
$^1$H NMR (CDCl$_3$) δ: 7.39-7.29 (m, 5H); 5.85 (m, 1H); 5.19 (m, 1H); 5.10 (m, 1H); 4.55-4.51 (m, 2H); 3.82 (m, 1H); 3.73 (m, 1H); 3.65 (m, 1H); 3.27 (m, 1H); 3.18-3.12 (m, 2H); 2.97 (t, J=7.4 Hz, 1H); 2.85 (m, 1H); 1.46-1.41 (m, 9H).

MS (ESI, m/z): 318.1 [M+H$^+$] for C$_{19}$H$_{28}$NO$_3$; t$_R$=0.72 min.

(2R,3R)-isomer:
$^1$H NMR (CDCl$_3$) δ: 7.44-7.29 (m, 5H); 5.86 (m, 1H); 5.22 (m, 1H); 5.11 (m, 1H); 4.60-4.54 (m, 2H); 3.62-3.51 (m, 2H); 3.50-3.43 (m, 2H); 3.30 (m, 1H); 3.08 (m, 1H); 2.90-2.82 (m, 2H); 1.52-1.44 (m, 9H).

MS (ESI, m/z): 318.1 [M+H$^+$] for C$_{19}$H$_{28}$NO$_3$; t$_R$=0.72 min.

BK.iv. ((2R,3R)-1-allyl-3-((benzyloxy)methyl)azetidin-2-yl)methanol

Starting from the (2R,3R)-configured intermediate BK.iii (7.8 g; 24.6 mmol) and proceeding in analogy to Preparation BH, step BH.ii, the title compound was obtained, without purification, as a colourless oil (6 g; >95% yield).

$^1$H NMR (CDCl$_3$) δ: 7.42-7.29 (m, 5H); 5.78 (m, 1H); 5.21 (m, 1H); 5.08-5.15 (m, 1H); 4.50-4.59 (m, 2H); 3.56-3.62 (m, 1H); 3.40-3.55 (m, 4H); 3.12-3.24 (m, 2H); 3.03-3.12 (m, 1H); 2.91-3.03 (m, 1H); 2.66-2.79 (m, 2H).

MS (ESI, m/z): 248.1 [M+H$^+$] for C$_{15}$H$_{22}$NO$_2$; t$_R$=0.57 min.

BK.v. (2R,3R)-1-allyl-3-((benzyloxy)methyl)-2-(((tert-butyldiphenylsilyl)oxy)methyl)azetidine Starting from intermediate BK.iv (6.0 g; 24.3 mmol) and proceeding in analogy to Preparation AK, step AK.i, the title compound was obtained, after purification by CC (Hept-EA), as a colourless oil (11.7 g; >95% yield).

$^1$H NMR (CDCl$_3$) δ: 7.73-7.67 (m, 5H); 7.49-7.29 (m, 10H); 5.78 (m, 1H); 5.17 (m, 1H); 5.05 (m, 1H); 4.58-4.44 (m, 2H); 3.81 (m, 1H); 3.71 (m, 1H); 3.60-3.44 (m, 3H); 3.33 (m, 1H); 3.15 (m, 1H); 3.00 (m, 1H); 2.72 (m, 1H); 2.54 (m, 1H); 1.12-1.03 (m, 9H).

MS (ESI, m/z): 486.2 [M+H$^+$] for C$_{31}$H$_{39}$NO$_2$Si; t$_R$=0.94 min.

BK.vi. Tert-butyl (2R,3R)-3-((benzyloxy)methyl)-2-(((tert-butyldiphenylsilyl)oxy)methyl)azetidine-1-carboxylate To a solution of intermediate BK.v (11.7 g; 24.1 mmol) in a DCM-EtOH mixture (1:2; 200 mL) was added N-methyl barbituric acid (5.64 g; 36.1 mmol) and Pd(PPh$_3$)$_4$ (1.39 g; 1.2 mmol). The reaction mixture was stirred at rt for 30 min. The solvent was removed in vacuo and the residue was dissolved in DCM (200 mL) and Boc$_2$O (7.88 g; 36.1 mmol) was added and the mixture was stirred for 18 h. The solvent was removed in vacuo and the evaporation residue was directly subjected to CC (Hept-EA) to afford the title compound as a colorless oil (13.5 g; >95% yield).

¹H NMR (CDCl₃) δ: 7.73-7.65 (m, 4H); 7.48-7.31 (m, 11H); 4.55 (s, 2H); 4.06-3.96 (m, 2H); 3.78 (m, 1H); 3.69-3.59 (m, 3H); 2.91 (m, 1H); 2.75 (m, 1H); 1.40 (s, 9H); 1.08 (s, 9H).

MS (ESI, m/z): 546.1 [M+H⁺] for $C_{33}H_{44}NO_4Si$; $t_R$=1.16 min.

BK.vii. Tert-butyl (2R,3R)-2-(((tert-butyldiphenylsilyl)oxy)methyl)-3-(hydroxymethyl)azetidine-1-carboxylate To a solution of intermediate BK.vi (14 g; 25.7 mmol) in MeOH (200 mL) was added Pd/C (2 g; 10 wt %). The mixture was stirred under a hydrogen atmosphere. After 5 days, the suspension was filtered and the filtrate was concentrated. Purification by CC (Hept-EA) provided the product as a colourless oil (4.45 g, 38% yield), along with reisolated starting material.

¹H NMR (CDCl₃) δ: 7.69 (m, 4H); 7.36-7.50 (m, 6H); 4.11-4.00 (m, 1H); 3.97-3.90 (m, 2H); 3.88-3.84 (m, 1H); 3.84-3.76 (m, 2H); 3.67-3.57 (m, 1H); 2.82-2.69 (m, 1H); 1.39 (s, 9H); 1.14-1.06 (m, 9H).

MS (ESI, m/z): 456.14 [M+H⁺] for $C_{26}H_{37}NO_4Si$; $t_R$=1.04 min.

BK.viii. ((2R,3R)-3-(bromoethynyl)azetidin-2-yl)methanol

Starting from intermediate BK.vii (1.2 g; 3.88 mmol) and proceeding successively in analogy to Preparation J, step J.iii (81% yield) and Preparation BH, steps BH.vii to BH.ix (77%, 88% and >95% yield), the title compound was obtained as a brown oil (0.129 g).

¹H NMR (d6-DMSO) δ: 4.01 (m, 1H); 3.67-3.56 (m, 2H); 3.50 (d, J=4.7 Hz, 2H); 3.44-3.24 (overlapped m, 3H).

MS (ESI, m/z): 190.02 [M+H⁺] for $C_6H_8NOSBr$; $t_R$=0.22 min.

Preparation BL: (2R,3R)-3-(bromoethynyl)-2-methylazetidine

BL.i. Tert-butyl (2S,3R)-3-((benzyloxy)methyl)-2-(hydroxymethyl)azetidine-1-carboxylate Starting from the (2S,3R)-isomer of intermediate BK.iii (8 g; 25.2 mmol), and proceeding successively in analogy to Preparation BH, step BH.ii (95% yield) and Preparation BK, step BK.vi (86% yield), the title compound was obtained, after purification by CC (Hept-EA), as a colourless oil (6.7 g).

¹H NMR (CDCl₃) δ: 7.44-7.30 (m, 5H); 4.61-4.50 (m, 2H); 4.47 (m, 1H); 4.00-3.87 (m, 2H); 3.84-3.73 (m, 2H); 3.59 (m, 1H); 3.47 (m, 1H); 2.92 (m, 1H); 1.47 (m, 9H).

MS (ESI, m/z): 308.1 [M+H⁺] for $C_{17}H_{25}NO_4$; $t_R$=0.85 min.

BL.ii. Tert-butyl (2S,3R)-3-((benzyloxy)methyl)-2-(iodomethyl)azetidine-1-carboxylate To a solution of intermediate BL.i (6.5 g; 21.1 mmol) in DCM (200 mL) was added PPh₃ (11.08 g; 42.3 mmol), imidazole (2.88 g; 42.3 mmol) and iodine (10.19 g; 40.2 mmol). The reaction mixture was stirred at rt overnight. The reaction mixture was concentrated to about half the original volume and the residue was taken up in Et₂O. The solids were filtered off and the filtrate was concentrated to dryness. The residue was purified by CC (Hept-EA) to afford the title compound as a colourless oil (3.5 g; 40% yield).

¹H NMR (CDCl₃) δ: 7.41-7.31 (m, 5H); 4.58 (s, 2H); 4.53 (m, 1H); 3.92 (t, J=8.5 Hz, 1H); 3.89-3.86 (m, 2H); 3.73 (dd, J=5.0, 8.3 Hz, 1H); 3.55 (m, 1H); 3.44 (dd, J=9.7, 11.0 Hz, 1H); 2.91 (m, 1H); 1.46 (s, 9H).

MS (ESI, m/z): 417.8 [M+H⁺] for $C_{17}H_{24}NO_3I$; $t_R$=0.99 min.

BL.iii. Tert-butyl (2R,3R)-3-((benzyloxy)methyl)-2-methylazetidine-1-carboxylate A solution of intermediate BL.ii (3.5 g; 8.39 mmol) in THF (50 mL) was cooled to 0° C. and a solution of LiBH₄ (2M in THF; 15 mL; 30 mmol) was added. The mixture mixture was allowed to warm to rt and stirred for 3 days. The reaction was quenched by addition of water (100 mL) and diluted with EA (200 mL). The phases were separated and the aq. phase was extracted with EA (200 mL). The evaporation residue was subjected to CC (Hept-EA) to give the product as a colourless oil (1.3 g, 53% yield).

¹H NMR (CDCl₃) δ: 7.44-7.29 (m, 5H); 4.58-4.51 (m, 2H); 4.41 (m, 1H); 3.95 (m, 1H); 3.74 (m, 1H); 3.63-3.47 (m, 2H); 2.83 (m, 1H); 1.51-1.46 (m, 9H); 1.37-1.33 (m, 3H).

MS (ESI, m/z): 292.1 [M+H⁺] for $C_{17}H_{25}NO_3$; $t_R$=0.94 min.

BL.iv. (2R,3R)-3-(bromoethynyl)-2-methylazetidine

Starting from intermediate BL.iii (1.3 g; 4.46 mmol), and proceeding successively in analogy to Preparation BK, step BK.vii (>95% yield), Preparation J, step J.iii (39% yield) and Preparation BH, steps BH.vi to BH.viii (49% yield over three steps), the title compound was obtained as a white solid (0.18 g).

¹H NMR (d6-DMSO) δ: 4.19 (m, 1H); 3.83 (t, J=8.6 Hz, 1H); 3.60 (m, 1H); 3.47 (dd, J=6.4, 8.4 Hz, 1H); 1.30 (d, J=6.6 Hz, 3H).

MS (ESI, m/z): 292.1 [M+H⁺] for $C_{17}H_{25}NO_3$; $t_R$=0.94 min.

Preparation BM: ((2S,3S)-3-(bromoethynyl)azetidin-2-yl)methanol

BM.i. Tert-butyl (2S,3S)-3-((benzyloxy)methyl)-2-(((tert-butyldiphenylsilyl)oxy)methyl)azetidine-1-carboxylate Starting from (S)-benzyl glycidyl ether (40 g; 244 mmol) and proceeding in analogy to Preparation BK, steps BK.i to BK.vi, the title compound was obtained as a colourless oil (13.3 g).

¹H NMR (CDCl₃) δ: 7.73-7.65 (m, 4H); 7.48-7.31 (m, 11H); 4.55 (s, 2H); 4.06-3.96 (m, 2H); 3.77 (m, 1H); 3.64 (m, 3H); 2.91 (m, 1H); 2.75 (m, 1H); 1.40 (s, 9H); 1.08 (s, 9H).

MS (ESI, m/z): 546.1 [M+H⁺] for $C_{33}H_{44}NO_4Si$; $t_R$=1.16 min.

BM.ii. ((2S,3S)-3-(bromoethynyl)azetidin-2-yl)methanol

Starting from intermediate BM.i (13.3 g; 27.4 mmol) and proceeding successively in analogy to Preparation BK, step BK.vii, Preparation G, step G.ii, Preparation H, steps H.iv and H.v, and Preparation I, step I.ii, the title compound was obtained as a white solid (0.169 g).

$^1$H NMR (d6-DMSO) δ: 4.63 (t, J=5.7 Hz, 1H); 3.68 (m, 1H); 3.34-3.30 (overlapped m, 4H); 3.08 (m, 1H).

Preparation BN:
(2S,3S)-3-(bromoethynyl)-2-(fluoromethyl)azetidine

BN.i. Tert-butyl (2S,3S)-3-((benzyloxy)methyl)-2-(((methylsulfonyl)oxy)methyl)azetidine-1-carboxylate Starting from intermediate BM.i (3.5 g; 6.41 mmol) and proceeding successively in analogy to Preparation Y, step Y.i and Preparation BH, step BH.iii, the title compound was obtained, after purification by CC (Hept-EA), as a colourless oil (1.9 g).

MS (ESI, m/z): 386.0 [M+H$^+$] for $C_{18}H_{27}NO_6S$; $t_R$=0.89 min.

BN.ii. Tert-butyl (2S,3S)-3-((benzyloxy)methyl)-2-(fluoromethyl)azetidine-1-carboxylate A solution of intermediate BN.i (1.9 g; 4.93 mmol) in a TBAF in THF solution (1M; 34 mL; 34 mmol) was refluxed for 3 h. After cooling, the solution was partitioned between EA (100 mL) and water (30 mL). The org. layer was further washed with brine. The evaporation residue was purified by CC (Hept-EA) to afford the title compound as a colourless oil (1.2 g, 79% yield).

MS (ESI, m/z): 310.0 [M+H$^+$] for $C_{17}H_{24}NO_3F$; $t_R$=0.92 min.

BN.iii. (2S,3S)-3-(bromoethynyl)-2-(fluoromethyl)azetidine

Starting from intermediate BN.ii (1.2 g; 3.88 mmol) and proceeding successively in analogy to Preparation BK, step BK.vii (80% yield), Preparation J, step J.iii (68% yield) and Preparation BH, steps BH.vii to BH.ix (80%, 83% and >62% yield), the title compound was obtained as a brown oil (0.164 g).

$^1$H NMR (d6-DMSO) δ: 4.45 (d, J=4.4 Hz, 1H); 4.36 (d, J=4.4 Hz, 1H); 4.13-4.01 (m, 2H); 3.51-3.46 (m, 2H); 3.30 (overlapped m, 1H).

Preparation BO:
(3R*,4S*)-4-(bromoethynyl)pyrrolidin-3-ol trifluoroacetate

Starting from tert-butyl (3S*,4R*)-3-ethynyl-4-hydroxypyrrolidine-1-carboxylate (prepared as described in Longshaw et al., J. Med. Chem. (2010), 53, 6730-6746; 1.2 g; 5.68 mmol) and proceeding successively in analogy to Preparation J, step J.v (84% yield) and Preparation I, step I.ii (>95% yield), the title compound was obtained as a brown oil (0.675 g).

MS (ESI, m/z): 231.0 [M+MeCN+H$^+$] for $C_6H_8NO_4Br$; $t_R$=0.21 min.

Preparation BP: ((2R,4R)-4-(bromoethynyl)-1-(oxetan-3-yl)pyrrolidin-2-yl)methanol Starting from intermediate BJ.v (0.450 g; 1.87 mmol) and 3-oxetanone (0.162 g; 2.25 mmol) and proceeding in analogy to Preparation AN, the title compound was obtained, after purification by CC (DCM-MeOH), as a yellowish oil (0.083 g; 17% yield).

MS (ESI, m/z): 260.0 [M+H$^+$] for $C_{10}H_{14}NO_2Br$; $t_R$=0.32 min.

Preparation BQ: 3-(2-((di-tert-butoxyphosphoryl)oxy)phenyl)propanoic Acid

BQ.i. Methyl 3-(2-((di-tert-butoxyphosphoryl)oxy)phenyl)propanoate

To a solution of methyl 3-(2-hydroxyphenyl)propionate (5 g; 30 mmol) in THF (102 mL), cooled at 0° C., was added tetrazole (0.45M in MeCN; 92 mL; 0.042 mol) and di-tert-butyl diisopropylphosphoramidite (12 mL; 36 mmol). The reaction mixture was heated at 40° C. for 24 h. After cooling to 0° C., 30% aq. $H_2O_2$ (22 mL) was added dropwise at 0° C., keeping IT below 10° C. The solution was stirred for 1.5 h at 0° C. Water (200 mL) was added. The aq. layer was extracted with EA (3×100 mL) and the org. layers were washed with 10% aq. $NaHSO_3$ (100 mL). The evaporation residue was purified by CC (Hept-EA) to afford the title compound as a colourless oil (6.2 g; 60% yield).

$^1$H NMR (d6-DMSO) δ: 7.35-7.20 (m, 3H); 7.11 (m, 1H); 3.60 (s, 3H); 2.94-2.85 (m, 2H); 2.66-2.56 (m, 2H); 1.45 (s, 18H).

MS (ESI, m/z): 373.0 [M+H$^+$] for $C_{18}H_{29}O_6P$; $t_R$=0.91 min.

BQ.ii. 3-(2-((di-tert-butoxyphosphoryl)oxy)phenyl)propanoic Acid

To a solution of intermediate BQ.i (4.3 g; 0.011 mol) in THF-MeOH-water (2-2-1; 100 mL) was added LiOH.$H_2O$ (1.94 g; 46 mmol). The reaction mixture was stirred at rt for 1.5 h. The volatiles were removed in vacuo and the residue was diluted with water (20 mL) and washed with TBME (2×100 mL). This org. layer was discarded. The aq. layer was acidified with 10% aq. citric acid (100 mL) and extracted with EA (3×100 mL). The evaporation residue afforded the title compound as a white solid (3.2 g; 79% yield).

$^1$H NMR (d6-DMSO) δ: 12.14 (s, 1H); 7.30-7.26 (m, 2H); 7.24 (m, 1H); 7.11 (t, J=7.2 Hz, 1H); 2.88-2.82 (m, 2H); 2.55-2.51 (overlapped m, 2H); 1.45 (s, 18H).

MS (ESI, m/z): 359.0 [M+H$^+$] for $C_{17}H_{27}O_6P$; $t_R$=0.81 min.

EXAMPLES OF COMPOUNDS ACCORDING TO THE INVENTION

Examples 1 and 2: (2R)—N-hydroxy-4-(6-((4-((1R)-1-hydroxy-2-morpholinoethyl)phenyl)ethynyl)-3-oxo-1H-pyrrolo[1,2-c]imidazol-2(3H)-yl)-2-methyl-2-(methylsulfonyl)butanamide and (2R)—N-hydroxy-4-(6-((4-((1S)-1-hydroxy-2-morpholinoethyl)phenyl)ethynyl)-3-oxo-1H-pyrrolo[1,2-c]imidazol-2(3H)-yl)-2-methyl-2-(methylsulfonyl)butanamide Starting from the compound of Preparation D (0.1 g; 0.23 mmol) and either the first-eluting enantiomer ("1$^{st}$ variant") or the second-eluting enantiomer ("2$^{nd}$ variant") of Preparation E (each time 0.095 g (0.28 mmol)), and proceeding successively in analogy to Procedure A (1$^{st}$ variant: 62% yield; 2$^{nd}$ variant: 85% yield) and Procedure B (1$^{st}$ variant:

33% yield; 2$^{nd}$ variant: 10% yield), the title compounds were obtained, after purification by CC (DCM-MeOH), in the 1$^{st}$ variant case, as a yellow solid (0.026 g) and, in the 2$^{nd}$ variant case, as a yellow solid (0.01 g).

1$^{st}$ Variant Product:
$^1$H NMR (d6-DMSO) δ: 10.94 (br. s, 1H); 9.18 (br. s, 1H); 7.47-7.41 (m, 3H); 7.38-7.35 (m, 2H); 6.26 (d, J=1.2 Hz, 1H); 5.14 (d, J=4.0 Hz, 1H); 4.73 (m, 1H); 4.46 (s, 2H); 3.55 (t, J=4.6 Hz, 4H); 3.49 (m, 1H); 3.39 (m, 1H); 3.07 (s, 3H); 2.59 (m, 1H); 2.50-2.43 (overlapped m, 6H); 1.97 (m, 1H); 1.53 (s, 3H).
MS (ESI, m/z): 545.06 [M+H$^+$] for $C_{26}H_{32}N_4O_7S$; $t_R$=0.54 min.

2$^{nd}$ Variant Product:
$^1$H NMR (d6-DMSO) δ: 10.94 (br. s, 1H); 9.18 (br. s, 1H); 7.47-7.41 (m, 3H); 7.38-7.35 (m, 2H); 6.26 (d, J=1.2 Hz, 1H); 5.14 (d, J=4.0 Hz, 1H); 4.73 (m, 1H); 4.46 (s, 2H); 3.55 (t, J=4.6 Hz, 4H); 3.49 (m, 1H); 3.39 (m, 1H); 3.07 (s, 3H); 2.59 (m, 1H); 2.50-2.43 (overlapped m, 6H); 1.97 (m, 1H); 1.53 (s, 3H).
MS (ESI, m/z): 545.06 [M+H$^+$] for $C_{26}H_{32}N_4O_7S$; $t_R$=0.54 min.

Example 3: (2R)-4-(6-((4-((2-oxa-6-azaspiro[3.3] heptan-6-yl)methyl)phenyl)ethynyl)-3-oxo-1H-pyrrolo[1,2-c]imidazol-2(3H)-yl)-N-hydroxy-2-methyl-2-(methylsulfonyl)butanamide Starting from the compound of Preparation D (0.125 g; 0.29 mmol) and the compound of Preparation F (0.1 g; 0.317 mmol) and proceeding successively in analogy to Procedure A (50% yield) and Procedure C (22% yield), the title compound was obtained, after purification by prep-HPLC (Method 1), as a brownish solid (0.007 g).
$^1$H NMR (d6-DMSO) δ: 10.95 (m, 1H); 9.20 (m, 1H); 7.46 (s, 1H); 7.42 (d, J=8.2 Hz, 2H); 7.26 (d, J=7.9 Hz, 2H); 6.27 (d, J=1.2 Hz, 1H); 4.61 (s, 4H); 4.46 (s, 2H); 3.51 (m, 2H); 3.48 (m, 1H); 3.43-3.37 (m, 1H); 3.30 (s, 4H); 3.07 (s, 3H); 2.61 (m, 1H); 1.98 (m, 1H); 1.54 (s, 3H).
MS (ESI, m/z): 527.13 [M+H$^+$] for $C_{26}H_{30}N_4O_6S$; $t_R$=0.54 min.

Example 4: (2R)-4-(6-((4-((6-amino-3-azabicyclo[3.1.0]hexan-3-yl)methyl)phenyl)ethynyl)-3-oxo-1H-pyrrolo[1,2-c]imidazol-2(3H)-yl)-N-hydroxy-2-methyl-2-(methylsulfonyl)butanamide Starting from the compound of Preparation D (0.2 g; 0.47 mmol) and the compound of Preparation G (0.196 g; 0.47 mmol) and proceeding successively in analogy to Procedure A (44% yield) and Procedure D (10% yield), the title compound was obtained, after purification by prep-HPLC (Method 1), as a white solid (0.010 g).
$^1$H NMR (d6-DMSO) δ: 7.46 (d, J=0.8 Hz, 1H); 7.42 (d, J=8.2 Hz, 2H); 7.26 (d, J=8.2 Hz, 2H); 6.27 (d, J=1.2 Hz, 1H); 4.46 (s, 2H); 3.53 (s, 2H); 3.50 (m, 1H); 3.43-3.39 (m, 1H); 3.07 (s, 3H); 2.86 (d, J=8.7 Hz, 2H); 2.64 (m, 1H); 2.59 (d, J=3.3 Hz, 2H); 2.46 (s, 1H); 2.37 (m, 1H); 2.31 (d, J=8.5 Hz, 2H); 1.98 (m, 1H); 1.53 (s, 3H).
MS (ESI, m/z): 526.11 [M+H$^+$] for $C_{26}H_{31}N_5O_5S$; $t_R$=0.48 min.

Example 5: (3R)-4-((2-(4-(hydroxyamino)-3-methyl-3-(methylsulfonyl)-4-oxobutyl)-3-oxo-2,3-dihydro-1H-pyrrolo[1,2-c]imidazol-6-yl)ethynyl) benzyl 4-hydroxypiperidine-1-carboxylate Starting from the compound of Preparation D (0.2 g; 0.47 mmol) and the compound of Preparation H (0.256 g; 0.708 mmol) and proceeding successively in analogy to Procedure A (61% yield) and Procedure C (86% yield), the title compound was obtained, after purification by CC (DCM-MeOH), as a beige solid (0.010 g).
$^1$H NMR (d6-DMSO) δ: 10.96 (s, 1H); 9.19 (s, 1H); 7.48-7.50 (m, 3H); 7.37 (d, J=8.2 Hz, 2H); 6.28 (d, J=0.8 Hz, 1H); 5.09 (s, 2H); 4.75 (d, J=4.1 Hz, 1H); 4.47 (s, 2H); 3.74-3.72 (m, 2H); 3.66 (m, 1H); 3.51 (m, 1H); 3.40 (m, 1H); 3.17 (d, J=5.2 Hz, 3H); 3.08 (overlapped s, 2H); 2.60 (m, 1H); 1.98 (m, 1H); 1.75-1.68 (m, 2H); 1.54 (s, 3H); 1.34-1.24 (m, 2H).
MS (ESI, m/z): 573.1 [M+H$^+$] for $C_{27}H_{32}N_4O_8S$; $t_R$=0.70 min.

Example 6: (2R)-4-(6-((4-(1-acetyl-3-hydroxyazetidin-3-yl)phenyl)ethynyl)-3-oxo-1H-pyrrolo[1,2-c]imidazol-2(3H)-yl)-N-hydroxy-2-methyl-2-(methylsulfonyl)butanamide Starting from the compound of Preparation D (0.182 g; 0.43 mmol) and the compound of Preparation I (0.150 g; 0.473 mmol) and proceeding successively in analogy to Procedure A (68% yield) and Procedure C (36% yield), the title compound was obtained, after purification by prep-HPLC (Method 2) as a white solid (0.056 g).
$^1$H NMR (d6-DMSO) δ: 10.98 (br. s, 1H); 9.21 (br. s, 1H); 7.60-7.50 (m, 4H); 7.51-7.48 (m, 1H); 6.49 (br. s, 1H); 6.31-6.28 (m, 1H); 4.48 (s, 2H); 4.38 (d, J=9.0 Hz, 1H); 4.27 (d, J=9.0 Hz, 1H); 4.04 (d, J=10.0 Hz, 1H); 4.01 (d, J=10.0 Hz, 1H); 3.58-3.46 (m, 1H); 3.47-3.35 (overlapped m, 1H); 3.09 (s, 3H); 2.68-2.55 (overlapped m, 1H); 2.05-1.94 (m, 1H); 1.86 (s, 3H); 1.55 (s, 3H).
MS (ESI, m/z): 528.93 [M+H$^+$] for $C_{25}H_{28}N_4O_7S$; $t_R$=0.63 min.

Example 7: (2R)-4-(6-(((1R,2R)-2-((S)-1,2-dihydroxyethyl)cyclopropyl)buta-1,3-diyn-1-yl)-3-oxo-1H-pyrrolo[1,2-c]imidazol-2(3H)-yl)-N-hydroxy-2-methyl-2-(methylsulfonyl)butanamide Starting from the compound of Preparation D (0.25 g; 0.59 mmol) and the compound of Preparation J (0.157 g; 0.766 mmol) and proceeding successively in analogy to Procedure E (54% yield) and Procedure D (19% yield), the title compound was obtained, after purification by prep-HPLC (Method 3), as a white solid (0.013 g).
$^1$H NMR (d6-DMSO) δ: 11.00-10.94 (br. s, 1H); 9.25-9.12 (br. s, 1H); 7.52 (s, 1H); 6.23 (d, J=1.2 Hz, 1H); 4.69 (d, J=5.1 Hz, 1H); 4.61 (t, J=5.7 Hz, 1H); 4.42 (s, 2H); 3.48 (m, 1H); 3.41-3.36 (overlapped m, 3H); 3.29 (m, 1H); 3.06 (s, 3H); 2.59 (m, 1H); 1.96 (m, 1H); 1.52 (s, 3H); 1.46 (m, 1H); 1.35 (m, 1H); 0.93 (m, 1H); 0.80 (m, 1H).
MS (ESI, m/z): 464.02 [M+H$^+$] for $C_{21}H_{25}N_3O_7S$; $t_R$=0.48 min.

Example 8: (3R)-5-(2-(4-(hydroxyamino)-3-methyl-3-(methylsulfonyl)-4-oxobutyl)-3-oxo-2,3-dihydro-1H-pyrrolo[1,2-c]imidazol-6-yl)penta-2,4-diyn-1-yl 4-hydroxypiperidine-1-carboxylate Starting from the compound of Preparation D (0.2 g; 0.47 mmol) and the compound of Preparation K (0.161 g; 0.52 mmol) and proceeding successively in analogy to Procedure E (41% yield) and Procedure C (77% yield), the title compound was obtained, after purification by CC (DCM-MeOH), as a yellowish solid (0.077 g).

¹H NMR (d6-DMSO) δ: 10.97 (s, 1H); 9.21 (s, 1H); 7.66 (s, 1H); 6.32 (s, 1H); 4.87 (s, 2H); 4.79 (d, J=4.0 Hz, 1H); 4.46 (s, 2H); 3.73-3.65 (m, 3H); 3.51 (m, 1H); 3.42 (overlapped m, 1H); 3.16-3.09 (m, 2H); 3.08 (overlapped s, 3H); 2.63 (overlapped m, 1H); 1.95 (m, 1H); 1.75-1.71 (m, 2H); 1.54 (s, 3H); 1.38-1.25 (m, 2H).

MS (ESI, m/z): 521.07 [M+H$^+$] for $C_{23}H_{28}N_4O_8S$; $t_R$=0.66 min.

Example 9: (2R)—N-hydroxy-2-methyl-2-(methylsulfonyl)-4-(3-oxo-6-(5-(2-oxooxazolidin-3-yl)penta-1,3-diyn-1-yl)-1H-pyrrolo[1,2-c]imidazol-2(3H)-yl)butanamide Starting from the compound of Preparation D (0.2 g; 0.47 mmol) and the compound of Preparation L (0.145 g; 0.7 mmol) and proceeding successively in analogy to Procedure E (75% yield) and Procedure C (27% yield), the title compound was obtained, after purification by CC (DCM-MeOH), as a yellowish solid (0.044 g).

¹H NMR (d6-DMSO) δ: 10.95 (s, 1H); 9.18 (s, 1H); 7.63 (s, 1H); 6.29 (d, J=1.2 Hz, 1H); 4.44 (s, 2H); 4.35-4.30 (m, 2H); 4.24 (s, 2H); 3.62-3.56 (m, 2H); 3.49 (m, 1H); 3.40 (m, 1H); 3.06 (s, 3H); 2.60 (m, 1H); 1.96 (m, 1H); 1.53 (s, 3H).

MS (ESI, m/z): 463.0 [M+H$^+$] for $C_{20}H_{22}N_4O_7S$; $t_R$=0.65 min.

Example 10: (3R)-4-((2-(4-(hydroxyamino)-3-methyl-3-(methylsulfonyl)-4-oxobutyl)-3-oxo-2,3-dihydro-1H-pyrrolo[1,2-c]imidazol-6-yl)ethynyl) benzyl 3-hydroxyazetidine-1-carboxylate Starting from the compound of Preparation D (0.1 g; 0.23 mmol) and the compound of Preparation M (0.145 g; 0.7 mmol) and proceeding successively in analogy to Procedure A (57% yield) and Procedure C (72% yield), the title compound was obtained, after purification by CC (DCM-MeOH), as a yellowish solid (0.048 g).

¹H NMR (d6-DMSO) δ: 10.95 (s, 1H); 9.18 (s, 1H); 7.63 (s, 1H); 6.29 (d, J=1.2 Hz, 1H); 4.44 (s, 2H); 4.35-4.30 (m, 2H); 4.24 (s, 2H); 3.62-3.56 (m, 2H); 3.49 (m, 1H); 3.40 (m, 1H); 3.06 (s, 3H); 2.60 (m, 1H); 1.96 (m, 1H); 1.53 (s, 3H).

MS (ESI, m/z): 545.1 [M+H$^+$] for $C_{25}H_{28}N_4O_8S$; $t_R$=0.47 min.

Example 11: (3R)-4-((2-(4-(hydroxyamino)-3-methyl-3-(methylsulfonyl)-4-oxobutyl)-3-oxo-2,3-dihydro-1H-pyrrolo[1,2-c]imidazol-6-yl)ethynyl) benzyl (2-hydroxyethyl)(methyl)carbamate Starting from the compound of Preparation D (0.1 g; 0.23 mmol) and the compound of Preparation N (0.119 g; 0.35 mmol) and proceeding successively in analogy to Procedure A (57% yield) and Procedure C (74% yield), the title compound was obtained, after purification by CC (DCM-MeOH), as a brownish solid (0.052 g).

¹H NMR (d6-DMSO) δ: 10.96 (d, J=1.1 Hz, 1H); 9.20 (d, J=1.4 Hz, 1H); 7.48 (m, 3H); 7.38 (d, J=6.7 Hz, 2H); 6.28 (d, J=1.2 Hz, 1H); 5.09 (s, 2H); 4.73 (m, 1H); 4.47 (s, 2H); 3.53-3.48 (m, 2H); 3.50-3.37 (overlapped m, 2H); 3.31-3.25 (m, 2H); 3.08 (s, 3H); 2.91 (m, 3H); 2.60 (m, 1H); 1.99 (m, 1H); 1.54 (s, 3H).

MS (ESI, m/z): 547.1 [M+H$^+$] for $C_{25}H_{30}N_4O_8S$; $t_R$=0.69 min.

Example 12: (2R)—N-hydroxy-4-(6-((4-((RS)-(5-(hydroxymethyl)-2-oxooxazolidin-3-yl)methyl)phenyl)ethynyl)-3-oxo-1H-pyrrolo[1,2-c]imidazol-2(3H)-yl)-2-methyl-2-(methylsulfonyl)butanamide Starting from the compound of Preparation D (0.15 g; 0.35 mmol) and the compound of Preparation O (0.142 g; 0.425 mmol) and proceeding successively in analogy to Procedure A (97% yield) and Procedure C (22% yield), the title compound was obtained, after purification by prep-HPLC (Method 3), as a yellowish foam (0.041 g).

¹H NMR (d6-DMSO) δ: 7.50-7.47 (m, 3H); 7.31 (d, J=8.3 Hz, 2H); 6.28 (d, J=1.2 Hz, 1H); 5.18-5.09 (m, 1H); 4.54 (m, 1H); 4.47 (s, 2H); 4.37 (d, J=3.2 Hz, 2H); 3.58-3.21 (overlapped m, 6H); 3.08 (s, 3H); 2.64-2.58 (m, 1H); 1.98 (m, 1H); 1.54-1.51 (m, 3H).

MS (ESI, m/z): 545.11 [M+H$^+$] for $C_{25}H_{28}N_4O_8S$; $t_R$=0.65 min.

Example 13: (2R)-4-(6-((4-(((3S*,4S*)-4-amino-3-fluoropiperidin-1-yl)methyl)phenyl)ethynyl)-3-oxo-1H-pyrrolo[1,2-c]imidazol-2(3H)-yl)-N-hydroxy-2-methyl-2-(methylsulfonyl)butanamide Starting from the compound of Preparation D (0.1 g; 0.23 mmol) and the compound of Preparation P (0.116 g; 0.26 mmol) and proceeding successively in analogy to Procedure A (>95% yield) and Procedure C (30% yield), the title compound was obtained, after purification by prep-HPLC (Method 1), as a white solid (0.041 g).

¹H NMR (d6-DMSO) δ: 7.45 (s, 1H); 7.45 (d, J=8.4 Hz, 2H); 7.31 (d, J=8.2 Hz, 2H); 6.27 (d, J=1.2 Hz, 1H); 4.46 (s, 2H); 4.09-4.23 (m, 1H); 3.54 (m, 2H); 3.50 (m, 2H); 3.07 (s, 3H); 3.04-2.99 (m, 1H); 2.68-2.64 (m, 2H); 2.62-2.58 (m, 1H); 2.05-1.95 (m, 3H); 1.78-1.72 (m, 1H); 1.53 (s, 3H); 1.35-1.24 (m, 1H).

MS (ESI, m/z): 546.03 [M+H$^+$] for $C_{26}H_{32}N_5O_5FS$; $t_R$=0.50 min.

Example 14: (2R)-4-(6-((4-((4-amino-3,3-difluoropiperidin-1-yl)methyl)phenyl)ethynyl)-3-oxo-1H-pyrrolo[1,2-c]imidazol-2(3H)-yl)-N-hydroxy-2-methyl-2-(methylsulfonyl)butanamide Starting from the compound of Preparation D (0.1 g; 0.23 mmol) and the compound of Preparation Q (0.121 g; 0.26 mmol) and proceeding successively in analogy to Procedure A (54% yield) and Procedure C (61% yield), the title compound was obtained, after purification by prep-HPLC (Method 1), as a white solid (0.043 g).

¹H NMR (d6-DMSO) δ: 7.47 (s, 1H); 7.46 (d, J=6.5 Hz, 2H); 7.32 (d, J=8.3 Hz, 2H); 6.27 (d, J=1.2 Hz, 1H); 4.46 (s, 2H); 3.58 (s, 2H); 3.50 (m, 1H); 3.43-3.37 (m, 1H); 3.08 (s, 3H); 2.94 (m, 1H); 2.89-2.79 (m, 1H); 2.69 (d, J=11.4 Hz, 1H); 2.65-2.58 (m, 1H); 2.38-2.30 (m, 1H); 2.18 (m, 1H); 1.98 (m, 1H); 1.76 (m, 1H); 1.54 (s, 3H); 1.49-1.43 (m, 1H).

MS (ESI, m/z): 563.62 [M+H$^+$] for $C_{26}H_{31}N_5O_5F_2S$; $t_R$=0.56 min.

Example 15: (2R)-4-(6-((4-(3-fluoroazetidin-3-yl)phenyl)ethynyl)-3-oxo-1H-pyrrolo[1,2-c]imidazol-2(3H)-yl)-N-hydroxy-2-methyl-2-(methylsulfonyl)butanamide Starting from the compound of Preparation D (0.13 g; 0.3 mmol) and the compound of Preparation R (0.106 g; 0.33 mmol) and proceeding successively in analogy to Procedure A (68% yield) and Procedure C (59% yield), the title compound was obtained, after purification by prep-HPLC (Method 1), as a white solid (0.058 g).

$^1$H NMR (d6-DMSO) δ: 7.61-7.53 (m, 4H); 7.50-7.48 (m, 1H); 6.31-6.27 (m, 1H); 4.47 (s, 2H); 4.06-3.87 (m, 2H); 3.84-3.68 (m, 2H); 3.55-3.46 (m, 1H); 3.46-3.22 (overlapped m, 1H); 3.07 (s, 3H); 2.65-2.55 (overlapped m, 1H); 2.03-1.94 (m, 1H); 1.53 (s, 3H).

MS (ESI, m/z): 488.96 [M+H$^+$] for $C_{23}H_{25}N_4O_5FS$; $t_R$=0.56 min.

Example 16: (2R)-4-(6-((4-(3-fluoro-1-(oxetan-3-yl)azetidin-3-yl)phenyl)ethynyl)-3-oxo-1H-pyrrolo[1,2-c]imidazol-2(3H)-yl)-N-hydroxy-2-methyl-2-(methylsulfonyl)butanamide Starting from the compound of Preparation D (0.13 g; 0.3 mmol) and the compound of Preparation S (0.116 g; 0.33 mmol) and proceeding successively in analogy to Procedure A (46% yield) and Procedure C (54% yield), the title compound was obtained, after purification by prep-HPLC (Method 1), as a white solid (0.040 g).

$^1$H NMR (d6-DMSO) δ: 10.90 (br. s, 1H); 9.19 (br. s, 1H); 7.58 (d, J=8.6 Hz, 2H); 7.50 (d, J=8.3 Hz, 2H); 7.51-7.48 (m, 1H); 6.32-6.27 (m, 1H); 4.62 (t, J=6.7 Hz, 2H); 4.47 (s, 2H); 4.42 (d, J=5.2 Hz, 1H); 3.92-3.87 (m, 1H); 3.74-3.62 (m, 4H); 3.55-3.46 (m, 1H); 3.45-3.36 (m, 1H); 3.07 (s, 3H); 2.66-2.56 (overlapped m, 1H); 2.03-1.93 (m, 1H); 1.54 (s, 3H).

MS (ESI, m/z): 545.19 [M+H$^+$] for $C_{26}H_{29}N_4O_6FS$; $t_R$=0.57 min.

Example 17: (3R)-4-((2-(4-(hydroxyamino)-3-methyl-3-(methylsulfonyl)-4-oxobutyl)-3-oxo-2,3-dihydro-1H-pyrrolo[1,2-c]imidazol-6-yl)ethynyl)benzyl 4-methylpiperazine-1-carboxylate Starting from the compound of Preparation D (0.1 g; 0.23 mmol) and the compound of Preparation T (0.128 g; 0.35 mmol) and proceeding successively in analogy to Procedure A (51% yield) and Procedure C (27% yield), the title compound was obtained, after purification by CC (DCM-MeOH), as a yellowish solid (0.018 g).

$^1$H NMR (d6-DMSO) δ: 10.96 (s, 1H); 9.20 (s, 1H); 7.51-7.47 (m, 3H); 7.38 (d, J=8.2 Hz, 2H); 6.28 (d, J=1.0 Hz, 1H); 5.10 (s, 2H); 4.47 (s, 2H); 3.50 (m, 1H); 3.43-3.37 (m, 5H); 3.08 (s, 3H); 2.60 (m, 1H); 2.30-2.26 (m, 4H); 2.19 (s, 3H); 1.99 (m, 1H); 1.54 (s, 3H).

MS (ESI, m/z): 572.1 [M+H$^+$] for $C_{27}H_{33}N_5O_7S$; $t_R$=0.60 min.

Example 18: (2R)-4-(6-((3-fluoroazetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide

18.i. (2R)-4-(6-((3-fluoroazetidin-3-yl)buta-1,3-diyn-1-yl)-3-oxo-1H-pyrrolo[1,2-c]imidazol-2(3H)-yl)-2-methyl-2-(methylsulfonyl)-N-((tetrahydro-2H-pyran-2-yl)oxy)butanamide Starting from the compound of Preparation D (0.195 g; 0.46 mmol) and the compound of Preparation U (0.111 g; 0.51 mmol) and proceeding in analogy to Procedure E, the title compound was obtained, after purification by CC (DCM-MeOH), as a greenish solid (0.097 g; 41% yield).

$^1$H NMR (d6-DMSO) δ: 7.68 (d, J=5.4 Hz, 1H); 6.31 (m, 1H); 4.85 (m, 0.5H); 4.48 (m, 0.5H); 4.47-4.38 (m, 2H); 4.01 (m, 0.5H); 3.94 (m, 0.5H); 3.53-3.38 (m, 3H); 4.05-3.36 (overlapped m, 4H); 3.06 (s, 1.5H); 3.03 (s, 1.5H); 2.62 (m, 1H); 1.97 (m, 1H); 1.63 (m, 2H); 1.56 (s, 1.5H); 1.54 (s, 1.5H); 1.56-1.47 (overlapped m, 4H).

MS (ESI, m/z): 521.25 [M+H$^+$] for $C_{24}H_{29}N_4O_6FS$; $t_R$=0.61 min.

18.ii. (2R)-4-(6-((3-fluoroazetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide Starting from intermediate 18.i (0.036 g; 0.07 mmol) and proceeding in analogy to Procedure B, the title compound was obtained, after purification by prep-HPLC (Method 1), as a yellowish solid (0.08 g; 27% yield).

MS (ESI, m/z): 478.0 [M+MeCN+H$^+$] for $C_{19}H_{21}N_4O_5FS$; $t_R$=0.52 min.

Example 19: (2R)-4-(6-((3-fluoro-1-(oxetan-3-yl)azetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide Starting from the compound of Preparation D (0.126 g; 0.297 mmol) and the compound of Preparation V (0.073 g; 0.31 mmol) and proceeding successively in analogy to Procedure E (46% yield) and Procedure B (41% yield), the title compound was obtained, after purification by CC (DCM-MeOH), as a yellowish solid (0.022 g).

$^1$H NMR (d6-DMSO) δ: 10.93 (m, 1H); 9.18 (s, 1H); 7.70 (s, 1H); 6.33 (m, 1H); 4.56 (t, J=6.7 Hz, 2H); 4.44 (s, 2H); 4.33 (dd, J=5.2, 6.6 Hz, 2H); 3.81 (m, 1H); 3.71-3.66 (m, 2H); 3.58 (dd, J=9.9, 20.1 Hz, 2H); 3.48 (m, 1H); 3.39 (m, 1H); 3.06 (s, 3H); 2.59 (m, 1H); 1.97 (m, 1H); 1.52 (s, 3H).

MS (ESI, m/z): 493.01 [M+H$^+$] for $C_{22}H_{25}N_4O_6FS$; $t_R$=0.52 min.

Example 20: (2R)-4-(6-((4-(3-fluoro-1-methylazetidin-3-yl)phenyl)ethynyl)-3-oxo-1H-pyrrolo[1,2-c]imidazol-2(3H)-yl)-N-hydroxy-2-methyl-2-(methylsulfonyl)butanamide Starting from the compound of Preparation D (0.1 g; 0.23 mmol) and the compound of Preparation W (0.084 g; 0.28 mmol) and proceeding successively in analogy to Procedure A (72% yield) and Procedure B (55% yield), the title compound was obtained, after purification by prep-HPLC (Method 1), as a yellowish solid (0.043 g).

$^1$H NMR (d6-DMSO) δ: 10.95 (br. s, 1H); 9.19 (br. s, 1H); 7.60-7.52 (m, 4H); 7.49 (d, J=0.9 Hz, 1H); 6.29 (d, J=1.2 Hz, 1H); 4.46 (s, 2H); 3.68-3.60 (m, 2H); 3.54-3.47 (m, 3H); 3.40 (m, 1H); 3.07 (s, 3H); 2.62 (m, 1H); 2.38 (s, 3H); 1.98 (m, 1H); 1.53 (s, 3H).

MS (ESI, m/z): 503.09 [M+H$^+$] for $C_{24}H_{27}N_4O_5FS$; $t_R$=0.57 min.

Example 21: (2R)-4-(6-((1-(dimethylamino)cyclopropyl)buta-1,3-diyn-1-yl)-3-oxo-1H-pyrrolo[1,2-c]imidazol-2(3H)-yl)-N-hydroxy-2-methyl-2-(methylsulfonyl)butanamide

21.i. (2R)-4-(6-((1-aminocyclopropyl)buta-1,3-diyn-1-yl)-3-oxo-1H-pyrrolo[1,2-c]imidazol-2(3H)-yl)-2-methyl-2-(methylsulfonyl)-N—(((R)-tetrahydro-2H-pyran-2-yl)oxy)butanamide Starting from the compound of Preparation D (2.5 g; 5.9 mmol) and the compound of Preparation X (1.43 g; 7.31 mmol) and proceeding in analogy to Procedure E, the title compound was obtained, after purification by CC (DCM–Hept–MeOH), as a yellowish solid (2.47 g; 83% yield).

$^1$H NMR (d6-DMSO) δ: (mixture of isomers) 11.28 (m, 1H); 7.53 (d, J=1.0 Hz, 0.5H); 7.52 (d, J=0.9 Hz, 0.5H); 6.24 (m, 1H); 4.86 (m, 0.5H); 4.49 (m, 0.5H); 4.46-4.37 (m, 2H); 4.03 (m, 0.5H); 3.95 (m, 0.5H); 3.56-3.37 (m, 3H); 3.06 (s, 1.5H); 3.04 (s, 1.5H); 2.62 (m, 1H); 1.98 (m, 1H); 1.72-1.60 (m, 2H); 1.59-1.43 (overlapped m, 4H); 1.56 (s, 1.5H); 1.54 (s, 1.5H); 0.97-0.89 (m, 2H); 0.88-0.82 (m, 2H).

MS (ESI, m/z): 503.1 [M+H$^+$] for C$_{24}$H$_{30}$N$_4$O$_6$S; t$_R$=0.59 min.

21.ii. (2R)-4-(6-((1-(dimethylamino)cyclopropyl)buta-1,3-diyn-1-yl)-3-oxo-1H-pyrrolo[1,2-c]imidazol-2(3H)-yl)-2-methyl-2-(methylsulfonyl)-N—(((R)-tetrahydro-2H-pyran-2-yl)oxy)butanamide To a solution of intermediate 21.i (0.150 g; 0.3 mmol) in DCM (4 mL) were added formaldehyde (37% aq., 0.06 mL, 0.76 mmol), NaBH(OAc)$_3$ (0.062 g, 0.76 mmol) and Na$_2$SO$_4$ (0.21 g). The reaction mixture was stirred at rt for 5 h. Sat. aq. NaHCO$_3$ (5 mL) was added. The two layers were separated and the aq. layer was extracted with DCM-MeOH (9-1; 3×5 mL). The evaporation residue was purified by CC (Hept-EA-MeOH) to afford the title product as a light yellow foam (0.1 g; 66% yield).

MS (ESI, m/z): 531.0 [M+H$^+$] for C$_{26}$H$_{34}$N$_4$O$_6$S; t$_R$=0.59 min.

21.iii. (2R)-4-(6-((1-(dimethylamino)cyclopropyl)buta-1,3-diyn-1-yl)-3-oxo-1H-pyrrolo[1,2-c]imidazol-2(3H)-yl)-N-hydroxy-2-methyl-2-(methylsulfonyl)butanamide Starting from intermediate 21.ii (0.1 g; 0.18 mmol) and proceeding in analogy to Procedure C, the title compound was obtained, after purification by CC (DCM-MeOH), as a yellowish solid (0.038 g; 47% yield).

$^1$H NMR (d6-DMSO) δ: 10.95 (s, 1H); 9.19 (s, 1H); 7.58 (m, 1H); 6.27 (m, 1H); 4.44 (s, 2H); 3.49 (m, 1H); 3.39 (m, 1H); 3.06 (s, 3H); 2.60 (m, 1H); 2.26 (s, 6H); 1.97 (m, 1H); 1.53 (s, 3H); 1.00-0.97 (m, 2H); 0.92-0.88 (m, 2H).

MS (ESI, m/z): 447.1 [M+H$^+$] for C$_{21}$H$_{26}$N$_4$O$_5$S; t$_R$=0.54 min.

Example 22: (3R)-(1-((2-(4-(hydroxyamino)-3-methyl-3-(methylsulfonyl)-4-oxobutyl)-3-oxo-2,3-dihydro-1H-pyrrolo[1,2-c]imidazol-6-yl)buta-1,3-diyn-1-yl)cyclopropyl)methyl 3-hydroxyazetidine-1-carboxylate Starting from the compound of Preparation D (0.1 g; 0.23 mmol) and the compound of Preparation Y (0.097 g; 0.35 mmol) and proceeding successively in analogy to Procedure E (87% yield) and Procedure C (80% yield), the title compound was obtained, after purification by CC (DCM-MeOH), as a yellowish foam (0.086 g).

$^1$H NMR (d6-DMSO) δ: 10.94 (s, 1H); 9.18 (s, 1H); 7.56 (d, J=0.7 Hz, 1H); 6.25 (d, J=1.2 Hz, 1H); 5.72 (d, J=6.5 Hz, 1H); 4.48-4.44 (m, 1H); 4.43 (s, 2H); 4.04-4.19 (m, 2H); 3.93 (s, 2H); 3.73-3.64 (m, 1H); 3.48 (m, 1H); 3.39 (m, 1H); 3.06 (s, 3H); 2.59 (m, 1H); 1.97 (m, 1H); 1.53 (s, 3H); 1.06-0.99 (m, 4H).

MS (ESI, m/z): 533.0 [M+H$^+$] for C$_{24}$H$_{28}$N$_4$O$_8$S; t$_R$=0.68 min.

Example 23: (3R)-(1-((2-(4-(hydroxyamino)-3-methyl-3-(methylsulfonyl)-4-oxobutyl)-3-oxo-2,3-dihydro-1H-pyrrolo[1,2-c]imidazol-6-yl)buta-1,3-diyn-1-yl)cyclopropyl)methyl 4-methylpiperazine-1-carboxylate Starting from the compound of Preparation D (0.1 g; 0.23 mmol) and the compound of Preparation Z (0.107 g; 0.35 mmol) and proceeding successively in analogy to Procedure E (76% yield) and Procedure C (12% yield), the title compound was obtained, after purification by prep-HPLC (Method 3), as a yellowish solid (0.012 g).

$^1$H NMR (d6-DMSO) δ: 10.95 (m, 1H); 9.15 (m, 1H); 7.55 (d, J=0.9 Hz, 1H); 6.25 (d, J=1.2 Hz, 1H); 4.43 (s, 2H); 3.98 (s, 2H); 3.55-3.46 (overlapped m, 4H and 2H); 3.06 (s, 3H); 2.59 (overlapped m, 1H); 2.29 (m, 4H); 2.18 (s, 3H); 1.96 (m, 1H); 1.52 (s, 3H); 1.07-1.04 (m, 2H); 1.02-1.00 (m, 2H).

MS (ESI, m/z): 560.1 [M+H$^+$] for C$_{26}$H$_{33}$N$_5$O$_7$S; t$_R$=0.61 min.

Example 24: (3R)-5-(2-(4-(hydroxyamino)-3-methyl-3-(methylsulfonyl)-4-oxobutyl)-3-oxo-2,3-dihydro-1H-pyrrolo[1,2-c]imidazol-6-yl)penta-2,4-diyn-1-yl 3-hydroxyazetidine-1-carboxylate Starting from the compound of Preparation D (0.1 g; 0.23 mmol) and the compound of Preparation AA (0.083 g; 0.35 mmol) and proceeding successively in analogy to Procedure E (83% yield) and Procedure C (60% yield), the title compound was obtained, after purification by CC (DCM-MeOH), as a yellowish foam (0.057 g).

$^1$H NMR (d6-DMSO) δ: 10.95 (s, 1H); 9.18 (s, 1H); 7.64 (d, J=0.3 Hz, 1H); 6.30 (d, J=1.2 Hz, 1H); 5.74 (m, 1H); 4.82 (s, 2H); 4.46 (m, 1H); 4.44 (overlapped s, 2H); 4.18-4.11 (m, 2H); 3.75-3.69 (m, 2H); 3.50 (m, 1H); 3.41 (m, 1H); 3.06 (s, 3H); 2.59 (m, 1H); 1.97 (m, 1H); 1.53 (s, 3H).

MS (ESI, m/z): 493.0 [M+H$^+$] for C$_{21}$H$_{24}$N$_4$O$_8$S; t$_R$=0.63 min.

Example 25: (2R)—N-hydroxy-2-methyl-2-(methylsulfonyl)-4-(6-((4-(2-(methylsulfonyl)ethoxy)phenyl)ethynyl)-3-oxo-1H-pyrrolo[1,2-c]imidazol-2(3H)-yl)butanamide Starting from the compound of Preparation D (0.09 g; 0.21 mmol) and 1-iodo-4-(2-(methylsulfonyl)ethoxy)benzene (0.101 g; 0.25 mmol) and proceeding successively in analogy to Procedure A (50% yield) and Procedure C (50% yield), the title compound was obtained, after purification by prep-HPLC (Method 3), as a white solid (0.028 g).

$^1$H NMR (d6-DMSO) δ: 10.92 (br. s, 1H); 9.17 (br. s, 1H); 7.45 (d, J=8.8 Hz, 2H); 7.42 (s, 1H); 7.02 (d, J=8.8 Hz, 2H); 6.25 (d, J=1.0 Hz, 1H); 4.45 (s, 2H); 4.38 (t, J=5.5 Hz, 2H); 3.61 (t, J=5.5 Hz, 2H); 3.49 (m, 1H); 3.39 (m, 1H); 3.08 (s, 3H); 3.07 (s, 3H); 2.59 (m, 1H); 1.97 (m, 1H); 1.53 (s, 3H).

MS (ESI, m/z): 538.01 [M+H$^+$] for C$_{23}$H$_{27}$N$_3$O$_8$S$_2$; t$_R$=0.69 min.

Example 26: azetidin-3-yl (3R)-(4-((2-(4-(hydroxyamino)-3-methyl-3-(methylsulfonyl)-4-oxobutyl)-3-oxo-2,3-dihydro-1H-pyrrolo[1,2-c]imidazol-6-yl)ethynyl)benzyl)carbamate Starting from the compound of Preparation D (0.1 g; 0.23 mmol) and the compound of Preparation AB (0.116 g; 0.26 mmol) and proceeding successively in analogy to Procedure A (45% yield) and Procedure B (51% yield), the title compound was obtained, after purification by prep-HPLC (Method 1), as a white solid (0.029 g).

$^1$H NMR (d6-DMSO) δ: 7.86 (t, J=6.1 Hz, 1H); 7.40-7.49 (m, 3H); 7.26 (d, J=8.1 Hz, 2H); 6.27 (s, 1H); 5.15-4.98 (m, 1H); 4.46 (s, 2H); 4.19 (d, J=6.0 Hz, 2H); 3.81-3.53 (m, 2H); 3.53-3.44 (m, 2H); 3.43-3.21 (overlapped m, 2H); 3.07 (s, 3H); 2.65-2.55 (overlapped m, 1H); 2.03-1.92 (m, 1H), 1.53 (s, 3H).

MS (ESI, m/z): 544.09 [M+H$^+$] for $C_{25}H_{29}NO_5O_7S$; $t_R$=0.57 min.

Example 27: 1-methylazetidin-3-yl (3R)-(4-((2-(4-(hydroxyamino)-3-methyl-3-(methylsulfonyl)-4-oxobutyl)-3-oxo-2,3-dihydro-1H-pyrrolo[1,2-c]imidazol-6-yl)ethynyl)benzyl)carbamate Starting from the compound of Preparation D (0.1 g; 0.23 mmol) and the compound of Preparation AC (0.102 g; 0.29 mmol) and proceeding successively in analogy to Procedure A (23% yield) and Procedure B (28% yield), the title compound was obtained, after purification by prep-HPLC (Method 1), as a white solid (0.09 g).

$^1$H NMR (d6-DMSO) δ: 7.86 (t, J=6.2 Hz, 1H); 7.48-7.41 (m, 3H); 7.26 (d, J=8.2 Hz, 2H); 6.28-6.26 (m, 1H); 4.85-4.78 (m, 1H); 4.46 (s, 2H); 4.19 (d, J=6.2 Hz, 2H); 3.57-3.51 (m, 2H); 3.50-3.46 (m, 1H); 3.44-3.36 (overlapped m, 1H); 3.08 (s, 3H); 2.93-2.86 (m, 2H); 2.65-2.56 (overlapped m, 1H); 2.25 (s, 3H); 2.02-1.93 (m, 1H); 1.54 (s, 3H).

MS (ESI, m/z): 558.10 [M+H$^+$] for $C_{26}H_{31}N_5O_7S$; $t_R$=0.57 min.

Example 28: (2R)—N-hydroxy-4-(6-((RS)-(4-(1-hydroxy-2-((2-methoxyethyl)(methyl)amino)ethyl)phenyl)ethynyl)-3-oxo-1H-pyrrolo[1,2-c]imidazol-2(3H)-yl)-2-methyl-2-(methylsulfonyl)butanamide Starting from the compound of Preparation D (0.1 g; 0.23 mmol) and the compound of Preparation AD (0.105 g; 0.28 mmol) and proceeding successively in analogy to Procedure A (74% yield) and Procedure B (40% yield), the title compound was obtained, after purification by prep-HPLC (Method 1), as a yellowish solid (0.039 g).

$^1$H NMR (d6-DMSO) δ: 10.94 (br. s, 1H); 9.19 (br. s, 1H); 7.45-7.43 (m, 2H); 7.42 (s, 1H); 7.37-7.34 (m, 2H); 6.26 (m, 1H); 5.02 (m, 1H); 4.65 (m, 1H); 4.46 (s, 2H); 3.50 (m, 1H); 3.43-3.34 (m, 3H); 3.20 (s, 3H); 3.07 (s, 3H); 2.62-2.54 (m, 3H); 2.50 (overlapped m, 2H); 2.27 (s, 3H); 1.97 (m, 1H); 1.53 (s, 3H).

MS (ESI, m/z): 547.03 [M+H$^+$] for $C_{26}H_{34}N_4O_7S$ $t_R$=0.56 min.

Example 29: (2R)—N-hydroxy-2-methyl-2-(methylsulfonyl)-4-(6-(((1R,2R)-2-(morpholinomethyl)cyclopropyl)buta-1,3-diyn-1-yl)-3-oxo-1H-pyrrolo[1,2-c]imidazol-2(3H)-yl)butanamide Starting from the compound of Preparation D (0.1 g; 0.23 mmol) and the compound of Preparation AE (0.075 g, 0.3 mmol) and proceeding successively in analogy to Procedure E (90% yield) and Procedure C (19% yield), the title compound was obtained, after purification by CC (DCM-MeOH), as a yellowish solid (0.020 g).

$^1$H NMR (d6-DMSO) δ: 10.98 (s, 1H); 9.18 (s, 1H); 7.52 (s, 1H); 6.23 (m, 1H); 4.42 (s, 2H); 3.58 (t, J=4.4 Hz, 4H); 3.47 (m, 1H); 3.38 (m, 1H); 3.05 (s, 3H); 2.57 (m, 1H); 2.41-2.34 (m, 5H); 2.11 (dd, J=7.4, 12.8 Hz, 1H); 1.95 (m, 1H); 1.52 (s, 3H); 1.38 (m, 1H); 1.30 (m, 1H); 0.97 (m, 1H); 0.77 (m, 1H).

MS (ESI, m/z): 503.15 [M+H$^+$] for $C_{24}H_{30}N_4O_6S$; $t_R$=0.55 min.

Example 30: (2R)—N-hydroxy-2-methyl-4-(6-((1-methylazetidin-3-yl)buta-1,3-diyn-1-yl)-3-oxo-1H-pyrrolo[1,2-c]imidazol-2(3H)-yl)-2-(methylsulfonyl)butanamide

30.i. (2R)-4-(6-((1-acetylazetidin-3-yl)buta-1,3-diyn-1-yl)-3-oxo-1H-pyrrolo[1,2-c]imidazol-2(3H)-yl)-2-methyl-2-(methylsulfonyl)-N-((tetrahydro-2H-pyran-2-yl)oxy)butanamide and (2R)-4-(6-(azetidin-3-ylbuta-1,3-diyn-1-yl)-3-oxo-1H-pyrrolo[1,2-c]imidazol-2(3H)-yl)-2-methyl-2-(methylsulfonyl)-N-((tetrahydro-2H-pyran-2-yl)oxy)butanamide Starting from the compound of Preparation D (0.15 g; 0.35 mmol) and the compound of Preparation AF (0.097 g; 0.49 mmol) and proceeding in analogy to Procedure E (89% yield), the crude reaction mixture was purified by CC (DCM-MeOH) affording first the acetamide as a yellowish solid (first eluting compound; 0.03 g; 12% yield). A second compound, characterized as the free amine, was subsequently eluted and obtained as a greenish solid (second eluting compound; 0.067 g; 28% yield).

First Eluting Compound:

$^1$H NMR (d6-DMSO) δ: 11.32 (br. s, 1H); 7.58 (m, 1H); 6.27 (m, 1H); 4.85 (m, 0.5H); 4.48 (s, 0.5H); 4.44-4.34 (m, 3H); 4.14-4.08 (m, 2H); 3.97 (m, 1H); 3.76 (m, 1H); 3.66 (m, 1H); 3.55-3.37 (m, 3H); 3.06 (s, 1.5H); 3.03 (s, 1.5H); 2.52 (m, 1H); 1.98 (m, 1H); 1.75 (s, 3H); 1.68-1.56 (m, 2H); 1.55 (s, 1.5H); 1.54 (s, 1.5H); 1.55-1.48 (overlapped m, 4H).

MS (ESI, m/z): 545.13 [M+H$^+$] for $C_{26}H_{32}N_4O_7S$; $t_R$=0.80 min.

Second Eluting Compound:

MS (ESI, m/z): 503.19 [M+H$^+$] for $C_{24}H_{30}N_4O_6S$; $t_R$=0.59 min.

30.ii. (2R)—N-hydroxy-2-methyl-4-(6-((1-methylazetidin-3-yl)buta-1,3-diyn-1-yl)-3-oxo-1H-pyrrolo[1,2-c]imidazol-2(3H)-yl)-2-(methylsulfonyl)butanamide Starting from intermediate 30.i (second eluting compound; 0.15 g; 0.3 mmol) proceeding successively in analogy to the procedure of Example 21, step 21.ii (64% yield) and Procedure B (58% yield), the title compound was obtained, after purification by prep-HPLC (Method 1), as a white solid (0.0479 g).

$^1$H NMR (d6-DMSO) δ: 10.94 (br. s, 1H); 9.19 (br. s, 1H); 7.56 (d, J=1.0 Hz, 1H); 6.25 (d, J=1.2 Hz, 1H); 4.43 (s, 2H); 3.53-3.44 (m, 3H); 3.39 (m, 1H); 3.30 (overlapped m, 1H); 3.06 (s, 3H); 2.99-2.94 (m, 2H); 2.58 (m, 1H); 2.18 (s, 3H); 1.96 (m, 1H); 1.52 (s, 3H).

MS (ESI, m/z): 433.02 [M+H$^+$] for $C_{20}H_{24}N_4O_5S$; $t_R$=0.50 min.

Example 31: (2R)-4-(6-(azetidin-3-ylbuta-1,3-diyn-1-yl)-3-oxo-1H-pyrrolo[1,2-c]imidazol-2(3H)-yl)-2-methyl-2-(methylsulfonyl)-N-((tetrahydro-2H-pyran-2-yl)oxy)butanamide Starting from intermediate 30.i (second eluting compound; 0.05 g; 0.1 mmol) and proceeding in analogy to Procedure B, the title compound was obtained, after purification by prep-HPLC (Method 1), as a white solid (0.02 g; 48% yield).

$^1$H NMR (d6-DMSO) δ: 8.99 (br. s, 1H); 7.56 (s, 1H); 6.25 (d, J=1.2 Hz, 1H); 4.43 (s, 2H); 3.63-3.55 (m, 3H); 3.54-3.44 (m, 3H); 3.37 (overlapped m, 1H); 3.05 (s, 3H); 2.56 (overlapped m, 1H); 1.94 (m, 1H); 1.49 (s, 3H).

MS (ESI, m/z): 419.04 [M+H$^+$] for $C_{19}H_{22}N_4O_5S$; $t_R$=0.49 min.

Example 32: (2R)-4-(6-((1-acetylazetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide Starting from intermediate 30.i (first eluting compound, 0.03 g; 0.3 mmol) and proceeding in analogy to Procedure B, the title compound was obtained, after purification by prep-HPLC (Method 1), as a white solid (0.015 g; 59% yield).

$^1$H NMR (d6-DMSO) δ: 10.95 (br. s, 1H); 8.90 (br. s, 1H); 7.59 (s, 1H); 6.26 (s, 1H); 4.43 (s, 2H); 4.37 (t, J=8.5 Hz, 1H); 4.07-4.13 (m, 2H); 3.76 (m, 1H); 3.66 (m, 1H); 3.48 (m, 1H); 3.38 (m, 1H); 3.05 (s, 3H); 2.56 (m, 1H); 1.92 (m, 1H); 1.75 (s, 3H); 1.47 (s, 3H).

MS (ESI, m/z): 461.02 [M+H$^+$] for $C_{21}H_{24}N_4O_6S$; $t_R$=0.67 min.

Example 33: (2R)-4-(6-((3-fluoro-1-methylazetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide Starting from intermediate 18.i (0.097 g; 0.18 mmol), and proceeding successively in analogy to the procedures of Example 21, step 21.ii (49% yield) and Procedure C (38% yield), the title compound was obtained, after purification by CC (DCM-MeOH), as a yellowish solid (0.015 g).

$^1$H NMR (d6-DMSO) δ: 10.94 (s, 1H); 9.18 (s, 1H); 7.69 (m, 1H); 6.32 (m, 1H); 4.44 (s, 2H); 3.61-3.56 (m, 2H); 3.52-3.36 (m, 4H); 3.06 (s, 3H); 2.59 (m, 1H); 2.30 (s, 3H); 1.97 (m, 1H); 1.52 (s, 3H).

MS (ESI, m/z): 451.01 [M+H$^+$] for $C_{20}H_{23}N_4O_5FS$; $t_R$=0.51 min.

Example 34: (2R)—N-hydroxy-2-methyl-4-(6-((1-methylpiperidin-4-yl)buta-1,3-diyn-1-yl)-3-oxo-1H-pyrrolo[1,2-c]imidazol-2(3H)-yl)-2-(methylsulfonyl)butanamide Starting from the compound of Preparation D (0.1 g; 0.23 mmol) and the compound of Preparation AG (0.065 g; 0.26 mmol) and proceeding successively in analogy to Procedure F (30% yield) and Procedure B (51% yield), the title compound was obtained, after purification by prep-HPLC (Method 1), as a white solid (0.016 g).

$^1$H NMR (d6-DMSO) δ: 7.57 (s, 1H); 6.27 (s, 1H); 4.44 (s, 2H); 3.59-3.33 (overlapped m, 4H); 3.07 (s, 3H); 2.66-2.50 (overlapped m, 3H); 2.15 (s, 3H); 2.12-2.02 (m, 1H); 2.01-1.91 (m, 1H); 1.86-1.75 (m, 2H); 1.64-1.53 (m, 2H); 1.53 (s, 3H).

MS (ESI, m/z): 461.06 [M+H$^+$] for $C_{22}H_{28}N_4O_5S$; $t_R$=0.53 min.

Example 35: (2R)—N-hydroxy-2-methyl-2-(methylsulfonyl)-4-(6-((1-(oxetan-3-yl)piperidin-4-yl)buta-1,3-diyn-1-yl)-3-oxo-1H-pyrrolo[1,2-c]imidazol-2(3H)-yl)butanamide Starting from the compound of Preparation D (0.1 g; 0.23 mmol) and the compound of Preparation AH (0.075 g; 0.26 mmol) and proceeding successively in analogy to Procedure F (78% yield) and Procedure B (12% yield), the title compound was obtained, after purification by prep-HPLC (Method 1), as a white solid (0.011 g).

$^1$H NMR (d6-DMSO) δ: 10.96 (br. s, 1H); 9.21 (br. s, 1H); 7.57 (s, 1H); 6.27 (s, 1H); 4.52 (t, J=6.5 Hz, 2H); 4.44 (s, 2H); 4.41 (t, J=6.1 Hz, 2H); 3.55-3.45 (m, 1H); 3.45-3.34 (overlapped m, 2H); 3.08 (s, 3H); 2.70-2.54 (overlapped m, 2H); 2.49-2.43 (overlapped m, 1H); 2.09-1.90 (m, 4H); 1.89-1.77 (m, 2H); 1.65-1.53 (m, 2H); 1.54 (s, 3H).

MS (ESI, m/z): 503.08 [M+H$^+$] for $C_{24}H_{30}N_4O_6S$; $t_R$=0.53 min.

Example 36: (2R)-4-(6-((4-(((3S*,4S*)-3-fluoro-4-hydroxypiperidin-1-yl)methyl)phenyl)ethynyl)-3-oxo-1H-pyrrolo[1,2-c]imidazol-2(3H)-yl)-N-hydroxy-2-methyl-2-(methylsulfonyl)butanamide Starting from the compound of Preparation D (0.1 g; 0.23 mmol) and the compound of Preparation AI (0.087 g; 0.26 mmol) and proceeding successively in analogy to Procedure A (50% yield) and Procedure B (78% yield), the title compound was obtained, after purification by prep-HPLC (Method 1), as a white solid (0.050 g).

$^1$H NMR (d6-DMSO) δ: 7.46-7.43 (m, 3H); 7.31 (d, J=8.3 Hz, 2H); 6.26 (d, J=1.2 Hz, 1H); 5.16 (d, J=4.8 Hz, 1H); 4.46 (s, 2H); 4.30 (m, 0.5H); 4.20 (m, 0.5H); 3.53 (s, 2H); 3.51-3.35 (m, 3H); 3.07 (s, 3H); 2.92 (m, 1H); 2.62-2.55 (m, 2H); 2.14-2.00 (m, 2H); 1.95 (m, 1H); 1.78 (m, 1H); 1.50 (s, 3H); 1.41 (m, 1H).

MS (ESI, m/z): 547.10 [M+H$^+$] for $C_{26}H_{31}N_4O_6FS$; $t_R$=0.54 min.

Example 37: (2R)-4-(6-((4-(((S)-3,3-difluoro-4-hydroxypiperidin-1-yl)methyl)phenyl)ethynyl)-3-oxo-1H-pyrrolo[1,2-c]imidazol-2(3H)-yl)-N-hydroxy-2-methyl-2-(methylsulfonyl)butanamide Starting from the compound of Preparation D (0.1 g; 0.23 mmol) and the compound of Preparation AJ (0.091 g; 0.26 mmol) and proceeding successively in analogy to Procedure A (59% yield) and Procedure B (74% yield), the title compound was obtained, after purification by prep-HPLC (Method 1), as a yellowish solid (0.058 g).

$^1$H NMR (d6-DMSO) δ: 9.18 (br. s, 1H); 7.44-7.47 (m, 3H); 7.31 (d, J=8.2 Hz, 2H); 6.27 (d, J=1.2 Hz, 1H); 5.50 (d, J=5.3 Hz, 1H); 4.46 (s, 2H); 3.66 (m, 1H); 3.59 (overlapped m, 1H); 3.58 (s, 2H), 3.50 (m, 1H); 3.39 (m, 1H); 3.07 (s, 3H); 2.78 (m, 1H); 2.63-2.54 (m, 2H); 2.28 (m, 1H); 1.97 (m, 1H); 1.77 (m, 1H); 1.62 (m, 1H); 1.53 (s, 3H).

MS (ESI, m/z): 565.07 [M+H$^+$] for $C_{26}H_{30}N_4O_6F_2S$; $t_R$=0.56 min.

Example 38: (2R)—N-hydroxy-2-methyl-4-(6-((1-(methylamino)cyclopropyl)buta-1,3-diyn-1-yl)-3-oxo-1H-pyrrolo[1,2-c]imidazol-2(3H)-yl)-2-(methylsulfonyl)butanamide Starting from the compound of Preparation D (0.1 g; 0.23 mmol) and the compound of Preparation AK (0.070 g; 0.33 mmol) and proceeding successively in analogy to Procedure E (62% yield) and Procedure B (62% yield), the title compound was obtained, after purification by prep-HPLC (Method 1), as a yellowish solid (0.039 g).

$^1$H NMR (d6-DMSO) δ: 10.91 (br. s, 1H); 9.16 (br. s, 1H); 7.54 (d, J=0.9 Hz, 1H); 6.24 (d, J=1.2 Hz, 1H); 4.42 (s, 2H); 3.48 (m, 1H); 3.38 (m, 1H); 3.05 (s, 3H); 2.72 (br. s, 1H); 2.57 (m, 1H); 2.31 (d, J=1.8 Hz, 3H); 1.96 (m, 1H); 1.51 (s, 3H); 0.95-0.90 (m, 2H), 0.87-0.81 (m, 2H).

MS (ESI, m/z): 474.05 [M+H$^+$] for $C_{20}H_{24}N_4O_5S$; $t_R$=0.52 min.

Example 39: 1-methylazetidin-3-yl (3R)-(5-(2-(4-(hydroxyamino)-3-methyl-3-(methylsulfonyl)-4-oxobutyl)-3-oxo-2,3-dihydro-1H-pyrrolo[1,2-c]imidazol-6-yl)penta-2,4-diyn-1-yl)carbamate Starting from the compound of Preparation D (0.25 g; 0.59 mmol) and the compound of Preparation AL (0.24 g; 0.88 mmol) and proceeding successively in analogy to Procedure E (40% yield), Example 21, step 21.ii (88% yield) and Procedure D (30% yield), the title compound was obtained, after purification by prep-HPLC (Method 1), as a white solid (0.013 g).

$^1$H NMR (d6-DMSO) δ: 10.93 (m, 1H); 9.16 (m, 1H); 7.84 (t, J=5.7 Hz, 1H); 7.59 (d, J=0.8 Hz, 1H); 6.26 (m, 1H); 4.83 (m, 1H); 4.44 (s, 2H); 3.96 (d, J=5.7 Hz, 2H); 3.54 (m, 2H); 3.48 (m, 1H); 3.40 (m, 1H); 3.06 (s, 3H); 2.90-2.86 (m, 2H); 2.58 (m, 1H); 2.24 (s, 3H); 1.96 (m, 1H); 1.52 (s, 3H).

MS (ESI, m/z): 506.0 [M+H$^+$] for $C_{22}H_{27}N_5O_7S$; $t_R$=0.53 min.

Example 40: (2R)—N-hydroxy-4-(6-(5-(4-hydroxypiperidin-1-yl)penta-1,3-diyn-1-yl)-3-oxo-1H-pyrrolo[1,2-c]imidazol-2(3H)-yl)-2-methyl-2-(methylsulfonyl)butanamide Starting from the compound of Preparation D (0.15 g; 0.35 mmol) and the compound of Preparation AM (0.108 g; 0.4 mmol) and proceeding successively in analogy to Procedure E (37% yield) and Procedure C (54% yield), the title compound was obtained, after purification by prep-HPLC (Method 1), as a white solid (0.013 g).

$^1$H NMR (d6-DMSO) δ: 10.95 (s, 1H); 9.19 (s, 1H); 7.59 (s, 1H); 6.28 (d, J=1.1 Hz, 1H); 4.44 (m, 2H); 3.49-3.44 (m, 4H); 3.07 (s, 3H); 2.69 (m, 2H); 2.61-2.57 (m, 1H); 2.23 (t, J=9.5 Hz, 2H); 1.97 (m, 1H); 1.74-1.71 (m, 2H); 1.53 (s, 3H); 1.40 (m, 2H); 1.10 (t, J=7.0 Hz, 2H).

MS (ESI, m/z): 477.04 [M+H$^+$] for $C_{22}H_{28}N_4O_6S$; $t_R$=0.49 min.

Example 41: (2R)—N-hydroxy-4-(6-((1-(2-hydroxyethyl)azetidin-3-yl)buta-1,3-diyn-1-yl)-3-oxo-1H-pyrrolo[1,2-c]imidazol-2(3H)-yl)-2-methyl-2-(methylsulfonyl)butanamide Starting from the compound of Preparation D (0.1 g; 0.23 mmol) and the compound of Preparation AN (0.09 g; 0.28 mmol) and proceeding successively in analogy to Procedure E (78% yield), Preparation Y, step Y.i (70% yield) and Procedure B (98% yield), the title compound was obtained, after purification by prep-HPLC (Method 1), as a white solid (0.049 g).

$^1$H NMR (d6-DMSO) δ: 10.94 (br. s, 1H); 9.20 (br. s, 1H); 7.57 (d, J=1.0 Hz, 1H); 6.26 (q, J=1.3 Hz, 1H); 4.43 (s, 2H); 4.42 (t, J=5.5 Hz, 1H); 3.51 (t, J=6.9 Hz, 2H); 3.54-3.45 (overlapped m, 1H); 3.34 (overlapped m, 4H); 3.06 (s, 3H); 3.03 (t, J=6.9 Hz, 2H); 2.59 (m, 1H); 2.43 (t, J=6.0 Hz, 2H); 1.97 (m, 1H); 1.53 (s, 3H).

MS (ESI, m/z): 463.0 [M+H$^+$] for $C_{26}H_{34}N_4O_7S$; $t_R$=0.49 min.

Example 42: (2R)-4-(6-((4-(((3R*,4S*)-3-fluoro-4-hydroxypiperidin-1-yl)methyl)phenyl)ethynyl)-3-oxo-1H-pyrrolo[1,2-c]imidazol-2(3H)-yl)-N-hydroxy-2-methyl-2-(methylsulfonyl)butanamide Starting from the compound of Preparation D (0.1 g; 0.23 mmol) and the compound of Preparation AO (0.087 g; 0.26 mmol) and proceeding successively in analogy to Procedure F (78% yield) and Procedure B (61% yield), the title compound was obtained, after purification by prep-HPLC (Method 1), as a white solid (0.049 g).

$^1$H NMR (d6-DMSO) δ: 11.00-10.88 (m, 1H); 9.28-9.09 (m, 1H); 7.48-7.41 (m, 3H); 7.32 (d, J=7.7 Hz, 2H); 6.37-6.17 (m, 1H); 4.98-4.80 (m, 1H); 4.60-4.57 (m, 0.5H); 4.54-4.49 (m, 0.5H); 4.46 (s, 2H); 4.18-4.01 (m, 1H); 3.50 (m, 2H); 3.46-3.36 (m, 1H); 3.23-3.14 (m, 2H); 3.10-3.04 (m, 3H); 2.87-2.70 (m, 1H); 2.69-2.56 (m, 2H); 2.24-2.09 (m, 1H); 2.08-1.90 (m, 1H); 1.81-1.63 (m, 1H); 1.62-1.56 (m, 1H); 1.54 (s, 3H).

MS (ESI, m/z): 547.09 [M+H$^+$] for $C_{26}H_{31}N_4O_6FS$; $t_R$=0.52 min.

Example 43: (2R)—N-hydroxy-4-(6-((4-((3-hydroxyazetidin-1-yl)methyl)phenyl)ethynyl)-3-oxo-1H-pyrrolo[1,2-c]imidazol-2(3H)-yl)-2-methyl-2-(methylsulfonyl)butanamide Starting from the compound of Preparation D (0.1 g; 0.23 mmol) and the compound of Preparation AP (0.075 g; 0.26 mmol) and proceeding successively in analogy to Procedure F (47% yield) and Procedure C (52% yield), the title compound was obtained, after purification by prep-HPLC (Method 1), as a white solid (0.029 g).

$^1$H NMR (d6-DMSO) δ: 10.95 (m, 1H); 9.21-9.19 (m, 1H); 7.46 (s, 1H); 7.42 (d, J=8.1 Hz, 2H); 7.28 (d, J=8.1 Hz, 2H); 6.27 (d, J=1.2 Hz, 1H); 5.32 (d, J=6.3 Hz, 1H); 4.46 (s, 2H); 4.19 (m, 1H); 3.57 (s, 2H); 3.49 (m, 3H); 3.08 (s, 3H); 2.77 (s, 2H); 2.65-2.58 (m, 2H); 2.01-1.95 (m, 1H); 1.54 (s, 3H).

MS (ESI, m/z): 501.04 [M+H$^+$] for $C_{24}H_{28}N_4O_6S$; $t_R$=0.53 min.

Example 44: (2R)-4-(6-(((1R,2R)-2-((dimethylamino)methyl)cyclopropyl)buta-1,3-diyn-1-yl)-3-oxo-1H-pyrrolo[1,2-c]imidazol-2(3H)-yl)-N-hydroxy-2-methyl-2-(methylsulfonyl)butanamide Starting from the compound of Preparation D (0.115 g; 0.27 mmol) and the compound of Preparation AQ (0.084 g; 0.38 mmol) and proceeding successively in analogy to Procedure E (38% yield), Example 21, step 21.ii (42% yield) and Procedure B (27% yield), the title compound was obtained, after purification by prep-HPLC (Method 1), as a yellowish solid (0.005 g).

$^1$H NMR (d6-DMSO) δ: 7.53 (s, 1H); 6.23 (s, 1H); 4.42 (s, 2H); 3.48 (m, 1H); 3.42-3.28 (overlapped m, 1H); 3.05 (s, 3H); 2.58 (m, 1H); 2.31 (m, 1H); 2.23-2.17 (m, 6H); 2.09 (m, 1H); 1.95 (m, 1H); 1.52 (s, 3H); 1.38 (m, 1H); 1.29 (m, 1H); 0.98 (m, 1H); 0.78 (m, 1H).

MS (ESI, m/z): 461.14 [M+H⁺] for C₂₂H₂₈N₄O₅S; $t_R$=0.55 min.

Example 45: (2R)—N-hydroxy-4-(6-((4-hydroxy-1-(oxetan-3-yl)piperidin-4-yl)buta-1,3-diyn-1-yl)-3-oxo-1H-pyrrolo[1,2-c]imidazol-2(3H)-yl)-2-methyl-2-(methylsulfonyl)butanamide Starting from the compound of Preparation D (0.1 g; 0.24 mmol) and the compound of Preparation AR (0.069 g; 0.26 mmol) and proceeding successively in analogy to Procedure E (56% yield) and Procedure B (70% yield), the title compound was obtained, after purification by prep-HPLC (Method 1), as a yellowish solid (0.047 g).
¹H NMR (d6-DMSO) δ: 10.80 (br. s, 1H); 9.17 (br. s, 1H); 7.59 (s, 1H); 6.28 (d, J=1.2 Hz, 1H); 5.75 (br. s, 1H); 4.51 (t, J=6.5 Hz, 2H); 4.44 (s, 2H); 4.40 (t, J=6.5 Hz, 2H); 3.54-3.45 (m, 1H); 3.44-3.35 (overlapped m, 2H); 3.06 (s, 3H); 2.65-2.54 (overlapped m, 1H); 2.47-2.34 (overlapped m, 2H); 2.22-2.06 (m, 2H); 2.03-1.90 (m, 1H); 1.86-1.78 (m, 2H); 1.77-1.61 (m, 2H); 1.52 (s, 3H).
MS (ESI, m/z): 519.03 [M+H⁺] for C₂₄H₃₀N₄O₇S; $t_R$=0.49 min.

Example 46: (2R)-4-(6-((4-fluoro-1-methylpiperidin-4-yl)buta-1,3-diyn-1-yl)-3-oxo-1H-pyrrolo[1,2-c]imidazol-2(3H)-yl)-N-hydroxy-2-methyl-2-(methylsulfonyl)butanamide Starting from the compound of Preparation D (0.13 g; 0.3 mmol) and the compound of Preparation AS (0.074 g; 0.33 mmol) and proceeding successively in analogy to Procedure E (68% yield) and Procedure B (72% yield), the title compound was obtained, after purification by prep-HPLC (Method 1), as a yellowish solid (0.071 g).
¹H NMR (d6-DMSO) δ: 10.90 (br. s, 1H); 9.19 (br. s, 1H); 7.68 (s, 1H); 6.32 (d, J=1.2 Hz, 1H); 4.45 (s, 2H); 3.55-3.46 (m, 1H); 3.45-3.36 (overlapped m, 1H); 3.06 (s, 3H); 2.66-2.55 (overlapped m, 1H); 2.48-2.29 (overlapped m, 4H); 2.19 (s, 3H); 2.04-1.93 (m, 5H), 1.53 (s, 3H).
MS (ESI, m/z): 479.06 [M+H⁺] for C₂₂H₂₇N₄O₅S; $t_R$=0.56 min.

Example 47: (2R)-4-(6-((4-fluoro-1-(oxetan-3-yl)piperidin-4-yl)buta-1,3-diyn-1-yl)-3-oxo-1H-pyrrolo[1,2-c]imidazol-2(3H)-yl)-N-hydroxy-2-methyl-2-(methylsulfonyl)butanamide Starting from the compound of Preparation D (0.13 g; 0.30 mmol) and the compound of Preparation AT (0.088 g; 0.34 mmol) and proceeding successively in analogy to Procedure E (87% yield) and Procedure B (61% yield), the title compound was obtained, after purification by prep-HPLC (Method 1), as a yellowish solid (0.084 g).
¹H NMR (d6-DMSO) δ: 10.70 (br. s, 1H); 9.16 (br. s, 1H); 7.68 (s, 1H); 6.33-6.31 (m, 1H); 4.53 (t, J=6.6 Hz, 2H); 4.45 (s, 2H); 4.42 (t, J=6.1 Hz, 2H); 3.54-3.35 (overlapped m, 3H); 3.06 (s, 3H); 2.68-2.56 (overlapped m, 1H); 2.42-2.22 (overlapped m, 4H); 2.07-1.92 (m, 5H); 1.52 (s, 3H).
MS (ESI, m/z): 521.11 [M+H⁺] for C₂₄H₂₉N₄O₆FS; $t_R$=0.55 min.

Example 48: (2R)—N-hydroxy-4-(6-((4-hydroxy-1-methylpiperidin-4-yl)buta-1,3-diyn-1-yl)-3-oxo-1H-pyrrolo[1,2-c]imidazol-2(3H)-yl)-2-methyl-2-(methylsulfonyl)butanamide Starting from the compound of Preparation D (0.062 g; 0.15 mmol) and intermediate AR.ii (0.051 g; 0.16 mmol) and proceeding successively in analogy to Procedure E (44% yield), Preparation W (50% yield) and Procedure B (61% yield), the title compound was obtained, after purification by prep-HPLC (Method 1), as a white solid (0.009 g).
¹H NMR (d6-DMSO) δ: 7.59 (s, 1H); 6.29-6.27 (m, 1H); 5.70 (br. s, 1H); 4.44 (s, 2H); 3.55-3.44 (m, 1H); 3.43-3.29 (overlapped m, 1H); 3.06 (s, 3H); 2.66-2.54 (overlapped m, 1H); 2.53-2.44 (overlapped m, 2H); 2.28-2.14 (m, 2H); 2.16 (s, 3H); 2.00-1.90 (m, 1H); 1.85-1.75 (m, 2H); 1.74-1.62 (m, 2H); 1.52 (s, 3H).
MS (ESI, m/z): 477.0 [M+H⁺] for C₂₂H₂₈N₄O₆S; $t_R$=0.49 min.

Example 49: (2R)-4-(6-((4-((3-fluoroazetidin-1-yl)methyl)phenyl)ethynyl)-3-oxo-1H-pyrrolo[1,2-c]imidazol-2(3H)-yl)-N-hydroxy-2-methyl-2-(methylsulfonyl)butanamide Starting from the compound of Preparation D (0.15 g; 0.354 mmol) and the compound of Preparation AU (0.244 g; 0.595 mmol) and proceeding successively in analogy to Procedure F (62% yield) and Procedure B (52% yield), the title compound was obtained, after purification by prep-HPLC (Method 1), as a brownish solid (0.034 g).
¹H NMR (d6-DMSO) δ: 10.95 (d, 1H); 9.20 (s, 1H); 7.46 (s, 1H); 7.43 (d, J=8.1 Hz, 2H); 7.30 (d, J=8.2 Hz, 2H); 6.27 (d, J=1.2 Hz, 1H); 5.24 (t, J=5.3 Hz, 0.5H); 5.12 (m, 0.5H); 4.46 (s, 2H); 3.64 (s, 2H); 3.48-3.58 (m, 3H); 3.16 (m, 1H); 3.12 (m, 1H); 3.08 (s, 3H); 2.65-2.58 (m, 1H); 2.01-1.96 (m, 1H); 1.54 (s, 3H).
MS (ESI, m/z): 503.0 [M+H⁺] for C₂₄H₂₇N₄O₅FS; $t_R$=0.56 min.

Example 50: (3R)-5-(2-(4-(hydroxyamino)-3-methyl-3-(methylsulfonyl)-4-oxobutyl)-3-oxo-2,3-dihydro-1H-pyrrolo[1,2-c]imidazol-6-yl)penta-2,4-diyn-1-yl 4-methylpiperazine-1-carboxylate Starting from the compound of Preparation D (0.15 g; 0.354 mmol) and the compound of Preparation AV (0.139 g; 0.531 mmol) and proceeding successively in analogy to Procedure E (93% yield) and Procedure D (63% yield), the title compound was obtained, after purification by prep-HPLC (Method 1), as a beige solid (0.107 g).
¹H NMR (d6-DMSO) δ: 10.94 (m, 1H); 9.18 (m, 1H); 7.64 (s, 1H); 6.30 (s, 1H); 4.87 (s, 2H); 4.44 (s, 2H); 3.49 (m, 1H); 3.43-3.34 (overlapped m, 5H); 3.06 (s, 3H); 2.60 (m, 1H); 2.28 (s, 4H); 2.18 (s, 3H); 1.96 (m, 1H); 1.53 (s, 3H).
MS (ESI, m/z): 520.00 [M+H⁺] for C₂₃H₂₉N₅O₇S; $t_R$=0.55 min.

Example 51: (2R)-4-(6-((1-((R)-2,3-dihydroxypropyl)azetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide Starting from intermediate 30.i (second-eluting compound; 0.15 g; 0.3 mmol) and (R)-2,2-dimethyl-1,3-dioxolane-4-carboxaldehyde (50% in DCM; 0.31 mL) and proceeding successively in analogy to Preparation V (61% yield) and Procedure B (58% yield), the title compound was obtained, after purification by prep-HPLC (Method 1), as a white solid (0.032 g).
¹H NMR (d6-DMSO) δ: 10.94 (m, 1H); 9.20 (m, 1H); 7.57 (d, J=0.7 Hz, 1H); 6.26 (d, J=1.2 Hz, 1H); 4.52-4.40 (m, 4H); 3.56-3.45 (m, 3H); 3.43-3.31 (overlapped m, 3H); 3.30-3.23 (m, 2H); 3.08-3.01 (overlapped m, 2H); 3.07 (s, 3H); 2.60 (m, 1H); 2.54-2.40 (overlapped m, 1H); 2.29 (dd, J=6.7, 12.0 Hz, 1H); 1.97 (m, 1H); 1.53 (s, 3H).

MS (ESI, m/z): 493.00 [M+H$^+$] for C$_{22}$H$_{28}$N$_7$O$_7$S; t$_R$=0.48 min.

Example 52: (2R)—N-hydroxy-2-methyl-4-(6-((1-(methyl-d2)azetidin-3-yl)buta-1,3-diyn-1-yl)-3-oxo-1H-pyrrolo[1,2-c]imidazol-2(3H)-yl)-2-(methylsulfonyl)butanamide

52.i. (2R)-4-(6-(azetidin-3-ylbuta-1,3-diyn-1-yl)-3-oxo-1H-pyrrolo[1,2-c]imidazol-2(3H)-yl)-2-methyl-2-(methylsulfonyl)-N-((2RS)-(tetrahydro-2H-pyran-2-yl)oxy)butanamide Starting from the compound of Preparation D (0.6 g; 1.42 mmol) and the compound of Preparation AF (0.363 g; 1.85 mmol) and proceeding in analogy to Procedure E, the title compound was obtained, after purification by CC (DCM-MeOH), as a greenish solid (0.445 g; 62% yield).

$^1$H NMR (d6-DMSO) δ (mixture of isomers): 11.34 (m, 1H); 7.56 (s, 0.5H); 7.55 (s, 0.5H); 6.26 (m, 1H); 4.85 (s, 0.5H); 4.49 (m, 0.5H); 4.47-4.37 (m, 2H); 4.01 (m, 0.5H); 3.95 (m, 0.5H); 3.28-3.67 (overlapped m, 8H); 3.07 (s, 1.5H); 3.04 (s, 1.5H); 2.62 (m, 1H); 1.97 (m, 1H); 1.73-1.60 (m, 2H); 1.59-1.43 (overlapped m, 4H); 1.56 (s, 1.5H); 1.54 (s, 1.5H).

MS (ESI, m/z): 503.19 [M+H$^+$] for C$_{24}$H$_{30}$N$_4$O$_6$S; t$_R$=0.59 min.

52.ii. (2R)—N-hydroxy-2-methyl-4-(6-((1-(methyl-d2)azetidin-3-yl)buta-1,3-diyn-1-yl)-3-oxo-1H-pyrrolo[1,2-c]imidazol-2(3H)-yl)-2-(methylsulfonyl)butanamide Starting from intermediate 52.i (0.1 g; 0.2 mmol) and 20% aq. formaldehyde-d2 (0.096 g; 0.6 mmol) and proceeding successively in analogy to Example 21, step 21.ii (86% yield) and Procedure B (22% yield), the title compound was obtained, after purification by prep-HPLC (Method 1), as a white solid (0.016 g).

$^1$H NMR (d6-DMSO) δ: 10.93 (m, 1H); 9.21 (m, 1H); 7.57 (d, J=0.8 Hz, 1H); 6.26 (d, J=1.2 Hz, 1H); 4.44 (s, 2H); 3.52-3.45 (m, 3H); 3.43-3.30 (overlapped m, 2H); 3.07 (s, 3H); 2.99-2.95 (m, 2H); 2.60 (m, 1H); 2.14 (m, 1H); 1.97 (m, 1H); 1.53 (s, 3H).

MS (ESI, m/z): 435.0 [M+H$^+$] for C$_{20}$H$_{22}$N$_4$O$_5$D$_2$S; t$_R$=0.50 min.

Example 53: (2R)-4-(6-(((2S,4S)-4-fluoropyrrolidin-2-yl)buta-1,3-diyn-1-yl)-3-oxo-1H-pyrrolo[1,2-c]imidazol-2(3H)-yl)-N-hydroxy-2-methyl-2-(methylsulfonyl)butanamide hydrochloride Starting from the compound of Preparation D (0.14 g; 0.33 mmol) and the compound of Preparation AW (0.105 g; 0.36 mmol) and proceeding successively in analogy to Procedure E (99% yield) and Procedure D (18% yield), the title compound was obtained, after purification by CC (DCM-MeOH), as a greenish solid (0.445 g).

$^1$H NMR (d6-DMSO) δ: 10.96 (s, 1H); 10.25 (br. s, 1H); 9.20 (s, 1H); 7.70 (s, 1H); 6.33 (s, 1H); 5.49 (m, 1H); 4.81 (m, 1H); 4.45 (s, 2H); 3.63-3.33 (overlapped m, 4H); 3.06 (s, 3H); 2.76-2.56 (m, 2H); 2.33 (m, 1H); 1.97 (m, 1H); 1.53 (s, 3H).

MS (ESI, m/z): 450.98 [M+H$^+$] for C$_{20}$H$_{24}$N$_4$O$_5$ClFS; t$_R$=0.51 min.

Example 54: (2R)-4-(6-((1-ethylazetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide Starting from intermediate 52.i (0.345 g; 0.686 mmol) and acetaldehyde (5M in THF; 0.42 mL; 2.1 mmol) and proceeding successively in analogy to Example 21, step 21.ii (19% yield) and Procedure B (65% yield), the title compound was obtained, after purification by prep-HPLC (Method 1), as a white solid (0.037 g).

$^1$H NMR (d6-DMSO) δ: 10.72 (br. s, 1H); 9.20 (br. s, 1H); 7.57 (s, 1H); 6.26 (s, 1H); 4.43 (s, 2H); 3.54-3.42 (m, 3H); 3.41-3.28 (overlapped m, 2H); 3.06 (s, 3H); 2.93 (t, J=6.5 Hz, 2H); 2.65-2.55 (m, 1H); 2.35 (q, J=7.1 Hz, 2H); 2.02-1.90 (m, 1H); 1.52 (s, 3H); 0.84 (t, J=7.2 Hz, 3H).

MS (ESI, m/z): 447.04 [M+H$^+$] for C$_{21}$H$_{26}$N$_4$O$_5$S; t$_R$=0.52 min.

Example 55: (2R)-4-(6-((1-(cyclopropylmethyl)azetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide Starting from intermediate 52.i (0.345 g; 0.686 mmol) and cyclopropanecarboxaldehyde (0.157 mL; 2.1 mmol) and proceeding successively in analogy to Example 21, step 21.ii (28% yield) and Procedure B (66% yield), the title compound was obtained, after purification by prep-HPLC (Method 1), as a white solid (0.060 g).

$^1$H NMR (d6-DMSO) δ: 10.90 (br. s, 1H); 9.22 (br. s, 1H); 7.57 (s, 1H); 6.26 (s, 1H); 4.43 (s, 2H); 3.51 (t, J=7.0 Hz, 2H); 3.54-3.44 (overlapped m, 1H); 3.43-3.28 (overlapped m, 2H); 3.06 (s, 3H); 2.99 (t, J=6.6 Hz, 2H); 2.65-2.56 (m, 1H); 2.21 (d, J=6.7 Hz, 2H); 2.03-1.91 (m, 1H); 1.53 (s, 3H); 0.75-0.62 (m, 1H); 0.40-0.32 (m, 2H); 0.10-0.01 (m, 2H).

MS (ESI, m/z): 473.06.04 [M+H$^+$] for C$_{23}$H$_{28}$N$_4$O$_5$S; t$_R$=0.56 min.

Example 56: (2R)-4-(6-(((1S,2S)-2-((R)-1,2-dihydroxyethyl)cyclopropyl)buta-1,3-diyn-1-yl)-3-oxo-1H-pyrrolo[1,2-c]imidazol-2(3H)-yl)-N-hydroxy-2-methyl-2-(methylsulfonyl)butanamide Starting from the compound of Preparation D (0.2 g; 0.47 mmol) and the compound of Preparation AX (0.118 g; 0.57 mmol) and proceeding successively in analogy to Procedure E (90% yield) and Procedure D (63% yield), the title compound was obtained, after purification by prep-HPLC (Method 3), as a white solid (0.124 g).

$^1$H NMR (d6-DMSO) δ: 11.09-10.72 (br. s, 1H); 9.32-8.98 (br. s, 1H); 7.52 (m, 1H); 6.23 (m, 1H); 4.70 (d, J=4.8 Hz, 1H); 4.61 (t, J=5.6 Hz, 1H); H); 4.46-4.39 (br. s, 2H); 3.48 (m, 1H); 3.32-3.23 (overlapped m, 3H); 3.29 (m, 1H); 3.12-3.01 (m, 3H); 2.64-2.53 (overlapped m, 1H); 1.96 (m, 1H); 1.52 (s, 3H); 1.46 (m, 1H); 1.35 (m, 1H); 0.93 (m, 1H); 0.80 (m, 1H).

MS (ESI, m/z): 464.02 [M+H$^+$] for C$_{21}$H$_{25}$N$_3$O$_7$S; t$_R$=0.59 min.

Example 57: (2R)-4-(6-((1-cyclopropylazetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide To a solution of intermediate 52.i (0.050 g, 0.0995 mmol) in EtOH (0.5 mL) and MeOH (0.5 mL) were added sequentially (1-ethoxycyclopropoxy)trimethylsilane (0.12 mL; 0.597 mmol), 3Å molecular sieves (0.050 g), AcOH (0.0569 mL; 0.995 mmol) and sodium cyanoborohydride (0.03 g; 0.448 mmol). The reaction mixture was stirred at 75° C. for 2 h. The reaction mixture was cooled at rt and filtered. The filtrate was concentrated in vacuo and the residue was purified by prep-HPLC (Method 1) to afford the title product as a white solid (0.015 g; 34% yield).

$^1$H NMR (d6-DMSO) δ: 10.95 (br. s, 1H); 9.19 (br. s, 1H); 7.57 (s, 1H); 6.26 (d, J=1.1 Hz, 1H); 4.44 (s, 2H); 3.52 (t, J=7.2 Hz, 2H); 3.53-3.44 (overlapped m, 1H); 3.43-3.25 (overlapped m, 2H); 3.14 (t, J=6.7 Hz, 2H); 3.07 (s, 3H); 2.66-2.52 (overlapped m, 1H); 2.03-1.92 (m, 1H); 1.89-1.81 (m, 1H); 1.53 (s, 3H); 0.39-0.28 (m, 2H); 0.25-0.16 (m, 2H).

MS (ESI, m/z): 459.03 [M+H$^+$] for $C_{22}H_{26}N_4O_5S$; $t_R$=0.54 min.

Example 58: (2R)—N-hydroxy-2-methyl-2-(methylsulfonyl)-4-(3-oxo-6-((1-(2,2,2-trifluoroethyl)azetidin-3-yl)buta-1,3-diyn-1-yl)-1H-pyrrolo[1,2-c]imidazol-2(3H)-yl)butanamide 58.i. (2R)-2-methyl-2-(methylsulfonyl)-4-(3-oxo-6-((1-(2,2,2-trifluoroethyl)azetidin-3-yl)buta-1,3-diyn-1-yl)-1H-pyrrolo[1,2-c]imidazol-2(3H)-yl)-N-((tetrahydro-2H-pyran-2-yl)oxy)butanamide To a suspension of intermediate 52.i (0.05 g; 0.0995 mmol) in THF (1 mL) was added DIPEA (0.0341 mL; 0.199 mmol). The mixture was cooled at 0° C. and 2,2,2-trifluoroethyl trifluoromethanesulfonate (0.022 mL; 0.15 mmol) was added. The reaction mixture was stirred at 50° C. for 2 h. DCM (10 mL) and sat. NaHCO$_3$ (10 mL) were added. The two layers were separated and the aq. layer was extracted with DCM (2×10 mL). The evaporation residue afforded the title product as a yellow foam (0.049 g; 86% yield).

MS (ESI, m/z): 585.08 [M+H$^+$] for $C_{26}H_{31}N_4O_6F_3S$; $t_R$=0.83 min.

58.ii. (2R)—N-hydroxy-2-methyl-2-(methylsulfonyl)-4-(3-oxo-6-((1-(2,2,2-trifluoroethyl)azetidin-3-yl)buta-1,3-diyn-1-yl)-1H-pyrrolo[1,2-c]imidazol-2(3H)-yl)butanamide Starting from the intermediate 58.i (0.049 g; 0.085 mmol) and proceeding in analogy to Procedure B, the title compound was obtained, after purification by prep-HPLC (Method 1), as a white solid (0.020 g; 47% yield).

$^1$H NMR (d6-DMSO) δ: 10.82 (br. s, 1H); 9.16 (br. s, 1H); 7.58 (s, 1H); 6.27 (d, J=1.2 Hz, 1H); 4.44 (s, 2H); 3.66 (t, J=7.3 Hz, 2H); 3.52-3.46 (m, 2H); 3.43-3.39 (overlapped m, 1H); 3.30 (t, J=6.9 Hz, 2H); 3.23 (q, J=10.1 Hz, 2H); 3.06 (s, 3H); 2.62-2.56 (overlapped m, 1H); 2.02-1.91 (m, 1H); 1.52 (s, 3H).

MS (ESI, m/z): 501.0 [M+H$^+$] for $C_{21}H_{23}N_4O_5F_3S$; $t_R$=0.70 min.

Example 59: (2R)-4-(6-((1-isopropylazetidin-3-yl)buta-1,3-diyn-1-yl)-3-oxo-1H-pyrrolo[1,2-c]imidazol-2(3H)-yl)-2-methyl-2-(methylsulfonyl)-N-((tetrahydro-2H-pyran-2-yl)oxy)butanamide Starting from the intermediate 52.i (0.095 g; 0.19 mmol) and acetone (0.042 mL; 0.57 mmol) and proceeding successively in analogy to Example 21, step 21.ii (62% yield) and Procedure B (65% yield), the title compound was obtained, after purification by prep-HPLC (Method 1), as a white solid (0.037 g).

$^1$H NMR (d6-DMSO) δ: 10.94 (m, 1H); 9.20 (m, 1H); 7.57 (s, 1H); 6.26 (d, J=1.2 Hz, 1H); 4.43 (s, 2H); 3.54-3.23 (overlapped m, 5H); 3.06 (s, 3H); 2.99-2.90 (m, 2H); 2.59 (m, 1H); 2.25 (m, 1H); 1.97 (m, 1H); 1.53 (s, 3H); 0.83 (d, J=6.2 Hz, 6H).

MS (ESI, m/z): 461.0 [M+H$^+$] for $C_{22}H_{28}N_4O_5S$; $t_R$=0.54 min.

Example 60: (2R)—N-hydroxy-2-methyl-4-(6-((1-(methyl-d)azetidin-3-yl)buta-1,3-diyn-1-yl)-3-oxo-1H-pyrrolo[1,2-c]imidazol-2(3H)-yl)-2-(methylsulfonyl)butanamide 60.i. (2R)-2-methyl-4-(6-((1-(methyl-d)azetidin-3-yl)buta-1,3-diyn-1-yl)-3-oxo-1H-pyrrolo[1,2-c]imidazol-2(3H)-yl)-2-(methylsulfonyl)-N-((tetrahydro-2H-pyran-2-yl)oxy)butanamide To a suspension of intermediate 52.i (0.05 g; 0.11 mmol) in MeOH (1.5 mL) were added 37% aq. formaldehyde (0.02 mL, 0.3 mmol), AcOH (0.1 mL) and NaBD$_4$ (0.08 g; 0.37 mmol). After 2 h stirring, sat. aq. Na$_2$CO$_3$ (10 mL) and DCM (8 mL) were added. The two layers were separated and the aq. layer was extracted with a DCM-MeOH mixture (9-1, 3×10 mL). The evaporation residue was purified by CC (Hept-EA-MeOH) to afford the title compound as a yellow gum (0.04 g; 80% yield).

MS (ESI, m/z): 518.02 [M+H$^+$] for $C_{22}H_{28}N_4O_5S$; $t_R$=0.60 min.

60.ii. (2R)—N-hydroxy-2-methyl-4-(6-((1-(methyl-d)azetidin-3-yl)buta-1,3-diyn-1-yl)-3-oxo-1H-pyrrolo[1,2-c]imidazol-2(3H)-yl)-2-(methylsulfonyl)butanamide Starting from intermediate 60.i (0.041 g; 0.08 mmol) and proceeding in analogy to Procedure B, the title compound was obtained, after purification by prep-HPLC (Method 1), as a white solid (0.024 g; 70% yield).

$^1$H NMR (d6-DMSO) δ: 10.93 (m, 1H); 9.20 (m, 1H); 7.57 (s, 1H); 6.26 (d, J=1.2 Hz, 1H); 4.44 (s, 2H); 3.53-3.46 (m, 3H); 3.43-3.31 (overlapped m, 2H); 3.06 (s, 3H); 3.01-2.97 (m, 2H); 2.60 (m, 1H); 2.18 (s, 2H); 1.97 (m, 1H); 1.53 (s, 3H).

MS (ESI, m/z): 433.9 [M+H$^+$] for $C_{20}H_{23}N_4O_5DS$; $t_R$=0.50 min.

Example 61: (2R)-4-(6-((1-(2-fluoroethyl)azetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide Starting from intermediate 52.i (0.05 g; 0.0995 mmol) and 1-iodo-2-fluoroethane (0.038 mL; 0.43 mmol) and proceeding successively in analogy to Example 58, step 58.i (45% yield) and Procedure B (59% yield), the title compound was obtained, after purification by prep-HPLC (Method 1), as a white solid (0.012 g).

$^1$H NMR (d6-DMSO) δ: 10.94 (br. s, 1H); 9.18 (br. s, 1H); 7.57 (s, 1H); 6.27 (d, J=1.2 Hz, 1H); 4.49-4.39 (m, 3H); 4.33 (t, J=4.8 Hz, 1H); 3.55 (t, J=7.2 Hz, 2H); 3.52-3.45 (m, 1H); 3.44-3.36 (overlapped m, 2H); 3.08 (t, J=6.3 Hz, 2H); 3.06

(s, 3H); 2.69 (t, J=4.8 Hz, 1H); 2.63 (overlapped t, J=4.4 Hz, 1H); 2.58-2.62 (overlapped m, 1H); 1.93-2.01 (m, 1H); 1.53 (s, 3H).

MS (ESI, m/z): 465.1 [M+H$^+$] for $C_{21}H_{25}N_4O_5FS$; $t_R$=0.52 min.

Example 62: (2R)-4-(6-((1-cyclobutylazetidin-3-yl) buta-1,3-diyn-1-yl)-3-oxo-1H-pyrrolo[1,2-c]imidazol-2(3H)-yl)-N-hydroxy-2-methyl-2-(methylsulfonyl)butanamide Starting from intermediate 52.i (0.05 g; 0.0995 mmol) and cyclobutananone (0.022 mL; 0.3 mmol) and proceeding successively in analogy to Example 21, step 21.ii (45% yield) and Procedure B (66% yield), the title compound was obtained, after purification by prep-HPLC (Method 1), as a white solid (0.012 g).

$^1$H NMR (d6-DMSO) δ: 10.95 (br. s, 1H); 9.19 (br. s, 1H); 7.57 (s, 1H); 6.26 (d, J=1.2 Hz, 1H); 4.44 (s, 2H); 3.54-3.44 (m, 1H); 3.43-3.37 (m, 2H); 3.36-3.27 (overlapped m, 1H); 3.06 (s, 3H); 3.03 (t, J=7.1 Hz, 1H); 3.01-2.96 (m, 2H); 2.62-2.57 (overlapped m, 1H); 2.56-2.47 (overlapped m, 1H); 2.01-1.92 (m, 1H); 1.91-1.82 (m, 2H); 1.77-1.55 (m, 4H); 1.53 (s, 3H).

MS (ESI, m/z): 473.06 [M+H$^+$] for $C_{23}H_{28}N_4O_5S$; $t_R$=0.56 min.

Example 63: (2R)-4-(6-((1-(1,1-dioxidothietan-3-yl) azetidin-3-yl)buta-1,3-diyn-1-yl)-3-oxo-1H-pyrrolo [1,2-c]imidazol-2(3H)-yl)-N-hydroxy-2-methyl-2-(methylsulfonyl)butanamide Starting from intermediate 52.i (0.05 g; 0.0995 mmol) and thietan-3-one 1,1-dioxide (0.038 g; 0.3 mmol) and proceeding in analogy to Example 21, step 21.ii, the title compound was obtained, after purification by prep-HPLC (Method 1), as a white solid (0.010 g; 19% yield).

$^1$H NMR (d6-DMSO) δ: 10.94 (br. s, 1H); 9.17 (br. s, 1H); 7.58 (s, 1H); 6.27 (d, J=1.2 Hz, 1H); 4.44 (s, 2H); 4.19-4.28 (m, 2H); 3.85-3.92 (m, 2H); 3.54 (t, J=7.5 Hz, 2H); 3.45-3.51 (m, 1H); 3.28-3.44 (overlapped m, 3H); 3.10 (t, J=6.7 Hz, 3H); 3.06 (s, 3H); 2.53-2.62 (overlapped m, 1H); 1.91-2.02 (m, 1H); 1.53 (s, 3H).

MS (ESI, m/z): 522.98 [M+H$^+$] for $C_{22}H_{26}N_4O_7S_2$; $t_R$=0.57 min.

Example 64: (2R)—N-hydroxy-4-(6-((1-(3-hydroxypropyl)azetidin-3-yl)buta-1,3-diyn-1-yl)-3-oxo-1H-pyrrolo[1,2-c]imidazol-2(3H)-yl)-2-methyl-2-(methylsulfonyl)butanamide Starting from intermediate 52.i (0.09 g; 0.18 mmol) and 3-trityloxypropionaldehyde (commercial; 0.15 g; 0.47 mmol) and proceeding successively in analogy to Example 21, step 21.ii (48% yield) and Procedure B (55% yield), the title compound was obtained, after purification by prep-HPLC (Method 1), as a white solid (0.020 g).

$^1$H NMR (d6-DMSO) δ: 10.92 (m, 1H); 9.19 (m, 1H); 7.57 (s, 1H); 6.26 (d, J=1.2 Hz, 1H); 4.50-4.35 (overlapped m, 1H); 4.44 (s, 2H); 3.53-3.45 (m, 3H); 3.43-3.31 (overlapped m, 4H); 3.07 (s, 3H); 2.94 (t, J=6.7 Hz, 2H); 2.60 (m, 1H); 2.38 (t, J=7.1 Hz, 2H); 1.97 (m, 1H); 1.53 (s, 3H); 1.39 (quint, J=6.7 Hz, 2H).

MS (ESI, m/z): 477.0 [M+H$^+$] for $C_{22}H_{28}N_4O_6S$; $t_R$=0.50 min.

Example 65: (2R)-4-(6-((1,3-dimethylazetidin-3-yl) buta-1,3-diyn-1-yl)-3-oxo-1H-pyrrolo[1,2-c]imidazol-2(3H)-yl)-N-hydroxy-2-methyl-2-(methylsulfonyl)butanamide Starting from the compound of Preparation D (0.3 g; 0.7 mmol) and the compound of Preparation AY (0.179 g; 0.85 mmol) and proceeding successively in analogy to Procedure E (73% yield), Example 21, step 21.ii (>95% yield) and Procedure B (58% yield), the title compound was obtained, after purification by prep-HPLC (Method 1), as a white solid (0.08 g).

$^1$H NMR (d6-DMSO) δ: 10.92 (br. s, 1H), 9.19 (br. s, 1H); 7.56 (s, 1H); 6.26 (d, J=1.2 Hz, 1H); 4.44 (s, 2H); 3.54-3.45 (m, 1H); 3.44-3.27 (overlapped m, 1H); 3.21-3.12 (m, 4H); 3.06 (s, 3H); 2.64-2.53 (overlapped m, 1H); 2.21 (s, 3H); 2.03-1.90 (m, 1H); 1.52 (s, 3H); 1.48 (s, 3H).

MS (ESI, m/z): 447.03 [M+H$^+$] for $C_{21}H_{26}N_4O_5S$; $t_R$=0.55 min.

Example 66: (2R)-4-(6-((3-fluoro-1-(2-hydroxyethyl)azetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide Starting from intermediate 18.i (0.053 g; 0.1 mmol) and (tert-butyldimethylsilyloxy)acetaldehyde (0.053 g; 0.3 mmol) and proceeding successively in analogy to Example 21, step 21.ii (46% yield), Preparation Y, step Y.i (>95% yield) and Procedure B (68% yield), the title compound was obtained, after purification by prep-HPLC (Method 1), as a white solid (0.013 g).

$^1$H NMR (d6-DMSO) δ: 10.95 (s, 1H); 9.19 (d, J=1.0 Hz, 1H); 7.71 (s, 1H); 6.34 (d, J=1.1 Hz, 1H); 4.62 (d, J=0.8 Hz, 1H); 4.45 (s, 2H); 3.97-3.61 (m, 4H); 3.54-3.30 (overlapped m, 4H); 3.07 (s, 3H); 2.76-2.63 (m, 2H); 2.60 (m, 1H); 1.97 (m, 1H); 1.53 (s, 3H).

MS (ESI, m/z): 481.0 [M+H$^+$] for $C_{21}H_{25}N_4O_7FS$; $t_R$=0.51 min.

Example 67: (2R)—N-hydroxy-4-(6-((1-(3-hydroxy-2-(hydroxymethyl)propyl)azetidin-3-yl)buta-1,3-diyn-1-yl)-3-oxo-1H-pyrrolo[1,2-c]imidazol-2 (3H)-yl)-2-methyl-2-(methylsulfonyl)butanamide Starting from intermediate 52.i (0.1 g; 0.2 mmol) and 2-(4-methoxyphenyl)-1,3-dioxane-5-carbaldehyde (prepared as described in Ko et al., *Organic Letters* (2007), 9, 141-144, 0.133 g; 0.60 mmol) and proceeding successively in analogy to Example 21, step 21.ii (66% yield) and Procedure B (53% yield), the title compound was obtained, after purification by prep-HPLC (Method 1), as a white solid (0.044 g).

$^1$H NMR (d6-DMSO) δ: 10.93 (m, 1H); 9.18 (m, 1H); 7.57 (s, 1H); 6.26 (d, J=1.0 Hz, 1H); 4.57-4.27 (overlapped m, 2H); 4.44 (s, 2H); 3.49 (m, 3H); 3.43-3.31 (m, 6H); 3.07 (s, 3H); 2.97 (t, J=6.7 Hz, 2H); 2.60 (m, 1H); 2.35 (d, J=6.7 Hz, 2H); 1.97 (m, 1H); 1.53 (s, 3H); 1.47 (m, 1H).

MS (ESI, m/z): 507.1 [M+H$^+$] for $C_{23}H_{30}N_4O_7S$; $t_R$=0.50 min.

Example 68: (2R)-4-(6-((1-(2,2-difluoroethyl)azetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide Starting from intermediate 52.i (0.05 g; 0.0995 mmol) and 2,2-difluoroethyl trifluoromethanesulfonate (0.021 mL; 0.15 mmol) and proceeding successively in analogy to Example 58, step 58.i (35% yield) and Procedure B (35% yield), the title compound was obtained, after purification by prep-HPLC (Method 1), as a white solid (0.006 g).

MS (ESI, m/z): 483.01 [M+H$^+$] for $C_{21}H_{24}N_4O_5F_2S$; $t_R$=0.54 min.

Example 69: (2R)—N-hydroxy-4-(6-((1-(3-hydroxycyclobutyl)azetidin-3-yl)buta-1,3-diyn-1-yl)-3-oxo-1H-pyrrolo[1,2-c]imidazol-2(3H)-yl)-2-methyl-2-(methylsulfonyl)butanamide Starting from intermediate 52.i (0.1 g; 0.199 mmol) and 3-oxocyclobutyl acetate (0.076 g; 0.60 mmol) and proceeding successively in analogy to Example 21, step 21.ii (40% yield), Preparation J, step J.ii (>95% yield) and Procedure B (38% yield), the title compound was obtained, after purification by prep-HPLC (Method 1), as a white solid (0.014 g).

MS (ESI, m/z): 489.01 [M+H$^+$] for $C_{23}H_{28}N_4O_6S$; $t_R$=0.51 min.

Example 70: (2R)-4-(6-((1-cyclohexylazetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide Starting from intermediate 52.i (0.07 g; 0.139 mmol) and cyclohexanone (0.022 mL; 0.21 mmol) and proceeding successively in analogy to Example 21, step 21.ii (>95% yield) and Procedure D (>95% yield), the title compound was obtained, after purification by prep-HPLC (Method 1), as a white solid (0.075 g).

$^1$H NMR (d6-DMSO) δ: 10.9 (s, 1H); 9.2 (s, 1H) 7.55 (s, 1H) 6.22 (s, 1H); 4.43 (s, 2H); 3.52-3.44 (overlapped m, 3H); 3.44-3.36 (overlapped m, 2H); 3.29 (m, 1H); 3.05 (s, 3H); 2.99-2.90 (m, 2H); 2.60 (overlapped m, 1H); 2.05-1.88 (m, 2H); 1.70-1.56 (m, 4H); 1.55-1.44 (m, 4H); 1.19-1.11 (m, 3H); 0.98-0.81 (m, 2H).

MS (ESI, m/z): 510.10 [M+H$^+$] for $C_{25}H_{32}N_4O_5S$; $t_R$=0.62 min.

Examples 71 and 72: (2R)-4-(6-(((3R)-3-fluoro-1-methylpyrrolidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide Trifluoroacetic Acid Salt and (2R)-4-(6-(((3S)-3-fluoro-1-methylpyrrolidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide Trifluoro Acetic Acid Salt Starting from the compound of Preparation D (0.15 g; 0.35 mmol) and the compound of Preparation AZ (0.102 g; 0.49 mmol) and proceeding successively in analogy to Procedure E (89% yield) and Procedure B (37% yield), the title compounds were obtained, after purification by prep-HPLC (Method 1), as a white solid (0.100 g; 72% yield). The latter compounds (0.058 g) were separated by semi-preparative chiral HPLC Method B (Hept-EtOH 1-9 containing 0.1% TFA; flow rate: 16 mL/min; UV detection at 210 nM); the respective retention times were 6.4 and 7.8 min. Both enantiomers, respectively first-eluting enantiomer (0.031 g) and second-eluting enantiomer (0.027 g) were obtained as yellowish solids (the absolute configuration of each enantiomer has not been assigned).

First-Eluting Enantiomer:
$^1$H NMR (d6-DMSO) δ: 10.95 (br. s, 1H); 10.49 (br. s, 1H); 9.18 (br. s, 1H); 7.73 (s, 1H); 6.33 (s, 1H); 4.45 (s, 2H); 3.58-3.39 (m, 6H); 3.06 (s, 3H); 2.89 (s, 3H); 2.68 (m, 1H); 2.59 (m, 1H); 2.42 (m, 1H); 1.96 (m, 1H); 1.52 (s, 3H).

MS (ESI, m/z): 465.03 [M+H$^+$] for $C_{21}H_{25}N_4O_5ClFS$; $t_R$=0.52 min.

Second-Eluting Enantiomer:
$^1$H NMR (d6-DMSO) δ: 10.95 (br. s, 1H); 10.49 (br. s, 1H); 9.18 (br. s, 1H); 7.73 (s, 1H); 6.33 (s, 1H); 4.45 (s, 2H); 3.58-3.39 (m, 6H); 3.06 (s, 3H); 2.89 (s, 3H); 2.68 (m, 1H); 2.59 (m, 1H); 2.42 (m, 1H); 1.96 (m, 1H); 1.52 (s, 3H).

MS (ESI, m/z): 465.03 [M+H$^+$] for $C_{21}H_{25}N_4O_5ClFS$; $t_R$=0.52 min.

Example 73: (2R)-4-(6-((1-cyclopentylazetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide Starting from intermediate 52.i (0.08 g; 0.159 mmol) and cyclopentanone (0.021 mL; 0.21 mmol) and proceeding successively in analogy to Example 21, step 21.ii (>95% yield) and Procedure D (73% yield), the title compound was obtained, after purification by prep-HPLC (Method 1), as a white solid (0.050 g).

$^1$H NMR (d6-DMSO) δ: 9.21-9.05 (s, 1H); 7.62-7.46 (s, 1H); 6.31-6.17 (s, 1H); 11.04-10.80 (s, 1H); 4.45-4.42 (m, 2H); 3.56-3.53 (overlapped m, 2H); 3.52-3.46 (overlapped m, 1H); 3.35 (overlapped m, 1H); 3.06 (s, 3H); 2.93-2.90 (m, 2H); 2.67-2.64 (m, 2H); 2.50 (m, 1H); 2.30 (m, 1H); 1.90 (m, 1H); 1.62-1.55 (m, 2H); 1.52 (m, 3H); 1.49-1.42 (m, 4H); 1.29-1.20 (m, 2H).

MS (ESI, m/z): 487.07 [M+H$^+$] for $C_{24}H_{30}N_4O_5S$; $t_R$=0.59 min.

Example 74: (2R)—N-hydroxy-2-methyl-2-(methylsulfonyl)-4-(3-oxo-6-((1-(tetrahydro-2H-pyran-4-yl)azetidin-3-yl)buta-1,3-diyn-1-yl)-1H-pyrrolo[1,2-c]imidazol-2(3H)-yl)butanamide Starting from intermediate 52.i (0.08 g; 0.159 mmol) and tetrahydro-4H-pyran-4-one (0.022 mL; 0.24 mmol) and proceeding successively in analogy to Example 21, step 21.ii (80% yield) and Procedure D (82% yield), the title compound was obtained, after purification by prep-HPLC (Method 1), as a white solid (0.060 g).

$^1$H NMR (d6-DMSO) δ: 10.90 (s, 1H); 9.20 (s, 1H); 7.55 (s, 1H); 6.25 (s, 1H); 4.42 (s, 2H); 3.85-3.71 (m, 2H) 3.50-3.46 (overlapped m, 3H); 3.40 (overlapped m, 1H); 3.31-3.23 (m, 3H); 3.09 (s, 3H); 3.01-2.91 (m, 2H); 2.57 (m, 1H); 2.21 (m, 1H); 1.89 (m, 1H); 1.59-1.55 (m, 2H); 1.52-1.47 (m, 3H); 1.16-1.03 (m, 2H).

MS (ESI, m/z): 503.00 [M+H$^+$] for $C_{24}H_{30}N_4O_6S$; $t_R$=0.53 min.

Example 75: (2R)—N-hydroxy-2-methyl-2-(methylsulfonyl)-4-(3-oxo-6-((1-(thietan-3-yl)azetidin-3-yl)buta-1,3-diyn-1-yl)-1H-pyrrolo[1,2-c]imidazol-2(3H)-yl)butanamide Starting from intermediate 52.i (0.08 g; 0.159 mmol) and thietan-3-one (0.021 g; 0.24 mmol) and proceeding successively in analogy to Example 21, step 21.ii (13% yield) and Procedure D (78% yield), the title compound was obtained, after purification by prep-HPLC (Method 1), as a white solid (0.008 g).

¹H NMR (d6-DMSO) δ: 10.9 (s, 1H); 9.19 (s, 1H) 7.55 (s, 1H); 6.25 (s, 1H); 4.47-4.33 (m, 2H); 3.85 (m, 1H); 3.49-3.44 (m, 3H); 3.42-3.36 (m, 2H); 3.20-3.15 (m, 2H); 3.12 (t, J=6.6 Hz, 2H); 3.06 (s, 3H); 3.01-2.96 (m, 2H); 2.58 (m, 1H); 1.95 (m, 1H); 1.53-1.49 (m, 3H).

MS (ESI, m/z): 491.02 [M+H$^+$] for $C_{22}H_{26}N_4O_5S_2$; $t_R$=0.53 min.

Example 76: (2R)-4-(6-(((3RS)-1-cyclopropyl-3-fluoropyrrolidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide 76.i. (2R)-4-(6-((3-fluoropyrrolidin-3-yl)buta-1,3-diyn-1-yl)-3-oxo-1H-pyrrolo[1,2-c]imidazol-2(3H)-yl)-2-methyl-2-(methylsulfonyl)-N-(((2RS)-tetrahydro-2H-pyran-2-yl)oxy)butanamide Starting from the compound of Preparation D (0.5 g; 1.18 mmol) and intermediate AZ.i (0.378 g; 1.65 mmol) and proceeding in analogy to Procedure E (62% yield), the title compound was obtained as a yellow foam (0.388 g; 62% yield).

¹H NMR (d6-DMSO) δ: 7.66 (m, 0.5H); 7.65 (m, 0.5H); 6.31 (m, 1H); 4.85 (m, 0.5H); 4.49 (m, 0.5H); 4.44-4.40 (m, 2H); 4.01 (m, 1H); 3.55-3.36 (m, 3H); 3.24 (m, 1H); 3.06 (s, 1.5H); 3.03 (s, 1.5H); 3.01-2.84 (m, 3H); 2.61 (m, 1H); 2.24 (m, 1H); 2.11 (m, 1H); 1.95 (m, 1H); 1.69-1.59 (m, 2H); 1.55 (s, 1.5H); 1.54 (s, 1.5H); 1.51-1.43 (m, 4H).

MS (ESI, m/z): 535.18 [M+H$^+$] for $C_{25}H_{31}N_4O_6FS$; $t_R$=0.61 min.

76.ii. (2R)-4-(6-((1-cyclopropyl-3-fluoropyrrolidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide Starting from intermediate 76.i (0.15 g; 0.28 mmol) and proceeding successively in analogy to Example 57 (37% yield) and Procedure B (54% yield), the title compound was obtained, after purification by prep-HPLC (Method 1), as a white solid (0.036 g).

¹H NMR (d6-DMSO) δ: 10.90 (br. s, 1H); 9.18 (br. s, 1H); 7.67 (d, J=0.4 Hz, 1H); 6.31 (d, J=1.2 Hz, 1H); 4.44 (s, 2H); 3.49 (m, 1H); 3.39 (m, 1H); 3.17 (m, 1H); 3.06 (s, 3H); 2.99 (m, 1H); 2.92 (m, 1H); 2.73 (m, 1H); 2.59 (m, 1H); 2.35-2.23 (m, 2H); 1.96 (m, 1H); 1.77 (m, 1H); 1.52 (s, 3H); 0.42-0.38 (m, 2H); 0.37-0.29 (m, 2H).

MS (ESI, m/z): 491.02 [M+H$^+$] for $C_{23}H_{27}N_4O_5FS$; $t_R$=0.57 min.

Example 77: (2R)-4-(6-(((3RS)-3-fluoro-1-(2-hydroxyethyl)pyrrolidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide Starting from intermediate 76.i (0.14 g; 0.26 mmol) and proceeding successively in analogy to Preparation AN (66% yield), Preparation Y, step Y.i. (>95% yield) and Procedure B (59% yield), the title compound was obtained, after purification by prep-HPLC (Method 1), as an off-white solid (0.049 g).

¹H NMR (d6-DMSO) δ: 10.94 (br. s, 1H); 9.18 (br. s, 1H); 7.67 (s, 1H); 6.31 (d, J=1.2 Hz, 1H); 4.51 (t, J=5.4 Hz, 1H); 4.44 (s, 2H); 3.52-3.45 (m, 3H); 3.39 (m, 1H); 3.14 (m, 1H); 3.06 (s, 3H); 2.92-2.83 (m, 2H); 2.62-2.50 (overlapped m, 4H); 2.35-2.22 (m, 2H); 1.96 (m, 1H); 1.52 (s, 3H).

MS (ESI, m/z): 495.02 [M+H$^+$] for $C_{22}H_{27}N_4O_6FS$; $t_R$=0.53 min.

Example 78: (2R)-4-(6-(((3RS)-3-fluoropyrrolidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide Starting from intermediate 76.i (0.03 g; 0.056 mmol) and proceeding in analogy to Procedure B (25% yield), the title compound was obtained, after purification by prep-HPLC (Method 1), as an off-white solid (0.006 g).

¹H NMR (d6-DMSO) δ: 9.18 (br. s, 1H); 7.66 (s, 1H); 6.31 (d, J=1.1 Hz, 1H); 4.44 (s, 2H); 3.49 (m, 1H); 3.39 (m, 1H); 3.24 (m, 1H); 3.06 (s, 3H); 3.03-2.85 (m, 4H); 2.58 (m, 1H); 2.33-2.03 (m, 2H); 1.96 (m, 1H); 1.52 (s, 3H).

MS (ESI, m/z): 492.05 [M+MeCN+H$^+$] for $C_{20}H_{23}N_4O_5FS$; $t_R$=0.53 min.

Example 79: (2R)-4-(6-((3-ethyl-1-methylazetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide Starting from the compound of Preparation D (0.2 g; 0.47 mmol) and the compound of Preparation BA (0.159 g; 0.70 mmol) and proceeding successively in analogy to Procedure E (52% yield), Example 21, step 21.ii (>95% yield) and Procedure B (63% yield), the title compound was obtained, after purification by prep-HPLC (Method 1), as a white solid (0.072 g).

¹H NMR (d6-DMSO) δ: 10.94 (br. s, 1H); 9.21 (br. s, 1H); 7.57 (d, J=0.9 Hz, 1H); 6.27 (d, J=1.2 Hz, 1H); 4.44 (s, 2H); 3.54-3.44 (m, 1H); 3.44-3.27 (overlapped m, 1H); 3.20-3.13 (m, 4H); 3.07 (s, 3H); 2.60 (overlapped m, 1H); 2.22 (s, 3H); 1.96 (m, 1H); 1.78 (q, J=7.4 Hz, 2H); 1.53 (s, 3H); 0.93 (t, J=7.3 Hz, 3H).

MS (ESI, m/z): 461.07 [M+H$^+$] for $C_{22}H_{23}N_4O_5FS$; $t_R$=0.57 min.

Example 80: (2R)—N-hydroxy-2-methyl-2-((methyl-d2)sulfonyl)-4-(6-((1-methylazetidin-3-yl)buta-1,3-diyn-1-yl)-3-oxo-1H-pyrrolo[1,2-c]imidazol-2(3H)-yl)butanamide 80.i. (2R)-2-methyl-4-(6-((1-methylazetidin-3-yl)buta-1,3-diyn-1-yl)-3-oxo-1H-pyrrolo[1,2-c]imidazol-2(3H)-yl)-2-(methylsulfonyl)-N-((2RS)-(tetrahydro-2H-pyran-2-yl)oxy)butanamide Starting from the compound of Preparation D (5.50 g; 13 mmol) and the compound of Preparation BB (2.71 g; 15.6 mmol) and proceeding in analogy to Procedure E, the title compound was obtained, after purification by CC (Hept-EA-MeOH), as a yellowish foam solid (5.09 g; 76% yield).

¹H NMR (d6-DMSO) mixture of diastereomers δ: 11.35 (m, 1H); 7.56 (d, J=0.8 Hz, 0.5H); 7.55 (d, J=0.8 Hz, 0.5H); 6.26 (m, 1H); 4.86 (m, 0.5H); 4.49 (m, 0.5H); 4.47-4.36 (m, 2H); 4.03 (m, 0.5H); 3.95 (m, 0.5H); 3.56-3.37 (m, 6H); 3.07 (s, 1.5H); 3.04 (s, 1.5H); 3.00-2.95 (m, 2H); 2.63 (m, 1H); 2.19 (s, 3H); 1.99 (m, 1H); 1.70-1.60 (m, 2H); 1.58-1.44 (overlapped m, 4H); 1.56 (s, 1.5H); 1.55 (s, 1.5H).

MS (ESI, m/z): 517.1 [M+H$^+$] for $C_{25}H_{32}N_4O_6S$; $t_R$=0.60 min.

80.ii. (2R)—N-hydroxy-2-methyl-2-((methyl-d₂) sulfonyl)-4-(6-((1-methylazetidin-3-yl)buta-1,3-diyn-1-yl)-3-oxo-1H-pyrrolo[1,2-c]imidazol-2(3H)-yl)butanamide To a solution of intermediate 80.i (0.049 g, 0.095 mmol) in THF (0.35 mL), cooled at −78° C., was added dropwise LDA (2M in THF; 0.05 mmol). The reaction mixture was stirred at −78° C. for 20 min and D₂O (0.04 mL) was added. The reaction mixture was allowed to warm to rt over 1.5 h. After cooling to 0° C., aq. HCl (2M, 0.3 mL) was added. After further 1.5 h stirring at rt, aq. NH₄OH (0.25 mL) was added and the resulting solution was purified by prep-HPLC (Method 1) to afford the title compound as a white solid (0.022 g; 53% yield).

¹H NMR (d6-DMSO) δ: 10.93 (br. s, 1H); 9.22 (br. s, 1H); 7.57 (d, J=0.9 Hz, 1H); 6.26 (m, 1H); 4.44 (s, 2H); 3.52-3.46 (m, 3H); 3.42-3.28 (overlapped m, 2H); 3.04 (m, 1H); 2.99-2.96 (m, 2H); 2.59 (m, 1H); 2.19 (s, 3H); 1.96 (m, 1H); 1.52 (s, 3H).

MS (ESI, m/z): 435.12 [M+H⁺] for $C_{20}H_{22}N_4O_5D_2S$; $t_R$=0.50 min.

Example 81: (2R)—N-hydroxy-4-(6-((1-(2-hydroxyethyl)azetidin-3-yl)buta-1,3-diyn-1-yl)-3-oxo-1H-pyrrolo[1,2-c]imidazol-2(3H)-yl)-2-methyl-2-((methyl-d3)sulfonyl)butanamide

81.i. (2R)-4-(6-((1-(2-hydroxyethyl)azetidin-3-yl)buta-1,3-diyn-1-yl)-3-oxo-1H-pyrrolo[1,2-c]imidazol-2(3H)-yl)-2-methyl-2-(methylsulfonyl)-N-((tetrahydro-2H-pyran-2-yl)oxy)butanamide Starting from the compound of Preparation D (0.56 g; 1.32 mmol) and the compound of Preparation AN (0.46 g; 1.44 mmol) and proceeding successively in analogy to Procedure E (68% yield) and Preparation Y, step Y.i (54% yield), the title compound was obtained, after purification by prep-HPLC (Method 1), as a white solid (0.265 g).

MS (ESI, m/z): 547.14 [M+H⁺] for $C_{26}H_{34}N_4O_7S$; $t_R$=0.59 min.

81.ii. (2R)—N-Hydroxy-4-(6-((1-(2-hydroxyethyl)azetidin-3-yl)buta-1,3-diyn-1-yl)-3-oxo-1H-pyrrolo[1,2-c]imidazol-2(3H)-yl)-2-methyl-2-((methyl-d3)sulfonyl)butanamide To a solution of intermediate 81.i (0.070 g; 0.128 mmol) in THF (0.30 mL), cooled to −20° C., was added a solution of LiHMDS (1M in THF; 0.4 mL; 0.4 mmol). The reaction mixture was stirred 15 min at 0° C. After cooling to −20° C., D₂O (0.05 mL) was added and the reaction mixture was allowed to warm to 20° C. over 1 h. After cooling to 0° C., 2M aq. HCl (0.7 mL; 1.4 mmol) was added. The reaction mixture was stirred at rt for 30 min, and aq. NH₄OH (0.05 mL) was added. The resulting solution was purified by prep-HPLC (Method 1) to afford the title compound as a white solid (0.012 g; 21% yield).

¹H NMR (d6-DMSO) δ: 11.12-10.82 (m, 1H); 9.20 (m, 1H); 7.57 (s, 1H); 6.26 (d, J=1.2 Hz, 1H); 4.44 (s, 2H); 4.41 (m, 1H); 3.53-3.46 (overlapped, 3H); 3.42-3.36 (overlapped m, 4H); 3.03 (t, J=6.9 Hz, 2H); 2.59 (m, 1H); 2.43 (t, J=6.0 Hz, 2H); 1.96 (m, 1H); 1.52 (s, 3H).

MS (ESI, m/z): 465.9 [M+H⁺] for $C_{21}H_{23}N_4O_6D_3S$; $t_R$=0.49 min.

Example 82: (2R)-4-(6-(((3RS)-1,3-dimethylpyrrolidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide Starting from the compound of Preparation D (0.25 g; 0.59 mmol) and the compound of Preparation BC (0.186 g; 0.826 mmol) and proceeding successively in analogy to Procedure E (67% yield), Example 21, step 21.ii (77% yield) and Procedure B (64% yield), the title compound was obtained, after purification by prep-HPLC (Method 1), as a white solid (0.058 g).

¹H NMR (d6-DMSO) δ: 10.94 (br. s, 1H); 9.19 (br. s, 1H); 7.54 (s, 1H); 6.24 (d, J=1.2 Hz, 1H); 4.42 (s, 2H); 3.48 (m, 1H); 3.38 (m, 1H); 3.06 (s, 3H); 2.64 (m, 1H); 2.59 (m, 1H); 2.55-2.50 (overlapped m, 2H); 2.43 (d, J=8.9 Hz, 1H); 2.23 (s, 3H); 2.07 (m, 1H); 1.96 (m, 1H); 1.78 (m, 1H); 1.52 (s, 3H); 1.33 (s, 3H).

MS (ESI, m/z): 461.09 [M+H⁺] for $C_{22}H_{28}N_4O_5S$; $t_R$=0.55 min.

Example 83: (2R)—N-hydroxy-2-methyl-4-(6-(((3RS)-1-methylpyrrolidin-3-yl)buta-1,3-diyn-1-yl)-3-oxo-1H-pyrrolo[1,2-c]imidazol-2(3H)-yl)-2-(methylsulfonyl)butanamide Starting from the compound of Preparation D (0.1 g; 0.24 mmol) and the compound of Preparation BD (0.05 g; 0.23 mmol) and proceeding successively in analogy to Procedure E (74% yield) and Procedure B (67% yield), the title compound was obtained, after purification by prep-HPLC (Method 1), as a white solid (0.052 g).

¹H NMR (d6-DMSO) δ: 10.80 (br. s, 1H); 9.21 (br. s, 1H); 7.54 (d, J=0.8 Hz, 1H); 6.25 (d, J=1.2 Hz, 1H); 4.43 (s, 2H); 3.49 (m, 1H); 3.40 (overlapped m, 1H); 3.12 (m, 1H); 3.06 (s, 3H); 2.77 (m, 1H); 2.58 (m, 1H); 2.53-2.43 (overlapped m, 2H); 2.36 (m, 1H); 2.24 (s, 3H); 2.16 (m, 1H); 1.95 (m, 1H); 1.77 (m, 1H); 1.52 (s, 3H).

MS (ESI, m/z): 488.09 [M+MeCN+H⁺] for $C_{21}H_{26}N_4O_5S$; $t_R$=0.52 min.

Example 84: (2R)-4-(6-(2-fluoro-4-((1-methylazetidin-3-yl)ethynyl)phenyl)-3-oxo-1H-pyrrolo[1,2-c]imidazol-2(3H)-yl)-N-hydroxy-2-methyl-2-(methylsulfonyl)butanamide

84.i. Tert-butyl (R)-3-((3-fluoro-4-(2-(4-methoxy-3-methyl-3-(methylsulfonyl)-4-oxobutyl)-3-oxo-2,3-dihydro-1H-pyrrolo[1,2-c]imidazol-6-yl)phenyl)ethynyl)azetidine-1-carboxylate To a mixture of the compound of Preparation BE (0.769 g; 1.44 mmol) was added a solution of intermediate AF.i (0.311 g; 1.72 mmol) in degassed THF (10 mL). Degassed TEA (1 mL, 7.18 mmol) was added followed by PdCl₂(PPh₃)₂ (0.185 g, 0.26 mmol) and CuI (0.104 g, 0.54 mmol). The reaction mixture was heated at 50° C. for 2 h. After cooling, the reaction mixture was concentrated in vacuo and the evaporation residue was purified by CC (Hept-EA-MeOH) to give the title compound as a yellow solid (0.706 g; 83% yield).

¹H NMR (d6-DMSO) δ: 7.75 (t, J=8.2 Hz, 1H); 7.55 (m, 1H); 7.35 (dd, J=1.6, 12.1 Hz, 1H); 7.28 (dd, J=1.6, 8.1 Hz, 1H); 6.62 (m, 1H); 4.44 (s, 2H); 4.20-4.14 (m, 2H); 3.89-3.83 (m, 2H); 3.71-3.62 (m, 2H); 3.53-3.46 (overlapped m, 1H); 3.51 (s, 3H); 3.13 (s, 3H); 2.64 (m, 1H); 2.08 (m, 1H); 1.60 (s, 3H); 1.39 (s, 9H).

MS (ESI, m/z): 588.09 [M+H⁺] for $C_{29}H_{34}N_3O_7FS$; $t_R$=0.97 min.

84.ii. Methyl (R)-4-(6-(4-(azetidin-3-ylethynyl)-2-fluorophenyl)-3-oxo-1H-pyrrolo[1,2-c]imidazol-2(3H)-yl)-2-methyl-2-(methylsulfonyl)butanoate hydrochloride Starting from intermediate 84.i (0.706 g; 1.2 mmol) and proceeding in analogy to Preparation U, step U.iii, the title compound was obtained, after co-evaporation in Et₂O, as a yellowish solid (0.678 g; >95% yield).

¹H NMR (d6-DMSO) δ: 9.22-9.09 (m, 2H); 7.79 (m, 1H); 7.56 (m, 1H); 7.36 (dd, J=1.6, 12.0 Hz, 1H); 7.29 (dd, J=1.6, 8.1 Hz, 1H); 6.62 (m, 1H); 4.44 (s, 2H); 4.25-4.19 (m, 2H); 4.06-3.95 (m, 3H); 3.66 (m, 1H); 3.51 (s, 3H); 3.50 (overlapped m, 1H); 3.13 (s, 3H); 2.64 (m, 1H); 2.09 (m, 1H); 1.60 (s, 3H).

MS (ESI, m/z): 488.22 [M+H⁺] for $C_{24}H_{26}N_3O_5FS$; $t_R$=0.65 min.

84.iii. Methyl (2R)-4-(6-(2-fluoro-4-((1-methylazetidin-3-yl)ethynyl)phenyl)-3-oxo-1H-pyrrolo[1,2-c]imidazol-2(3H)-yl)-2-methyl-2-(methylsulfonyl)butanoate Starting from intermediate 84.ii (0.219 g; 0.418 mmol) and proceeding in analogy to Example 21, step 21.ii, the title compound was obtained, after purification by CC (DCM-MeOH), as a yellowish solid (0.053 g; 25% yield).

¹H NMR (d6-DMSO) δ: 7.73 (t, J=8.3 Hz, 1H); 7.53 (s, 1H); 7.30 (dd, J=1.6, 12.2 Hz, 1H); 7.23 (dd, J=1.6, 8.1 Hz, 1H); 6.61 (m, 1H); 4.44 (s, 2H); 3.65 (m, 1H); 3.57-3.46 (overlapped m, 3H); 3.51 (s, 3H); 3.39 (m, 1H); 3.13 (s, 3H); 3.04-3.00 (m, 2H); 2.64 (m, 1H); 2.21 (m, 1H); 2.09 (m, 1H); 1.60 (s, 3H).

MS (ESI, m/z): 502.19 [M+H⁺] for $C_{25}H_{28}N_3O_5FS$; $t_R$=0.66 min.

84.iv. (R)-4-(6-(2-fluoro-4-((1-methylazetidin-3-yl)ethynyl)phenyl)-3-oxo-1H-pyrrolo[1,2-c]imidazol-2(3H)-yl)-2-methyl-2-(methylsulfonyl)butanoic Acid To an ice-chilled solution of intermediate 84.iii (0.065 g; 0.13 mmol) in THF (0.813 mL) and water (0.53 mL) was added LiOH (0.019 g; 0.26 mmol). The reaction mixture was stirred overnight at rt. The reaction was concentrated to dryness to afford the crude title compound as a yellow solid (0.078 g; >95% yield).

MS (ESI, m/z): 528.97 [M+MeCN+H⁺] for $C_{24}H_{26}N_3O_5FS$; $t_R$=0.61 min.

84.v. (2R)-4-(6-(2-fluoro-4-((1-methylazetidin-3-yl)ethynyl)phenyl)-3-oxo-1H-pyrrolo[1,2-c]imidazol-2(3H)-yl)-N-hydroxy-2-methyl-2-(methylsulfonyl)butanamide Starting from intermediate 84.iv (0.063 g; 0.13 mmol) and proceeding successively in analogy to Preparation D, step D.ii (34% yield) and Procedure B (37% yield), the title compound was obtained, after purification by prep-HPLC (Method 1), as a white solid (0.008 g).

¹H NMR (d6-DMSO) δ: 10.94 (br. s, 1H); 9.08 (br. s, 1H); 7.73 (t, J=8.2 Hz, 1H); 7.52 (s, 1H); 7.29 (dd, J=1.5, 12.2 Hz, 1H); 7.23 (dd, J=1.6, 8.1 Hz, 1H); 6.59 (s, 1H); 4.49 (s, 2H); 3.56-3.48 (m, 3H); 3.43-3.35 (m, 2H); 3.07 (s, 3H); 3.04-2.99 (m, 2H); 2.60 (m, 1H); 2.21 (s, 3H); 1.97 (m, 1H); 1.52 (s, 3H).

MS (ESI, m/z): 485.13 [M+H⁺] for $C_{24}H_{28}N_4O_5S$; $t_R$=0.55 min.

Example 85: (2R)—N-hydroxy-2-methyl-4-(6-(4-((1-methylazetidin-3-yl)ethynyl)phenyl)-3-oxo-1H-pyrrolo[1,2-c]imidazol-2(3H)-yl)-2-(methylsulfonyl)butanamide Starting from the compound of Preparation BF (0.538 g; 1.04 mmol) and intermediate AF.i (0.24 g; 1.32 mmol) and proceeding successively in analogy to Example 84, step 84.i (77% yield), Preparation U, step U.iii (>95% yield), Example 21, step 21.ii (55% yield), Example 84, step 84.iv (>95% yield), Preparation D, step D.ii (57% yield) and Procedure B (27% yield), the title compound was obtained, after purification by prep-HPLC (Method 1), as a white solid (0.029 g).

¹H NMR (d6-DMSO) δ: 10.95 (br. s, 1H); 9.17 (br. s, 1H); 7.66 (s, 1H); 7.65-7.62 (m, 2H); 7.37-7.34 (m, 2H); 6.56 (m, 1H); 4.48 (s, 2H); 3.56-3.52 (m, 2H); 3.50 (m, 1H); 3.42-3.35 (m, 2H); 3.07 (s, 3H); 3.01-2.99 (m, 2H); 2.59 (m, 1H); 2.21 (s, 3H); 1.98 (m, 1H); 1.53 (s, 3H).

MS (ESI, m/z): 485.13 [M+H⁺] for $C_{24}H_{28}N_4O_5S$; $t_R$=0.55 min.

Example 86: (2R)-2-(3-((4-(6-((1-(2-hydroxyethyl)azetidin-3-yl)buta-1,3-diyn-1-yl)-3-oxo-1H-pyrrolo[1,2-c]imidazol-2(3H)-yl)-2-methyl-2-(methylsulfonyl)butanamido)oxy)-3-oxopropyl)phenyl dihydrogen phosphate

86.i. (2R)-4-(6-((1-(2-((tert-butyldimethylsilyl)oxy)ethyl)azetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide Starting from the compound of Preparation D (6.0 g; 14.2 mmol) and the compound of Preparation AN (4.96 g; 15.6 mmol) and proceeding successively in analogy to Procedure E (78% yield), and Procedure C (43% yield on 0.3 mmol scale), the title compound was obtained, after purification by CC (DCM-MeOH containing 1% aq. NH₄OH), as a yellowish foam (0.075 g).

¹H NMR (d6-DMSO) δ: 10.6 (br. s, 1H); 9.18 (br. s, 1H), 7.32-7.69 (m, 1H); 6.26 (s, 1H); 4.43 (m, 2H); 3.57-3.43 (m, 5H); 3.42-3.37 (m, 2H); 3.06 (m, 3H); 3.04 (m, 2H); 2.60 (m, 1H); 2.46-2.43 (m, 2H); 1.98 (m, 1H); 1.52 (s, 3H); 0.90-0.85 (m, 9H); 0.03 (s, 6H).

MS (ESI, m/z): 577.0 [M+H⁺] for $C_{27}H_{40}N_4O_6SSi$; $t_R$=0.74 min.

86.ii. (R)-di-tert-butyl (2-(3-((4-(6-((1-(2-((tert-butyldimethylsilyl)oxy)ethyl)azetidin-3-yl)buta-1,3-diyn-1-yl)-3-oxo-1H-pyrrolo[1,2-c]imidazol-2(3H)-yl)-2-methyl-2-(methylsulfonyl)butanamido)oxy)-3-oxopropyl)phenyl) phosphate To a solution of the compound of Preparation BQ (0.125 g, 0.349 mmol) in DMF (3 mL) were added HOBT (0.067 g, 0.496 mmol), EDC (0.0899 g, 0.464 mmol), TEA (0.097 mL, 0.697 mmol) and intermediate 86.i (0.156 g, 0.271 mmol). The reaction proceeded at rt for 4 h. The reaction mixture was diluted with EA (25 mL) and aq. NaHCO₃ (25 mL). The two layers were separated. The evaporation residue was purified by CC (EA-Hept) to afford the title compound (0.120 g; 48% yield) as a yellow foam.

MS (ESI, m/z): 917.38.0 [M+H⁺] for $C_{44}H_{65}N_4O_{11}SPSSi$; $t_R$=0.92 min.

86.iii. (2R)-2-(3-((4-(6-((1-(2-hydroxyethyl)azetidin-3-yl)buta-1,3-diyn-1-yl)-3-oxo-1H-pyrrolo[1,2-c]imidazol-2(3H)-yl)-2-methyl-2-(methylsulfonyl)butanamido)oxy)-3-oxopropyl)phenyl dihydrogen phosphate Starting from intermediate 86.ii (0.12 g; 0.131 mmol) and proceeding in analogy to Procedure D (69% yield), the title compound was obtained, after purification by prep-HPLC (Method 3), as a white solid (0.062 g).

¹H NMR (d6-DMSO) δ: 7.57 (m, 1H); 7.44 (m, 1H); 7.20-7.06 (m, 2H); 6.92 (m, 1H); 6.21 (m, 1H); 4.53-4.39 (m, 2H); 4.21-4.05 (m, 2H); 3.96-3.84 (m, 2H); 3.73 (m, 1H); 3.59-3.52 (overlapped m, 5H); 3.12 (s, 3H); 3.11-3.01 (m, 2H); 3.00-2.85 (m, 2H); 2.60 (overlapped m, 2H); 1.96 (m, 1H); 1.54-1.64 (m, 3H).

MS (ESI, m/z): 691.1 [M+H⁺] for $C_{30}H_{35}N_4O_{11}PS$; $t_R$=0.55 min.

Example 87: (2R)-4-(6-(2-fluoro-4-((1-methylpiperidin-4-yl)ethynyl)phenyl)-3-oxo-1H-pyrrolo[1,2-c]imidazol-2(3H)-yl)-N-hydroxy-2-methyl-2-(methylsulfonyl)butanamide Starting from the compound of Preparation BE (0.254 g; 0.48 mmol) and tert-butyl 4-ethynylpiperidine-1-carboxylate (0.128 g; 0.61 mmol) and proceeding successively in analogy to Example 84, step 84.i (86% yield), Preparation U, step U.iii (>95% yield), Example 21, step 21.ii (74% yield), Example 84, step 84.iv (>95% yield), Preparation D, step D.ii (54% yield) and Procedure B (84% yield), the title compound was obtained, after precipitation at pH 9 and drying to a constant weight, as an off-white solid (0.073 g).

¹H NMR (d6-DMSO) δ: 10.88 (br. s, 1H); 9.23 (br. s, 1H); 7.72 (t, J=8.2 Hz, 1H); 7.51 (s, 1H); 7.26 (dd, J=1.5, 12.2 Hz, 1H); 7.21 (dd, J=1.5, 8.1 Hz, 1H); 6.59 (m, 1H); 4.49 (s, 2H); 3.52 (m, 1H); 3.41 (m, 1H); 3.07 (s, 3H); 2.65-2.58 (m, 4H); 2.15 (s, 3H); 2.11-2.04 (m, 2H); 1.99 (m, 1H); 1.88-1.83 (m, 2H); 1.65-1.57 (m, 2H); 1.54 (s, 3H).

MS (ESI, m/z): 531.1 [M+H⁺] for $C_{26}H_{31}N_4O_5FS$; $t_R$=0.60 min.

Example 88: (2R)-4-(6-(2-fluoro-4-((1-(2-hydroxyethyl)azetidin-3-yl)ethynyl)phenyl)-3-oxo-1H-pyrrolo[1,2-c]imidazol-2(3H)-yl)-N-hydroxy-2-methyl-2-(methylsulfonyl)butanamide Starting from intermediate 84.ii (0.251 g; 0.48 mmol) and proceeding successively in analogy to Preparation AN (95% yield), Example 84, step 84.iii (>95% yield), Preparation D, step D.ii (19% yield), Preparation Y, step Y.i (80% yield) and Procedure B (45% yield), the title compound was obtained, after purification by prep-HPLC (Method 1), as a white solid (0.014 g).

¹H NMR (d6-DMSO) δ: 10.66 (br. s, 1H); 9.18 (br. s, 1H); 7.73 (t, J=8.2 Hz, 1H); 7.52 (m, 1H); 7.30 (dd, J=1.5, 12.2 Hz, 1H); 7.23 (dd, J=1.5, 8.1 Hz, 1H); 6.59 (m, 1H); 4.50 (s, 2H); 4.41 (t, J=5.3 Hz, 1H); 3.58-3.55 (m, 2H); 3.51 (m, 1H); 3.45-3.30 (overlapped m, 4H); 3.07 (s, 3H); 3.08-3.05 (overlapped m, 2H); 2.60 (m, 1H); 2.45 (t, J=6.0 Hz, 2H); 1.98 (m, 1H); 1.53 (s, 3H).

MS (ESI, m/z): 533.13 [M+H⁺] for $C_{25}H_{29}N_4O_6FS$; $t_R$=0.56 min.

Example 89: (2R)—N-hydroxy-2-methyl-2-(methylsulfonyl)-4-(6-((1-(oxetan-3-yl)pyrrolidin-3-yl)buta-1,3-diyn-1-yl)-3-oxo-1H-pyrrolo[1,2-c]imidazol-2(3H)-yl)butanamide Starting from the compound of Preparation D (0.1 g; 0.24 mmol) and the compound of Preparation BG (0.058 g; 0.25 mmol) and proceeding successively in analogy to Procedure E (99% yield) and Procedure B (32% yield), the title compound was obtained, after purification by prep-HPLC (Method 1), as a white solid (0.037 g).

¹H NMR (d6-DMSO) δ: 10.90 (s, 1H); 9.19 (s, 1H); 7.55 (d, J=0.9 Hz, 1H); 6.25 (d, J=1.3 Hz, 1H); 4.56 (td, 2H); 4.46-4.41 (m, 4H); 3.60 (m, 1H); 3.49 (m, 1H); 3.39 (m, 1H); 3.15 (m, 1H); 3.06 (s, 3H); 2.82 (m, 1H); 2.62-2.52 (overlapped m, 4H); 2.42 (m, 1H); 2.17 (m, 1H); 1.96 (m, 1H); 1.79 (m, 1H); 1.52 (s, 3H).

MS (ESI, m/z): 489.1 [M+H⁺] for $C_{23}H_{28}N_4O_6S$; $t_R$=0.52 min.

Example 90: (2R)—N-hydroxy-4-(6-((1-((1r,3r)-3-hydroxycyclobutyl)azetidin-3-yl)buta-1,3-diyn-1-yl)-3-oxo-1H-pyrrolo[1,2-c]imidazol-2(3H)-yl)-2-methyl-2-(methylsulfonyl)butanamide 90.i. (1r,3r)-3-(3-((2-((2R)-4-(hydroxyamino)-3-methyl-3-(methylsulfonyl)-4-oxobutyl)-3-oxo-2,3-dihydro-1H-pyrrolo[1,2-c]imidazol-6-yl)buta-1,3-diyn-1-yl)azetidin-1-yl)cyclobutyl Acetate and (1s,3s)-3-(3-((2-((2R)-4-(hydroxyamino)-3-methyl-3-(methylsulfonyl)-4-oxobutyl)-3-oxo-2,3-dihydro-1H-pyrrolo[1,2-c]imidazol-6-yl)buta-1,3-diyn-1-yl)azetidin-1-yl)cyclobutyl Acetate Starting from intermediate 52.i (0.5 g; 0.995 mmol) and 3-oxocyclobutyl acetate (0.394 g; 2.98 mmol) and proceeding in analogy to Example 21, step 21.ii, the two title compounds were obtained, after purification by CC (DCM-MeOH+1% aq. NH₄OH) (Method 1), as white solids (0.194 g; 32% yield each). The (1r,3r)-isomer was assigned as the first eluting isomer, the (1s,3s)-isomer being the second eluting isomer.

First Eluting Isomer:
MS (ESI, m/z): 615.20 [M+H⁺] for $C_{30}H_{38}N_4O_8S$; $t_R$=0.66 min.

Second Eluting Isomer:
MS (ESI, m/z): 615.20 [M+H⁺] for $C_{30}H_{38}N_4O_8S$; $t_R$=0.65 min.

90.ii. (2R)—N-hydroxy-4-(6-((1-((1r,3r)-3-hydroxycyclobutyl)azetidin-3-yl)buta-1,3-diyn-1-yl)-3-oxo-1H-pyrrolo[1,2-c]imidazol-2(3H)-yl)-2-methyl-2-(methylsulfonyl)butanamide Starting from intermediate 90.i (first eluting isomer, 0.184 g; 0.3 mmol) and proceeding successively in analogy to Preparation J, step J.ii and Procedure B (69% yield over two steps), the title compound was obtained, after purification by prep-HPLC (Method 1), as a white solid (0.101 g).

¹H NMR (d6-DMSO) δ: 10.87 (br. s, 1H); 9.18 (br. s, 1H); 7.57 (d, J=0.9 Hz, 1H); 6.26 (d, J=1.3 Hz, 1H); 4.95 (d, J=6.4 Hz, 1H); 4.43 (s, 2H); 4.13-4.21 (m, 1H); 3.49 (m, 1H);

3.45-3.34 (m, 3H); 3.30 (overlapped m, 1H); 3.06 (s, 3H); 2.59 (overlapped m, 1H); 2.01-1.88 (m, 3H); 1.80-1.71 (m, 2H); 1.52 (s, 3H).

MS (ESI, m/z): 489.01 [M+H$^+$] for C$_{23}$H$_{28}$N$_4$O$_6$S; t$_R$=0.51 min.

Example 91: (2R)—N-hydroxy-4-(6-((1-((1s,3s)-3-hydroxycyclobutyl)azetidin-3-yl)buta-1,3-diyn-1-yl)-3-oxo-1H-pyrrolo[1,2-c]imidazol-2(3H)-yl)-2-methyl-2-(methylsulfonyl)butanamide Starting from intermediate 90.i (second eluting isomer, 0.193 g; 0.31 mmol) and proceeding in analogy to Preparation J, step J.ii and Procedure B (73% yield, two steps), the title compound was obtained, after purification by prep-HPLC (Method 1), as a white solid (0.112 g).

$^1$H NMR (d6-DMSO) δ: 10.87 (br. s, 1H); 9.18 (br. s, 1H); 7.57 (d, J=0.9 Hz, 1H); 6.26 (d, J=1.3 Hz, 1H); 4.95 (d, J=6.4 Hz, 1H); 4.43 (s, 2H); 4.17 (m, 1H); 3.49 (m, 1H); 3.45-3.34 (m, 3H); 3.30 (overlapped m, 1H); 3.06 (s, 3H); 2.59 (overlapped m, 1H); 2.01-1.88 (m, 3H); 1.80-1.71 (m, 2H); 1.52 (s, 3H).

MS (ESI, m/z): 489.01 [M+H$^+$] for C$_{23}$H$_{28}$N$_4$O$_6$S; t$_R$=0.51 min.

Example 92: (2R)-4-(6-(((2S,3R)-1,2-dimethylazetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide Starting from the compound of Preparation D (0.07 g; 0.165 mmol) and the compound of Preparation BH (0.072 g; 0.41 mmol) and proceeding successively in analogy to Procedure E (46% yield), Example 21, step 21.ii (83% yield) and Procedure B (66% yield), the title compound was obtained, after purification by prep-HPLC (Method 1), as a white solid (0.018 g).

$^1$H NMR (d6-DMSO) δ: 10.91 (br. s, 1H); 9.17 (br. s, 1H); 7.56 (s, 1H); 6.25 (s, 1H); 4.41 (s, 2H); 3.57-3.44 (m, 2H); 3.39 (m, 1H); 3.05 (s, 3H); 2.93-2.84 (m, 2H); 2.63 (m, 1H); 2.58 (m, 1H); 2.18 (s, 3H); 1.95 (m, 1H); 1.52 (s, 3H); 1.14 (d, J=5.4 Hz, 3H).

MS (ESI, m/z): 447.06 [M+H$^+$] for C$_{21}$H$_{26}$N$_4$O$_5$S; t$_R$=0.53 min.

Example 93: (2R)-4-(6-(((2R,3S)-1,2-dimethylazetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide Starting from the compound of Preparation D (0.07 g; 0.165 mmol) and the compound of Preparation BI (0.078 g; 0.45 mmol) and proceeding successively in analogy to Procedure E (41% yield), Example 21, step 21.ii (79% yield) and Procedure B (59% yield), the title compound was obtained, after purification by prep-HPLC (Method 1), as a white solid (0.012 g).

$^1$H NMR (d6-DMSO) δ: 10.93 (br. s, 1H); 9.17 (br. s, 1H); 7.56 (s, 1H); 6.25 (s, 1H); 4.42 (s, 2H); 3.56-3.45 (m, 2H); 3.38 (m, 1H); 3.07 (s, 3H); 2.92-2.86 (m, 2H); 2.63-2.56 (m, 2H); 2.18 (s, 3H); 1.97 (m, 1H); 1.52 (s, 3H); 1.14 (d, J=5.5 Hz, 3H).

MS (ESI, m/z): 447.07 [M+H$^+$] for C$_{21}$H$_{26}$N$_4$O$_5$S; t$_R$=0.53 min.

Example 94: (2R)—N-hydroxy-4-(6-(((3R,5R)-5-(hydroxymethyl)-1-methylpyrrolidin-3-yl)buta-1,3-diyn-1-yl)-3-oxo-1H-pyrrolo[1,2-c]imidazol-2(3H)-yl)-2-methyl-2-(methylsulfonyl)butanamide

94.i. (2R)—N-hydroxy-4-(6-(((3RS, 5R)-5-(hydroxymethyl)-1-methylpyrrolidin-3-yl)buta-1,3-diyn-1-yl)-3-oxo-1H-pyrrolo[1,2-c]imidazol-2(3H)-yl)-2-methyl-2-(methylsulfonyl)butanamide Starting from the compound of Preparation D (0.1 g; 0.236 mmol) and the compound of Preparation BJ (0.072 g; 0.32 mmol) and proceeding successively in analogy to Procedure E (75% yield), and Procedure B (66% yield), the title compound was obtained, after purification by prep-HPLC (Method 1), as a white solid (0.054 g).

$^1$H NMR (d6-DMSO) δ: mixture of isomers, 10.95 (m, 1H); 9.19 (m, 1H); 7.55 (d, J=0.9 Hz, 0.8H); 7.54 (d, J=1.0 Hz, 0.2H); 6.25 (m, 1H); 4.51 (m, 0.2H); 4.48 (t, J=5.5 Hz, 0.8H); 4.43 (br. s, 2H); 3.52-3.45 (m, 1H); 3.41-3.37 (m, 2H); 3.25 (m, 1H); 3.18 (m, 1H); 3.06 (s, 3H); 3.02 (m, 0.8H); 2.97 (m, 0.2H); 2.59 (m, 1H); 2.42-2.37 (m, 1H); 2.28 (s, 3H); 2.22 (m, 1H); 2.00-1.94 (m, 2H); 1.89 (m, 1H); 1.53 (s, 3H).

MS (ESI, m/z): 477.1 [M+H$^+$] for C$_{22}$H$_{28}$N$_4$O$_6$S; t$_R$=0.51 min.

94.ii. (2R)—N-hydroxy-4-(6-(((3R,5R)-5-(hydroxymethyl)-1-methylpyrrolidin-3-yl)buta-1,3-diyn-1-yl)-3-oxo-1H-pyrrolo[1,2-c]imidazol-2(3H)-yl)-2-methyl-2-(methylsulfonyl)butanamide Intermediate 94.i (0.044 g) was separated by semi-preparative chiral HPLC Method E (MeCN-EtOH 1-19+0.5% TFA; flow rate: 16 mL/min; UV detection at 278 nm); the respective retention times were 4.5 and 5.5 min. The title (3R,5R)-enantiomer, identified as the second eluting compound, was obtained as a yellowish solid (0.035 g).

$^1$H NMR (d$_6$-DMSO) δ: 10.9 (br. s, 1H); 9.18 (s, 1H); 7.60 (s, 1H); 6.27 (s, 1H); 4.43 (s, 2H); 3.81-3.73 (m, 2H), 3.67-3.57 (m, 3H); 3.49 (m, 1H); 3.42-3.33 (m, 2H); 3.24 (m, 1H); 3.06 (s, 3H); 2.90 (s, 3H); 2.59 (m, 1H); 2.28-2.17 (m, 2H); 1.96 (m, 1H); 1.52 (s, 3H).

MS (ESI, m/z): 477.1 [M+H$^+$] for C$_{22}$H$_{28}$N$_4$O$_6$S; t$_R$=0.51 min.

Example 95: (2R)—N-hydroxy-4-(6-(((2R,3R)-2-(hydroxymethyl)-1-methylazetidin-3-yl)buta-1,3-diyn-1-yl)-3-oxo-1H-pyrrolo[1,2-c]imidazol-2(3H)-yl)-2-methyl-2-(methylsulfonyl)butanamide Starting from the compound of Preparation D (0.15 g; 0.35 mmol) and the compound of Preparation BK (0.124 g; 0.65 mmol) and proceeding successively in analogy to Procedure E (82% yield), Preparation W (71% yield) and Procedure B (84% yield), the title compound was obtained, after purification by prep-HPLC (Method 1), as a white solid (0.079 g).

$^1$H NMR (d6-DMSO) δ: 10.94 (br. s, 1H); 9.17 (br. s, 1H); 7.56 (d, J=0.6 Hz, 1H); 6.25 (d, J=1.2 Hz, 1H); 4.66 (t, J=5.7 Hz, 1H); 4.43 (s, 2H); 3.53 (dd, J=6.1, 7.5 Hz, 1H); 3.47 (m, 1H); 3.41 (t, J=5.1 Hz, 2H); 3.38 (overlapped m, 1H); 3.06 (s, 3H); 3.06 (overlapped m, 1H); 2.95 (m, 1H); 2.67 (m, 1H); 2.58 (m, 1H); 2.23 (s, 3H); 1.96 (m, 1H); 1.52 (s, 3H).

MS (ESI, m/z): 463.1 [M+H$^+$] for C$_{21}$H$_{26}$N$_4$O$_6$S; t$_R$=0.50 min.

Example 96: (2R)-4-(6-(((2R,3R)-1,2-dimethylazetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide Starting from the compound of Preparation D (0.15 g; 0.35 mmol) and the compound of Preparation BL (0.10 g; 0.575 mmol) and proceeding successively in analogy to Procedure E (69% yield), Preparation W (97% yield) and Procedure B (79% yield), the title compound was obtained, after purification by prep-HPLC (Method 1), as a white solid (0.083 g).

$^1$H NMR (d6-DMSO) δ: 10.94 (br. s, 1H); 9.18 (br. s, 1H); 7.57 (d, J=0.9 Hz, 1H); 6.27 (d, J=1.2 Hz, 1H); 4.43 (s, 2H); 3.48 (m, 1H); 3.39 (m, 1H); 3.35 (overlapped m, 1H); 3.20 (dd, J=2.4, 6.3 Hz, 1H); 3.14 (m, 1H); 3.06 (s, 3H); 2.96 (m, 1H); 2.59 (m, 1H); 2.14 (s, 3H); 1.96 (m, 1H); 1.52 (s, 3H); 1.11 (d, J=6.2 Hz, 3H).

MS (ESI, m/z): 447.1 [M+H$^+$] for $C_{21}H_{26}N_4O_5S$; $t_R$=0.52 min.

Example 97: (2R)—N-hydroxy-4-(6-(((2S,3S)-2-(hydroxymethyl)-1-methylazetidin-3-yl)buta-1,3-diyn-1-yl)-3-oxo-1H-pyrrolo[1,2-c]imidazol-2(3H)-yl)-2-methyl-2-(methylsulfonyl)butanamide Starting from the compound of Preparation D (0.15 g; 0.35 mmol) and the compound of Preparation BM (0.160 g; 0.84 mmol) and proceeding successively in analogy to Procedure E (60% yield), Preparation W (94% yield) and Procedure B (56% yield), the title compound was obtained, after purification by prep-HPLC (Method 1), as a white solid (0.052 g).

$^1$H NMR (d6-DMSO) δ: 10.94 (br. s, 1H); 9.17 (br. s, 1H); 7.56 (d, J=0.6 Hz, 1H); 6.25 (d, J=1.2 Hz, 1H); 4.66 (t, J=5.7 Hz, 1H); 4.43 (s, 2H); 3.53 (dd, J=6.1, 7.5 Hz, 1H); 3.47 (m, 1H); 3.41 (t, J=5.1 Hz, 2H); 3.38 (overlapped m, 1H); 3.06 (s, 3H); 3.06 (overlapped m, 1H); 2.95 (m, 1H); 2.67 (m, 1H); 2.58 (m, 1H); 2.23 (s, 3H); 1.96 (m, 1H); 1.52 (s, 3H).

MS (ESI, m/z): 463.1 [M+H$^+$] for $C_{21}H_{26}N_4O_6S$; $t_R$=0.50 min.

Example 98: (2R)—N-hydroxy-4-(6-(((2S,3S)-2-(fluoromethyl)-1-methylazetidin-3-yl)buta-1,3-diyn-1-yl)-3-oxo-1H-pyrrolo[1,2-c]imidazol-2(3H)-yl)-2-methyl-2-(methylsulfonyl)butanamide Starting from the compound of Preparation D (0.15 g; 0.35 mmol) and the compound of Preparation BN (0.160 g; 0.83 mmol) and proceeding successively in analogy to Procedure E (80% yield), Preparation W (77% yield) and Procedure B (74% yield), the title compound was obtained, after purification by prep-HPLC (Method 1), as a white solid (0.052 g).

$^1$H NMR (d6-DMSO) δ: 10.94 (br. s, 1H); 9.18 (br. s, 1H); 7.58 (s, 1H); 6.26 (s, 1H); 4.53-4.32 (m, 4H); 3.57 (m, 1H); 3.48 (m, 1H); 3.39 (m, 1H); 3.24-3.16 (m, 2H); 3.05 (s, 3H); 2.75 (m, 1H); 2.59 (m, 1H); 2.25 (s, 3H); 1.95 (m, 1H); 1.51 (s, 3H).

MS (ESI, m/z): 465.0 [M+H$^+$] for $C_{21}H_{25}N_4O_5FS$; $t_R$=0.50 min.

Example 99: (2R)—N-hydroxy-4-(6-(((3S*,4R*)-4-hydroxy-1-methylpyrrolidin-3-yl)buta-1,3-diyn-1-yl)-3-oxo-1H-pyrrolo[1,2-c]imidazol-2(3H)-yl)-2-methyl-2-(methylsulfonyl)butanamide Starting from the compound of Preparation D (0.3 g; 0.708 mmol) and the compound of Preparation BO (0.675 g; 0.45 mmol) and proceeding successively in analogy to Procedure E (52% yield), Example 21, step 21.ii (49% yield) and Procedure B (46% yield), the title compound was obtained, after purification by prep-HPLC (Method 1), as a white solid (0.019 g).

$^1$H NMR (d6-DMSO) δ: 10.95 (m, 1H); 9.17-9.21 (m, 1H); 7.56 (d, J=1.0 Hz, 1H); 6.26 (d, J=1.2 Hz, 1H); 5.44 (d, J=5.3 Hz, 1H); 4.43 (s, 2H); 4.18 (m, 1H); 3.49 (m, 1H); 3.39 (m, 1H); 3.06 (s, 3H); 2.88-2.82 (m, 2H); 2.71 (dd, J=6.6, 9.7 Hz, 1H); 2.59 (m, 1H); 2.40-2.34 (m, 2H); 2.22 (s, 3H); 1.97 (m, 1H); 1.53 (s, 3H).

MS (ESI, m/z): 463.0 [M+H$^+$] for $C_{21}H_{26}N_4O_6S$; $t_R$=0.49 min.

Example 100: (2R)—N-hydroxy-4-(6-(((3R,5R)-5-(hydroxymethyl)-1-(oxetan-3-yl)pyrrolidin-3-yl)buta-1,3-diyn-1-yl)-3-oxo-1H-pyrrolo[1,2-c]imidazol-2(3H)-yl)-2-methyl-2-(methylsulfonyl)butanamide Starting from the compound of Preparation D (0.09 g; 0.213 mmol) and the compound of Preparation BP (0.072 g; 0.27 mmol) and proceeding successively in analogy to Procedure E (68% yield), and Procedure C (51% yield), the title compound was obtained, after purification by prep-HPLC (Method 1), as a white solid (0.036 g).

MS (ESI, m/z): 519.0 [M+H$^+$] for $C_{24}H_{30}N_4O_7S$; $t_R$=0.51 min.

Pharmacological Properties of the Invention Compounds
In Vitro Assays
Bacterial Growth Minimal Inhibitory Concentrations:
Experimental Methods:

Minimal Inhibitory Concentrations (MICs; mg/L) were determined in cation-adjusted Mueller-Hinton Broth by a microdilution method following the description given in "*Methods for Dilution Antimicrobial Susceptibility Tests for Bacteria that Grow Aerobically*", Approved standard, 7$^{th}$ ed., Clinical and Laboratory Standards Institute (CLSI) Document M7-A7, Wayne, Pa., USA (2006).

RESULTS

All Reference Example compounds were tested against against several Gram-negative bacteria. *K. pneumoniae* A-651 is a multiply resistant strain (in particular quinolone-resistant), while *E. coli* ATCC25922 and *P. aeruginosa* ATCC27853 are quinolone-sensitive strains. The corresponding antibacterial test results are given in Table 1 hereafter (MICs in mg/L).

TABLE 1

| Example No. | MIC for *E. coli* ATCC25922 | MIC for *P. aeruginosa* ATCC27853 | MIC for *K. Pneumoniae* A-651 |
|---|---|---|---|
| 1 | 1 | 2 | 2 |
| 2 | 1 | 1 | 1 |
| 3 | 0.25 | 1 | 1 |
| 4 | 2 | 2 | 2 |
| 5 | 0.25 | 2 | 1 |
| 6 | 2 | 1 | 4 |
| 7 | 0.5 | 0.5 | 2 |
| 8 | 1 | 2 | 2 |
| 9 | 2 | 8 | 4 |
| 10 | 0.25 | 1 | 0.25 |
| 11 | 0.5 | 2 | 0.5 |
| 12 | 1 | 4 | 2 |
| 13 | 1 | 1 | 1 |
| 14 | 0.5 | 1 | 2 |

TABLE 1-continued

| Example No. | MIC for E. coli ATCC25922 | MIC for P. aeruginosa ATCC27853 | MIC for K. Pneumoniae A-651 |
|---|---|---|---|
| 15 | 0.5 | 1 | 2 |
| 16 | 0.25 | 1 | 0.5 |
| 17 | 0.25 | 2 | 0.5 |
| 18 | 2 | 2 | 4 |
| 19 | 0.25 | 2 | 1 |
| 20 | 0.125 | 1 | 0.25 |
| 21 | 0.5 | 0.5 | 0.5 |
| 22 | 1 | 4 | 4 |
| 23 | 4 | 8 | 4 |
| 24 | 0.5 | 1 | 1 |
| 25 | 0.125 | 1 | 0.5 |
| 26 | 8 | 4 | 8 |
| 27 | 2 | 8 | 4 |
| 28 | 1 | 2 | 8 |
| 29 | 0.25 | 2 | 0.5 |
| 30 | 0.5 | 0.5 | 0.5 |
| 31 | 8 | 1 | 8 |
| 32 | 1 | 1 | 2 |
| 33 | 0.25 | 2 | 0.25 |
| 34 | 4 | 1 | 4 |
| 35 | 0.5 | 2 | 1 |
| 36 | 0.25 | 1 | 0.5 |
| 37 | 0.5 | 2 | 0.5 |
| 38 | 0.063 | 0.5 | 0.25 |
| 39 | 8 | 4 | 4 |
| 40 | 2 | 2 | 2 |
| 41 | 0.5 | 0.5 | 0.5 |
| 42 | 0.5 | 2 | 1 |
| 43 | 0.5 | 0.5 | 2 |
| 44 | 2 | 4 | 2 |
| 45 | 8 | >8 | 8 |
| 46 | 0.5 | 1 | 1 |
| 47 | 0.5 | 2 | 2 |
| 48 | >8 | 4 | >8 |
| 49 | <0.063 | 1 | 0.125 |
| 50 | 1 | 2 | 1 |
| 51 | 1 | 1 | 4 |
| 52 | 0.5 | 0.5 | 0.5 |
| 53 | 4 | 4 | 4 |
| 54 | 0.25 | 0.5 | 0.5 |
| 55 | 0.125 | 1 | 0.25 |
| 56 | 0.25 | 0.5 | 1 |
| 57 | 0.125 | 0.063 | 0.5 |
| 58 | 0.5 | 0.25 | 4 |
| 59 | 1 | 0.5 | 0.5 |
| 60 | 0.5 | 0.5 | 0.5 |
| 61 | 0.063 | 0.5 | 0.5 |
| 62 | 0.125 | 1 | 0.125 |
| 63 | 1 | 4 | 2 |
| 64 | 0.25 | 0.5 | 1 |
| 65 | 1 | 1 | 1 |
| 66 | 0.5 | 2 | 1 |
| 67 | 2 | 1 | 2 |
| 68 | 0.063 | 1 | 0.25 |
| 69 | 0.25 | 0.5 | 0.5 |
| 70 | 0.125 | 0.5 | 0.25 |
| 71 | 0.25 | 2 | 0.5 |
| 72 | 0.5 | 2 | 0.5 |
| 73 | 0.5 | 1 | 0.25 |
| 74 | 0.25 | 1 | 0.25 |
| 75 | 0.063 | 2 | 0.125 |
| 76 | 0.125 | 2 | 0.25 |
| 77 | 0.5 | 1 | 1 |
| 78 | 1 | 1 | 1 |
| 79 | 2 | 4 | 2 |
| 80 | 0.5 | 0.5 | 0.5 |
| 81 | 1 | 1 | 2 |
| 82 | 2 | 4 | 2 |
| 83 | 2 | 1 | 1 |
| 84 | 0.5 | 2 | 1 |
| 85 | 0.5 | 1 | 1 |
| 87 | 4 | 8 | >8 |
| 88 | 0.5 | 2 | 2 |
| 89 | 1 | 2 | 1 |
| 90 | 0.5 | 1 | 0.5 |
| 91 | 0.5 | 1 | 0.5 |
| 92 | 0.25 | 0.25 | 0.25 |
| 93 | 0.25 | 0.25 | 0.5 |
| 94 | 1 | 0.5 | 1 |
| 95 | 1 | 0.5 | 1 |
| 96 | 4 | 2 | 4 |
| 97 | 0.5 | 0.5 | 1 |
| 98 | 0.063 | 0.5 | 0.25 |
| 99 | 2 | 2 | 2 |
| 100 | 4 | 4 | 4 |
| Cipro | 0.063 | 0.25 | 8 |

The compound of Example 86 was tested against against wild-type E. coli A-1261 in the absence of alkaline phosphatase or esterase, in the presence of an alkaline phosphatase and in the presence of an esterase. The corresponding antibacterial test results are given in Table 2 hereafter (MICs in mg/L).

TABLE 2

| Active Example No. | Metabolite Reference Example No. | MIC for E. coli A-1261 | | |
|---|---|---|---|---|
| | | In the absence of alkaline phosphatase or esterase | In the presence of an alkaline phosphatase (2 i.U./mL) | In the presence of an esterase (10 i.U./mL) |
| 86 | 41 | 16 | 1 | 16 |

The invention claimed is:

1. A compound of formula I

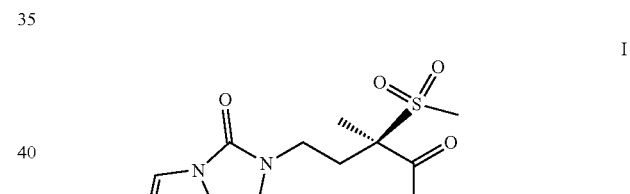

wherein

M is one of the groups $M^A$, $M^B$ and $M^C$ represented below

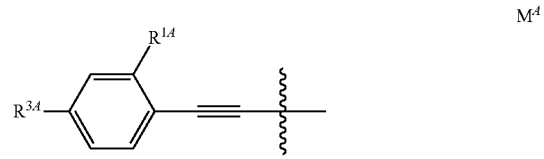

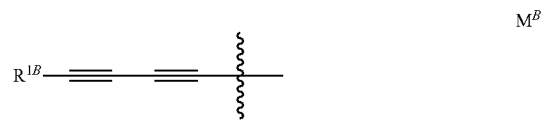

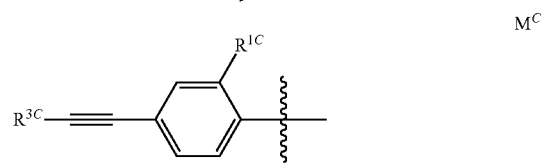

wherein

R$^{1A}$ represents hydrogen or fluorine;

R$^{3A}$ represents 3-fluoroazetidin-3-yl, 3-fluoro-1-methyl-azetidin-3-yl, 1-acetyl-3-hydroxyazetidin-3-yl, 3-fluoro-1-(oxetan-3-yl)azetidin-3-yl, (3-fluoroazetidin-1-yl)methyl, (3-hydroxyazetidin-1-yl)methyl, (5-(hydroxymethyl)-2-oxooxazolidin-3-yl)methyl, (4-hydroxy-3-fluoropiperidin-1-yl)methyl, (4-amino-3-fluoropiperidin-1-yl)methyl, (4-hydroxy-3,3-difluoropiperidin-1-yl)methyl, (4-amino-3,3-difluoropiperidin-1-yl)methyl, (6-amino-3-azabicyclo[3.1.0]hexan-3-yl)methyl, (2-oxa-6-azaspiro[3.3]heptan-6-yl)methyl, 2-morpholino-1-hydroxyethyl, 2-(methylsulfonyl)ethoxy, (3-hydroxyazetidin-1-yl)carbonyloxymethyl, (4-hydroxypiperidin-1-yl)carbonyloxymethyl, (4-methylpiperazin-1-yl)carbonyloxymethyl, N-(2-hydroxyethyl)-N-(methyl)carbamoyloxymethyl, 1-hydroxy-2-[(2-methoxyethyl)(methyl)amino]ethyl, azetidin-3-yloxycarbonylaminomethyl or (N-methylazetidin-3-yl)oxycarbonylaminomethyl;

R$^{1B}$ represents trans-2-(1,2-dihydroxyethyl)cycloprop-1-yl, 1-(methylamino)cydoprop-1-yl, 1-(dimethylamino)cycloprop-1-yl, 2-(dimethylaminomethyl)cycloprop-1-yl, 1-((3-hydroxyazetidinyl)-1-carbonyloxymethyl)cycloprop-1-yl, 2-(morpholinomethyl)cycloprop-1-yl, 1-((4-methylpiperazinyl)-1-carbonyloxymethyl)cycloprop-1-yl, 4-fluoropyrrolidin-2-yl, (2-oxooxazolidin-3-yl)methyl, 1-(3-hydroxyazetidine)-1-carbonyloxymethyl, (4-hydroxypiperidin-1-yl)carbonyloxymethyl, 1-(4-methylpiperazine)-1-carbonyloxymethyl or N-methylazetidin-3-yl)oxycarbonylaminomethyl, or R$^{1B}$ represents a group Q, Q being one of the groups Q$^A$, Q$^B$ and Q$^C$ represented below

Q$^A$

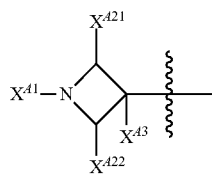

Q$^B$

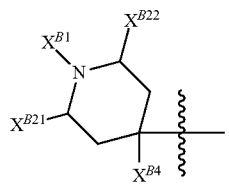

Q$^C$

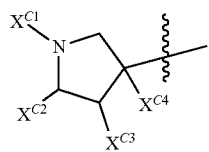

wherein

X$^{A1}$ represents H, methyl-d, methyl-d2, (C$_1$-C$_4$)alkyl, acetyl, ω-(C$_2$-C$_3$)haloalkyl, ω-hydroxy(C$_2$-C$_3$)alkyl, 2,3-dihydroxyprop-1-yl, 3-hydroxy-2-(hydroxymethyl)prop-1-yl, oxetan-3-yl, thietan-3-yl, 1,1-dioxidothietan-3-yl, (C$_3$-C$_6$)cycloalkyl, 3-hydroxycyclobut-1-yl, tetrahydropyran-4-yl or (C$_3$-C$_6$)cycloalkyl(C$_1$-C$_3$)alkyl, X$^{A21}$ and X$^{A22}$ each independently represent H, (C$_1$-C$_4$)alkyl, (C$_1$-C$_3$)haloalkyl or hydroxy(C$_1$-C$_3$)alkyl, and X$^{A3}$ represents H, (C$_1$-C$_3$)alkyl or halogen, provided that if X$^{A1}$ represents oxetan-3-yl, at least one of X$^{A21}$, X$^{A22}$ and X$^{A3}$ does not represent H;

X$^{B1}$ represents H, (C$_1$-C$_4$)alkyl, ω-hydroxy(C$_2$-C$_3$)alkyl, (C$_3$-C$_6$)cycloalkyl, oxetan-3-yl or tetrahydropyran-4-yl, X$^{B21}$ and X$^{B22}$ each independently represent H, (C$_1$-C$_4$)alkyl, (C$_1$-C$_3$)haloalkyl or hydroxy(C$_1$-C$_3$)alkyl, and X$^{B4}$ represents H, halogen, hydroxy or (C$_1$-C$_3$)alkyl;

X$^{C1}$ represents H, (C$_1$-C$_4$)alkyl, (C$_3$-C$_6$)cycloalkyl, ω-hydroxy(C$_2$-C$_3$)alkyl, oxetan-3-yl or tetrahydropyran-4-yl, X$^{C2}$ represents H, (C$_1$-C$_4$)alkyl, (C$_1$-C$_3$)haloalkyl or hydroxy(C$_1$-C$_3$)alkyl, X$^{C3}$ represents H, halogen, hydroxy, (C$_1$-C$_4$)alkyl, (C$_1$-C$_3$)haloalkyl, hydroxy(C$_1$-C$_3$)alkyl, and X$^{C4}$ represents H, (C$_1$-C$_3$)alkyl, halogen or hydroxy;

R$^{1C}$ represents hydrogen or fluorine;

R$^{3C}$ represents a group Q as defined before; and

R$^1$ represents H, PO$_3$H$_2$, SO$_3$H, phosphonooxymethyl or the group L represented below

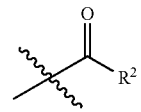

L wherein R$^2$ represents (C$_1$-C$_4$)alkylamino(C$_1$-C$_4$)alkyl, [di(C$_1$-C$_4$)alkylamino](C$_1$-C$_4$)alkyl, phosphonooxy(C$_1$-C$_4$)alkyl, phosphonooxymethoxy, 2-(phosphonooxy-(C$_1$-C$_4$)alkyl)-phenyl, (2-(phosphonooxy)-phenyl)-(C$_1$-C$_4$)alkyl, 2-(2-(phosphonooxy)-phenyl)-ethyl, or [2-(phosphonooxy-(C$_1$-C$_4$)alkyl)-phenyl]-(C$_1$-C$_4$)alkyl;

or a salt thereof.

2. A compound of formula I according to claim 1, which is a compound of formula I$_{CEP}$

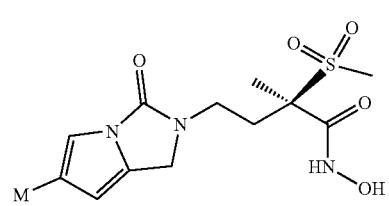

I$_{CEP}$ wherein

M is one of the groups M$^A$ and M$^B$ represented below

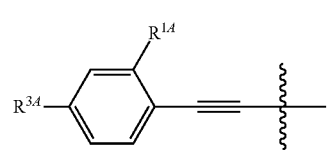

M$^A$

-continued

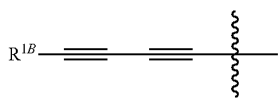
$M^B$ wherein $R^{1A}$ represents hydrogen or fluorine;

$R^{3A}$ represents 3-fluoroazetidin-3-yl, 3-fluoro-1-methyl-azetidin-3-yl, 1-acetyl-3-hydroxyazetidin-3-yl, 3-fluoro-1-(oxetan-3-yl)azetidin-3-yl, (3-fluoroazetidin-1-yl)methyl, (3-hydroxyazetidin-1-yl)methyl, (5-(hydroxymethyl)-2-oxooxazolidin-3-yl)methyl, (4-hydroxy-3-fluoropiperidin-1-yl)methyl, (4-amino-3-fluoropiperidin-1-yl)methyl, (4-hydroxy-3,3-difluoropiperidin-1-yl)methyl, (4-amino-3,3-difluoropiperidin-1-yl)methyl, (6-amino-3-azabicyclo[3.1.0]hexan-3-yl)methyl, (2-oxa-6-azaspiro[3.3]heptan-6-yl)methyl, 2-morpholino-1-hydroxyethyl, 2-(methylsulfonyl)ethoxy, (3-hydroxyazetidin-1-yl)carbonyloxymethyl, (4-hydroxypiperidin-1-yl)carbonyloxymethyl, (4-methylpiperazin-1-yl)carbonyloxymethyl, N-(2-hydroxyethyl)-N-(methyl)carbamoyloxymethyl, 1-hydroxy-2-[(2-methoxyethyl)(methyl)amino]ethyl, azetidin-3-yloxycarbonylaminomethyl or (N-methylazetidin-3-yl)oxycarbonylaminomethyl;

$R^{1B}$ represents trans-2-(1,2-dihydroxyethyl)cycloprop-1-yl, 1-(methylamino)cydoprop-1-yl, 1-(dimethylamino)cycloprop-1-yl, 2-(dimethylaminomethyl)cycloprop-1-yl, 1-((3-hydroxyazetidinyl)-1-carbonyloxymethyl)cycloprop-1-yl, 2-(morpholinomethyl)cycloprop-1-yl, 1-((4-methylpiperazinyl)-1-carbonyloxymethyl)cycloprop-1-yl, 4-fluoropyrrolidin-2-yl, (2-oxooxazolidin-3-yl)methyl, 1-(3-hydroxyazetidine)-1-carbonyloxymethyl, (4-hydroxypiperidin-1-yl)carbonyloxymethyl, 1-(4-methylpiperazine)-1-carbonyloxymethyl or N-methylazetidin-3-yl)oxycarbonylaminomethyl, or $R^{1B}$ represents a group Q, Q being one of the groups $Q^A$ and $Q^B$ represented below

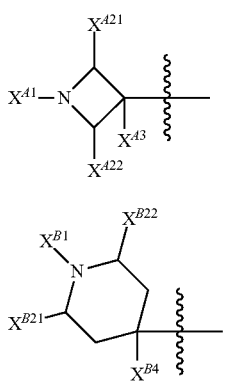

wherein $X^{A1}$ represents H, methyl-d, methyl-d2, $(C_1-C_4)$alkyl, acetyl, ω-$(C_2-C_3)$haloalkyl, ω-hydroxy$(C_2-C_3)$alkyl, 2,3-dihydroxyprop-1-yl, 3-hydroxy-2-(hydroxymethyl)prop-1-yl, oxetan-3-yl, 1,1-dioxidothietan-3-yl, $(C_3-C_6)$cycloalkyl or $(C_3-C_6)$cycloalkyl$(C_1-C_3)$alkyl, $X^{A21}$ and $X^{A22}$ each represent H, and $X^{A3}$ represents H, $(C_1-C_3)$alkyl or halogen,
provided that if $X^{A1}$ represents oxetan-3-yl, then $X^{A3}$ does not represent H;

$X^{B1}$ represents H, $(C_1-C_4)$alkyl or oxetan-3-yl, $X^{B21}$ and $X^{B22}$ each represent H, and $X^{B4}$ represents H, halogen or hydroxy;

or a salt thereof.

3. A compound of formula I according to claim 1, wherein M is the group $M^A$;
or a salt thereof.

4. A compound of formula I according to claim 3, wherein M is the group $M^A$ wherein $R^{1A}$ represents hydrogen or fluorine and $R^{3A}$ represents 3-fluoro-1-methyl-azetidin-3-yl, 3-fluoro-1-(oxetan-3-yl)azetidin-3-yl, (3-fluoroazetidin-1-yl)methyl, (3-hydroxyazetidin-1-yl)methyl, (4-hydroxy-3-fluoropiperidin-1-yl)methyl, (4-hydroxy-3,3-difluoropiperidin-1-yl)methyl, (6-amino-3-azabicyclo[3.1.0]hexan-3-yl)methyl, (2-oxa-6-azaspiro[3.3]heptan-6-yl)methyl, 2-(methylsulfonyl)ethoxy, (3-hydroxyazetidin-1-yl)carbonyloxymethyl, (4-methylpiperazin-1-yl)carbonyloxymethyl, N-(2-hydroxyethyl)-N-(methyl)carbamoyloxymethyl or azetidin-3-yloxycarbonylaminomethyl;
or a salt thereof.

5. A compound of formula I according to claim 1, wherein M is the group $M^B$;
or a salt thereof.

6. A compound of formula I according to claim 5, wherein M is the group $M^B$ and $R^{1B}$ represents trans-2-(1,2-dihydroxyethyl)cycloprop-1-yl, 1-(methylamino)cydoprop-1-yl, 1-(dimethylamino)cycloprop-1-yl, 2-(morpholinomethyl)cycloprop-1-yl or 1-(3-hydroxyazetidine)-1-carbonyloxymethyl;
or a salt thereof.

7. A compound of formula I according to claim 5, wherein M is the group $M^B$ wherein $R^{1B}$ represents the group $Q^A$ wherein $X^{A1}$ represents H, methyl-d, methyl-d2, $(C_1-C_4)$alkyl, ω-$(C_2-C_3)$haloalkyl, ω-hydroxy$(C_2-C_3)$alkyl, $(C_3-C_6)$cycloalkyl or $(C_3-C_6)$cycloalkyl$(C_1-C_3)$alkyl, $X^{A21}$ and $X^{A22}$ each represent H, and $X^{A3}$ represents H, $(C_1-C_3)$alkyl or fluorine;
or a salt thereof.

8. A compound of formula I according to claim 7, wherein M is the group $M^B$ wherein $R^{1B}$ represents the group $Q^A$ wherein $X^{A1}$ represents methyl, methyl-d, methyl-d2, 2-fluoro-ethyl, 2-hydroxy-ethyl, cycloprop-1-yl, 3-hydroxyprop-1-yl or 3-hydroxycyclobut-1-yl, $X^{A21}$ and $X^{A22}$ each represent H, and $X^{A3}$ represents H or fluorine;
or a salt thereof.

9. A compound of formula I according to claim 5, wherein M is the group $M^B$ wherein $R^{1B}$ represents the group $Q^A$ wherein $X^{A1}$ represents cycloprop-1-yl, 3-hydroxycyclobut-1-yl or cyclohex-1-yl, $X^{A21}$ and $X^{A22}$ each represent H, and $X^{A3}$ represents H;
or a salt thereof.

10. A compound of formula I according to claim 5, wherein M is the group $M^B$ wherein $R^{1B}$ represents the group $Q^A$ wherein $X^{A1}$ represents methyl or ethyl,
one of $X^{A21}$ and $X^{A22}$ represents methyl or fluoromethyl and the other represents H, and $X^{A3}$ represents H;
or a salt thereof.

11. A compound of formula I according to claim 5, wherein M is the group $M^B$ wherein $R^{1B}$ represents the group $Q^B$ wherein $X^{B1}$ represents H or methyl, $X^{B21}$ and $X^{B22}$ each represent H, and $X^{B4}$ represents H or fluorine;
or a salt thereof.

12. A compound of formula I according to claim 1, which is selected from the following:

(2R)—N-hydroxy-4-(6-((4-((1R)-1-hydroxy-2-morpholinoethyl)phenyl)ethynyl)-3-oxo-1H-pyrrolo[1,2-c]imidazol-2(3H)-yl)-2-methyl-2-(methylsulfonyl)butanamide;

(2R)—N-hydroxy-4-(6-((4-((1S)-1-hydroxy-2-morpholinoethyl)phenyl)ethynyl)-3-oxo-1H-pyrrolo[1,2-c]imidazol-2(3H)-yl)-2-methyl-2-(methylsulfonyl)butanamide;

(2R)-4-(6-((4-((2-oxa-6-azaspiro[3.3]heptan-6-yl)methyl)phenyl)ethynyl)-3-oxo-1H-pyrrolo[1,2-c]imidazol-2(3H)-yl)-N-hydroxy-2-methyl-2-(methylsulfonyl)butanamide;

(2R)-4-(6-((4-((6-amino-3-azabicyclo[3.1.0]hexan-3-yl)methyl)phenyl)ethynyl)-3-oxo-1H-pyrrolo[1,2-c]imidazol-2(3H)-yl)-N-hydroxy-2-methyl-2-(methylsulfonyl)butanamide;

(3R)-4-((2-(4-(hydroxyamino)-3-methyl-3-(methylsulfonyl)-4-oxobutyl)-3-oxo-2,3-dihydro-1H-pyrrolo[1,2-c]imidazol-6-yl)ethynyl)benzyl 4-hydroxypiperidine-1-carboxylate;

(2R)-4-(6-((4-(1-acetyl-3-hydroxyazetidin-3-yl)phenyl)ethynyl)-3-oxo-1H-pyrrolo[1,2-c]imidazol-2(3H)-yl)-N-hydroxy-2-methyl-2-(methylsulfonyl)butanamide;

(2R)-4-(6-(((1R,2R)-2-((S)-1,2-dihydroxyethyl)cyclopropyl)buta-1,3-diyn-1-yl)-3-oxo-1H-pyrrolo[1,2-c]imidazol-2(3H)-yl)-N-hydroxy-2-methyl-2-(methylsulfonyl)butanamide;

(3R)-5-(2-(4-(hydroxyamino)-3-methyl-3-(methylsulfonyl)-4-oxobutyl)-3-oxo-2,3-dihydro-1H-pyrrolo[1,2-c]imidazol-6-yl)penta-2,4-diyn-1-yl 4-hydroxypiperidine-1-carboxylate;

(2R)—N-hydroxy-2-methyl-2-(methylsulfonyl)-4-(3-oxo-6-(5-(2-oxooxazolidin-3-yl)penta-1,3-diyn-1-yl)-1H-pyrrolo[1,2-c]imidazol-2(3H)-yl)butanamide;

(3R)-4-((2-(4-(hydroxyamino)-3-methyl-3-(methylsulfonyl)-4-oxobutyl)-3-oxo-2,3-dihydro-1H-pyrrolo[1,2-c]imidazol-6-yl)ethynyl)benzyl 3-hydroxyazetidine-1-carboxylate;

(3R)-4-((2-(4-(hydroxyamino)-3-methyl-3-(methylsulfonyl)-4-oxobutyl)-3-oxo-2,3-dihydro-1H-pyrrolo[1,2-c]imidazol-6-yl)ethynyl)benzyl (2-hydroxyethyl)(methyl)carbamate;

(2R)—N-hydroxy-4-(6-((4-((5-(hydroxymethyl)-2-oxooxazolidin-3-yl)methyl)phenyl)ethynyl)-3-oxo-1H-pyrrolo[1,2-c]imidazol-2(3H)-yl)-2-methyl-2-(methylsulfonyl)butanamide;

(2R)-4-(6-((4-(((3S*,4S*)-4-amino-3-fluoropiperidin-1-yl)methyl)phenyl)ethynyl)-3-oxo-1H-pyrrolo[1,2-c]imidazol-2(3H)-yl)-N-hydroxy-2-methyl-2-(methylsulfonyl)butanamide;

(2R)-4-(6-((4-((4-amino-3,3-difluoropiperidin-1-yl)methyl)phenyl)ethynyl)-3-oxo-1H-pyrrolo[1,2-c]imidazol-2(3H)-yl)-N-hydroxy-2-methyl-2-(methylsulfonyl)butanamide;

(2R)-4-(6-((4-(3-fluoroazetidin-3-yl)phenyl)ethynyl)-3-oxo-1H-pyrrolo[1,2-c]imidazol-2(3H)-yl)-N-hydroxy-2-methyl-2-(methylsulfonyl)butanamide;

(2R)-4-(6-((4-(3-fluoro-1-(oxetan-3-yl)azetidin-3-yl)phenyl)ethynyl)-3-oxo-1H-pyrrolo[1,2-c]imidazol-2(3H)-yl)-N-hydroxy-2-methyl-2-(methylsulfonyl)butanamide;

(3R)-4-((2-(4-(hydroxyamino)-3-methyl-3-(methylsulfonyl)-4-oxobutyl)-3-oxo-2,3-dihydro-1H-pyrrolo[1,2-c]imidazol-6-yl)ethynyl)benzyl 4-methylpiperazine-1-carboxylate;

(2R)-4-(6-((3-fluoroazetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide;

(2R)-4-(6-((3-fluoro-1-(oxetan-3-yl) azetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide;

(2R)-4-(6-((4-(3-fluoro-1-methylazetidin-3-yl)phenyl)ethynyl)-3-oxo-1H-pyrrolo[1,2-c]imidazol-2(3H)-yl)-N-hydroxy-2-methyl-2-(methylsulfonyl)butanamide;

(2R)-4-(6-((1-(dimethylamino)cyclopropyl)buta-1,3-diyn-1-yl)-3-oxo-1H-pyrrolo[1,2-c]imidazol-2(3H)-yl)-N-hydroxy-2-methyl-2-(methylsulfonyl)butanamide;

(3R)-(1-((2-(4-(hydroxyamino)-3-methyl-3-(methylsulfonyl)-4-oxobutyl)-3-oxo-2,3-dihydro-1H-pyrrolo[1,2-c]imidazol-6-yl)buta-1,3-diyn-1-yl)cyclopropyl)methyl 3-hydroxyazetidine-1-carboxylate;

(3R)-(1-((2-(4-(hydroxyamino)-3-methyl-3-(methylsulfonyl)-4-oxobutyl)-3-oxo-2,3-dihydro-1H-pyrrolo[1,2-c]imidazol-6-yl)buta-1,3-diyn-1-yl)cyclopropyl)methyl 4-methylpiperazine-1-carboxylate;

(3R)-5-(2-(4-(hydroxyamino)-3-methyl-3-(methylsulfonyl)-4-oxobutyl)-3-oxo-2,3-dihydro-1H-pyrrolo[1,2-c]imidazol-6-yl)penta-2,4-diyn-1-yl 3-hydroxyazetidine-1-carboxylate;

(2R)—N-hydroxy-2-methyl-2-(methylsulfonyl)-4-(6-((4-(2-(methylsulfonyl)ethoxy)phenyl)ethynyl)-3-oxo-1H-pyrrolo[1,2-c]imidazol-2 (3H)-yl)butanamide;

azetidin-3-yl (3R)-(4-((2-(4-(hydroxyamino)-3-methyl-3-(methylsulfonyl)-4-oxobutyl)-3-oxo-2,3-dihydro-1H-pyrrolo[1,2-c]imidazol-6-yl)ethynyl)benzyl)carbamate;

1-methylazetidin-3-yl (3R)-(4-((2-(4-(hydroxyamino)-3-methyl-3-(methylsulfonyl)-4-oxobutyl)-3-oxo-2,3-dihydro-1H-pyrrolo[1,2-c]imidazol-6-yl)ethynyl)benzyl)carbamate;

(2R)—N-hydroxy-4-(6-((4-(1-hydroxy-2-((2-methoxyethyl)(methyl)amino)ethyl)phenyl)ethynyl)-3-oxo-1H-pyrrolo[1,2-c]imidazol-2(3H)-yl)-2-methyl-2-(methylsulfonyl)butanamide;

(2R)—N-hydroxy-2-methyl-2-(methylsulfonyl)-4-(6-(((1R,2R)-2-(morpholinomethyl)cyclopropyl)buta-1,3-diyn-1-yl)-3-oxo-1H-pyrrolo[1,2-c]imidazol-2(3H)-yl)butanamide;

(2R)—N-hydroxy-4-(6-((1-methylazetidin-3-yl)buta-1,3-diyn-1-yl)-3-oxo-1H-pyrrolo[1,2-c]imidazol-2(3H)-yl)-2-(methylsulfonyl)butanamide;

(2R)-4-(6-(azetidin-3-ylbuta-1,3-diyn-1-yl)-3-oxo-1H-pyrrolo[1,2-c]imidazol-2 (3H)-yl)-2-methyl-2-(methylsulfonyl)-N-((tetrahydro-2H-pyran-2-yl)oxy)butanamide;

(2R)-4-(6-((1-acetylazetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide;

(2R)-4-(6-((3-fluoro-1-methylazetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide;

(2R)—N-hydroxy-2-methyl-4-(6-((1-methylpiperidin-4-yl)buta-1,3-diyn-1-yl)-3-oxo-1H-pyrrolo[1,2-c]imidazol-2(3H)-yl)-2-(methylsulfonyl)butanamide;

(2R)—N-hydroxy-2-methyl-2-(methylsulfonyl)-4-(6-((1-(oxetan-3-yl)piperidin-4-yl)buta-1,3-diyn-1-yl)-3-oxo-1H-pyrrolo[1,2-c]imidazol-2(3H)-yl)butanamide;

(2R)-4-(6-((4-(((3S*,4S*)-3-fluoro-4-hydroxypiperidin-1-yl)methyl)phenyl)ethynyl)-3-oxo-1H-pyrrolo[1,2-c]imidazol-2(3H)-yl)-N-hydroxy-2-methyl-2-(methylsulfonyl)butanamide;

(2R)-4-(6-((4-(((S)-3,3-difluoro-4-hydroxypiperidin-1-yl)methyl)phenyl)ethynyl)-3-oxo-1H-pyrrolo[1,2-c]imidazol-2(3H)-yl)-N-hydroxy-2-methyl-2-(methylsulfonyl)butanamide;

(2R)—N-hydroxy-2-methyl-4-(6-((1-(methylamino)cyclopropyl)buta-1,3-diyn-1-yl)-3-oxo-1H-pyrrolo[1,2-c]imidazol-2(3H)-yl)-2-(methylsulfonyl)butanamide;

1-methylazetidin-3-yl (3R)-(5-(2-(4-(hydroxyamino)-3-methyl-3-(methylsulfonyl)-4-oxobutyl)-3-oxo-2,3-dihydro-1H-pyrrolo[1,2-c]imidazol-6-yl)penta-2,4-diyn-1-yl)carbamate;

(2R)—N-hydroxy-4-(6-(5-(4-hydroxypiperidin-1-yl)penta-1,3-diyn-1-yl)-3-oxo-1H-pyrrolo[1,2-c]imidazol-2(3H)-yl)-2-methyl-2-(methylsulfonyl)butanamide;

(2R)—N-hydroxy-4-(6-((1-(2-hydroxyethyl)azetidin-3-yl)buta-1,3-diyn-1-yl)-3-oxo-1H-pyrrolo[1,2-c]imidazol-2(3H)-yl)-2-methyl-2-(methylsulfonyl)butanamide;

(2R)-4-(6-((4-(((3R*,4S*)-3-fluoro-4-hydroxypiperidin-1-yl)methyl)phenyl)ethynyl)-3-oxo-1H-pyrrolo[1,2-c]imidazol-2(3H)-yl)-N-hydroxy-2-methyl-2-(methylsulfonyl)butanamide;

(2R)—N-hydroxy-4-(6-((4-((3-hydroxyazetidin-1-yl)methyl)phenyl)ethynyl)-3-oxo-1H-pyrrolo[1,2-c]imidazol-2(3H)-yl)-2-methyl-2-(methylsulfonyl)butanamide;

(2R)-4-(6-(((1R,2R)-2-((dimethylamino)methyl)cyclopropyl)buta-1,3-diyn-1-yl)-3-oxo-1H-pyrrolo[1,2-c]imidazol-2(3H)-yl)-N-hydroxy-2-methyl-2-(methylsulfonyl)butanamide;

(2R)—N-hydroxy-4-(6-((4-hydroxy-1-(oxetan-3-yl)piperidin-4-yl)buta-1,3-diyn-1-yl)-3-oxo-1H-pyrrolo[1,2-c]imidazol-2(3H)-yl)-2-methyl-2-(methylsulfonyl)butanamide;

(2R)-4-(6-((4-fluoro-1-methylpiperidin-4-yl)buta-1,3-diyn-1-yl)-3-oxo-1H-pyrrolo[1,2-c]imidazol-2(3H)-yl)-N-hydroxy-2-methyl-2-(methylsulfonyl)butanamide;

(2R)-4-(6-((4-fluoro-1-(oxetan-3-yl)piperidin-4-yl)buta-1,3-diyn-1-yl)-3-oxo-1H-pyrrolo[1,2-c]imidazol-2(3H)-yl)-N-hydroxy-2-methyl-2-(methylsulfonyl)butanamide;

(2R)—N-hydroxy-4-(6-((4-hydroxy-1-methylpiperidin-4-yl)buta-1,3-diyn-1-yl)-3-oxo-1H-pyrrolo[1,2-c]imidazol-2(3H)-yl)-2-methyl-2-(methylsulfonyl)butanamide;

(2R)-4-(6-((4-((3-fluoro azetidin-1-yl)methyl)phenyl)ethynyl)-3-oxo-1H-pyrrolo[1,2-c]imidazol-2(3H)-yl)-N-hydroxy-2-methyl-2-(methylsulfonyl)butanamide;

(3R)-5-(2-(4-(hydroxyamino)-3-methyl-3-(methylsulfonyl)-4-oxobutyl)-3-oxo-2,3-dihydro-1H-pyrrolo[1,2-c]imidazol-6-yl)penta-2,4-diyn-1-yl 4-methylpiperazine-1-carboxylate;

(2R)-4-(6-((1-((R)-2,3-dihydroxypropyl)azetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide;

(2R)—N-hydroxy-2-methyl-4-(6-((1-(methyl-d2)azetidin-3-yl)buta-1,3-diyn-1-yl)-3-oxo-1H-pyrrolo[1,2-c]imidazol-2(3H)-yl)-2-(methylsulfonyl)butanamide;

(2R)-4-(6-(((2S,4S)-4-fluoropyrrolidin-2-yl)buta-1,3-diyn-1-yl)-3-oxo-1H-pyrrolo[1,2-c]imidazol-2(3H)-yl)-N-hydroxy-2-methyl-2-(methylsulfonyl)butanamide;

(2R)-4-(6-((1-ethylazetidin-3-yl)buta-1,3-diyn-1-yl)-3-oxo-1H-pyrrolo[1,2-c]imidazol-2 (3H)-yl)-N-hydroxy-2-methyl-2-(methylsulfonyl)butanamide;

(2R)-4-(6-((1-(cyclopropylmethyl)azetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide;

(2R)-4-(6-(((1S,2S)-2-((R)-1,2-dihydroxyethyl)cyclopropyl)buta-1,3-diyn-1-yl)-3-oxo-1H-pyrrolo[1,2-c]imidazol-2(3H)-yl)-N-hydroxy-2-methyl-2-(methylsulfonyl)butanamide;

(2R)-4-(6-((1-cyclopropylazetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide;

(2R)—N-hydroxy-2-methyl-2-(methylsulfonyl)-4-(3-oxo-6-((1-(2,2,2-trifluoroethyl)azetidin-3-yl)buta-1,3-diyn-1-yl)-1H-pyrrolo[1,2-c]imidazol-2(3H)-yl)butanamide;

(2R)-4-(6-((1-isopropylazetidin-3-yl)buta-1,3-diyn-1-yl)-3-oxo-1H-pyrrolo[1,2-c]imidazol-2(3H)-yl-2-methyl-2-(methylsulfonyl)-N-((tetrahydro-2H-pyran-2-yl)oxy)butanamide;

(2R)—N-hydroxy-2-methyl-4-(6-((1-(methyl-d)azetidin-3-yl)buta-1,3-diyn-1-yl)-3-oxo-1H-pyrrolo[1,2-c]imidazol-2(3H)-yl-2-(methylsulfonyl)butanamide;

(2R)-4-(6-((1-(2-fluoroethyl)azetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide;

(2R)-4-(6-((1-cyclobutylazetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide;

(2R)-4-(6-((1-(1,1-dioxidothietan-3-yl)azetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide;

(2R)—N-hydroxy-4-(6-((1-(3-hydroxypropyl)azetidin-3-yl)buta-1,3-diyn-1-yl)-3-oxo-1H-pyrrolo[1,2-c]imidazol-2(3H)-yl)-2-methyl-2-(methylsulfonyl)butanamide;

(2R)-4-(6-((1,3-dimethylazetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide;

(2R)-4-(6-((3-fluoro-1-(2-hydroxyethyl)azetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide;

(2R)—N-hydroxy-4-(6-((1-(3-hydroxy-2-(hydroxymethyl)propyl)azetidin-3-yl)buta-1,3-diyn-1-yl)-3-oxo-1H-pyrrolo[1,2-c]imidazol-2(3H)-yl)-2-methyl-2-(methylsulfonyl)butanamide;

(2R)-4-(6-((1-(2,2-difluoroethyl)azetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide; and (2R)—N-hydroxy-4-(6-((1-(3-hydroxycyclobutyl)azetidin-3-yl)buta-1,3-diyn-1-yl)-3-oxo-1H-pyrrolo[1,2-c]imidazol-2(3H)-yl)-2-methyl-2-(methylsulfonyl)butanamide;

or a salt thereof.

13. A compound of formula I according to claim 1, which is selected from the following:

(2R)-4-(6-((1-cyclohexylazetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide;

(2R)-4-(6-(((3R)-3-fluoro-1-methylpyrrolidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide;

(2R)-4-(6-(((3S)-3-fluoro-1-methylpyrrolidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide;

(2R)-4-(6-((1-cyclopentylazetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide;

(2R)—N-hydroxy-2-methyl-2-(methylsulfonyl)-4-(3-oxo-6-((1-(tetrahydro-2H-pyran-4-yl)azetidin-3-yl)buta-1,3-diyn-1-yl)-1H-pyrrolo[1,2-c]imidazol-2 (3H)-yl)butanamide;

(2R)—N-hydroxy-2-methyl-2-(methylsulfonyl)-4-(3-oxo-6-((1-(thietan-3-yl)azetidin-3-yl)buta-1,3-diyn-1-yl)-1H-pyrrolo[1,2-c]imidazol-2(3H)-yl)butanamide;

(2R)-4-(6-((1-cyclopropyl-3-fluoropyrrolidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide;

(2R)-4-(6-((3-fluoro-1-(2-hydroxyethyl)pyrrolidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide;

(2R)-4-(6-((3-fluoropyrrolidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide;

(2R)-4-(6-((3-ethyl-1-methylazetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide;

(2R)-4-(6-((1,3-dimethylpyrrolidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide;

(2R)—N-hydroxy-2-methyl-4-(6-((1-methylpyrrolidin-3-yl)buta-1,3-diyn-1-yl)-3-oxo-1H-pyrrolo[1,2-c]imidazol-2(3H)-yl)-2-(methylsulfonyl)butanamide;

(2R)-4-(6-(2-fluoro-4-((1-methylazetidin-3-yl)ethynyl)phenyl)-3-oxo-1H-pyrrolo[1,2-c]imidazol-2(3H)-yl)-N-hydroxy-2-methyl-2-(methylsulfonyl)butanamide;

(2R)—N-hydroxy-2-methyl-4-(6-(4-((1-methylazetidin-3-yl)ethynyl)phenyl)-3-oxo-1H-pyrrolo[1,2-c]imidazol-2(3H)-yl)-2-(methylsulfonyl)butanamide;

(2R)-2-(3-((4-(6-((1-(2-hydroxyethyl)azetidin-3-yl)buta-1,3-diyn-1-yl)-3-oxo-1H-pyrrolo[1,2-c]imidazol-2(3H)-yl)-2-methyl-2-(methylsulfonyl)butanamido)oxy)-3-oxopropyl)phenyl dihydrogen phosphate;

(2R)-4-(6-(2-fluoro-4-((1-methylpiperidin-4-yl)ethynyl)phenyl)-3-oxo-1H-pyrrolo[1,2-c]imidazol-2(3H)-yl)-N-hydroxy-2-methyl-2-(methylsulfonyl)butanamide;

(2R)-4-(6-(2-fluoro-4-((1-(2-hydroxyethyl)azetidin-3-yl)ethynyl)phenyl)-3-oxo-1H-pyrrolo[1,2-c]imidazol-2(3H)-yl)-N-hydroxy-2-methyl-2-(methylsulfonyl)butanamide;

(2R)—N-hydroxy-2-methyl-2-(methylsulfonyl)-4-(6-((1-(oxetan-3-yl)pyrrolidin-3-yl)buta-1,3-diyn-1-yl)-3-oxo-1H-pyrrolo[1,2-c]imidazol-2(3H)-yl)butanamide;

(2R)—N-hydroxy-4-(6-((1-((1r,3r)-3-hydroxycyclobutyl)azetidin-3-yl)buta-1,3-diyn-1-yl)-3-oxo-1H-pyrrolo[1,2-c]imidazol-2(3H)-yl)-2-methyl-2-(methylsulfonyl)butanamide;

(2R)—N-hydroxy-4-(6-((1-((1s,3s)-3-hydroxycyclobutyl)azetidin-3-yl)buta-1,3-diyn-1-yl)-3-oxo-1H-pyrrolo[1,2-c]imidazol-2(3H)-yl)-2-methyl-2-(methylsulfonyl)butanamide;

(2R)-4-(6-(((2S,3R)-1,2-dimethylazetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide;

(2R)-4-(6-(((2R,3S)-1,2-dimethylazetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide;

(2R)—N-hydroxy-4-(6-(((3R,5R)-5-(hydroxymethyl)-1-methylpyrrolidin-3-yl)buta-1,3-diyn-1-yl)-3-oxo-1H-pyrrolo[1,2-c]imidazol-2(3H)-yl)-2-methyl-2-(methylsulfonyl)butanamide;

(2R)—N-hydroxy-4-(6-(((2R,3R)-2-(hydroxymethyl)-1-methylazetidin-3-yl)buta-1,3-diyn-1-yl)-3-oxo-1H-pyrrolo[1,2-c]imidazol-2(3H)-yl)-2-methyl-2-(methylsulfonyl)butanamide;

(2R)-4-(6-(((2R,3R)-1,2-dimethylazetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide;

(2R)—N-hydroxy-4-(6-(((2S,3S)-2-(hydroxymethyl)-1-methylazetidin-3-yl)buta-1,3-diyn-1-yl)-3-oxo-1H-pyrrolo[1,2-c]imidazol-2(3H)-yl)-2-methyl-2-(methylsulfonyl)butanamide;

(2R)—N-hydroxy-4-(6-(((2S,3S)-2-(fluoromethyl)-1-methylazetidin-3-yl)buta-1,3-diyn-1-yl)-3-oxo-1H-pyrrolo[1,2-c]imidazol-2(3H)-yl)-2-methyl-2-(methylsulfonyl)butanamide;

(2R)—N-hydroxy-4-(6-(((3S*,4R*)-4-hydroxy-1-methylpyrrolidin-3-yl)buta-1,3-diyn-1-yl)-3-oxo-1H-pyrrolo[1,2-c]imidazol-2(3H)-yl)-2-methyl-2-(methylsulfonyl)butanamide; and (2R)—N-hydroxy-4-(6-(((3R,5R)-5-(hydroxymethyl)-1-(oxetan-3-yl)pyrrolidin-3-yl)buta-1,3-diyn-1-yl)-3-oxo-1H-pyrrolo[1,2-c]imidazol-2(3H)-yl)-2-methyl-2-(methylsulfonyl)butanamide;

or a salt thereof.

14. A pharmaceutical composition containing, as active principle, a compound of formula I as defined in claim 1, or a pharmaceutically acceptable salt thereof, and at least one therapeutically inert excipient.

15. A compound of formula I according to claim 5, wherein M is the group $M^B$, wherein $R^{1B}$ represents the group $Q^A$, wherein $X^{A1}$ represents methyl, methyl-d, methyl-d2, 2-fluoro-ethyl, 2-hydroxy-ethyl, cycloprop-1-yl, 3-hydroxy-prop-1-yl or 3-hydroxycyclobut-1-yl; $X^{A21}$ and $X^{A22}$ each represent H; and $X^{A3}$ represents H;

or a salt thereof.

16. A compound of formula I according to claim 1, wherein $R^1$ represents (2-(phosphonooxy)-phenyl)-$(C_1-C_4)$alkyl;

or a salt thereof.

17. A compound of formula I according to claim 1, wherein $R^1$ represents H; or a salt thereof.

18. A compound of formula I according to claim 5, wherein $R^1$ represents (2-(phosphonooxy)-phenyl)-$(C_1-C_4)$alkyl;

or a salt thereof.

19. A compound of formula I according to claim 5, wherein $R^1$ represents H;

or a salt thereof.

20. A compound of formula I according to claim 15, wherein $R^1$ represents (2-(phosphonooxy)-phenyl)-($C_1$-$C_4$) alkyl;
or a salt thereof.

21. A compound of formula I according to claim 15, wherein $R^1$ represents H;
or a salt thereof.

22. A compound of formula I according to claim 15, which is selected from the following:
- (2R)—N-hydroxy-2-methyl-4-(6-((1-methylazetidin-3-yl)buta-1,3-diyn-1-yl)-3-oxo-1H-pyrrolo[1,2-c]imidazol-2(3H)-yl)-2-(methylsulfonyl)butanamide;
- (2R)—N-hydroxy-4-(6-((1-(2-hydroxyethyl)azetidin-3-yl)buta-1,3-diyn-1-yl)-3-oxo-1H-pyrrolo[1,2-c]imidazol-2(3H)-yl)-2-methyl-2-(methylsulfonyl)butanamide;
- (2R)—N-hydroxy-2-methyl-4-(6-((1-(methyl-d2)azetidin-3-yl)buta-1,3-diyn-1-yl)-3-oxo-1H-pyrrolo[1,2-c]imidazol-2(3H)-yl)-2-(methylsulfonyl)butanamide;
- (2R)-4-(6-((1-cyclopropylazetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide;
- (2R)—N-hydroxy-2-methyl-4-(6-((1-(methyl-d)azetidin-3-yl)buta-1,3-diyn-1-yl)-3-oxo-1H-pyrrolo[1,2-c]imidazol-2(3H)-yl)-2-(methylsulfonyl)butanamide;
- (2R)-4-(6-((1-(2-fluoroethyl)azetidin-3-yl)buta-1,3-diyn-1-yl)-3-oxo-1H-pyrrolo[1,2-c]imidazol-2(3H)-yl)-N-hydroxy-2-methyl-2-(methylsulfonyl)butanamide;
- (2R)—N-hydroxy-4-(6-((1-(3-hydroxypropyl)azetidin-3-yl)buta-1,3-diyn-1-yl)-3-oxo-1H-pyrrolo[1,2-c]imidazol-2(3H)-yl)-2-methyl-2-(methylsulfonyl)butanamide;
- (2R)—N-hydroxy-4-(6-((1-(3-hydroxycyclobutyl)azetidin-3-yl)buta-1,3-diyn-1-yl)-3-oxo-1H-pyrrolo[1,2-c]imidazol-2(3H)-yl)-2-methyl-2-(methylsulfonyl)butanamide; and
- (2R)-2-(3-((4-(6-((1-(2-hydroxyethyl)azetidin-3-yl)buta-1,3-diyn-1-yl)-3-oxo-1H-pyrrolo[1,2-c]imidazol-2(3H)-yl)-2-methyl-2-(methylsulfonyl)butanamido)oxy)-3-oxopropyl)phenyl dihydrogen phosphate;
or a salt thereof.

23. The compound of formula I according to claim 22, which is (2R)—N-hydroxy-4-(6-((1-(2-hydroxyethyl)azetidin-3-yl)buta-1,3-diyn-1-yl)-3-oxo-1H-pyrrolo[1,2-c]imidazol-2(3H)-yl)-2-methyl-2-(methylsulfonyl)butanamide;
or a salt thereof.

24. The compound of formula I according to claim 22, which is (2R)-2-(3-((4-(6-((1-(2-hydroxyethyl)azetidin-3-yl)buta-1,3-diyn-1-yl)-3-oxo-1H-pyrrolo[1,2-c]imidazol-2(3H)-yl)-2-methyl-2-(methylsulfonyl)butanamido)oxy)-3-oxopropyl)phenyl dihydrogen phosphate;
or a salt thereof.

25. A pharmaceutical composition containing, as active principle, a compound of formula I as defined in claim 1, or a pharmaceutically acceptable salt thereof, and at least one therapeutically inert excipient.

26. A pharmaceutical composition containing, as active principle, the compound defined in claim 23, or a pharmaceutically acceptable salt thereof, and at least one therapeutically inert excipient.

27. A pharmaceutical composition containing, as active principle, the compound defined in claim 24, or a pharmaceutically acceptable salt thereof, and at least one therapeutically inert excipient.

28. A method of treatment of a bacterial infection, comprising administering to a subject in need thereof a compound of formula I as defined in claim 1, or a pharmaceutically acceptable salt thereof.

29. A method of treatment of a bacterial infection, comprising administering to a subject in need thereof the compound defined in claim 23, or a pharmaceutically acceptable salt thereof.

30. A method of treatment of a bacterial infection, comprising administering to a subject in need thereof the compound defined in claim 24, or a pharmaceutically acceptable salt thereof.

31. A method of treatment of a bacterial infection, comprising administering to a subject in need thereof the pharmaceutical composition defined in claim 26.

32. A method of treatment of a bacterial infection, comprising administering to a subject in need thereof the pharmaceutical composition defined in claim 27.

33. The method according to claim 28, wherein the bacterial infection is a Gram-negative bacterial infection.

34. The method according to claim 29, wherein the bacterial infection is a Gram-negative bacterial infection.

35. The method according to claim 30, wherein the bacterial infection is a Gram-negative bacterial infection.

36. The method according to claim 31, wherein the bacterial infection is a Gram-negative bacterial infection.

37. The method according to claim 32, wherein the bacterial infection is a Gram-negative bacterial infection.

38. A pharmaceutical composition comprising (2R)—N-hydroxy-4-(6-((1-(2-hydroxyethyl)azetidin-3-yl)buta-1,3-diyn-1-yl)-3-oxo-1H-pyrrolo[1,2-c]imidazol-2(3H)-yl)-2-methyl-2-(methylsulfonyl)butanamide, or a salt thereof.

39. A pharmaceutical composition comprising (2R)-2-(3-((4-(6-((1-(2-hydroxyethyl)azetidin-3-yl)buta-1,3-diyn-1-yl)-3-oxo-1H-pyrrolo[1,2-c]imidazol-2(3H)-yl)-2-methyl-2-(methylsulfonyl)butanamido)oxy)-3-oxopropyl)phenyl dihydrogen phosphate, or a salt thereof.

* * * * *